United States Patent
Chandran et al.

(10) Patent No.: US 9,234,885 B2
(45) Date of Patent: Jan. 12, 2016

(54) METHODS AND ASSAYS FOR TREATING FILOVIRIDAE INFECTIONS

(75) Inventors: Kartik Chandran, Brooklyn, NY (US); Sean Whelan, Cambridge, MA (US); Thijn Brummelkamp, Amsterdam (NL); Jan Carette, Palo Alto, CA (US); Matthijs Raaben, De Belt (NL)

(73) Assignees: Albert Einstein College of Medicine, Inc., Bronx, NY (US); President and Fellows of Harvard College, Cambridge, MA (US); Whitehead Institute For Biomedical Research, Cambridge, MA (US)

( * ) Notice: Subject to any disclaimer, the term of this patent is extended or adjusted under 35 U.S.C. 154(b) by 47 days.

(21) Appl. No.: 13/979,179

(22) PCT Filed: Jan. 24, 2012

(86) PCT No.: PCT/US2012/022349
§ 371 (c)(1),
(2), (4) Date: Sep. 25, 2013

(87) PCT Pub. No.: WO2012/103081
PCT Pub. Date: Aug. 2, 2012

(65) Prior Publication Data
US 2014/0018338 A1    Jan. 16, 2014

Related U.S. Application Data

(60) Provisional application No. 61/435,858, filed on Jan. 25, 2011.

(51) Int. Cl.
*G01N 33/50* (2006.01)
*A61K 31/55* (2006.01)
*A61K 31/566* (2006.01)
*C12Q 1/70* (2006.01)
*G01N 33/569* (2006.01)
*A61K 31/5685* (2006.01)

(52) U.S. Cl.
CPC ............ *G01N 33/5035* (2013.01); *A61K 31/55* (2013.01); *A61K 31/566* (2013.01); *A61K 31/5685* (2013.01); *C12Q 1/70* (2013.01); *G01N 33/56983* (2013.01); *C12N 2760/14034* (2013.01); *C12N 2760/14111* (2013.01); *C12N 2760/14211* (2013.01); *C12N 2760/20243* (2013.01)

(58) Field of Classification Search
CPC .................................................. G01N 33/5035
See application file for complete search history.

(56) References Cited

U.S. PATENT DOCUMENTS

| 5,837,701 A * | 11/1998 | Bleiweiss et al. ............. 514/217 |
| 2002/0168771 A1 | 11/2002 | Gamerman |
| 2007/0087008 A1 | 4/2007 | Hodge et al. |
| 2010/0221357 A1 | 9/2010 | Ostroff |

OTHER PUBLICATIONS

CDC Ebola Hemorrhagic Fever Information Packet, 2009.*
CDC Marburg Hemorrhagic Fever Fact Sheet, 2010.*
Feldmann H, Geisbert TW. Ebola haemorrhagic fever. Lancet. Mar. 5, 2011;377(9768):849-62.*
Cote M et al., entitled "Small molecule inhibitors reveal Niemann-Pick C1 is essential for Ebola virus infection," Nature, Aug. 24, 2011, 477(7364): 344-348.
Shoemaker C J et al., entitled "Multiple Cationic Amphiphiles Induce a Niemann-Pick C Phenotype and Inhibit Ebola Virus Entry and Infection," PLOS ONE, Feb. 2013, vol. 8, Issue 2, e56265, 13 pages.
Johansen L M et al., entitled "FDA-Approved Selective Estrogen Receptor Modulators Inhibit Ebola Virus Infection," Science Translation Medicine, Jun. 19, 2013, vol. 5, Issue 90, 190ra79, 15 pages.
Cai X et al., entitled "PIKfyve, a Class III PI Kinase, Is the Target of the Small Molecular IL-12/IL-23 Inhibitor Apilimod and a Player in Toll-like Receptor Signaling," Chemistry & Biology 20, 912-921, Jul. 25, 2013.
International Search Report, dated Apr. 13, 2012 in connection with PCT International Application No. PCT/2012/022349, 6 pages.
Written Opinion of the International Searching Authority, dated Apr. 13, 2012 in connection with PCT International Application No. PCT/2012/022349, 5 pages.
Carette J E et al., entitled "Ebola virus entry requires the cholesterol transporter Niemann-Pick C1," Nature, vol. 477, Sep. 15, 2011, 340-343.

* cited by examiner

*Primary Examiner* — Paul Zarek
(74) *Attorney, Agent, or Firm* — Amster, Rothstein & Ebenstein LLP

(57) ABSTRACT

Methods and assays for treating a subject with a filovirus infection using an agent that inhibits Niemann-Pick CI (NPCI), VPSII, VPSI6, VPSI8, VPS33A, VPS39, VPS41, BLOCISI, BLOCIS2, GNPTAB, PIKFYVE, ARHGAP23 or FIG4. Methods for screening for an agent that treats and/or prevents infection of a subject with a filovirus, where the methods comprise determining whether the agent inhibits one or more of Niemann-Pick CI (NPCI), VPSII, VPSI6, VPSI8, VPS33A, VPS39, VPS41. BLOCISI, BLOCIS2, GNPTAB, PIKFYVE, ARHGAP23 or FIG4, wherein an agent that inhibits one or more of NPCI, VPSII, VPSI6, VPSI8, VPS33A, VPS39, VPS41, BLOCISI, BLOCIS2, GNPTAB, PIKFYVE, ARHGAP23 or FIG4 is a candidate for treating and/or preventing an infection with a filovirus and wherein an agent that does not inhibit NPCI, VPSII, VPSI6, VPSI8, VPS33A. VPS39, VPS41, BLOCISI, BLOCIS2, GNPTAB, PIKFYVE, ARHGAP23 or FIG4 is not a candidate for treating and/or preventing an infection with a filovirus.

9 Claims, 34 Drawing Sheets

HAP1 cells mutagenized with gene trap
(complexity ~ 100 x 10$^6$)

unselected control selected with rVSV-GP-Ebola deep sequence insertion sites deep sequence insertion sites isolate clonal derivatives count independent insertions per gene count independent insertions per gene functional studies control dataset ~430,000 insertions experimental dataset ~700 insertions calculate per gene the significance of enrichment in experimental dataset Expected (based on control)

Observed gene with multiple insertions and high significance of enrichment

Significance

Genes in experimental dataset

SEQUENCE LISTING

```
<160> NUMBER OF SEQ ID NOS: 39

<210> SEQ ID NO 1
<211> LENGTH: 1278
<212> TYPE: PRT
<213> ORGANISM: Homo sapiens

<400> SEQUENCE: 1

Met Thr Ala Arg Gly Leu Ala Leu Gly Leu Leu Leu Leu Leu Leu Cys
1               5                   10                  15

Pro Ala Gln Val Phe Ser Gln Ser Cys Val Trp Tyr Gly Glu Cys Gly
            20                  25                  30

Ile Ala Tyr Gly Asp Lys Arg Tyr Asn Cys Glu Tyr Ser Gly Pro Pro
        35                  40                  45

Lys Pro Leu Pro Lys Asp Gly Tyr Asp Leu Val Gln Glu Leu Cys Pro
    50                  55                  60

Gly Phe Phe Phe Gly Asn Val Ser Leu Cys Cys Asp Val Arg Gln Leu
65                  70                  75                  80

Gln Thr Leu Lys Asp Asn Leu Gln Leu Pro Leu Gln Phe Leu Ser Arg
                85                  90                  95

Cys Pro Ser Cys Phe Tyr Asn Leu Leu Asn Leu Phe Cys Glu Leu Thr
            100                 105                 110

Cys Ser Pro Arg Gln Ser Gln Phe Leu Asn Val Thr Ala Thr Glu Asp
        115                 120                 125

Tyr Val Asp Pro Val Thr Asn Gln Thr Lys Thr Asn Val Lys Glu Leu
    130                 135                 140

Gln Tyr Tyr Val Gly Gln Ser Phe Ala Asn Ala Met Tyr Asn Ala Cys
145                 150                 155                 160

Arg Asp Val Glu Ala Pro Ser Ser Asn Asp Lys Ala Leu Gly Leu Leu
                165                 170                 175
```

```
Cys Gly Lys Asp Ala Asp Ala Cys Asn Ala Thr Asn Trp Ile Glu Tyr
            180                 185                 190

Met Phe Asn Lys Asp Asn Gly Gln Ala Pro Phe Thr Ile Thr Pro Val
        195                 200                 205

Phe Ser Asp Phe Pro Val His Gly Met Glu Pro Met Asn Asn Ala Thr
    210                 215                 220

Lys Gly Cys Asp Glu Ser Val Asp Glu Val Thr Ala Pro Cys Ser Cys
225                 230                 235                 240

Gln Asp Cys Ser Ile Val Cys Gly Pro Lys Pro Gln Pro Pro Pro Pro
                245                 250                 255

Pro Ala Pro Trp Thr Ile Leu Gly Leu Asp Ala Met Tyr Val Ile Met
            260                 265                 270

Trp Ile Thr Tyr Met Ala Phe Leu Leu Val Phe Phe Gly Ala Phe Phe
        275                 280                 285

Ala Val Trp Cys Tyr Arg Lys Arg Tyr Phe Val Ser Glu Tyr Thr Pro
    290                 295                 300

Ile Asp Ser Asn Ile Ala Phe Ser Val Asn Ala Ser Asp Lys Gly Glu
305                 310                 315                 320

Ala Ser Cys Cys Asp Pro Val Ser Ala Ala Phe Glu Gly Cys Leu Arg
                325                 330                 335

Arg Leu Phe Thr Arg Trp Gly Ser Phe Cys Val Arg Asn Pro Gly Cys
            340                 345                 350

Val Ile Phe Phe Ser Leu Val Phe Ile Thr Ala Cys Ser Ser Gly Leu
        355                 360                 365

Val Phe Val Arg Val Thr Thr Asn Pro Val Asp Leu Trp Ser Ala Pro
    370                 375                 380

Ser Ser Gln Ala Arg Leu Glu Lys Glu Tyr Phe Asp Gln His Phe Gly
385                 390                 395                 400

Pro Phe Phe Arg Thr Glu Gln Leu Ile Ile Arg Ala Pro Leu Thr Asp
                405                 410                 415

Lys His Ile Tyr Gln Pro Tyr Pro Ser Gly Ala Asp Val Pro Phe Gly
            420                 425                 430

Pro Pro Leu Asp Ile Gln Ile Leu His Gln Val Leu Asp Leu Gln Ile
        435                 440                 445

Ala Ile Glu Asn Ile Thr Ala Ser Tyr Asp Asn Glu Thr Val Thr Leu
    450                 455                 460

Gln Asp Ile Cys Leu Ala Pro Leu Ser Pro Tyr Asn Thr Asn Cys Thr
465                 470                 475                 480

Ile Leu Ser Val Leu Asn Tyr Phe Gln Asn Ser His Ser Val Leu Asp
                485                 490                 495

His Lys Lys Gly Asp Asp Phe Phe Val Tyr Ala Asp Tyr His Thr His
            500                 505                 510

Phe Leu Tyr Cys Val Arg Ala Pro Ala Ser Leu Asn Asp Thr Ser Leu
        515                 520                 525

Leu His Asp Pro Cys Leu Gly Thr Phe Gly Gly Pro Val Phe Pro Trp
    530                 535                 540

Leu Val Leu Gly Gly Tyr Asp Asp Gln Asn Tyr Asn Asn Ala Thr Ala
545                 550                 555                 560

Leu Val Ile Thr Phe Pro Val Asn Asn Tyr Tyr Asn Asp Thr Glu Lys
                565                 570                 575

Leu Gln Arg Ala Gln Ala Trp Glu Lys Glu Phe Ile Asn Phe Val Lys
            580                 585                 590

Asn Tyr Lys Asn Pro Asn Leu Thr Ile Ser Phe Thr Ala Glu Arg Ser
```

-continued

```
            595                 600                 605
Ile Glu Asp Glu Leu Asn Arg Glu Ser Asp Ser Asp Val Phe Thr Val
    610                 615                 620

Val Ile Ser Tyr Ala Ile Met Phe Leu Tyr Ile Ser Leu Ala Leu Gly
625                 630                 635                 640

His Met Lys Ser Cys Arg Arg Leu Leu Val Asp Ser Lys Val Ser Leu
                    645                 650                 655

Gly Ile Ala Gly Ile Leu Ile Val Leu Ser Ser Val Ala Cys Ser Leu
                660                 665                 670

Gly Val Phe Ser Tyr Ile Gly Leu Pro Leu Thr Leu Ile Val Ile Glu
            675                 680                 685

Val Ile Pro Phe Leu Val Leu Ala Val Gly Val Asp Asn Ile Phe Ile
690                 695                 700

Leu Val Gln Ala Tyr Gln Arg Asp Glu Arg Leu Gln Gly Glu Thr Leu
705                 710                 715                 720

Asp Gln Gln Leu Gly Arg Val Leu Gly Glu Val Ala Pro Ser Met Phe
                725                 730                 735

Leu Ser Ser Phe Ser Glu Thr Val Ala Phe Phe Leu Gly Ala Leu Ser
                740                 745                 750

Val Met Pro Ala Val His Thr Phe Ser Leu Phe Ala Gly Leu Ala Val
            755                 760                 765

Phe Ile Asp Phe Leu Leu Gln Ile Thr Cys Phe Val Ser Leu Leu Gly
770                 775                 780

Leu Asp Ile Lys Arg Gln Glu Lys Asn Arg Leu Asp Ile Phe Cys Cys
785                 790                 795                 800

Val Arg Gly Ala Glu Asp Gly Thr Ser Val Gln Ala Ser Glu Ser Cys
                805                 810                 815

Leu Phe Arg Phe Phe Lys Asn Ser Tyr Ser Pro Leu Leu Leu Lys Asp
                820                 825                 830

Trp Met Arg Pro Ile Val Ile Ala Ile Phe Val Gly Val Leu Ser Phe
            835                 840                 845

Ser Ile Ala Val Leu Asn Lys Val Asp Ile Gly Leu Asp Gln Ser Leu
850                 855                 860

Ser Met Pro Asp Asp Ser Tyr Met Val Asp Tyr Phe Lys Ser Ile Ser
865                 870                 875                 880

Gln Tyr Leu His Ala Gly Pro Pro Val Tyr Phe Val Leu Glu Glu Gly
                885                 890                 895

His Asp Tyr Thr Ser Ser Lys Gly Gln Asn Met Val Cys Gly Gly Met
                900                 905                 910

Gly Cys Asn Asn Asp Ser Leu Val Gln Gln Ile Phe Asn Ala Ala Gln
            915                 920                 925

Leu Asp Asn Tyr Thr Arg Ile Gly Phe Ala Pro Ser Ser Trp Ile Asp
            930                 935                 940

Asp Tyr Phe Asp Trp Val Lys Pro Gln Ser Ser Cys Cys Arg Val Asp
945                 950                 955                 960

Asn Ile Thr Asp Gln Phe Cys Asn Ala Ser Val Val Asp Pro Ala Cys
                965                 970                 975

Val Arg Cys Arg Pro Leu Thr Pro Glu Gly Lys Gln Arg Pro Gln Gly
                980                 985                 990

Gly Asp Phe Met Arg Phe Leu Pro Met Phe Leu Ser Asp Asn Pro Asn
            995                 1000                1005

Pro Lys Cys Gly Lys Gly Gly His Ala Ala Tyr Ser Ser Ala Val
    1010            1015                1020
```

Asn Ile Leu Leu Gly His Gly Thr Arg Val Gly Ala Thr Tyr Phe
1025                1030                1035

Met Thr Tyr His Thr Val Leu Gln Thr Ser Ala Asp Phe Ile Asp
1040                1045                1050

Ala Leu Lys Lys Ala Arg Leu Ile Ala Ser Asn Val Thr Glu Thr
1055                1060                1065

Met Gly Ile Asn Gly Ser Ala Tyr Arg Val Phe Pro Tyr Ser Val
1070                1075                1080

Phe Tyr Val Phe Tyr Glu Gln Tyr Leu Thr Ile Asp Asp Thr
1085                1090                1095

Ile Phe Asn Leu Gly Val Ser Leu Gly Ala Ile Phe Leu Val Thr
1100                1105                1110

Met Val Leu Leu Gly Cys Glu Leu Trp Ser Ala Val Ile Met Cys
1115                1120                1125

Ala Thr Ile Ala Met Val Leu Val Asn Met Phe Gly Val Met Trp
1130                1135                1140

Leu Trp Gly Ile Ser Leu Asn Ala Val Ser Leu Val Asn Leu Val
1145                1150                1155

Met Ser Cys Gly Ile Ser Val Glu Phe Cys Ser His Ile Thr Arg
1160                1165                1170

Ala Phe Thr Val Ser Met Lys Gly Ser Arg Val Glu Arg Ala Glu
1175                1180                1185

Glu Ala Leu Ala His Met Gly Ser Ser Val Phe Ser Gly Ile Thr
1190                1195                1200

Leu Thr Lys Phe Gly Gly Ile Val Val Leu Ala Phe Ala Lys Ser
1205                1210                1215

Gln Ile Phe Gln Ile Phe Tyr Phe Arg Met Tyr Leu Ala Met Val
1220                1225                1230

Leu Leu Gly Ala Thr His Gly Leu Ile Phe Leu Pro Val Leu Leu
1235                1240                1245

Ser Tyr Ile Gly Pro Ser Val Asn Lys Ala Lys Ser Cys Ala Thr
1250                1255                1260

Glu Glu Arg Tyr Lys Gly Thr Glu Arg Glu Arg Leu Leu Asn Phe
1265                1270                1275

<210> SEQ ID NO 2
<211> LENGTH: 4827
<212> TYPE: DNA
<213> ORGANISM: Homo sapiens

<400> SEQUENCE: 2
gaagggcaac acgggaccct tgaagcgggg tcgcggcggc gccccagccc gggccaggga      60
gtcccggcag cggcacctcc cagaaagggc ggagccgacg acgccttctt ccttcctgac     120
cggcgcgcgc agcctgctgc cgcggtcagc gcctgctcct gctcctccgc tcctcctgcg     180
cggggtgctg aaacagcccg gggaagtaga gccgcctccg gggagcccaa ccagccgaac     240
gccgccggcg tcagcagcct tgcgcggcca cagcatgacc gctcgcggcc tggcccttgg     300
cctcctcctg ctgctactgt gtccagcgca ggtgttttca cagtcctgtg tttggtatgg     360
agagtgtgga attgcatatg gggacaagag gtacaattgc gaatattctg cccaccaaa     420 accattgcca aaggatggat atgacttagt gcaggaactc tgtccaggat tcttctttgg     480
caatgtcagt ctctgttgtg atgttcggca gcttcagaca ctaaaagaca acctgcagct     540
gcctctacag tttctgtcca gatgtccatc ctgtttttat aacctactga acctgttttg     600

```
tgagctgaca tgtagccctc gacagagtca gtttttgaat gttacagcta ctgaagatta      660
tgttgatcct gttacaaacc agacgaaaac aaatgtgaaa gagttacaat actacgtcgg      720
acagagtttt gccaatgcaa tgtacaatgc ctgccgggat gtggaggccc cctcaagtaa      780
tgacaaggcc ctgggactcc tgtgtgggaa ggacgctgac gcctgtaatg ccaccaactg      840
gattgaatac atgttcaata aggacaatgg acaggcacct tttaccatca ctcctgtgtt      900
ttcagatttt ccagtccatg ggatggagcc catgaacaat gccaccaaag gctgtgacga      960
gtctgtggat gaggtcacag caccatgtag ctgccaagac tgctctattg tctgtggccc     1020
caagccccag cccccacctc ctcctgctcc ctggacgatc cttggcttgg acgccatgta     1080
tgtcatcatg tggatcacct acatggcgtt tttgcttgtg ttttttggag cattttttgc     1140
agtgtggtgc tacagaaaac ggtatttttgt ctccgagtac actccatcg atagcaatat     1200 agcttttttct gttaatgcaa gtgacaaagg agaggcgtcc tgctgtgacc ctgtcagcgc     1260
agcatttgag ggctgcttga ggcggctgtt cacacgctgg gggtcttttct gcgtccgaaa     1320 ccctggctgt gtcattttct tctcgctggt cttcattact gcgtgttcgt caggcctggt     1380
gtttgtccgg gtcacaacca atccagttga cctctggtca gcccccagca gccaggctcg     1440
cctggaaaaa gagtactttg accagcactt tgggcctttc ttccggacgg agcagctcat     1500
catccgggcc cctctcactg acaaacacat ttaccagcca tacccttcgg gagctgatgt     1560
acccttggga cctccgcttg acatacagat actgcaccag gttcttgact acaaatagc     1620 catcgaaaac attactgcct cttatgacaa tgagactgtg acacttcaag acatctgctt     1680
ggcccctctt tcaccgtata acacgaactg caccattttg agtgtgttaa attacttcca     1740
gaacagccat tccgtgctgg accacaagaa aggggacgac ttctttgtgt atgccgatta     1800
ccacacgcac tttctgtact gcgtacgggc tcctgcctct ctgaatgata caagtttgct     1860
ccatgacccc tgtctgggta cgtttggtgg accagtgttc ccgtggcttg tgttgggagg     1920
ctatgatgat caaaactaca ataacgccac tgcccttgtg attaccttcc ctgtcaataa     1980
ttactataat gatacagaga agctccagag ggcccaggcc tgggaaaaag agtttattaa     2040
ttttgtgaaa aactacaaga atcccaatct gaccatttcc ttcactgctg aacgaagtat     2100
tgaagatgaa ctaaatcgtg aaagtgacag tgatgtcttc accgttgtaa ttagctatgc     2160
catcatgttt ctatatattt ccctagcctt ggggcacatg aaaagctgtc gcaggcttct     2220
ggtggattcg aaggtctcac taggcatcgc gggcatcttg atcgtgctga gctcggtggc     2280
ttgctccttg ggtgtcttca gctacattgg gttgcccttg accctcattg tgattgaagt     2340
catcccgttc ctggtgctgg ctgttggagt ggacaacatc ttcattctgg tgcaggccta     2400
ccagagagat gaacgtcttc aaggggaaac cctggatcag cagctgggca gggtcctagg     2460
agaagtggct cccagtatgt tcctgtcatc ctttttctgag actgtagcat ttttcttagg     2520
agcattgtcc gtgatgccag ccgtgcacac cttctctctc tttgcgggat tggcagtctt     2580
cattgacttt cttctgcaga ttacctgttt cgtgagtctc ttggggttag acattaaacg     2640
tcaagagaaa aatcggctag acatcttttg ctgtgtcaga ggtgctgaag atggaacaag     2700
cgtccaggcc tcagagagct gttttgtttcg cttcttcaaa aactcctatt ctccacttct     2760
gctaaaggac tggatgagac caattgtgat agcaatattt gtgggtgttc tgtcattcag     2820
catcgcagtc ctgaacaaag tagatattgg attggatcag tctctttcga tgccagatga     2880
ctcctacatg gtggattatt tcaaatccat cagtcagtac ctgcatgcgg gtccgcctgt     2940
```

```
gtactttgtc ctggaggaag ggcacgacta cacttcttcc aaggggcaga acatggtgtg   3000
cggcggcatg ggctgcaaca atgattccct ggtgcagcag atatttaacg cggcgcagct   3060
ggacaactat acccgaatag gcttcgcccc ctcgtcctgg atcgacgatt atttcgactg   3120
ggtgaagcca cagtcgtctt gctgtcgagt ggacaatatc actgaccagt tctgcaatgc   3180
ttcagtggtt gaccctgcct gcgttcgctg caggcctctg actccggaag gcaaacagag   3240
gcctcagggg ggagacttca tgagattcct gcccatgttc ctttcggata acctaaccc   3300 caagtgtggc aaggggggac atgctgccta tagttctgca gttaacatcc tccttggcca   3360
tggcaccagg gtcggagcca cgtacttcat gacctaccac accgtgctgc agacctctgc   3420
tgactttatt gacgctctga gaaagcccg acttatagcc agtaatgtca ccgaaaccat   3480
gggcattaac ggcagtgcct accgagtatt tccttacagt gtgttttatg tcttctacga   3540
acagtacctg accatcattg acgacactat cttcaacctc ggtgtgtccc tgggcgcgat   3600
atttctggtg accatggtcc tcctgggctg tgagctctgg tctgcagtca tcatgtgtgc   3660
caccatcgcc atggtcttgg tcaacatgtt tggagttatg tggctctggg gcatcagtct   3720
gaacgctgta tccttggtca acctggtgat gagctgtggc atctccgtgg agttctgcag   3780
ccacataacc agagcgttca cggtgagcat gaaaggcagc cgcgtggagc gcgcggaaga   3840
ggcacttgcc cacatgggca gctccgtgtt cagtggaatc acacttacaa aatttggagg   3900
gattgtggtg ttggcttttg ccaaatctca aattttccag atattctact caggatgta   3960 tttggccatg gtcttactgg gagccactca cggattaata tttctccctg tcttactcag   4020
ttacataggc cctcagtaa ataaagccaa agttgtgcc actgaagagc gatacaaagg   4080
aacagagcgc gaacggcttc taaatttcta gcccctcgc agggcatcct gactgaactg   4140
tgtctaaggc tcggtcggtt taccactgga cgggtgctgc atcggcaagg ccaagttgaa   4200
caccggatgg tgccaaccat cggttgtttg gcagcagctt tgaacgtagc gcctgtgaac   4260
tcaggaatgc acagttgact tgggaagcag tattactaga tctggaggca accacaggac   4320
actaaacttc tcccagcctc ttcaggaaag aaacctcatt ctttggcaag caggaggtga   4380
cactagatgc tgtgaatgt gatccgctca ctgacactct gtaaaggcca atcaatgcac   4440
tgtctgtctc tccttttagg agtaagccat cccacaagtt ctataccata tttttagtga   4500
cagttgaggt tgtagataca ctttataaca ttttatagtt taaagagctt tattaatgca   4560
ataaattaac tttgtacaca ttttatata aaaaaacagc aagtgatttc agaatgttgt   4620
aggcctcatt agagcttggt ctccaaaaat ctgttgaaa aaagcaacat gttcttcaca   4680
gtgttcccct agaaaggaag agatttaatt gccagttaga tgtggcatga atgagggac   4740 aaagaaagca tctcgtaggt gtgtctactg ggttttaact tattttctt taataaaata   4800 cattgttttc ctaaaaaaaa aaaaaaa                                     4827
```

<210> SEQ ID NO 3
<211> LENGTH: 941
<212> TYPE: PRT
<213> ORGANISM: Homo sapiens

<400> SEQUENCE: 3

Met Ala Ala Tyr Leu Gln Trp Arg Arg Phe Val Phe Phe Asp Lys Glu
1               5                   10                  15

Leu Val Lys Glu Pro Leu Ser Asn Asp Gly Ala Ala Pro Gly Ala Thr
            20                  25                  30

Pro Ala Ser Gly Ser Ala Ala Ser Lys Phe Leu Cys Leu Pro Pro Gly

```
                35                  40                  45
Ile Thr Val Cys Asp Ser Gly Arg Gly Ser Leu Val Phe Gly Asp Met
 50                  55                  60
Glu Gly Gln Ile Trp Phe Leu Pro Arg Ser Leu Gln Leu Thr Gly Phe
 65                  70                  75                  80
Gln Ala Tyr Lys Leu Arg Val Thr His Leu Tyr Gln Leu Lys Gln His
                 85                  90                  95
Asn Ile Leu Ala Ser Val Gly Glu Asp Glu Gly Ile Asn Pro Leu
                100                 105                 110
Val Lys Ile Trp Asn Leu Glu Lys Arg Asp Gly Gly Asn Pro Leu Cys
                115                 120                 125
Thr Arg Ile Phe Pro Ala Ile Pro Gly Thr Glu Pro Thr Val Val Ser
130                 135                 140
Cys Leu Thr Val His Glu Asn Leu Asn Phe Met Ala Ile Gly Phe Thr
145                 150                 155                 160
Asp Gly Ser Val Thr Leu Asn Lys Gly Asp Ile Thr Arg Asp Arg His
                165                 170                 175
Ser Lys Thr Gln Ile Leu His Lys Gly Asn Tyr Pro Val Thr Gly Leu
                180                 185                 190
Ala Phe Arg Gln Ala Gly Lys Thr Thr His Leu Phe Val Val Thr Thr
                195                 200                 205
Glu Asn Val Gln Ser Tyr Ile Val Ser Gly Lys Asp Tyr Pro Arg Val
210                 215                 220
Glu Leu Asp Thr His Gly Cys Gly Leu Arg Cys Ser Ala Leu Ser Asp
225                 230                 235                 240
Pro Ser Gln Asp Leu Gln Phe Ile Val Ala Gly Asp Glu Cys Val Tyr
                245                 250                 255
Leu Tyr Gln Pro Asp Glu Arg Gly Pro Cys Phe Ala Phe Glu Gly His
                260                 265                 270
Lys Leu Ile Ala His Trp Phe Arg Gly Tyr Leu Ile Ile Val Ser Arg
                275                 280                 285
Asp Arg Lys Val Ser Pro Lys Ser Glu Phe Thr Ser Arg Asp Ser Gln
290                 295                 300
Ser Ser Asp Lys Gln Ile Leu Asn Ile Tyr Asp Leu Cys Asn Lys Phe
305                 310                 315                 320
Ile Ala Tyr Ser Thr Val Phe Glu Asp Val Asp Val Leu Ala Glu
                325                 330                 335
Trp Gly Ser Leu Tyr Val Leu Thr Arg Asp Gly Arg Val His Ala Leu
                340                 345                 350
Gln Glu Lys Asp Thr Gln Thr Lys Leu Glu Met Leu Phe Lys Lys Asn
                355                 360                 365
Leu Phe Glu Met Ala Ile Asn Leu Ala Lys Ser Gln His Leu Asp Ser
                370                 375                 380
Asp Gly Leu Ala Gln Ile Phe Met Gln Tyr Gly Asp His Leu Tyr Ser
385                 390                 395                 400
Lys Gly Asn His Asp Gly Ala Val Gln Gln Tyr Ile Arg Thr Ile Gly
                405                 410                 415
Lys Leu Glu Pro Ser Tyr Val Ile Arg Lys Phe Leu Asp Ala Gln Arg
                420                 425                 430
Ile His Asn Leu Thr Ala Tyr Leu Gln Thr Leu His Arg Gln Ser Leu
                435                 440                 445
Ala Asn Ala Asp His Thr Thr Leu Leu Leu Asn Cys Tyr Thr Lys Leu
                450                 455                 460
```

```
Lys Asp Ser Ser Lys Leu Glu Glu Phe Ile Lys Lys Ser Glu Ser
465                 470                 475                 480

Glu Val His Phe Asp Val Glu Thr Ala Ile Lys Val Leu Arg Gln Ala
            485                 490                 495

Gly Tyr Tyr Ser His Ala Leu Tyr Leu Ala Glu Asn His Ala His His
                500                 505                 510

Glu Trp Tyr Leu Lys Ile Gln Leu Glu Asp Ile Lys Asn Tyr Gln Glu
            515                 520                 525

Ala Leu Arg Tyr Ile Gly Lys Leu Pro Phe Glu Gln Ala Glu Ser Asn
530                 535                 540

Met Lys Arg Tyr Gly Lys Ile Leu Met His His Ile Pro Glu Gln Thr
545                 550                 555                 560

Thr Gln Leu Leu Lys Gly Leu Cys Thr Asp Tyr Arg Pro Ser Leu Glu
                565                 570                 575

Gly Arg Ser Asp Arg Glu Ala Pro Gly Cys Arg Ala Asn Ser Glu Glu
            580                 585                 590

Phe Ile Pro Ile Phe Ala Asn Asn Pro Arg Glu Leu Lys Ala Phe Leu
            595                 600                 605

Glu His Met Ser Glu Val Gln Pro Asp Ser Pro Gln Gly Ile Tyr Asp
610                 615                 620

Thr Leu Leu Glu Leu Arg Leu Gln Asn Trp Ala His Glu Lys Asp Pro
625                 630                 635                 640

Gln Val Lys Glu Lys Leu His Ala Glu Ala Ile Ser Leu Leu Lys Ser
                645                 650                 655

Gly Arg Phe Cys Asp Val Phe Asp Lys Ala Leu Val Leu Cys Gln Met
            660                 665                 670

His Asp Phe Gln Asp Gly Val Leu Tyr Leu Tyr Glu Gln Gly Lys Leu
            675                 680                 685

Phe Gln Gln Ile Met His Tyr His Met Gln His Glu Gln Tyr Arg Gln
690                 695                 700

Val Ile Ser Val Cys Glu Arg His Gly Glu Gln Asp Pro Ser Leu Trp
705                 710                 715                 720

Glu Gln Ala Leu Ser Tyr Phe Ala Arg Lys Glu Glu Asp Cys Lys Glu
                725                 730                 735

Tyr Val Ala Ala Val Leu Lys His Ile Glu Asn Lys Asn Leu Met Pro
            740                 745                 750

Pro Leu Leu Val Val Gln Thr Leu Ala His Asn Ser Thr Ala Thr Leu
            755                 760                 765

Ser Val Ile Arg Asp Tyr Leu Val Gln Lys Leu Gln Lys Gln Ser Gln
770                 775                 780

Gln Ile Ala Gln Asp Glu Leu Arg Val Arg Arg Tyr Arg Glu Glu Thr
785                 790                 795                 800

Thr Arg Ile Arg Gln Glu Ile Gln Glu Leu Lys Ala Ser Pro Lys Ile
                805                 810                 815

Phe Gln Lys Thr Lys Cys Ser Ile Cys Asn Ser Ala Leu Glu Leu Pro
            820                 825                 830

Ser Val His Phe Leu Cys Gly His Ser Phe His Gln His Cys Phe Glu
            835                 840                 845

Ser Tyr Ser Glu Ser Asp Ala Asp Cys Pro Thr Cys Leu Pro Glu Asn
            850                 855                 860

Arg Lys Val Met Asp Met Ile Arg Ala Gln Glu Gln Lys Arg Asp Leu
865                 870                 875                 880
```

| | | | | | | | | | | | |
|---|---|---|---|---|---|---|---|---|---|---|---|
| His | Asp | Gln | Phe | Gln | His | Gln | Leu | Lys | Cys | Ser | Asn | Asp | Ser | Phe | Ser |
| | | | | 885 | | | | 890 | | | | 895 | | | |
| Val | Ile | Ala | Asp | Tyr | Phe | Gly | Arg | Gly | Val | Phe | Asn | Lys | Leu | Thr | Leu |
| | | | 900 | | | | | 905 | | | | | 910 | | |
| Leu | Thr | Asp | Pro | Pro | Thr | Ala | Arg | Leu | Thr | Ser | Ser | Leu | Glu | Ala | Gly |
| | | | 915 | | | | | 920 | | | | | 925 | | |
| Leu | Gln | Arg | Asp | Leu | Leu | Met | His | Ser | Arg | Arg | Gly | Thr |
| | | | 930 | | | | 935 | | | | 940 | |

<210> SEQ ID NO 4
<211> LENGTH: 3279
<212> TYPE: DNA
<213> ORGANISM: Homo sapiens

<400> SEQUENCE: 4

```
ctcacgtgac aaagctcccg gaggtgggag ccctgggcca aaatggcggc ctacctgcag      60
tggcggcgct tcgttttctt cgacaaggag ctggtgaagg agccgctgag caatgatggg     120
gccgctcccg ggccacacc tgcttctgga tccgctgctt ccaagttcct ttgcctccct     180
cctggcatca ctgtctgcga ctcaggccga gggagcctgg tctttggaga tatggaaggc     240
cagatctggt tcttgccacg ttccctacag cttacaggct ccaagcctta caaactacgg     300
gtgacacacc tgtaccaact gaagcagcac aatattctgg catctgttgg agaagatgaa     360
gagggcatca ccccttggt taagatctgg aacctggaga gagagatgg tggcaatcca     420
ctctgcactc gaatcttccc tgctattcca ggaacagagc caactgttgt atcttgtttg     480
actgtccatg aaaatctcaa ctttatggcc attggtttca cagatggcag tgttacattg     540
aacaaaggag acatcacccg ggaccggcat agcaagaccc agattttgca caagggcaac     600
tatcctgtaa ctggattggc ctttcgccaa gcaggaaaga ccactcactt gtttgttgtg     660
acaacagaga acgtccagtc ctatatagtt tctggaaaag actaccctcg cgtggagttg     720
gacacccatg gttgtggcct gcgctgctca gcccttaagtg acccttctca ggacctgcag     780
ttcattgtgg ccggggatga gtgtgtctac ttgtaccagc ctgatgaacg tgggccctgc     840
ttcgcctttg agggccataa gctcattgcc cactggttta gaggctacct tatcattgtc     900
tcccgtgacc ggaaggtttc tcccaagtca gagtttacca gcagggattc acagagctcc     960
gacaagcaga ttctaaacat ctatgacctg tgcaacaagt tcatagccta tagcaccgtc    1020
tttgaggatg tagtggatgt gcttgctgag tggggctccc tgtacgtgct gacgcgggat    1080
gggcgggtcc acgcactgca ggagaaggac acacagacca aactggagat gctgtttaag    1140
aagaacctat ttgagatggc gattaacctt gccaagagcc agcatctgga cagtgatggg    1200
ctggcccaga ttttcatgca gtatggagac catctctaca gcaagggcaa ccacgatggg    1260
gctgtccagc aatatatccg aaccattgga agttggagc catcctacgt gatccgcaag    1320
tttctggatg cccagcgcat tcacaacctg actgcctacc tgcagaccct gcaccgacaa    1380
tccctggcca atgccgacca taccaccctg ctcctcaact gctataccaa gctcaaggac    1440
agctcgaagc tggaggagtt catcaagaaa aagagtgaga gtgaagtcca ctttgatgtg    1500
gagacagcca tcaaggtcct ccggcaggct ggctactact cccatgccct gtatctggcg    1560
gagaaccatg cacatcatga gtggtacctg aagatccagc tagaagacat taagaattat    1620
caggaagccc ttcgatacat cggcaagctg cctttttgagc aggcagagag caacatgaag    1680
cgctacggca agatcctcat gcaccacata ccagagcaga caactcagtt gctgaaggga    1740
ctttgtactg attatcggcc cagcctcgaa ggccgcagcg ataggaggc cccaggctgc    1800
```

```
agggccaact ctgaggagtt catccccatc tttgccaata acccgcgaga gctgaaagcc    1860
ttcctagagc acatgagtga agtgcagcca gactcacccc aggggatcta cgacacactc    1920
cttgagctgc gactgcagaa ctgggcccac gagaaggatc cacaggtcaa agagaagctt    1980
cacgcagagg ccatttccct gctgaagagt ggtcgcttct gcgacgtctt tgacaaggcc    2040
ctggtcctgt gccagatgca cgacttccag gatggtgtcc tttacctttA tgagcagggg    2100
aagctgttcc agcagatcat gcactaccac atgcagcacg agcagtaccg gcaggtcatc    2160
agcgtgtgtg agcgccatgg ggagcaggac ccctccttgt gggagcaggc cctcagctac    2220
ttcgctcgca aggaggagga ctgcaaggag tatgtggcag ctgtcctcaa gcatatcgag    2280
aacaagaacc tcatgccacc tcttctagtg gtgcagaccc tggcccacaa ctccacagcc    2340
acactctccg tcatcaggga ctacctggtc caaaaactac agaaacagag ccagcagatt    2400
gcacaggatg agctgcgggt gcggcggtac cgagaggaga ccacccgtat ccgccaggag    2460
atccaagagc tcaaggccag tcctaagatt ttccaaaaga ccaagtgcag catctgtaac    2520
agtgccttgg agttgccctc agtccacttc ctgtgtggcc actccttcca ccaacactgc    2580
tttgagagtt actcggaaag tgatgctgac tgccccacct gcctccctga aaaccggaag    2640
gtcatggata tgatccgggc ccaggaacag aaacgagatc ccatgatca attccagcat    2700
cagctcaagt gctccaatga cagctttttct gtgattgctg actactttgg cagaggtgtt    2760
ttcaacaaat tgactctgct gaccgacccct cccacagcca gactgacctc cagcctggag    2820
gctgggctgc aacgcgacct actcatgcac tccaggaggg gcacttaagc agcctggagg    2880
aagatgtggg caacagtgga ggaccaagag aacagacaca atgggacctg gcgggcgtt    2940
acacagaagg ctggctgaca tgcccagggc tccactctca tctaatgtca cagccctcag    3000
aactaaagcg gactttcttt ccctgccttc ttatttagtc agcttgccat ccctcctctt    3060
cactagcagt gtagatcatt ccagatcagt gggggagggc acctcagcaa cctctgagtg    3120
tggacaatag ctgctttctt ctctatccaa gagcaccagg ctgtgcttgg gtccttgctc    3180
tcagagtcta taaataaaag aatataatga tttgggagct taaaaaaaaa aaaaaaaaaa    3240
aaaaaaaaaa aaaaaaaaaa aaaaaaaaaa aaaaaaaaa                          3279
```

<210> SEQ ID NO 5
<211> LENGTH: 839
<212> TYPE: PRT
<213> ORGANISM: Homo sapiens

<400> SEQUENCE: 5

```
Met Asp Cys Tyr Thr Ala Asn Trp Asn Pro Leu Gly Asp Ser Ala Phe
1               5                   10                  15

Tyr Arg Lys Tyr Glu Leu Tyr Ser Met Asp Trp Asp Leu Lys Glu Glu
            20                  25                  30

Leu Arg Asp Cys Leu Val Ala Ala Pro Tyr Gly Gly Pro Ile Ala
        35                  40                  45

Leu Leu Arg Asn Pro Trp Arg Lys Glu Lys Ala Ala Ser Val Arg Pro
    50                  55                  60

Val Leu Asp Ile Tyr Ser Ala Ser Gly Met Pro Leu Ala Ser Leu Leu
65                  70                  75                  80

Trp Lys Ser Gly Pro Val Val Ser Leu Gly Trp Ser Ala Glu Glu Glu
                85                  90                  95

Leu Leu Cys Val Gln Glu Asp Gly Ala Val Leu Val Tyr Gly Leu His
                100                 105                 110
```

```
Gly Asp Phe Arg Arg His Phe Ser Met Gly Asn Glu Val Leu Gln Asn
            115                 120                 125

Arg Val Leu Asp Ala Arg Ile Phe His Thr Glu Phe Gly Ser Gly Val
        130                 135                 140

Ala Ile Leu Thr Gly Ala His Arg Phe Thr Leu Ser Ala Asn Val Gly
145                 150                 155                 160

Asp Leu Lys Leu Arg Arg Met Pro Glu Val Pro Gly Leu Gln Ser Ala
                165                 170                 175

Pro Ser Cys Trp Thr Val Leu Cys Gln Asp Arg Val Ala His Ile Leu
            180                 185                 190

Leu Ala Val Gly Pro Asp Leu Tyr Leu Leu Asp His Ala Ala Cys Ser
        195                 200                 205

Ala Val Thr Pro Pro Gly Leu Ala Pro Gly Val Ser Ser Phe Leu Gln
210                 215                 220

Met Ala Val Ser Phe Thr Tyr Arg His Leu Ala Leu Phe Thr Asp Thr
225                 230                 235                 240

Gly Tyr Ile Trp Met Gly Thr Ala Ser Leu Lys Glu Lys Leu Cys Glu
                245                 250                 255

Phe Asn Cys Asn Ile Arg Ala Pro Pro Lys Gln Met Val Trp Cys Ser
            260                 265                 270

Arg Pro Arg Ser Lys Glu Arg Ala Val Val Ala Trp Glu Arg Arg
        275                 280                 285

Leu Met Val Val Gly Asp Ala Pro Glu Ser Ile Gln Phe Val Leu Asp
        290                 295                 300

Glu Asp Ser Tyr Leu Val Pro Glu Leu Asp Gly Val Arg Ile Phe Ser
305                 310                 315                 320

Arg Ser Thr His Glu Phe Leu His Glu Val Pro Ala Ala Ser Glu Glu
                325                 330                 335

Ile Phe Lys Ile Ala Ser Met Ala Pro Gly Ala Leu Leu Leu Glu Ala
            340                 345                 350

Gln Lys Glu Tyr Glu Lys Gly Ser Gln Lys Ala Asp Glu Tyr Leu Arg
        355                 360                 365

Glu Ile Gln Glu Leu Gly Gln Leu Thr Gln Ala Val Gln Cys Ile
370                 375                 380

Glu Ala Ala Gly His Glu His Gln Pro Asp Met Gln Lys Ser Leu Leu
385                 390                 395                 400

Arg Ala Ala Ser Phe Gly Lys Cys Phe Leu Asp Arg Phe Pro Pro Asp
                405                 410                 415

Ser Phe Val His Met Cys Gln Asp Leu Arg Val Leu Asn Ala Val Arg
            420                 425                 430

Asp Tyr His Ile Gly Ile Pro Leu Thr Tyr Ser Gln Tyr Lys Gln Leu
        435                 440                 445

Thr Ile Gln Val Leu Leu Asp Arg Leu Val Leu Arg Arg Leu Tyr Pro
450                 455                 460

Leu Ala Ile Gln Ile Cys Glu Tyr Leu Arg Leu Pro Glu Val Gln Gly
465                 470                 475                 480

Val Ser Arg Ile Leu Ala His Trp Ala Cys Tyr Lys Val Gln Gln Lys
                485                 490                 495

Asp Val Ser Asp Glu Asp Val Ala Arg Ala Ile Asn Gln Lys Leu Gly
            500                 505                 510

Asp Thr Pro Gly Val Ser Tyr Ser Asp Ile Ala Ala Arg Ala Tyr Gly
        515                 520                 525
```

```
Cys Gly Arg Thr Glu Leu Ala Ile Lys Leu Leu Glu Tyr Glu Pro Arg
        530                 535                 540

Ser Gly Glu Gln Val Pro Leu Leu Leu Lys Met Lys Arg Ser Lys Leu
545                 550                 555                 560

Ala Leu Ser Lys Ala Ile Glu Ser Gly Asp Thr Asp Leu Val Phe Thr
                565                 570                 575

Val Leu Leu His Leu Lys Asn Glu Leu Asn Arg Gly Asp Phe Phe Met
            580                 585                 590

Thr Leu Arg Asn Gln Pro Met Ala Leu Ser Leu Tyr Arg Gln Phe Cys
        595                 600                 605

Lys His Gln Glu Leu Gly Thr Leu Lys Asp Leu Tyr Asn Gln Asp Asp
    610                 615                 620

Asn His Gln Glu Leu Gly Ser Phe His Ile Arg Ala Ser Tyr Ala Ala
625                 630                 635                 640

Glu Glu Arg Ile Glu Gly Arg Val Ala Ala Leu Gln Thr Ala Ala Asp
                645                 650                 655

Ala Phe Tyr Lys Ala Lys Asn Glu Phe Ala Ala Lys Ala Thr Glu Asp
            660                 665                 670

Gln Met Arg Leu Leu Arg Leu Gln Arg Arg Leu Glu Asp Glu Leu Gly
        675                 680                 685

Gly Gln Phe Leu Asp Leu Ser Leu His Asp Thr Val Thr Thr Leu Ile
    690                 695                 700

Leu Gly Gly His Asn Lys Arg Ala Glu Gln Leu Ala Arg Asp Phe Arg
705                 710                 715                 720

Ile Pro Asp Lys Arg Leu Trp Trp Leu Lys Leu Thr Ala Leu Ala Asp
                725                 730                 735

Leu Glu Asp Trp Glu Glu Leu Gly Lys Phe Ser Lys Ser Lys Lys Ser
            740                 745                 750

Pro Ile Gly Tyr Leu Pro Phe Val Glu Ile Cys Met Lys Gln His Asn
        755                 760                 765

Lys Tyr Glu Ala Lys Lys Tyr Ala Ser Arg Val Gly Pro Glu Gln Lys
    770                 775                 780

Val Lys Ala Leu Leu Leu Val Gly Asp Val Ala Gln Ala Ala Asp Val
785                 790                 795                 800

Ala Ile Glu His Arg Asn Glu Ala Glu Leu Ser Leu Val Leu Ser His
                805                 810                 815

Cys Thr Gly Ala Thr Asp Gly Ala Thr Ala Asp Lys Ile Gln Arg Ala
            820                 825                 830

Arg Ala Gln Ala Gln Lys Lys
        835

<210> SEQ ID NO 6
<211> LENGTH: 2769
<212> TYPE: DNA
<213> ORGANISM: Homo sapiens

<400> SEQUENCE: 6
ctaggtgggt gtcccctcgg tgcttcccag ctgccgtctg caccagccat ggactgctac    60
acggcgaact ggaacccact cggggactct gccttttacc ggaaatatga gctgtacagc   120
atggactggg acctgaagga ggaactcagg gattgcctgg tggctgctgc acctatgggg   180
ggccccattg cactgctgag gaaccctctg cggaaggaga agctgctag tgtgaggcca    240 gtgctcgata tatactctgc ttccggcatg cctctggcca gctgctgtg gaagagtgga    300 cccgtggtgt ccctgggctg gtcagctgag gaggagctgc tctgtgtgca ggaagatggt   360
```

```
gctgtactgg tttatgggct tcatggtgac ttccggagac acttcagcat gggcaatgaa    420
gtgctccaga accgggttct ggatgcccgg atctttcaca ctgagtttgg ttccggagtg    480
gccatcctca caggggccca ccgcttcacc ctcagtgcca atgtgggtga cctcaaactc    540
cgccggatgc cagaggtgcc aggtctgcaa agtgcaccct cctgctggac tgtgctgtgc    600
caggaccgag tggcacacat tcttctggct gtggggcctg acctttacct cttggaccat    660
gcagcctgct ccgcagtgac gcccctggc ctggccccag gagtaagcag cttcctacag    720
atggctgtct ccttcaccta ccgacacctg gcactcttca cagacacagg ctacatctgg    780
atggggacag catcactcaa ggagaagcta tgtgagttca actgcaacat ccgggcacct    840
ccaaagcaga tggtctggtg cagccgtcct cgtagcaagg agagggccgt ggtggtggcc    900
tgggaaaggc ggctgatggt ggtgggcgat gcacccgaga gcatccagtt tgtgctggat    960
gaggactcct acctggtgcc tgagctcgat ggggtccgca tcttctcccg cagcacccac   1020
gagttcctgc atgaggttcc agcggccagc gaggaaatct tcaaaattgc tcaatggcc    1080
cccggggcgc tgctcctgga ggctcagaag gagtatgaga agagagccaa gaaggcggac   1140
gagtacctgc gggagatcca ggagctgggc cagctgaccc aggccgtgca gcagtgcatt   1200
gaggctgcag acatgagcca ccagccagac atgcagaaga gtctgctcag gccgcctcc   1260
ttcggaaagt gtttcctgga cagatttcca cccgacagct tcgtgcacat tgtcaggac   1320
ctgcgtgtgc tcaatgctgt tcgggactat cacatcggga tcccgctcac ctatagccaa   1380
tataagcagc tcaccatcca ggtgctgctg acaggctcg tgttgcggag actttacccc   1440
ctggccatcc agatatgcga gtacttgcgc cttcctgaag tacagggcgt cagcaggatc   1500
ctggcccact gggcctgcta caaggtgcaa cagaaggatg tctcagatga ggatgtggct   1560
cgagccatta accagaagct gggggacacg cctggtgtct cttactccga cattgctgca   1620
cgagcctatg ttgtggccg cacggagctg gccatcaagc tgctggagta tgagccacgc   1680
tcaggggagc aggtaccccct ctcctaaag atgaagagga gcaaactggc actaagcaag   1740
gccatcgaga gcggggacac tgacctggtg ttcacggtgt tgctgcacct gaagaacgag   1800
ctgaaccgag gagatttttt catgacccct tcggaatcagc ccatggccct cagtttgtac   1860
cgacagttct gtaagcatca ggagctagac acgctgaagg acctttacaa tcaggatgac   1920
aatcaccagg aattgggcag cttccacatc cgagccagct atgctgcaga gagcgtatt   1980
gaggggcgag tagcagctct gcagacagcc gccgatgcct tctacaaggc caagaatgag   2040
tttgcagcca aggctacaga ggatcaaatg cggctcctac ggctgcagcg gcgcctagaa   2100
gacgagctgg ggggccagtt cctagacctg tctctacatg acacagttac caccctcatt   2160
cttggcggtc acaacaagcg tgcagagcag ctggcacgtg acttccgcat ccctgacaag   2220
aggctctggt ggctgaagct gactgccctg gcagatttgg aagattggga agagctagag   2280
aagtttttcca agagcaagaa atcacccatt ggctacctgc cttttgtgga gatctgcatg   2340
aaacaacata caaatacga agccaagaag tatgcttccc gcgtgggtcc cgagcagaag   2400
gtcaaggctt tgcttcttgt tggcgatgtg gctcaggctg cagatgtggc catcgaacac   2460
cggaatgagg ctgagctgag cctcgtattg tcccactgca cggagccac agatgggcc   2520
acagctgaca agattcaacg ggccagggca caagcccaga agaagtgagg agtccatcct   2580
gtacatctca gcaagggggt tcctccccta gcacctgggc ttggcagaag ggccatagtt   2640
catccagctc ctccccctaga gcaatgctga ggagcggggg catggtagca gggctgtctg   2700
```

```
gttttaaata aagttggaac acttcaaaaa aaaaaaaaaa aaaaaaaaaa aaaaaaaaaa    2760
aaaaaaaaa                                                             2769
```

<210> SEQ ID NO 7
<211> LENGTH: 973
<212> TYPE: PRT
<213> ORGANISM: Homo sapiens

<400> SEQUENCE: 7

```
Met Ala Ser Ile Leu Asp Glu Tyr Glu Asn Ser Leu Ser Arg Ser Ala
1               5                   10                  15

Val Leu Gln Pro Gly Cys Pro Ser Val Gly Ile Pro His Ser Gly Tyr
            20                  25                  30

Val Asn Ala Gln Leu Glu Lys Glu Val Pro Ile Phe Thr Lys Gln Arg
        35                  40                  45

Ile Asp Phe Thr Pro Ser Glu Arg Ile Thr Ser Leu Val Val Ser Ser
    50                  55                  60

Asn Gln Leu Cys Met Ser Leu Gly Lys Asp Thr Leu Leu Arg Ile Asp
65                  70                  75                  80

Leu Gly Lys Ala Asn Glu Pro Asn His Val Glu Leu Gly Arg Lys Asp
                85                  90                  95

Asp Ala Lys Val His Lys Met Phe Leu Asp His Thr Gly Ser His Leu
            100                 105                 110

Leu Ile Ala Leu Ser Ser Thr Glu Val Leu Tyr Val Asn Arg Asn Gly
        115                 120                 125

Gln Lys Val Arg Pro Leu Ala Arg Trp Lys Gly Gln Leu Val Glu Ser
    130                 135                 140

Val Gly Trp Asn Lys Ala Leu Gly Thr Glu Ser Ser Thr Gly Pro Ile
145                 150                 155                 160

Leu Val Gly Thr Ala Gln Gly His Ile Phe Glu Ala Glu Leu Ser Ala
                165                 170                 175

Ser Glu Gly Gly Leu Phe Gly Pro Ala Pro Asp Leu Tyr Phe Arg Pro
            180                 185                 190

Leu Tyr Val Leu Asn Glu Glu Gly Gly Pro Ala Pro Val Cys Ser Leu
        195                 200                 205

Glu Ala Glu Arg Gly Pro Asp Gly Arg Ser Phe Val Ile Ala Thr Thr
    210                 215                 220

Arg Gln Arg Leu Phe Gln Phe Ile Gly Arg Ala Ala Glu Gly Ala Glu
225                 230                 235                 240

Ala Gln Gly Phe Ser Gly Leu Phe Ala Ala Tyr Thr Asp His Pro Pro
                245                 250                 255

Pro Phe Arg Glu Phe Pro Ser Asn Leu Gly Tyr Ser Glu Leu Ala Phe
            260                 265                 270

Tyr Thr Pro Lys Leu Arg Ser Ala Pro Arg Ala Phe Ala Trp Met Met
        275                 280                 285

Gly Asp Gly Val Leu Tyr Gly Ala Leu Asp Cys Gly Arg Pro Asp Ser
    290                 295                 300

Leu Leu Ser Glu Glu Arg Val Trp Glu Tyr Pro Glu Gly Val Gly Pro
305                 310                 315                 320

Gly Ala Ser Pro Pro Leu Ala Ile Val Leu Thr Gln Phe His Phe Leu
                325                 330                 335

Leu Leu Leu Ala Asp Arg Val Glu Ala Val Cys Thr Leu Thr Gly Gln
            340                 345                 350

Val Val Leu Arg Asp His Phe Leu Glu Lys Phe Gly Pro Leu Lys His
```

-continued

```
            355                 360                 365
Met Val Lys Asp Ser Ser Thr Gly Gln Leu Trp Ala Tyr Thr Glu Arg
    370                 375                 380
Ala Val Phe Arg Tyr His Val Gln Arg Glu Ala Arg Asp Val Trp Arg
385                 390                 395                 400
Thr Tyr Leu Asp Met Asn Arg Phe Asp Leu Ala Lys Glu Tyr Cys Arg
                405                 410                 415
Glu Arg Pro Asp Cys Leu Asp Thr Val Leu Ala Arg Glu Ala Asp Phe
            420                 425                 430
Cys Phe Arg Gln Arg Arg Tyr Leu Glu Ser Ala Arg Cys Tyr Ala Leu
            435                 440                 445
Thr Gln Ser Tyr Phe Glu Glu Ile Ala Leu Lys Phe Leu Glu Ala Arg
    450                 455                 460
Gln Glu Glu Ala Leu Ala Glu Phe Leu Gln Arg Lys Leu Ala Ser Leu
465                 470                 475                 480
Lys Pro Ala Glu Arg Thr Gln Ala Thr Leu Leu Thr Thr Trp Leu Thr
                485                 490                 495
Glu Leu Tyr Leu Ser Arg Leu Gly Ala Leu Gln Gly Asp Pro Glu Ala
            500                 505                 510
Leu Thr Leu Tyr Arg Glu Thr Lys Glu Cys Phe Arg Thr Phe Leu Ser
            515                 520                 525
Ser Pro Arg His Lys Glu Trp Leu Phe Ala Ser Arg Ala Ser Ile His
    530                 535                 540
Glu Leu Leu Ala Ser His Gly Asp Thr Glu His Met Val Tyr Phe Ala
545                 550                 555                 560
Val Ile Met Gln Asp Tyr Glu Arg Val Val Ala Tyr His Cys Gln His
                565                 570                 575
Glu Ala Tyr Glu Glu Ala Leu Ala Val Leu Ala Arg His Arg Asp Pro
            580                 585                 590
Gln Leu Phe Tyr Lys Phe Ser Pro Ile Leu Ile Arg His Ile Pro Arg
            595                 600                 605
Gln Leu Val Asp Ala Trp Ile Glu Met Gly Ser Arg Leu Asp Ala Arg
    610                 615                 620
Gln Leu Ile Pro Ala Leu Val Asn Tyr Ser Gln Gly Gly Glu Val Gln
625                 630                 635                 640
Gln Val Ser Gln Ala Ile Arg Tyr Met Glu Phe Cys Val Asn Val Leu
                645                 650                 655
Gly Glu Thr Glu Gln Ala Ile His Asn Tyr Leu Leu Ser Leu Tyr Ala
            660                 665                 670
Arg Gly Arg Pro Asp Ser Leu Leu Ala Tyr Leu Glu Gln Ala Gly Ala
            675                 680                 685
Ser Pro His Arg Val His Tyr Asp Leu Lys Tyr Ala Leu Arg Leu Cys
    690                 695                 700
Ala Glu His Gly His His Arg Ala Cys Val His Val Tyr Lys Val Leu
705                 710                 715                 720
Glu Leu Tyr Glu Glu Ala Val Asp Leu Ala Leu Gln Val Asp Val Asp
                725                 730                 735
Leu Ala Lys Gln Cys Ala Asp Leu Pro Glu Glu Asp Glu Glu Leu Arg
            740                 745                 750
Lys Lys Leu Trp Leu Lys Ile Ala Arg His Val Val Gln Glu Glu Glu
            755                 760                 765
Asp Val Gln Thr Ala Met Ala Cys Leu Ala Ser Cys Pro Leu Leu Lys
    770                 775                 780
```

```
Ile Glu Asp Val Leu Pro Phe Phe Pro Asp Phe Val Thr Ile Asp His
785                 790                 795                 800

Phe Lys Glu Ala Ile Cys Ser Ser Leu Lys Ala Tyr Asn His His Ile
            805                 810                 815

Gln Glu Leu Gln Arg Glu Met Glu Ala Thr Ala Ser Ala Gln Arg
        820                 825                 830

Ile Arg Arg Asp Leu Gln Glu Leu Arg Gly Arg Tyr Gly Thr Val Glu
        835                 840                 845

Pro Gln Asp Lys Cys Ala Thr Cys Asp Phe Pro Leu Leu Asn Arg Pro
850                 855                 860

Phe Tyr Leu Phe Leu Cys Gly His Met Phe His Ala Asp Cys Leu Leu
865                 870                 875                 880

Gln Ala Val Arg Pro Gly Leu Pro Ala Tyr Lys Gln Ala Arg Leu Glu
                885                 890                 895

Glu Leu Gln Arg Lys Leu Gly Ala Ala Pro Pro Ala Lys Gly Ser
            900                 905                 910

Ala Arg Ala Lys Glu Ala Glu Gly Gly Ala Ala Thr Ala Gly Pro Ser
        915                 920                 925

Arg Glu Gln Leu Lys Ala Asp Leu Asp Glu Leu Val Ala Ala Glu Cys
        930                 935                 940

Val Tyr Cys Gly Glu Leu Met Ile Arg Ser Ile Asp Arg Pro Phe Ile
945                 950                 955                 960

Asp Pro Gln Arg Tyr Glu Glu Gln Leu Ser Trp Leu
                965                 970

<210> SEQ ID NO 8
<211> LENGTH: 3922
<212> TYPE: DNA
<213> ORGANISM: Homo sapiens

<400> SEQUENCE: 8
gcccgcgtca cggggggcggg agtcagctga gctgccgggg cgaggttggg atcacctggc    60
accggctgaa gggagcctgt gatttttttg tagcggggc gggagtaag gtgcaagact     120 gcgccagatt caaggacgag ggctgcccga ttatctcgct gcataaggca agagcaagag    180
gatcctcagg attttaaaga ggaggcgacg gctgcaggtt cccaggatct gtcagaggct    240
ggggagttac agcttccatt ctggggcgac ggggacccccg ggggggtagc ccttttgtaa   300
tccccaggcc ccgacaaag agcccagagg ccgggcacca tggcgtccat cctggatgag     360
tacgagaact cgctgtcccg ctcggccgtc ttgcagcccg gctgccctag cgtgggcatc    420
ccccactcgg ggtatgtgaa tgcccagctg gagaaggaag tgcccatctt cacaaagcag    480
cgcattgact tcaccccttc cgagcgcatt accagtcttg tcgtctccag caatcagctg    540
tgcatgagcc tgggcaagga tacactgctc cgcattgact gggcaaggc aaatgagccc    600 aaccacgtgg agctgggacg taaggatgac gcaaaagttc acaagatgtt ccttgaccat    660
actggctctc acctgctgat tgccctgagc agcacggagg tcctctacgt gaaccgaaat    720
ggacagaagg tacggccact agcacgctgg aaggggcagc tggtggagag tgtgggttgg    780
aacaaggcac tgggcacgga gagcagcaca ggccccatcc tggtcgggac tgcccaaggc    840
cacatctttg aagcagagct ctcagccagc gaaggtgggc ttttcggccc tgctccggat    900
ctctacttcc gccattgta cgtgctaaat gaagaagggg gtccagcacc tgtgtgctcc    960
cttgaggccg agcggggccc tgatgggcgt agctttgtta ttgccaccac tcggcagcgc   1020
```

```
ctcttccagt tcataggccg agcagcagag ggggctgagg cccagggttt ctcagggctc    1080
tttgcagctt acacggacca cccacccca ttccgtgagt ttcccagcaa cctgggctac     1140
agtgagttgg ccttctacac ccccaagctg cgctccgcac cccgggcctt cgcctggatg   1200 atggggatg tgtgttgta tggggcattg actgtgggc gccctgactc tctgctgagc      1260
gaggagcgag tctgggagta cccagagggg gtagggcctg gggccagccc accectagcc   1320 atcgtcttga cccagttcca cttcctgctg ctactggcag accgggtgga ggcagtgtgc   1380
acactgaccg ggcaggtggt gctgcgggat cacttcctgg agaaatttgg gccgctgaag   1440
cacatggtga aggactcctc cacaggccag ctgtgggcct acactgagcg ggctgtcttc   1500
cgctaccacg tgcaacggga ggcccgagat gtctggcgca cctatctgga catgaaccgc   1560
ttcgatctgg ccaaagagta ttgtcgagag cggcccgact gcctggacac ggtcctggcc   1620
cgggaggccg atttctgctt tcgccagcgt cgctacctgg agagcgcacg ctgctatgcc   1680
ctgacccaga gctactttga ggagattgcc ctcaagttcc tggaggcccg acaggaggag   1740
gctctggctg agttcctgca gcgaaaactg gccagtttga agccagccga acgtacccag   1800 gcccacactgc tgaccacctg gctgacagag ctctacctga gccggcttgg ggctctgcag   1860
ggcgacccag aggccctgac tctctaccga gaaaccaagg aatgctttcg aaccttcctc   1920
agcagccccc gccacaaaga gtggctcttt gccagccggg cctctatcca tgagctgctc   1980
gccagtcatg gggacacaga acacatggtg tactttgcag tgatcatgca ggactatgag   2040
cgggtggtgg cttaccactg tcagcacgag gcctacgagg aggccctggc cgtgctcgcc   2100
cgccaccgtg accccagct cttctacaag ttctcaccca tcctcatccg tcacatcccc   2160
cgccagcttg tagatgcctg gattgagatg ggcagccggc tggatgctcg tcagctcatt   2220
cctgccctgg tgaactacag ccagggtggt gaggtccagc aggtgagcca ggccatccgc   2280
tacatggagt tctgcgtgaa cgtgctgggg gagactgagc aggccatcca caactacctg   2340
ctgtcactgt atgcccgtgg ccggccggac tcactactgg cctatctgga gcaggctggg   2400
gccagccccc accgggtgca ttacgacctc aagtatgcgc tgcggctctg cgccgagcat   2460
ggccaccacc gcgcttgtgt ccatgtctac aaggtcctag agctgtatga ggaggccgtg   2520
gacctggccc tgcaggtgga tgtggacctg gccaagcagt gtgcagacct gcctgaggag   2580
gatgaggaat gcgcaagaa gctgtggctg aagatcgcac ggcacgtggt gcaggaagag   2640
gaagatgtac agacagccat ggcttgcctg gctagctgcc ccttgctcaa gattgaggat   2700
gtgctgccct tcctgctga tttcgtcacc atcgaccact tcaaggaggc gatctgcagc   2760
tcacttaagg cctacaacca cccacatccag gagctgcagc gggagatgga agaggctaca   2820
gccagtgccc agcgcatccg cgcgagacctg caggagctgc ggggccgcta cggcactgtg   2880
gagccccagg acaaatgtgc cacctgcgac ttccccctgc tcaaccgccc tttttacctc   2940
ttcctctgtg gccatatgtt ccatgctgac tgcctgctgc aggctgtgcg acctggcctg   3000
ccagcctaca gcaggcccg gctggaggag ctgcagagga agctgggggc tgctccaccc   3060
ccagccaagg gctctgcccg ggccaaggag gccgagggtg gggctgccac ggcagggccc   3120
agccgggaac agctcaaggc tgacctggat gagttggtgg ccgctgagtg tgtgtactgt   3180
ggggagctga tgatccgctc tatcgaccgg ccgttcatcg accccagcg ctacgaggag   3240 gagcagctca gttggctgta gagggtgtc acctttgatg gggggtgggc aatgggagc     3300 agtggcttga acccacttga gaaggctgcc tcctaggctc tgctcagtca tcttgcaatt   3360
gccacactgt gaccacgttg acgggagtag agtagcgctg ttggccagga ggtgtcaggt   3420
```

```
gtgagtgtat tctgccagct tttcatgctg ttcttcagag ctgcagttat gccagaccat    3480
cagcctgcct cccagtagag gcccttcacc tggagaagtc agaaatctga cccaattcca    3540 cccctgcct ctagcacctc ttctgtccct gtcattcccc acacacgtcc tgttcacctc    3600
gagagagaga gagagagagc acctttcttc cgtctgttca ctctgcggcc tctggaatcc    3660
cagctcttct ctctcagaag aagccttctc ttcctcctgc ctgtaggtgt cccagaagtg    3720
agaaggcagc cttcgaagtc ctgggcattg ggtgagaaag tgatgctagt tggggcatgc    3780
ttttgtgcac actctctggg gctccagtgt gaagggtgcc ctggggctga gggccttgtg    3840
gaggatggtc ggtggtggtg atggaggtgg agagcattaa actgtctgca ctgcaaaaaa    3900
aaaaaaaaaa aaaaaaaaaa aa                                             3922
```

<210> SEQ ID NO 9
<211> LENGTH: 596
<212> TYPE: PRT
<213> ORGANISM: Homo sapiens

<400> SEQUENCE: 9

```
Met Ala Ala His Leu Ser Tyr Gly Arg Val Asn Leu Asn Val Leu Arg
1               5                   10                  15

Glu Ala Val Arg Arg Glu Leu Arg Glu Phe Leu Asp Lys Cys Ala Gly
                20                  25                  30

Ser Lys Ala Ile Val Trp Asp Glu Tyr Leu Thr Gly Pro Phe Gly Leu
            35                  40                  45

Ile Ala Gln Tyr Ser Leu Leu Lys Glu His Glu Val Glu Lys Met Phe
        50                  55                  60

Thr Leu Lys Gly Asn Arg Leu Pro Ala Ala Asp Val Lys Asn Ile Ile
65                  70                  75                  80

Phe Phe Val Arg Pro Arg Leu Glu Leu Met Asp Ile Ile Ala Glu Asn
                85                  90                  95

Val Leu Ser Glu Asp Arg Arg Gly Pro Thr Arg Asp Phe His Ile Leu
            100                 105                 110

Phe Val Pro Arg Arg Ser Leu Leu Cys Glu Gln Arg Leu Lys Asp Leu
        115                 120                 125

Gly Val Leu Gly Ser Phe Ile His Arg Glu Glu Tyr Ser Leu Asp Leu
    130                 135                 140

Ile Pro Phe Asp Gly Asp Leu Leu Ser Met Glu Ser Glu Gly Ala Phe
145                 150                 155                 160

Lys Glu Cys Tyr Leu Glu Gly Asp Gln Thr Ser Leu Tyr His Ala Ala
                165                 170                 175

Lys Gly Leu Met Thr Leu Gln Ala Leu Tyr Gly Thr Ile Pro Gln Ile
            180                 185                 190

Phe Gly Lys Gly Glu Cys Ala Arg Gln Val Ala Asn Met Met Ile Arg
        195                 200                 205

Met Lys Arg Glu Phe Thr Gly Ser Gln Asn Ser Ile Phe Pro Val Phe
    210                 215                 220

Asp Asn Leu Leu Leu Leu Asp Arg Asn Val Asp Leu Leu Thr Pro Leu
225                 230                 235                 240

Ala Thr Gln Leu Thr Tyr Glu Gly Leu Ile Asp Glu Ile Tyr Gly Ile
                245                 250                 255

Gln Asn Ser Tyr Val Lys Leu Pro Pro Glu Lys Phe Ala Pro Lys Lys
            260                 265                 270

Gln Gly Asp Gly Gly Lys Asp Leu Pro Thr Glu Ala Lys Lys Leu Gln
```

```
                275                 280                 285
Leu Asn Ser Ala Glu Glu Leu Tyr Ala Glu Ile Arg Asp Lys Asn Phe
    290                 295                 300

Asn Ala Val Gly Ser Val Leu Ser Lys Lys Ala Lys Ile Ile Ser Ala
305                 310                 315                 320

Ala Phe Glu Glu Arg His Asn Ala Lys Thr Val Gly Glu Ile Lys Gln
                325                 330                 335

Phe Val Ser Gln Leu Pro His Met Gln Ala Ala Arg Gly Ser Leu Ala
            340                 345                 350

Asn His Thr Ser Ile Ala Glu Leu Ile Lys Asp Val Thr Thr Ser Glu
        355                 360                 365

Asp Phe Phe Asp Lys Leu Thr Val Glu Gln Glu Phe Met Ser Gly Ile
    370                 375                 380

Asp Thr Asp Lys Val Asn Asn Tyr Ile Glu Asp Cys Ile Ala Gln Lys
385                 390                 395                 400

His Ser Leu Ile Lys Val Leu Arg Leu Val Cys Leu Gln Ser Val Cys
                405                 410                 415

Asn Ser Gly Leu Lys Gln Lys Val Leu Asp Tyr Tyr Lys Arg Glu Ile
            420                 425                 430

Leu Gln Thr Tyr Gly Tyr Glu His Ile Leu Thr Leu His Asn Leu Glu
        435                 440                 445

Lys Ala Gly Leu Leu Lys Pro Gln Thr Gly Arg Asn Asn Tyr Pro
    450                 455                 460

Thr Ile Arg Lys Thr Leu Arg Leu Trp Met Asp Val Asn Glu Gln
465                 470                 475                 480

Asn Pro Thr Asp Ile Ser Tyr Val Tyr Ser Gly Tyr Ala Pro Leu Ser
                485                 490                 495

Val Arg Leu Ala Gln Leu Leu Ser Arg Pro Gly Trp Arg Ser Ile Glu
            500                 505                 510

Glu Val Leu Arg Ile Leu Pro Gly Pro His Phe Glu Glu Arg Gln Pro
        515                 520                 525

Leu Pro Thr Gly Leu Gln Lys Lys Arg Gln Pro Gly Glu Asn Arg Val
    530                 535                 540

Thr Leu Ile Phe Phe Leu Gly Gly Val Thr Phe Ala Glu Ile Ala Ala
545                 550                 555                 560

Leu Arg Phe Leu Ser Gln Leu Glu Asp Gly Gly Thr Gly Tyr Val Ile
                565                 570                 575

Ala Thr Thr Lys Leu Met Asn Gly Thr Ser Trp Ile Gly Ala Leu Met
            580                 585                 590

Glu Lys Pro Phe
        595

<210> SEQ ID NO 10
<211> LENGTH: 2628
<212> TYPE: DNA
<213> ORGANISM: Homo sapiens

<400> SEQUENCE: 10
gtgcgctgcc gtaccggtca cgtggacgtt tggtcacgtg actgcgtccg tggtcctccc      60
gtaggaaccg gcggactcgg ttggcgttgt ggggcagggg gtggtggagc aagatggcgg     120
ctcatctgtc ctacggccga gtgaacctaa acgtgttgcg cgaggcggtg cgtcgcgagc     180
tgcgcgagtt cctggacaag tgcgcaggaa gcaaggcaat agtttgggat gaatacctaa     240
ctggaccctt tggcctgatt gcacagtatt cactattgaa ggaacatgaa gtggaaaaaa     300
```

```
tgttcacact taaaggaaat cgtttgccgg cagctgatgt gaagaatata attttttttg      360
tcagacccag gctagagttg atggatataa tcgctgaaaa cgtgctcagt gaagatagac      420
gaggcccaac gagagatttt catattctgt ttgtgccacg ccgtagcctg ttgtgcgaac      480
agcggttgaa ggatctgggt gtcttgggat cctttattca cagggaggag tacagcttag      540
atctcattcc attcgatggg gatctcttat ccatggaatc agagggtgca ttcaaagagt      600
gctacctgga gggtgaccag acgagcctgt accacgcagc caaggggctg atgaccctgc      660
aagctctgta tggaacgatc ccccagatct ttgggaaagg agaatgcgct cggcaagtgg      720
ccaatatgat gatcaggatg aagagagagt ttacaggaag ccagaattca atatttcctg      780
tttttgataa tctcttgttg cttgatcgga atgtggattt attaacacct cttgccactc      840
agctgacata tgaaggactc attgatgaaa tttatggcat tcagaacagt tatgtgaaat      900
tacctccaga gaaatttgca cctaagaaac agggcgatgg tggtaaggac ctccccacgg      960
aagcaaagaa gctgcagctg aattctgcag aggagctcta tgctgagatc cgagataaga     1020
acttcaacgc agttggctct gtgctcagca agaaagcaaa gatcatctct gcagcattcg     1080
aggaaagaca caatgctaag accgtggggg agatcaagca gtttgtttcc cagttgcccc     1140
acatgcaggc agcaaggggc tcgcttgcaa accatacctc aattgcagaa ttgatcaaag     1200
atgtcactac ttctgaagac tttttttgata aattaaccgt ggaacaggag tttatgtctg     1260
gaatagacac tgataaggtc aacaattaca ttgaggattg tatcgcccaa aagcactcgt     1320
tgatcaaggt gttaagacta gtttgcctcc aatccgtgtg taatagtggg ctcaaacaaa     1380
aagttttgga ttattacaaa agagagattc tccagacata cggctatgag cacatattga     1440
ccttacacaa cctggagaag gccggcctgc tgaaaccgca gacgggggc agaaacaatt       1500 acccaactat acggaaaaca ttacgcctct ggatggatga tgttaatgag caaaaccccca      1560 cggacatatc gtatgtgtac agtgggtatg ccccgctcag tgtgcggctg gcccagctgc     1620
tttcccggcc tggctggcgg agcatcgagg aggtcctccg catcctccca gggccccact     1680
ttgaggagcg gcagccactg cccacaggac tgcagaagaa acgtcaaccg ggagaaaacc     1740
gagtgactct gatattttc cttggggggcg taaccttcgc tgaaattgct gccctgcgat      1800
ttctctccca gttggaagat ggaggtacag aatatgtcat tgccaccact aaactaatga     1860
atggaaccag ttgatagag gctctgatgg aaaaacctttt ctaggatgtt cagaggagac     1920
ttaacaagtg tactgcagaa taaactacct ctttgaagaa attgctgaaa ggaagtaaaa     1980
ccccatagaa gaaacatggg aatacagaat atattctggg gtcagcttct taaattatac     2040
tactgtttac tgctttctcc gtctcttttg tattcccttt tttttttttcc tttgagacgg     2100 agtcttgctc tgtcacccag actagagtgc agtggcacgg tctcacctca ctgcaacctc     2160
cacctcctag gttcaagcaa ttctcctgcc tcagcctcct gagtagctgg gactacaggc     2220
atgcaccacc acaccggct aattttttgta tttttagtag ccatggtgtt tcaccatgtt      2280
ggccaggctg gtctcaaact cctgacctca ggtgatccac ctgcctcggc ctcccacagt     2340
gctgggatta caggcctgag ccaccgtgcc tggcccctaa tctgctgaag aagaagaat      2400 agaagaaaat caacctgagt aaaagcagca ctggttttga gttttctaag ctcagggtct     2460
tcattagaga cctctggaaa tacattaagg atggtggggg tagataatcc attcagccag     2520
acaaacgggg ccagctctta aaataagaaa gctgagactg aggaggtgaa actgaaaata     2580 aaagagaaa gttcatcctc taaaaaaaaa aaaaaaaaaa aaaaaaaa                   2628
```

<210> SEQ ID NO 11
<211> LENGTH: 875
<212> TYPE: PRT
<213> ORGANISM: Homo sapiens

<400> SEQUENCE: 11

```
Met His Asp Ala Phe Glu Pro Val Pro Ile Leu Glu Lys Leu Pro Leu
1               5                   10                  15
Gln Ile Asp Cys Leu Ala Ala Trp Glu Glu Trp Leu Leu Val Gly Thr
            20                  25                  30
Lys Gln Gly His Leu Leu Leu Tyr Arg Ile Arg Lys Asp Val Gly Cys
        35                  40                  45
Asn Arg Phe Glu Val Thr Leu Glu Lys Ser Asn Lys Asn Phe Ser Lys
    50                  55                  60
Lys Ile Gln Gln Ile His Val Val Ser Gln Phe Lys Ile Leu Val Ser
65                  70                  75                  80
Leu Leu Glu Asn Asn Ile Tyr Val His Asp Leu Leu Thr Phe Gln Gln
                85                  90                  95
Ile Thr Thr Val Ser Lys Ala Lys Gly Ala Ser Leu Phe Thr Cys Asp
            100                 105                 110
Leu Gln His Thr Glu Thr Gly Glu Glu Val Leu Arg Met Cys Val Ala
        115                 120                 125
Val Lys Lys Lys Leu Gln Leu Tyr Phe Trp Lys Asp Arg Glu Phe His
    130                 135                 140
Glu Leu Gln Gly Asp Phe Ser Val Pro Asp Val Pro Lys Ser Met Ala
145                 150                 155                 160
Trp Cys Glu Asn Ser Ile Cys Val Gly Phe Lys Arg Asp Tyr Tyr Leu
                165                 170                 175
Ile Arg Val Asp Gly Lys Gly Ser Ile Lys Glu Leu Phe Pro Thr Gly
            180                 185                 190
Lys Gln Leu Glu Pro Leu Val Ala Pro Leu Ala Asp Gly Lys Val Ala
        195                 200                 205
Val Gly Gln Asp Asp Leu Thr Val Val Leu Asn Glu Glu Gly Ile Cys
    210                 215                 220
Thr Gln Lys Cys Ala Leu Asn Trp Thr Asp Ile Pro Val Ala Met Glu
225                 230                 235                 240
His Gln Pro Pro Tyr Ile Ile Ala Val Leu Pro Arg Tyr Val Glu Ile
                245                 250                 255
Arg Thr Phe Glu Pro Arg Leu Leu Val Gln Ser Ile Glu Leu Gln Arg
            260                 265                 270
Pro Arg Phe Ile Thr Ser Gly Gly Ser Asn Ile Ile Tyr Val Ala Ser
        275                 280                 285
Asn His Phe Val Trp Arg Leu Ile Pro Val Pro Met Ala Thr Gln Ile
    290                 295                 300
Gln Gln Leu Leu Gln Asp Lys Gln Phe Glu Leu Ala Leu Gln Leu Ala
305                 310                 315                 320
Glu Met Lys Asp Asp Ser Asp Ser Glu Lys Gln Gln Ile His His
                325                 330                 335
Ile Lys Asn Leu Tyr Ala Phe Asn Leu Phe Cys Gln Lys Arg Phe Asp
            340                 345                 350
Glu Ser Met Gln Val Phe Ala Lys Leu Gly Thr Asp Pro Thr His Val
        355                 360                 365
Met Gly Leu Tyr Pro Asp Leu Leu Pro Thr Asp Tyr Arg Lys Gln Leu
    370                 375                 380
```

```
Gln Tyr Pro Asn Pro Leu Pro Val Leu Ser Gly Ala Glu Leu Glu Lys
385                 390                 395                 400

Ala His Leu Ala Leu Ile Asp Tyr Leu Thr Gln Lys Arg Ser Gln Leu
            405                 410                 415

Val Lys Lys Leu Asn Asp Ser Asp His Gln Ser Ser Thr Ser Pro Leu
        420                 425                 430

Met Glu Gly Thr Pro Thr Ile Lys Ser Lys Lys Leu Leu Gln Ile
            435                 440                 445

Ile Asp Thr Thr Leu Leu Lys Cys Tyr Leu His Thr Asn Val Ala Leu
        450                 455                 460

Val Ala Pro Leu Leu Arg Leu Glu Asn Asn His Cys His Ile Glu Glu
465                 470                 475                 480

Ser Glu His Val Leu Lys Lys Ala His Lys Tyr Ser Glu Leu Ile Ile
            485                 490                 495

Leu Tyr Glu Lys Lys Gly Leu His Glu Lys Ala Leu Gln Val Leu Val
            500                 505                 510

Asp Gln Ser Lys Lys Ala Asn Ser Pro Leu Lys Gly His Glu Arg Thr
        515                 520                 525

Val Gln Tyr Leu Gln His Leu Gly Thr Glu Asn Leu His Leu Ile Phe
530                 535                 540

Ser Tyr Ser Val Trp Val Leu Arg Asp Phe Pro Glu Asp Gly Leu Lys
545                 550                 555                 560

Ile Phe Thr Glu Asp Leu Pro Glu Val Glu Ser Leu Pro Arg Asp Arg
            565                 570                 575

Val Leu Gly Phe Leu Ile Glu Asn Phe Lys Gly Leu Ala Ile Pro Tyr
            580                 585                 590

Leu Glu His Ile Ile His Val Trp Glu Glu Thr Gly Ser Arg Phe His
            595                 600                 605

Asn Cys Leu Ile Gln Leu Tyr Cys Glu Lys Val Gln Gly Leu Met Lys
        610                 615                 620

Glu Tyr Leu Leu Ser Phe Pro Ala Gly Lys Thr Pro Val Pro Ala Gly
625                 630                 635                 640

Glu Glu Glu Gly Glu Leu Gly Glu Tyr Arg Gln Lys Leu Leu Met Phe
                645                 650                 655

Leu Glu Ile Ser Ser Tyr Tyr Asp Pro Gly Arg Leu Ile Cys Asp Phe
            660                 665                 670

Pro Phe Asp Gly Leu Leu Glu Glu Arg Ala Leu Leu Leu Gly Arg Met
        675                 680                 685

Gly Lys His Glu Gln Ala Leu Phe Ile Tyr Val His Ile Leu Lys Asp
        690                 695                 700

Thr Arg Met Ala Glu Glu Tyr Cys His Lys His Tyr Asp Arg Asn Lys
705                 710                 715                 720

Asp Gly Asn Lys Asp Val Tyr Leu Ser Leu Leu Arg Met Tyr Leu Ser
            725                 730                 735

Pro Pro Ser Ile His Cys Leu Gly Pro Ile Lys Leu Glu Leu Leu Glu
            740                 745                 750

Pro Lys Ala Asn Leu Gln Ala Ala Leu Gln Val Leu Glu Leu His His
        755                 760                 765

Ser Lys Leu Asp Thr Thr Lys Ala Leu Asn Leu Leu Pro Ala Asn Thr
        770                 775                 780

Gln Ile Asn Asp Ile Arg Ile Phe Leu Glu Lys Val Leu Glu Glu Asn
785                 790                 795                 800
```

```
Ala Gln Lys Lys Arg Phe Asn Gln Val Leu Lys Asn Leu Leu His Ala
            805                 810                 815

Glu Phe Leu Arg Val Gln Glu Glu Arg Ile Leu His Gln Val Lys
        820                 825                 830

Cys Ile Ile Thr Glu Glu Lys Val Cys Met Val Cys Lys Lys Lys Ile
        835                 840                 845

Gly Asn Ser Ala Phe Ala Arg Tyr Pro Asn Gly Val Val Val His Tyr
    850                 855                 860

Phe Cys Ser Lys Glu Val Asn Pro Ala Asp Thr
865                 870                 875

<210> SEQ ID NO 12
<211> LENGTH: 4851
<212> TYPE: DNA
<213> ORGANISM: Homo sapiens

<400> SEQUENCE: 12
```

| | | | | | |
|---|---|---|---|---|---|
| ggggttgacg | atggctgtgt | tgttgaaggg | cctgtagccg | ggggttcct | ggccggatcc | 60 |
| cggtctaccc | ttagcccaga | ctcgttccgg | accccagccc | ggcccggaac | actctgggcg | 120 |
| agacggcggt | ggcaactctc | cccttgccgc | catgcacgac | gctttcgagc | cagtgccgat | 180 |
| cctagaaaag | ctgcctctgc | aaatcgactg | tctggctgcc | tgggaggaat | ggcttcttgt | 240 |
| gggaaccaaa | caaggacatc | ttcttctcta | taggattcgg | aaggacgttg | gttgcaacag | 300 |
| atttgaagtg | acactagaga | atccaataa | gaacttctcc | aaaaagattc | agcagatcca | 360 |
| tgtggtttcc | cagtttaaga | ttctggtcag | cttgttagaa | aataacattt | atgtccatga | 420 |
| cctattgaca | tttcaacaaa | tcactacggt | ttcaaaggca | aagggagcat | cactgtttac | 480 |
| ttgtgacctc | cagcacacag | agaccggtga | ggaggtgtta | cggatgtgtg | tggcagtaaa | 540 |
| aaagaagctg | cagctctatt | tctggaagga | cagggaattt | catgaattgc | aggggacttt | 600 |
| tagtgtgcca | gatgtgccca | agtccatggc | gtggtgtgaa | aattctatct | gtgtgggttt | 660 |
| caagagagac | tactacctaa | taagggtgga | tggaaagggg | tccatcaaag | agctctttcc | 720 |
| aacaggaaaa | cagctggagc | ccttagttgc | acctctggca | gatggaaaag | tggctgtggg | 780 |
| ccaggatgat | ctcaccgtgg | tactcaatga | ggaagggatc | tgcacacaga | aatgtgccct | 840 |
| gaactggacg | gacataccag | tggccatgga | gcaccagcct | ccctacatca | ttgcagtgtt | 900 |
| gcctcgatat | gttgagatcc | gaacatttga | accgaggctt | ctggtccaaa | gcattgaatt | 960 |
| gcaaaggccc | cgtttcatta | cctcaggagg | atcaaacatt | atctatgtgg | ccagcaatca | 1020 |
| ttttgtttgg | agactcatcc | ctgtccccat | ggcaacccaa | atccaacaac | ttctccagga | 1080 |
| caagcagttt | gaattggctc | tgcagctcgc | agaaatgaaa | gatgattctg | acagtgaaaa | 1140 |
| gcagcaacaa | attcatcaca | tcaagaactt | gtatgccttc | aacctcttct | gccagaagcg | 1200 |
| ttttgatgag | tccatgcagg | tctttgctaa | acttggcaca | gatcccaccc | atgtgatggg | 1260 |
| cctgtaccct | gacctgctgc | ccacagacta | cagaaagcag | ttgcagtatc | caacccatt | 1320 |
| gcctgtgctc | tccggggctg | aattggagaa | ggctcactta | gctctgattg | actacctgac | 1380 |
| acagaaacga | agtcaattgg | taaagaagct | gaatgactct | gatcaccagt | caagcacctc | 1440 |
| accgctcatg | gaaggcactc | ccaccatcaa | atccaagaag | aagctgctac | aaatcatcga | 1500 |
| caccaccctg | ctcaagtgct | atctccatac | aaatgtggcc | ctggtggccc | ccttgctacg | 1560 |
| cctggagaac | aatcactgcc | acatcgagga | gagcgagcac | gtgctaaaga | aggctcacaa | 1620 |
| gtacagtgag | cttatcatcc | tgtatgagaa | gaagggggctc | cacgagaaag | ctctgcaggt | 1680 |

```
gctcgtggac cagtccaaga aagccaactc ccctctgaaa ggccacgaga ggacagtgca    1740
gtatctgcag catctgggca cagaaaacct gcatttgatt ttctcctact cagtgtgggt    1800
gctgagagac ttcccagaag atggcctgaa gatatttact gaagatctcc cggaagtgga    1860
gtctctgcca cgtgatcgag tcctcggctt cttaatagag aattttaagg gtctggctat    1920
tccttatctg gaacacatca tccatgtttg ggaggagaca ggctctcggt ccacaactg     1980 cctgatccag ctatactgtg agaaggtgca aggtctgatg aaggagtatc tcctgtcctt    2040
ccctgcaggc aaaacccag tcccagctgg agaggaagag ggtgagctgg gagaataccg     2100
gcaaaagctc ctcatgttct ggagatttc cagctactat gatccaggcc ggctcatctg     2160
tgattttccc tttgatggcc tcttagaaga acgagctctc ctgttggggc gcatggggaa    2220
acatgaacaa gctcttttca tttatgtcca catcttgaag gatacaagga tggctgagga    2280
gtactgccac aaacactatg accgaaacaa agatggcaac aaagatgtgt atctgtccct    2340
gcttcggatg tacctgtcgc cccccagcat tcactgcctg gggccaatca agctggaact    2400
actggagcca aaagccaacc tccaggccgc tctgcaggtc ctcgagctac accacagcaa    2460
actggacacc accaaggccc tcaaccttct gccagcaaac actcagatca atgacatacg    2520
catcttcctg gaaaaggtct tggaagaaaa tgcacaaaag aaacggttca atcaagtgct    2580
caagaacctt ctccatgcag aattcctgag ggtccaggaa gagcggattt tacaccagca    2640
ggtgaagtgc atcatcacag aggagaaggt gtgcatggtg tgtaagaaga agattgggaa    2700
cagtgcattt gcaagatacc ccaatggagt ggtcgtccat tacttctgtt ccaaagaggt    2760
aaacccagct gacacttgag cccagcatcc tggggatcca gcggatggac agcttggctc    2820
tcccagagag gtgaaggagc acctggcctt aggaatcctg gctgccacca ccacaaggct    2880
ccccatttgg acattactgg ctatcttgtg ccctggaaca actctgaatt aattagactc    2940
atggtctggc attgccagct tttaatggg aaaagagatt agttatacct tataccatta     3000
tgttgtgggc aattccagag aattcagtac ctgcttggtc aggaggatgt gcaccatctt    3060
gcctttgcac accagtcacc tgaacaagga aacttgtcac aagtgtttgt aaccatgggg    3120
ttgttcatca agggcttttc tattaagtac atgacttcac aaggaccgct cagcatggct    3180
cactggagag ttccatgaga gaacagcact caagcttctg gccgcatgga cccgatggct    3240
cgcattctgt gtagtgtttt acgtctccat ggtaactgtg ccctgcaccc ctcggtagcc    3300
gccctgttag ttttcagtct ccttttcttt ctcaccattt atcacttccc tcactgccct    3360
acccaggctt tctctcccac ttccctgact ctgggaataa ctaatattta agcaaggtaa    3420
gatgagaagc aaggggtctc agttctagga atacagtgct agttgattgt caggtatgtt    3480
gtaaatagac cctcttttggc catacactcc atgcctagat gcctcggaga gcatcattct    3540
ctgcctaggc aaggccctgc atcccttgcc tcaggccggg ctgagtgtga ctgcagctcc    3600
tgaggatggg cctgccctgt ctggggtatg cgtgatccct agatacatgt tcccacagag    3660
gtgcctgctc cgtcttcgct caccagacac tcaggcaggc tggcttagtc tttgtgcgtg    3720
gcgattttgt gctctgggcc ctttctcttt ttccagccag tttccattca cttgccttac    3780
agcctgccct ggccgtcact ccccagcttt gttcagcaat ggtgtggttg gagagttgtg    3840
ctgggatagc gcaggaaggt gggtcccggc aacacgcagg ggatgagtgg acctggaact    3900
gacaatggcg tgctgccaag tgttcctgag aggtgtttag gcacagcaga ggggacgcgg    3960
ggggcaagaa cagcaggacg ctggtttaaa ataactcac cgcccaaacct gtggagcagt     4020 gtggggcatc ctgccagagg tgcacaggct ggagtttcag gcactgcagg ctgatgacac    4080
```

```
acagggagag tggccctgcc tcctgtcctc cccggggttt ttgcagactc gaagtctcac    4140
tgcaccagtg tctttgatgg tggtgagggt gggtgatggt gcccagcacc aacagtttta    4200
gtggcctgtc cttgacctgc cgtggtcctt tgtaaactat ggctccatgc tgtgtgacag    4260
atcaacgtgc tgatggtaag tagactaggc ttccccaggc atgccgtccg tgggggcctg    4320
aagagacagt gagtgccatt ggccccattc gcagatgtgg gagactctgc tcaggcctgt    4380
gaggctggga gcccttcac cagagttcgg aggagcagtg tgtggcgcca cgtcccgact    4440
ggccataccc acacagaagc agtgctgccc ggggcctcat ctgggccagc ttggactctg    4500
cttcctccag gagcagcagg gaagctctgg gccacctccc tggatagcag gaacttgacc    4560
tgccatgtgt gccctgcctt cctggccagc tgtgcttgtt atcttccatt ctcacaaact    4620
gtctttgaag caatagaata aagaatgtgt gttttctttc ctggtataca tacatgatcc    4680
catgctccca agctccattc ttccttccct caactctctg ccctccacag agctatggag    4740
aaggctggag atgaaagctt tgtagtgagg actgataaag atctcatcac tgctccttat    4800
aataaaccta ataaagcaag aaaccaagcc taaaaaaaaa aaaaaaaaa a              4851
```

<210> SEQ ID NO 13
<211> LENGTH: 854
<212> TYPE: PRT
<213> ORGANISM: Homo sapiens

<400> SEQUENCE: 13

```
Met Ala Glu Ala Glu Glu Gln Glu Thr Gly Ser Leu Glu Glu Ser Thr
1               5                   10                  15

Asp Glu Ser Glu Glu Glu Ser Glu Glu Pro Lys Leu Lys Tyr
            20                  25                  30

Glu Arg Leu Ser Asn Gly Val Thr Glu Ile Leu Gln Lys Asp Ala Ala
        35                  40                  45

Ser Cys Met Thr Val His Asp Lys Phe Leu Ala Leu Gly Thr His Tyr
    50                  55                  60

Gly Lys Val Tyr Leu Leu Asp Val Gln Gly Asn Ile Thr Gln Lys Phe
65                  70                  75                  80

Asp Val Ser Pro Val Lys Ile Asn Gln Ile Ser Leu Asp Glu Ser Gly
                85                  90                  95

Glu His Met Gly Val Cys Ser Asp Gly Lys Val Gln Val Phe Gly
            100                 105                 110

Leu Tyr Ser Gly Glu Glu Phe His Glu Thr Phe Asp Cys Pro Ile Lys
        115                 120                 125

Ile Ile Ala Val His Pro His Phe Val Arg Ser Ser Cys Lys Gln Phe
    130                 135                 140

Val Thr Gly Gly Lys Lys Leu Leu Leu Phe Glu Arg Ser Trp Met Asn
145                 150                 155                 160

Arg Trp Lys Ser Ala Val Leu His Glu Gly Glu Gly Asn Ile Arg Ser
                165                 170                 175

Val Lys Trp Arg Gly His Leu Ile Ala Trp Ala Asn Asn Met Gly Val
            180                 185                 190

Lys Ile Phe Asp Ile Ile Ser Lys Gln Arg Ile Thr Asn Val Pro Arg
        195                 200                 205

Asp Asp Ile Ser Leu Arg Pro Asp Met Tyr Pro Cys Ser Leu Cys Trp
    210                 215                 220

Lys Asp Asn Val Thr Leu Ile Ile Gly Trp Gly Thr Ser Val Lys Val
225                 230                 235                 240
```

-continued

```
Cys Ser Val Lys Glu Arg His Ala Ser Glu Met Arg Asp Leu Pro Ser
            245                 250                 255

Arg Tyr Val Glu Ile Val Ser Gln Phe Glu Thr Glu Phe Tyr Ile Ser
        260                 265                 270

Gly Leu Ala Pro Leu Cys Asp Gln Leu Val Val Leu Ser Tyr Val Lys
    275                 280                 285

Glu Ile Ser Glu Lys Thr Glu Arg Glu Tyr Cys Ala Arg Pro Arg Leu
290                 295                 300

Asp Ile Ile Gln Pro Leu Ser Glu Thr Cys Glu Ile Ser Ser Asp
305                 310                 315                 320

Ala Leu Thr Val Arg Gly Phe Gln Glu Asn Glu Cys Arg Asp Tyr His
                325                 330                 335

Leu Glu Tyr Ser Glu Gly Glu Ser Leu Phe Tyr Ile Val Ser Pro Arg
            340                 345                 350

Asp Val Val Ala Lys Glu Arg Asp Gln Asp His Ile Asp Trp
        355                 360                 365

Leu Leu Glu Lys Lys Lys Tyr Glu Ala Leu Met Ala Ala Glu Ile
    370                 375                 380

Ser Gln Lys Asn Ile Lys Arg His Lys Ile Leu Asp Ile Gly Leu Ala
385                 390                 395                 400

Tyr Ile Asn His Leu Val Glu Arg Gly Asp Tyr Asp Ile Ala Ala Arg
                405                 410                 415

Lys Cys Gln Lys Ile Leu Gly Lys Asn Ala Ala Leu Trp Glu Tyr Glu
            420                 425                 430

Val Tyr Lys Phe Lys Glu Ile Gly Gln Leu Lys Ala Ile Ser Pro Tyr
        435                 440                 445

Leu Pro Arg Gly Asp Pro Val Leu Lys Pro Leu Ile Tyr Glu Met Ile
450                 455                 460

Leu His Glu Phe Leu Glu Ser Asp Tyr Glu Gly Phe Ala Thr Leu Ile
465                 470                 475                 480

Arg Glu Trp Pro Gly Asp Leu Tyr Asn Asn Ser Val Ile Val Gln Ala
                485                 490                 495

Val Arg Asp His Leu Lys Lys Asp Ser Gln Asn Lys Thr Leu Leu Lys
            500                 505                 510

Thr Leu Ala Glu Leu Tyr Thr Tyr Asp Lys Asn Tyr Gly Asn Ala Leu
        515                 520                 525

Glu Ile Tyr Leu Thr Leu Arg His Lys Asp Val Phe Gln Leu Ile His
530                 535                 540

Lys His Asn Leu Phe Ser Ser Ile Lys Asp Lys Ile Val Leu Leu Met
545                 550                 555                 560

Asp Phe Asp Ser Glu Lys Ala Val Asp Met Leu Leu Asp Asn Glu Asp
                565                 570                 575

Lys Ile Ser Ile Lys Lys Val Val Glu Glu Leu Glu Asp Arg Pro Glu
            580                 585                 590

Leu Gln His Val Tyr Leu His Lys Leu Phe Lys Arg Asp His His Lys
        595                 600                 605

Gly Gln Arg Tyr His Glu Lys Gln Ile Ser Leu Tyr Ala Glu Tyr Asp
    610                 615                 620

Arg Pro Asn Leu Leu Pro Phe Leu Arg Asp Ser Thr His Cys Pro Leu
625                 630                 635                 640

Glu Lys Ala Leu Glu Ile Cys Gln Gln Arg Asn Phe Val Glu Glu Thr
                645                 650                 655
```

| | | | | | | | | | | | | |
|---|---|---|---|---|---|---|---|---|---|---|---|---|
|Val|Tyr|Leu|Leu|Ser|Arg|Met|Gly|Asn|Ser|Arg|Ser|Ala|Lys|Met|
| | | |660| | | |665| | | |670| | | |

Ile Met Glu Glu Leu His Asp Val Asp Lys Ala Ile Glu Phe Ala Lys
            675                 680                 685

Glu Gln Asp Asp Gly Glu Leu Trp Glu Asp Leu Ile Leu Tyr Ser Ile
        690                 695                 700

Asp Lys Pro Pro Phe Ile Thr Gly Leu Leu Asn Asn Ile Gly Thr His
705                 710                 715                 720

Val Asp Pro Ile Leu Leu Ile His Arg Ile Lys Glu Gly Met Glu Ile
                725                 730                 735

Pro Asn Leu Arg Asp Ser Leu Val Lys Ile Leu Gln Asp Tyr Asn Leu
            740                 745                 750

Gln Ile Leu Leu Arg Glu Gly Cys Lys Lys Ile Leu Val Ala Asp Ser
        755                 760                 765

Leu Ser Leu Leu Lys Lys Met His Arg Thr Gln Met Lys Gly Val Leu
    770                 775                 780

Val Asp Glu Glu Asn Ile Cys Glu Ser Cys Leu Ser Pro Ile Leu Pro
785                 790                 795                 800

Ser Asp Ala Ala Lys Pro Phe Ser Val Val Val Phe His Cys Arg His
                805                 810                 815

Met Phe His Lys Glu Cys Leu Pro Met Pro Ser Met Asn Ser Ala Ala
            820                 825                 830

Gln Phe Cys Asn Ile Cys Ser Ala Lys Asn Arg Gly Pro Gly Ser Ala
        835                 840                 845

Ile Leu Glu Met Lys Lys
    850

<210> SEQ ID NO 14
<211> LENGTH: 4894
<212> TYPE: DNA
<213> ORGANISM: Homo sapiens

<400> SEQUENCE: 14

```
ctgtcaggtg actctcccgt ggcgccatgg cggaagcaga ggagcaggaa actgggtccc      60
ttgaagaatc tacagatgag tctgaggaag aagagagcga agaggaaccc aagctgaagt     120
atgaaaggct ttccaatggg gtaactgaaa tacttcagaa ggatgcagct agctgcatga     180
cagtccatga caagtttttg gcattgggca cacattatgg caaggtttat ttacttgatg     240
tccaggggaa catcactcag aagtttgatg taagtcctgt gaagataaat cagattagct     300
tggatgaaag tggagagcac atgggtgtgt gttcagagga tggcaaggtg caggtatttg     360
gactgtattc tggagaagaa tttcacgaga cttttgactg tcccattaaa attattgctg     420
tgcacccaca tttcgtgaga tccagttgca agcagtttgt gaccggaggg aagaagctgc     480
tactgtttga acggtcttgg atgaacagat ggaagtctgc tgttctgcat gaaggggaag     540
ggaacataag gagtgtgaag tggagaggcc atctgattgc ttgggccaat aatatgggtg     600
tgaagatttt tgacatcatc tcaaagcaaa gaatcaccaa tgtgccccgg atgatataa      660
gtcttcgccc agacatgtat ccctgcagcc tctgctggaa ggacaatgtg acactgatta     720
ttggctgggg gacttctgtc aaggtgtgct cagtgaagga acggcatgcc agtgaaatga     780
gggatttgcc aagtcgatat gttgaaatag tgtctcagtt tgaaactgaa ttctacatca     840
gtggacttgc acctctctgt gatcagcttg ttgtactttc gtatgtaaag gagatttcag     900
aaaaaacgga agagaatac tgtgccaggc ctagactgga catcatccag ccactttctg     960
```

```
agacttgtga agagatctct tctgatgctt tgacagtcag aggctttcag gagaatgaat    1020
gtagagatta tcatttagaa tactctgaag gggaatcact tttttacatc gtgagtccga    1080
gagatgttgt agtggccaag gaacgagacc aagatgatca cattgactgg ctccttgaaa    1140
agaagaaata tgaagaagca ttgatggcag ctgaaattag ccaaaaaaat attaaaagac    1200
ataagattct ggatattggc ttggcatata taaatcacct ggtggagaga ggagactatg    1260
acatagcagc acgcaaatgc cagaaaattc ttgggaaaaa tgcagcactc tgggaatatg    1320
aagtttataa atttaaagaa attggacagc ttaaggctat tagtccttat ttgccaagag    1380
gtgatccagt tctgaaacca ctcatctatg aaatgatctt acatgaattt ttggagagtg    1440
attatgaggg ttttgccaca ttgatccgag aatggcctgg agatctgtat aataattcag    1500
tcatagttca agcagttcgg gatcatttga gaaaagatag tcagaacaag actttactta    1560
aaaccctggc agaattgtac acctatgaca agaactatgg caatgctctg gaaatatact    1620
taacattaag acataaagac gttttttcagt tgatccacaa gcataatctt ttcagttcta    1680
tcaaggataa aattgtttta ttaatggatt ttgattcaga gaaagctgtt gacatgcttt    1740
tggacaatga agataaaatt tcaattaaaa aggtagtgga agaattggaa gacagaccag    1800
agctacagca tgtgtatttg cataagcttt tcaagagaga ccaccataag gggcagcgtt    1860
accatgaaaa acagatcagt ctttatgctg aatatgatcg accaaactta cttcccttc    1920
tccgagacag tacccattgc ccacttgaaa aggctcttga gatctgtcaa cagagaaact    1980
ttgtagaaga gacagtttat cttctgagcc gaatgggtaa tagccgaagt gccctgaaga    2040
tgattatgga ggaattacat gatgttgata aagcaatcga atttgccaag gagcaagatg    2100
atggagagct gtgggaagat ttgatttat attccattga caaaccacca tttattactg    2160
gcttgttaaa caacattggc acacatgttg acccaattct actgattcac cgtattaagg    2220
aaggaatgga gatccccaat ttgagagatt ccttggttaa aattctgcaa gactacaatt    2280
tgcaaattct gcttcgtgaa ggctgcaaga agattctcgt agctgactct ttgtccttac    2340
tgaagaaaat gcaccgaact caaatgaaag gtgttcttgt tgatgaggag aacatctgtg    2400
agtcgtgcct ttcccctatt cttccatcag atgcagctaa gcccttcagc gtggtggtct    2460
tccattgccg gcacatgttc cacaaggagt gcctgcccat gcccagcatg aactctgctg    2520
cacagttctg caacatctgc agtgctaaga accgtggacc aggaagtgca attttggaga    2580
tgaaaaaata gctcatttct ccttgtcagt ctccttgtca ccactctttt tgagactgtt    2640
tttgcaacaa caaagcatt tgttgacact cgtgctgtta agagatttgt ttatgtttat    2700
attatactca aaaacaattt cttcatctat tcctgtacta atggtttctc tttgcagttc    2760
acagagaatt tggggctctc ttcatgcctt gaaattttgg ggtccatagt gaatattttg    2820
ttattattt gtttggctca ttcttatat agtaatggaa acataagtct aggagttaga    2880
aatgaatttt ttagaccctta gtaaaaccat ttaaccataa aatggacaac tgagaattct    2940
cccagctgcc tgaaagcgtc gccaactgtg gttatcctgc aagctgctac ctgcaacttg    3000
gacgttgttt ccacgtgctc tgctggctac gattcttgca ttctgggttt ggctttttc    3060
tgtgtcatca actatggtta tcctctaaat aggcatttaa tgaaacattg tacaaattgt    3120
cactcatttg atgacacctg ggaataacat tagcaggctg atgtcctgca ccattatgtt    3180
tactaatcac atgttctgtg tgctgtgacg actgtcaaag agtatctggc catggcggac    3240
actcagcatt tgttgattga ataaatgtta gctcttctca ttgtgaagga ctcacttta    3300
ctgggataaa caaatgcagt taagaattct ggcacccttg taaggaagaa aagagagttc    3360
```

```
aacaccttcg agtctgagcg cttgtggcta gagtttgcca ggagggagga aaccagtgac   3420
cctgaaaact gagggtgcct caggagcagt gggaccacct gatgctgaag gacggactaa   3480
tgatgtttcc tcttgccttc tctggtgcct ccattgccct catggaacag agcatatcat   3540
agagggagaa aagtcaaact tgtaattgtg tcttacagtt actggcttca tcttccttgg   3600
gatatatggt catcctctaa tgagtgtaaa agtgcgcaaa acacatcctt attgttcctg   3660
atctcttagt cccataaatg ggaacaaata cagctttctg cttctttctt tttggggaaa   3720
ggacagggtg ctagtgagta ctgacagcat gccagctacc gaagtcaccc agccattccc   3780
atgagcagca gttcatttaa ttgtcacagc gtcgccagga agaagatctg ataaacctag   3840
gtttacagat aaagaaagca aaatgtagag atgttgttga ggtcacagag gtgactgcct   3900
aacttcagag cagggcttct gatccctta agaaattaca gggccagccg ggcatggtgg   3960
ctcacgcccg taatcccagg ctttgggag gccttggcag gtggatcacc tgagatcgca   4020
cgttcgagac cagcctgacc aacatggaga accccatct ctactaaaaa cacaaattag   4080
ccaggcgtgg tggtacatgc ctgtaatccc agctactcag gaggctgagg caggagaatc   4140
acttgacccc aggagacgta ggttgtggtg agctgagatc gcgccattgc actccagcct   4200
gggcaacaag agcaaaactc cgtctcaaaa aagaaaagaa aagaaaagaa atcatagggc   4260
caagttcaaa ggaaatgcac agaacatatc ttcacattag agttaagaat tctctagcaa   4320
acaacagatt tttttgttgt tgttagtcac aaatacttag aactggaagg ctcttttgtta  4380 ttattgaatg taccctcag ccttctcagc atttccttat cccaagacta gtgtgctttc   4440
tgctacactg ctagttttca gttttgttct tacccaattg ttttttcttt tcaacattac   4500
caatttacag attcagttta ttacatttac attaatcctc acttatgatt tgagcaagct   4560
catttccaga aaagtttact ttaagatcat caataggatt tgctaatttc agtgaagtca   4620
ttttgcttca ggggtaaatt atcctagtta ccaagtccta tttggacata agaaaatcc    4680 tacttataga aaaggagaaa ataattaaac agtcttcatt tttaagtaac tgatttaaaa   4740
ggaaaataat aaaatatgtt cgtttatcat ttcagaaatt gctgtaacac actggaaaat   4800
tcctgaacaa tatagatttt atcgttaata aaaaacacta gctttcgttc cttagaatgt   4860
cttttctttt gaataaacag tattgggtga ttta                              4894
```

<210> SEQ ID NO 15
<211> LENGTH: 153
<212> TYPE: PRT
<213> ORGANISM: Homo sapiens

<400> SEQUENCE: 15

```
Met Ala Pro Gly Ser Arg Gly Glu Arg Ser Ser Phe Arg Ser Arg Arg
1               5                   10                  15

Gly Pro Gly Val Pro Ser Pro Gln Pro Asp Val Thr Met Leu Ser Arg
            20                  25                  30

Leu Leu Lys Glu His Gln Ala Lys Gln Asn Glu Arg Lys Glu Leu Gln
        35                  40                  45

Glu Lys Arg Arg Arg Glu Ala Ile Thr Ala Ala Thr Cys Leu Thr Glu
    50                  55                  60

Ala Leu Val Asp His Leu Asn Val Gly Val Ala Gln Ala Tyr Met Asn
65                  70                  75                  80

Gln Arg Lys Leu Asp His Glu Val Lys Thr Leu Gln Val Gln Ala Ala
                85                  90                  95
```

```
Gln Phe Ala Lys Gln Thr Gly Gln Trp Ile Gly Met Val Glu Asn Phe
                100                 105                 110

Asn Gln Ala Leu Lys Glu Ile Gly Asp Val Glu Asn Trp Ala Arg Ser
            115                 120                 125

Ile Glu Leu Asp Met Arg Thr Ile Ala Thr Ala Leu Glu Tyr Val Tyr
130                 135                 140

Lys Gly Gln Leu Gln Ser Ala Pro Ser
145                 150
```

```
<210> SEQ ID NO 16
<211> LENGTH: 590
<212> TYPE: DNA
<213> ORGANISM: Homo sapiens

<400> SEQUENCE: 16
acacagcggt cacgtgacat ggccccgggg agccgaggtg agcgttccag cttccggagc     60
cggaggggc  ccggcgtacc cagccccag  cccgacgtga ccatgctgtc ccgcctccta    120
aaagaacacc aggccaagca gaatgaacgc aaggagctgc aggaaaagag gaggcgagag    180
gctatcactg cagcgacctg cctgacagaa gctttggtgg atcacctcaa tgtgggtgtg    240
gcccaggcct acatgaacca gagaaagctg gaccatgagg tgaagaccct acaggtccag    300
gctgcccaat ttgccaagca gacaggccag tggatcggaa tggtggagaa cttcaaccag    360
gcactcaagg aaattgggga tgtggagaac tgggctcgga gcatcgagct ggacatgcgc    420
accattgcca ctgcactgga atatgtctac aaagggcagc tgcagtctgc cccttcctag    480
cccctgttcc ctcccccaac cctatccctc tacctcacc  cgcaggggga aggagggagg    540
ctgacaagcc ttgaataaaa cacaagcctc cgtttctcaa aaaaaaaaa                590
```

```
<210> SEQ ID NO 17
<211> LENGTH: 142
<212> TYPE: PRT
<213> ORGANISM: Homo sapiens

<400> SEQUENCE: 17

Met Ala Ala Ala Ala Glu Gly Val Leu Ala Thr Arg Ser Asp Glu Pro
1               5                   10                  15

Ala Arg Asp Asp Ala Ala Val Glu Thr Ala Glu Glu Ala Lys Glu Pro
            20                  25                  30

Ala Glu Ala Asp Ile Thr Glu Leu Cys Arg Asp Met Phe Ser Lys Met
        35                  40                  45

Ala Thr Tyr Leu Thr Gly Glu Leu Thr Ala Thr Ser Glu Asp Tyr Lys
    50                  55                  60

Leu Leu Glu Asn Met Asn Lys Leu Thr Ser Leu Lys Tyr Leu Glu Met
65                  70                  75                  80

Lys Asp Ile Ala Ile Asn Ile Ser Arg Asn Leu Lys Asp Leu Asn Gln
                85                  90                  95

Lys Tyr Ala Gly Leu Gln Pro Tyr Leu Asp Gln Ile Asn Val Ile Glu
            100                 105                 110

Glu Gln Val Ala Ala Leu Glu Gln Ala Ala Tyr Lys Leu Asp Ala Tyr
        115                 120                 125

Ser Lys Lys Leu Glu Ala Lys Tyr Lys Lys Leu Glu Lys Arg
    130                 135                 140
```

```
<210> SEQ ID NO 18
<211> LENGTH: 1958
<212> TYPE: DNA
```

<213> ORGANISM: Homo sapiens

<400> SEQUENCE: 18

```
ccggaaacag cgcggggtcc gctatggcgg cggcagccga gggcgtactg gcgacccgga      60
gtgatgagcc cgcccgagac gatgccgccg tggagacagc tgaggaagca aaggagcctg     120
ctgaagctga catcactgag ctctgccggg acatgttctc caaaatggcc acttacctga     180
ctggggaact gacggccacc agtgaagact ataagctcct ggaaaatatg aataaactca     240
ccagcttgaa gtatcttgaa atgaaagata ttgctataaa cattagtagg aacttaaagg     300
acttaaaacca gaaatatgct ggactgcagc cttatctgga tcagatcaat gtcattgaag     360
agcaggtagc agctcttgag caggcagctt acaagttgga tgcatattca aaaaaactgg     420
aagccaagta caagaagctg gagaagcgat gagaaactta tttctatggg acagagtctt     480
tttttttaa tgtggaagaa tgtcttataa aacctgaatc ctgaggctga tgaattgtga     540
aaattcctca aaaggaaatt atgctggtca tcacaggaac atctcaacgt tcgagtaaac     600
tggaggactg tggctattcc tgaaccttct ttgagacaga atccctcaga atctcacact     660
tataacttcc tacctttac ttgaatgctt tgccatattc aggacagaga ctctcacaaa     720
gttcagaaaa cagctggact taccagtaaa atcaaatgag aggacctatt ttctctggta     780
gtggttgatt actacattat tttcttaagt ggctggtttt ttagttacta tgtaaatggt     840
cgttttctg ttaatgatgc taatgtgttg taaacaagat tctaaattta aaaggaaaa     900
caaaacaaac ttgttctttg cagcttatca ccttgtgaat gtcggtaact tacttttcca     960
taatattgca ataacataa atcttaaaa taattccaag ctgagtcttc tagattgagc    1020
agaaatggtg aaaggagtat tgataacttg gcgtatgtga tgggccctc ttgtttattt    1080
tctatgtgag tcacattgac atgcgatcag tttgggaaat gtgatgaaaa caaagactag    1140
atgggtatgt gtgtttatgt gttgggtagg gaggtgacga ttgccactca taaaataaag    1200
gatttttataa aataccttcc tactgtgtat gtaggatttg gggggatctt agggacctaa    1260
tcgacttctt tgcacactaa aaacatcaga caatgggaca tactgactga ccagtctagg    1320
ttgaaagata ggcagcctta cccagaacac aacattagca gctgggaagg tgtctgaggt    1380
ccccaattac atatcccaaa gagtttctta cttctgtttc tgtcatttcc cctctgttcc    1440
agacagtcat catttatcct ctgttcttcc tggactgttg ctgtggtctc ttctcatctt    1500
aactgtccct tccaaccacc ctccacactg ctgccagagc aatcttaaaa atgtaaactg    1560
gccctattac tcctgcttag aaccctgtag tgacttatca tggcctctga aaaatctaga    1620
ctttcattat gcatacaagt cccttgtgtt tttttgtttg tttatagaca gggtctctat    1680
tgtcacccag gctggagtgt ggtggtgtga taatagctca ccttgacctc ctaggctcaa    1740
ctgatcttcc cacctcagcc tcctgaatag ctgggactac cagcacgctc caccatgcct    1800
tgctaattat ttttttataca gatggagtct cactatgttg tccaggctgg tcttgaactg    1860
gcctcaagtg attctcttac cacagcctgc cagagtgctg agattgtagg catgaaccac    1920
cgtgcctaac ataaggcccc tatttaaaca ttttttctt                           1958
```

<210> SEQ ID NO 19
<211> LENGTH: 1256
<212> TYPE: PRT
<213> ORGANISM: Homo sapiens

<400> SEQUENCE: 19

Met Leu Phe Lys Leu Leu Gln Arg Gln Thr Tyr Thr Cys Leu Ser His

```
1               5                   10                  15
Arg Tyr Gly Leu Tyr Val Cys Phe Leu Gly Val Val Thr Ile Val
            20                  25                  30

Ser Ala Phe Gln Phe Gly Glu Val Val Leu Glu Trp Ser Arg Asp Gln
            35                  40                  45

Tyr His Val Leu Phe Asp Ser Tyr Arg Asp Asn Ile Ala Gly Lys Ser
            50                  55                  60

Phe Gln Asn Arg Leu Cys Leu Pro Met Pro Ile Asp Val Val Tyr Thr
65                  70                  75                  80

Trp Val Asn Gly Thr Asp Leu Glu Leu Leu Lys Glu Leu Gln Gln Val
                85                  90                  95

Arg Glu Gln Met Glu Glu Gln Lys Ala Met Arg Glu Ile Leu Gly
                100                 105                 110

Lys Asn Thr Thr Glu Pro Thr Lys Lys Ser Glu Lys Gln Leu Glu Cys
                115                 120                 125

Leu Leu Thr His Cys Ile Lys Val Pro Met Leu Val Leu Asp Pro Ala
            130                 135                 140

Leu Pro Ala Asn Ile Thr Leu Lys Asp Leu Pro Ser Leu Tyr Pro Ser
145                 150                 155                 160

Phe His Ser Ala Ser Asp Ile Phe Asn Val Ala Lys Pro Lys Asn Pro
                165                 170                 175

Ser Thr Asn Val Ser Val Val Phe Asp Ser Thr Lys Asp Val Glu
                180                 185                 190

Asp Ala His Ser Gly Leu Leu Lys Gly Asn Ser Arg Gln Thr Val Trp
            195                 200                 205

Arg Gly Tyr Leu Thr Thr Asp Lys Glu Val Pro Gly Leu Val Leu Met
210                 215                 220

Gln Asp Leu Ala Phe Leu Ser Gly Phe Pro Pro Thr Phe Lys Glu Thr
225                 230                 235                 240

Asn Gln Leu Lys Thr Lys Leu Pro Glu Asn Leu Ser Ser Lys Val Lys
                245                 250                 255

Leu Leu Gln Leu Tyr Ser Glu Ala Ser Val Ala Leu Leu Lys Leu Asn
            260                 265                 270

Asn Pro Lys Asp Phe Gln Glu Leu Asn Lys Gln Thr Lys Lys Asn Met
            275                 280                 285

Thr Ile Asp Gly Lys Glu Leu Thr Ile Ser Pro Ala Tyr Leu Leu Trp
            290                 295                 300

Asp Leu Ser Ala Ile Ser Gln Ser Lys Gln Asp Glu Asp Ile Ser Ala
305                 310                 315                 320

Ser Arg Phe Glu Asp Asn Glu Glu Leu Arg Tyr Ser Leu Arg Ser Ile
                325                 330                 335

Glu Arg His Ala Pro Trp Val Arg Asn Ile Phe Ile Val Thr Asn Gly
            340                 345                 350

Gln Ile Pro Ser Trp Leu Asn Leu Asp Asn Pro Arg Val Thr Ile Val
            355                 360                 365

Thr His Gln Asp Val Phe Arg Asn Leu Ser His Leu Pro Thr Phe Ser
            370                 375                 380

Ser Pro Ala Ile Glu Ser His Ile His Arg Ile Glu Gly Leu Ser Gln
385                 390                 395                 400

Lys Phe Ile Tyr Leu Asn Asp Asp Val Met Phe Gly Lys Asp Val Trp
                405                 410                 415

Pro Asp Asp Phe Tyr Ser His Ser Lys Gly Gln Lys Val Tyr Leu Thr
                420                 425                 430
```

```
Trp Pro Val Pro Asn Cys Ala Glu Gly Cys Pro Gly Ser Trp Ile Lys
        435                 440                 445

Asp Gly Tyr Cys Asp Lys Ala Cys Asn Asn Ser Ala Cys Asp Trp Asp
    450                 455                 460

Gly Gly Asp Cys Ser Gly Asn Ser Gly Gly Ser Arg Tyr Ile Ala Gly
465                 470                 475                 480

Gly Gly Gly Thr Gly Ser Ile Gly Val Gly Gln Pro Trp Gln Phe Gly
                485                 490                 495

Gly Gly Ile Asn Ser Val Ser Tyr Cys Asn Gln Gly Cys Ala Asn Ser
            500                 505                 510

Trp Leu Ala Asp Lys Phe Cys Asp Gln Ala Cys Asn Val Leu Ser Cys
        515                 520                 525

Gly Phe Asp Ala Gly Asp Cys Gly Gln Asp His Phe His Glu Leu Tyr
530                 535                 540

Lys Val Ile Leu Leu Pro Asn Gln Thr His Tyr Ile Pro Lys Gly
545                 550                 555                 560

Glu Cys Leu Pro Tyr Phe Ser Phe Ala Glu Val Ala Lys Arg Gly Val
                565                 570                 575

Glu Gly Ala Tyr Ser Asp Asn Pro Ile Ile Arg His Ala Ser Ile Ala
            580                 585                 590

Asn Lys Trp Lys Thr Ile His Leu Ile Met His Ser Gly Met Asn Ala
        595                 600                 605

Thr Thr Ile His Phe Asn Leu Thr Phe Gln Asn Thr Asn Asp Glu Glu
    610                 615                 620

Phe Lys Met Gln Ile Thr Val Glu Val Asp Thr Arg Glu Gly Pro Lys
625                 630                 635                 640

Leu Asn Ser Thr Ala Gln Lys Gly Tyr Glu Asn Leu Val Ser Pro Ile
                645                 650                 655

Thr Leu Leu Pro Glu Ala Glu Ile Leu Phe Glu Asp Ile Pro Lys Glu
            660                 665                 670

Lys Arg Phe Pro Lys Phe Lys Arg His Asp Val Asn Ser Thr Arg Arg
        675                 680                 685

Ala Gln Glu Glu Val Lys Ile Pro Leu Val Asn Ile Ser Leu Leu Pro
    690                 695                 700

Lys Asp Ala Gln Leu Ser Leu Asn Thr Leu Asp Leu Gln Leu Glu His
705                 710                 715                 720

Gly Asp Ile Thr Leu Lys Gly Tyr Asn Leu Ser Lys Ser Ala Leu Leu
                725                 730                 735

Arg Ser Phe Leu Met Asn Ser Gln His Ala Lys Ile Lys Asn Gln Ala
            740                 745                 750

Ile Ile Thr Asp Glu Thr Asn Asp Ser Leu Val Ala Pro Gln Glu Lys
        755                 760                 765

Gln Val His Lys Ser Ile Leu Pro Asn Ser Leu Gly Val Ser Glu Arg
    770                 775                 780

Leu Gln Arg Leu Thr Phe Pro Ala Val Ser Val Lys Val Asn Gly His
785                 790                 795                 800

Asp Gln Gly Gln Asn Pro Pro Leu Asp Leu Glu Thr Thr Ala Arg Phe
                805                 810                 815

Arg Val Glu Thr His Thr Gln Lys Thr Ile Gly Gly Asn Val Thr Lys
            820                 825                 830

Glu Lys Pro Pro Ser Leu Ile Val Pro Leu Glu Ser Gln Met Thr Lys
        835                 840                 845
```

Glu Lys Lys Ile Thr Gly Lys Glu Lys Glu Asn Ser Arg Met Glu Glu
850                 855                 860

Asn Ala Glu Asn His Ile Gly Val Thr Glu Val Leu Leu Gly Arg Lys
865                 870                 875                 880

Leu Gln His Tyr Thr Asp Ser Tyr Leu Gly Phe Leu Pro Trp Glu Lys
            885                 890                 895

Lys Lys Tyr Phe Gln Asp Leu Leu Asp Glu Glu Ser Leu Lys Thr
                900                 905                 910

Gln Leu Ala Tyr Phe Thr Asp Ser Lys Asn Thr Gly Arg Gln Leu Lys
            915                 920                 925

Asp Thr Phe Ala Asp Ser Leu Arg Tyr Val Asn Lys Ile Leu Asn Ser
930                 935                 940

Lys Phe Gly Phe Thr Ser Arg Lys Val Pro Ala His Met Pro His Met
945                 950                 955                 960

Ile Asp Arg Ile Val Met Gln Glu Leu Gln Asp Met Phe Pro Glu Glu
                965                 970                 975

Phe Asp Lys Thr Ser Phe His Lys Val Arg His Ser Glu Asp Met Gln
            980                 985                 990

Phe Ala Phe Ser Tyr Phe Tyr Tyr Leu Met Ser Ala Val Gln Pro Leu
            995                 1000                1005

Asn Ile Ser Gln Val Phe Asp Glu Val Asp Thr Asp Gln Ser Gly
1010                1015                1020

Val Leu Ser Asp Arg Glu Ile Arg Thr Leu Ala Thr Arg Ile His
1025                1030                1035

Glu Leu Pro Leu Ser Leu Gln Asp Leu Thr Gly Leu Glu His Met
1040                1045                1050

Leu Ile Asn Cys Ser Lys Met Leu Pro Ala Asp Ile Thr Gln Leu
1055                1060                1065

Asn Asn Ile Pro Pro Thr Gln Glu Ser Tyr Tyr Asp Pro Asn Leu
1070                1075                1080

Pro Pro Val Thr Lys Ser Leu Val Thr Asn Cys Lys Pro Val Thr
1085                1090                1095

Asp Lys Ile His Lys Ala Tyr Lys Asp Lys Asn Lys Tyr Arg Phe
1100                1105                1110

Glu Ile Met Gly Glu Glu Glu Ile Ala Phe Lys Met Ile Arg Thr
1115                1120                1125

Asn Val Ser His Val Val Gly Gln Leu Asp Asp Ile Arg Lys Asn
1130                1135                1140

Pro Arg Lys Phe Val Cys Leu Asn Asp Asn Ile Asp His Asn His
1145                1150                1155

Lys Asp Ala Gln Thr Val Lys Ala Val Leu Arg Asp Phe Tyr Glu
1160                1165                1170

Ser Met Phe Pro Ile Pro Ser Gln Phe Glu Leu Pro Arg Glu Tyr
1175                1180                1185

Arg Asn Arg Phe Leu His Met His Glu Leu Gln Glu Trp Arg Ala
1190                1195                1200

Tyr Arg Asp Lys Leu Lys Phe Trp Thr His Cys Val Leu Ala Thr
1205                1210                1215

Leu Ile Met Phe Thr Ile Phe Ser Phe Phe Ala Glu Gln Leu Ile
1220                1225                1230

Ala Leu Lys Arg Lys Ile Phe Pro Arg Arg Arg Ile His Lys Glu
1235                1240                1245

Ala Ser Pro Asn Arg Ile Arg Val 1250        1255

<210> SEQ ID NO 20
<211> LENGTH: 5644
<212> TYPE: DNA
<213> ORGANISM: Homo sapiens

<400> SEQUENCE: 20

| | | | | | |
|---|---|---|---|---|---|
| gctcccggaa | gcggcggccg | cggcgcggag | ccgagcgggc | gtccgtcgcc | ggagctgcaa | 60 |
| tgagcggcgc | ccggaggctg | tgacctgcgc | gcggcggccc | gaccggggcc | cctgaatggc | 120 |
| ggctcgctga | ggcggcggcg | gcggcggcgg | cggctcaggc | tcctcgggc | gtggcgtggc | 180 |
| ggtgaagggg | tgatgctgtt | caagctcctg | cagagacaga | cctatacctg | cctgtcccac | 240 |
| aggtatgggc | tctacgtgtg | cttcttgggc | gtcgttgtca | ccatcgtctc | cgccttccag | 300 |
| ttcggagagg | tggttctgga | atggagccga | gatcaatacc | atgttttgtt | tgattcctat | 360 |
| agagacaata | ttgctggaaa | gtcctttcag | aatcggcttt | gtctgcccat | gccgattgac | 420 |
| gttgtttaca | cctgggtgaa | tggcacagat | cttgaactac | tgaaggaact | acagcaggtc | 480 |
| agagaacaga | tggaggagga | gcagaaagca | atgagagaaa | tccttgggaa | aaacacaacg | 540 |
| gaacctacta | agaagagtga | gaagcagtta | gagtgtttgc | taacacactg | cattaaggtg | 600 |
| ccaatgcttg | tcctggaccc | agccctgcca | gccaacatca | ccctgaagga | cctgccatct | 660 |
| ctttatcctt | cttttcattc | tgccagtgac | attttcaatg | ttgcaaaacc | aaaaaaccct | 720 |
| tctaccaatg | tctcagttgt | tgttttttgac | agtactaagg | atgttgaaga | tgcccactct | 780 |
| ggactgctta | aggaaaatag | cagacagaca | gtatggaggg | gctacttgac | aacagataaa | 840 |
| gaagtccctg | gattagtgct | aatgcaagat | ttggctttcc | tgagtggatt | ccaccaaca | 900 |
| ttcaaggaaa | caaatcaact | aaaaacaaaa | ttgccagaaa | atctttcctc | taaagtcaaa | 960 |
| ctgttgcagt | tgtattcaga | ggccagtgta | gcgcttctaa | aactgaataa | ccccaaggat | 1020 |
| tttcaagaat | tgaataagca | aactaagaag | aacatgacca | ttgatggaaa | agaactgacc | 1080 |
| ataagtcctg | catatttatt | atgggatctg | agcgccatca | gccagtctaa | gcaggatgaa | 1140 |
| gacatctctg | ccagtcgttt | tgaagataac | gaagaactga | ggtactcatt | gcgatctatc | 1200 |
| gagaggcatg | caccatgggt | tcggaatatt | ttcattgtca | ccaacgggca | gattccatcc | 1260 |
| tggctgaacc | ttgacaatcc | tcgagtgaca | atagtaacac | accaggatgt | ttttcgaaat | 1320 |
| ttgagccact | tgcctacctt | tagttcacct | gctattgaaa | gtcacattca | tcgcatcgaa | 1380 |
| gggctgtccc | agaagtttat | ttacctaaat | gatgatgtca | tgtttgggaa | ggatgtctgg | 1440 |
| ccagatgatt | tttacagtca | ctccaaaggc | cagaaggttt | atttgacatg | gcctgtgcca | 1500 |
| aactgtgccg | agggctgccc | aggttcctgg | attaaggatg | ctattgtgaa | caaggcttgt | 1560 |
| aataattcag | cctgcgattg | ggatggtggg | gattgctctg | gaaacagtgg | agggagtcgc | 1620 |
| tatattgcag | gaggtggagg | tactgggagt | attggagttg | acagccctg | cagtttggt | 1680 |
| ggaggaataa | acagtgtctc | ttactgtaat | cagggatgtg | cgaattcctg | gctcgctgat | 1740 |
| aagttctgtg | accaagcatg | caatgtcttg | tcctgtgggt | ttgatgctgg | cgactgtggg | 1800 |
| caagatcatt | ttcatgaatt | gtataaagtg | atccttctcc | caaaccagac | tcactatatt | 1860 |
| attccaaaag | gtgaatgcct | gccttatttc | agctttgcag | aagtagccaa | agaggagtt | 1920 |
| gaaggtgcct | atagtgacaa | tccaataatt | cgacatgctt | ctattgccaa | caagtggaaa | 1980 |
| accatccacc | tcataatgca | cagtggaatg | aatgccacca | caatacattt | taatctcacg | 2040 |
| tttcaaaata | caaacgatga | agagttcaaa | atgcagataa | cagtggaggt | ggacacaagg | 2100 |

```
gagggaccaa aactgaattc tacagcccag aagggttacg aaaatttagt tagtcccata   2160
acacttcttc cagaggcgga aatccttttt gaggatattc ccaaagaaaa acgcttcccg   2220
aagtttaaga gacatgatgt taactcaaca aggagagccc aggaagaggt gaaaattccc   2280
ctggtaaata tttcactcct tccaaaagac gcccagttga gtctcaatac cttggatttg   2340
caactggaac atggagacat cactttgaaa ggatacaatt tgtccaagtc agccttgctg   2400
agatcatttc tgatgaactc acagcatgct aaaataaaaa atcaagctat aataacagat   2460
gaaacaaatg acagtttggt ggctccacag gaaaaacagg ttcataaaag catcttgcca   2520
aacagcttag gagtgtctga aagattgcag aggttgactt ttcctgcagt gagtgtaaaa   2580
gtgaatggtc atgaccaggg tcagaatcca cccctggact tggagaccac agcaagattt   2640
agagtggaaa ctcacaccca aaaaaccata ggcggaaatg tgacaaaaga aaagccccca   2700
tctctgattg ttccactgga aagccagatg acaaagaaa agaaaatcac agggaaagaa   2760
aaagagaaca gtagaatgga ggaaaatgct gaaaatcaca taggcgttac tgaagtgtta   2820
cttggaagaa agctgcagca ttacacagat agttacttgg gctttttgcc atgggagaaa   2880
aaaaagtatt tccaagatct tctcgacgaa gaagagtcat tgaagacaca attggcatac   2940
ttcactgata gcaaaaatac tgggaggcaa ctaaaagata catttgcaga ttccctcaga   3000
tatgtaaata aaattctaaa tagcaagttt ggattcacat cgcggaaagt ccctgctcac   3060
atgcctcaca tgattgaccg gattgttatg caagaactgc aagatatgtt ccctgaagaa   3120
tttgacaaga cgtcatttca caaagtgcgc cattctgagg atatgcagtt tgccttctct   3180
tatttttatt atctcatgag tgcagtgcag ccactgaata tatctcaagt ctttgatgaa   3240
gttgatacag atcaatctgg tgtcttgtct gacagagaaa tccgaacact ggctaccaga   3300
attcacgaac tgccgttaag tttgcaggat ttgacaggtc tggaacacat gctaataaat   3360
tgctcaaaaa tgcttcctgc tgatatcacg cagctaaata atattccacc aactcaggaa   3420
tcctactatg atcccaacct gccaccggtc actaaaagtc tagtaacaaa ctgtaaacca   3480
gtaactgaca aaatccacaa agcatataag gacaaaaaca aatataggtt tgaaatcatg   3540
ggagaagaag aaatcgcttt taaaatgatt cgtaccaacg tttctcatgt ggttggccag   3600
ttggatgaca taagaaaaaa ccctaggaag tttgtttgcc tgaatgacaa cattgaccac   3660
aatcataaag atgctcagac agtgaaggct gttctcaggg acttctatga atccatgttc   3720
cccataccct cccaatttga actgccaaga gagtatcgaa accgtttcct tcatatgcat   3780
gagctgcagg aatggagggc ttatcgagac aaattgaagt tttggaccca ttgtgtacta   3840
gcaacattga ttatgtttac tatattctca ttttttgctg agcagttaat tgcacttaag   3900
cggaagatat ttcccagaag gaggatacac aaagaagcta gtcccaatcg aatcagagta   3960
tagaagatct tcatttgaaa accatctacc tcagcattta ctgagcattt taaaactcag   4020
cttcacagag atgtctttgt gatgtgatgc ttagcagttt ggcccgaaga aggaaaaatat   4080 ccagtaccat gctgttttgt ggcatgaata tagcccactg accaggaatt atttaaccaa   4140
cccactgaaa acttgtgtgt tgagcagctc tgaactgatt ttactttttaa agaatttgct   4200 catggacctg tcatcctttt tataaaaagg ctcactgaca agagacagct gttaatttcc   4260
cacagcaatc attgcagact aactttatta ggagaagcct atgccagctg ggagtgattg   4320
ctaagaggct ccagtctttg cattccaaag ccttttgcta aagttttgca cttttttttt   4380
ttcatttccc attttttaagt agttactaag ttaactagtt attcttgctt ctgagtataa   4440
```

-continued

```
cgaattggga tgtctaaacc tattttata gatgttattt aaataatgca gcaatatcac    4500
ctcttattga caatacctaa attatgagtt ttattaatat ttaagactgt aaatggtctt    4560
aaaccactaa ctactgaaga gctcaatgat tgacatctga aatgctttgt aattattgac    4620
ttcagcccct aagaatgcta tgatttcacg tgcaggtcta atttcaaagg gctagagtta    4680
gtactactta ccagatgtaa ttatgttttg gaaatgtaca tattcaaaca gaagtgcctc    4740
attttagaaa tgagtagtgc tgatggcact ggcacattac agtggtgtct tgtttaatac    4800
tcattggtat attccagtag ctatctctct cagttggttt ttgatagaac agaggccagc    4860
aaactttctt tgtaaaaggc tggttagtaa attattgcag gccacctgtg tctttgtcat    4920
acattcttct tgctgttgtt tagtttgttt ttttcaaac aaccctctaa aaatgtaaaa    4980
accatgttta gcttgcagct gtacaaaaac tgcccaccag ccagatgtga ccctcaggcc    5040
atcatttgcc aatcactgag aattagtttt tgttgttgtt gttgttgttg tttttgagac    5100
agagtctctc tctgttgccc aggctggagt gcagtggcgc aatctcagct cactgcaacc    5160
tccgcctccc gggttcaagc agttctgtct cagccttctg agtagctggg actacaggtg    5220
catgccacca cccctgcta atttttgtat ttttagtaga acggggggtt ccaccatatt    5280
ggtcaggctt atcttgaact cctgacctca ggtgatccac ctgcctctgc ctcccaaagt    5340
gctgagatta caggcataag ccagtgcacc cagccgagaa ttagtatttt tatgtatggt    5400
taaaccttgg cgtctagcca tattttatgt cataatacaa tggatttgtg aagagcagat    5460
tccatgagta actctgacag gtattttaga tcatgatctc aacaatattc ttccaaaatg    5520
gcatacatct tttgtacaaa gaacttgaaa tgtaaatact gtgtttgtgc tgtaagagtt    5580
gtgtatttca aaaactgaaa tctcataaaa agttaaattt ttgtctgaca aaaaaaaaaa    5640
aaaa                                                                5644
```

<210> SEQ ID NO 21
<211> LENGTH: 2098
<212> TYPE: PRT
<213> ORGANISM: Homo sapiens

<400> SEQUENCE: 21

```
Met Ala Thr Asp Asp Lys Thr Ser Pro Thr Leu Asp Ser Ala Asn Asp
1               5                   10                  15

Leu Pro Arg Ser Pro Thr Ser Pro Ser His Leu Thr His Phe Lys Pro
                20                  25                  30

Leu Thr Pro Asp Gln Asp Glu Pro Pro Phe Lys Ser Ala Tyr Ser Ser
            35                  40                  45

Phe Val Asn Leu Phe Arg Phe Asn Lys Glu Arg Ala Glu Gly Gly Gln
        50                  55                  60

Gly Glu Gln Gln Pro Leu Ser Gly Ser Trp Ser Pro Gln Leu Pro
65                  70                  75                  80

Ser Arg Thr Gln Ser Val Arg Ser Pro Thr Pro Tyr Lys Lys Gln Leu
                85                  90                  95

Asn Glu Glu Leu Gln Arg Arg Ser Ser Ala Leu Asp Thr Arg Arg Lys
                100                 105                 110

Ala Glu Pro Thr Phe Gly Gly His Asp Pro Arg Thr Ala Val Gln Leu
            115                 120                 125

Arg Ser Leu Ser Thr Val Leu Lys Arg Leu Lys Glu Ile Met Glu Gly
        130                 135                 140

Lys Ser Gln Asp Ser Asp Leu Lys Gln Tyr Trp Met Pro Asp Ser Gln
145                 150                 155                 160
```

```
Cys Lys Glu Cys Tyr Asp Cys Ser Glu Lys Phe Thr Thr Phe Arg Arg
                165                 170                 175

Arg His His Cys Arg Leu Cys Gly Gln Ile Phe Cys Ser Arg Cys Cys
                180                 185                 190

Asn Gln Glu Ile Pro Gly Lys Phe Met Gly Tyr Thr Gly Asp Leu Arg
                195                 200                 205

Ala Cys Thr Tyr Cys Arg Lys Ile Ala Leu Ser Tyr Ala His Ser Thr
            210                 215                 220

Asp Ser Asn Ser Ile Gly Glu Asp Leu Asn Ala Leu Ser Asp Ser Ala
225                 230                 235                 240

Cys Ser Val Ser Val Leu Asp Pro Ser Glu Pro Arg Thr Pro Val Gly
                245                 250                 255

Ser Arg Lys Ala Ser Arg Asn Ile Phe Leu Glu Asp Asp Leu Ala Trp
                260                 265                 270

Gln Ser Leu Ile His Pro Asp Ser Ser Asn Thr Pro Leu Ser Thr Arg
            275                 280                 285

Leu Val Ser Val Gln Glu Asp Ala Gly Lys Ser Pro Ala Arg Asn Arg
        290                 295                 300

Ser Ala Ser Ile Thr Asn Leu Ser Leu Asp Arg Ser Gly Ser Pro Met
305                 310                 315                 320

Val Pro Ser Tyr Glu Thr Ser Val Ser Pro Gln Ala Asn Arg Thr Tyr
                325                 330                 335

Val Arg Thr Glu Thr Thr Glu Asp Glu Arg Lys Ile Leu Leu Asp Ser
                340                 345                 350

Val Gln Leu Lys Asp Leu Trp Lys Lys Ile Cys His His Ser Ser Gly
            355                 360                 365

Met Glu Phe Gln Asp His Arg Tyr Trp Leu Arg Thr His Pro Asn Cys
        370                 375                 380

Ile Val Gly Lys Glu Leu Val Asn Trp Leu Ile Arg Asn Gly His Ile
385                 390                 395                 400

Ala Thr Arg Ala Gln Ala Ile Ala Ile Gly Gln Ala Met Val Asp Gly
                405                 410                 415

Arg Trp Leu Asp Cys Val Ser His His Asp Gln Leu Phe Arg Asp Glu
                420                 425                 430

Tyr Ala Leu Tyr Arg Pro Leu Gln Ser Thr Glu Phe Ser Glu Thr Pro
            435                 440                 445

Ser Pro Asp Ser Asp Ser Val Asn Ser Val Glu Gly His Ser Glu Pro
        450                 455                 460

Ser Trp Phe Lys Asp Ile Lys Phe Asp Asp Ser Asp Thr Glu Gln Ile
465                 470                 475                 480

Ala Glu Glu Gly Asp Asp Asn Leu Ala Asn Ser Ala Ser Pro Ser Lys
                485                 490                 495

Arg Thr Ser Val Ser Ser Phe Gln Ser Thr Val Asp Ser Asp Ser Ala
                500                 505                 510

Ala Ser Ile Ser Leu Asn Val Glu Leu Asp Asn Val Asn Phe His Ile
            515                 520                 525

Lys Lys Pro Ser Lys Tyr Pro His Val Pro Pro His Pro Ala Asp Gln
        530                 535                 540

Lys Glu Tyr Leu Ile Ser Asp Thr Gly Gly Gln Gln Leu Ser Ile Ser
545                 550                 555                 560

Asp Ala Phe Ile Lys Glu Ser Leu Phe Asn Arg Arg Val Glu Glu Lys
                565                 570                 575
```

-continued

```
Ser Lys Glu Leu Pro Phe Thr Pro Leu Gly Trp His His Asn Asn Leu
            580                 585                 590

Glu Leu Leu Arg Glu Glu Asn Gly Glu Lys Gln Ala Met Glu Arg Leu
        595                 600                 605

Leu Ser Ala Asn His Asn His Met Met Ala Leu Leu Gln Gln Leu Leu
    610                 615                 620

His Ser Asp Ser Leu Ser Ser Ser Trp Arg Asp Ile Ile Val Ser Leu
625                 630                 635                 640

Val Cys Gln Val Val Gln Thr Val Arg Pro Asp Val Lys Asn Gln Asp
                645                 650                 655

Asp Asp Met Asp Ile Arg Gln Phe Val His Ile Lys Lys Ile Pro Gly
            660                 665                 670

Gly Lys Lys Phe Asp Ser Val Val Asn Gly Phe Val Cys Thr Lys
        675                 680                 685

Asn Ile Ala His Lys Lys Met Ser Ser Cys Ile Lys Asn Pro Lys Ile
    690                 695                 700

Leu Leu Leu Lys Cys Ser Ile Glu Tyr Leu Tyr Arg Glu Glu Thr Lys
705                 710                 715                 720

Phe Thr Cys Ile Asp Pro Ile Val Leu Gln Glu Arg Glu Phe Leu Lys
                725                 730                 735

Asn Tyr Val Gln Arg Ile Val Asp Val Arg Pro Thr Leu Val Leu Val
            740                 745                 750

Glu Lys Thr Val Ser Arg Ile Ala Gln Asp Met Leu Leu Glu His Gly
        755                 760                 765

Ile Thr Leu Val Ile Asn Val Lys Ser Gln Val Leu Glu Arg Ile Ser
    770                 775                 780

Arg Met Thr Gln Gly Asp Leu Val Met Ser Met Asp Gln Leu Leu Thr
785                 790                 795                 800

Lys Pro His Leu Gly Thr Cys His Lys Phe Tyr Met Gln Ile Phe Gln
                805                 810                 815

Leu Pro Asn Glu Gln Thr Lys Thr Leu Met Phe Phe Glu Gly Cys Pro
            820                 825                 830

Gln His Leu Gly Cys Thr Ile Lys Leu Arg Gly Gly Ser Asp Tyr Glu
        835                 840                 845

Leu Ala Arg Val Lys Glu Ile Leu Ile Phe Met Ile Cys Val Ala Tyr
    850                 855                 860

His Ser Gln Leu Glu Ile Ser Phe Leu Met Asp Glu Phe Ala Met Pro
865                 870                 875                 880

Pro Thr Leu Met Gln Asn Pro Ser Phe His Ser Leu Ile Glu Gly Arg
                885                 890                 895

Gly His Glu Gly Ala Val Gln Glu Gln Tyr Gly Gly Gly Ser Ile Pro
            900                 905                 910

Trp Asp Pro Asp Ile Pro Pro Glu Ser Leu Pro Cys Asp Asp Ser Ser
        915                 920                 925

Leu Leu Glu Leu Arg Ile Val Phe Glu Lys Gly Glu Gln Glu Asn Lys
    930                 935                 940

Asn Leu Pro Gln Ala Val Ala Ser Val Lys His Gln Glu His Ser Thr
945                 950                 955                 960

Thr Ala Cys Pro Ala Gly Leu Pro Cys Ala Phe Phe Ala Pro Val Pro
                965                 970                 975

Glu Ser Leu Leu Pro Leu Pro Val Asp Asp Gln Gln Asp Ala Leu Gly
            980                 985                 990

Ser Glu Gln Pro Glu Thr Leu Gln  Gln Thr Val Val Leu  Gln Asp Pro
```

-continued

```
                995                 1000                1005
Lys Ser Gln Ile Arg Ala Phe Arg Asp Pro Leu Gln Asp Asp Thr
    1010            1015            1020

Gly Leu Tyr Val Thr Glu Glu Val Thr Ser Ser Glu Asp Lys Arg
    1025            1030            1035

Lys Thr Tyr Ser Leu Ala Phe Lys Gln Glu Leu Lys Asp Val Ile
    1040            1045            1050

Leu Cys Ile Ser Pro Val Ile Thr Phe Arg Glu Pro Phe Leu Leu
    1055            1060            1065

Thr Glu Lys Gly Met Arg Cys Ser Thr Arg Asp Tyr Phe Ala Glu
    1070            1075            1080

Gln Val Tyr Trp Ser Pro Leu Leu Asn Lys Glu Phe Lys Glu Met
    1085            1090            1095

Glu Asn Arg Arg Lys Lys Gln Leu Leu Arg Asp Leu Ser Gly Leu
    1100            1105            1110

Gln Gly Met Asn Gly Ser Ile Gln Ala Lys Ser Ile Gln Val Leu
    1115            1120            1125

Pro Ser His Glu Leu Val Ser Thr Arg Ile Ala Glu His Leu Gly
    1130            1135            1140

Asp Ser Gln Ser Leu Gly Arg Met Leu Ala Asp Tyr Arg Ala Arg
    1145            1150            1155

Gly Gly Arg Ile Gln Pro Lys Asn Ser Asp Pro Phe Ala His Ser
    1160            1165            1170

Lys Asp Ala Ser Ser Thr Ser Ser Gly Gln Ser Gly Ser Lys Asn
    1175            1180            1185

Glu Gly Asp Glu Glu Arg Gly Leu Ile Leu Ser Asp Ala Val Trp
    1190            1195            1200

Ser Thr Lys Val Asp Cys Leu Asn Pro Ile Asn His Gln Arg Leu
    1205            1210            1215

Cys Val Leu Phe Ser Ser Ser Ala Gln Ser Ser Asn Ala Pro
    1220            1225            1230

Ser Ala Cys Val Ser Pro Trp Ile Val Thr Met Glu Phe Tyr Gly
    1235            1240            1245

Lys Asn Asp Leu Thr Leu Gly Ile Phe Leu Glu Arg Tyr Cys Phe
    1250            1255            1260

Arg Pro Ser Tyr Gln Cys Pro Ser Met Phe Cys Asp Thr Pro Met
    1265            1270            1275

Val His His Ile Arg Arg Phe Val His Gly Gln Gly Cys Val Gln
    1280            1285            1290

Ile Ile Leu Lys Glu Leu Asp Ser Pro Val Pro Gly Tyr Gln His
    1295            1300            1305

Thr Ile Leu Thr Tyr Ser Trp Cys Arg Ile Cys Lys Gln Val Thr
    1310            1315            1320

Pro Val Val Ala Leu Ser Asn Glu Ser Trp Ser Met Ser Phe Ala
    1325            1330            1335

Lys Tyr Leu Glu Leu Arg Phe Tyr Gly His Gln Tyr Thr Arg Arg
    1340            1345            1350

Ala Asn Ala Glu Pro Cys Gly His Ser Ile His His Asp Tyr His
    1355            1360            1365

Gln Tyr Phe Ser Tyr Asn Gln Met Val Ala Ser Phe Ser Tyr Ser
    1370            1375            1380

Pro Ile Arg Leu Leu Glu Val Cys Val Pro Leu Pro Lys Ile Phe
    1385            1390            1395
```

-continued

Ile Lys Arg Gln Ala Pro Leu Lys Val Ser Leu Leu Gln Asp Leu
1400                1405                1410

Lys Asp Phe Phe Gln Lys Val Ser Gln Val Tyr Val Ala Ile Asp
1415                1420                1425

Glu Arg Leu Ala Ser Leu Lys Thr Asp Thr Phe Ser Lys Thr Arg
1430                1435                1440

Glu Glu Lys Met Glu Asp Ile Phe Ala Gln Lys Glu Met Glu Glu
1445                1450                1455

Gly Glu Phe Lys Asn Trp Ile Glu Lys Met Gln Ala Arg Leu Met
1460                1465                1470

Ser Ser Ser Val Asp Thr Pro Gln Gln Leu Gln Ser Val Phe Glu
1475                1480                1485

Ser Leu Ile Ala Lys Lys Gln Ser Leu Cys Glu Val Leu Gln Ala
1490                1495                1500

Trp Asn Asn Arg Leu Gln Asp Leu Phe Gln Gln Glu Lys Gly Arg
1505                1510                1515

Lys Arg Pro Ser Val Pro Pro Ser Pro Gly Arg Leu Arg Gln Gly
1520                1525                1530

Glu Glu Ser Lys Ile Ser Ala Met Asp Ala Ser Pro Arg Asn Ile
1535                1540                1545

Ser Pro Gly Leu Gln Asn Gly Glu Lys Glu Asp Arg Phe Leu Thr
1550                1555                1560

Thr Leu Ser Ser Gln Ser Ser Thr Ser Ser Thr His Leu Gln Leu
1565                1570                1575

Pro Thr Pro Pro Glu Val Met Ser Glu Gln Ser Val Gly Gly Pro
1580                1585                1590

Pro Glu Leu Asp Thr Ala Ser Ser Ser Glu Asp Val Phe Asp Gly
1595                1600                1605

His Leu Leu Gly Ser Thr Asp Ser Gln Val Lys Glu Lys Ser Thr
1610                1615                1620

Met Lys Ala Ile Phe Ala Asn Leu Leu Pro Gly Asn Ser Tyr Asn
1625                1630                1635

Pro Ile Pro Phe Pro Phe Asp Pro Asp Lys His Tyr Leu Met Tyr
1640                1645                1650

Glu His Glu Arg Val Pro Ile Ala Val Cys Glu Lys Glu Pro Ser
1655                1660                1665

Ser Ile Ile Ala Phe Ala Leu Ser Cys Lys Glu Tyr Arg Asn Ala
1670                1675                1680

Leu Glu Glu Leu Ser Lys Ala Thr Gln Trp Asn Ser Ala Glu Glu
1685                1690                1695

Gly Leu Pro Thr Asn Ser Thr Ser Asp Ser Arg Pro Lys Ser Ser
1700                1705                1710

Ser Pro Ile Arg Leu Pro Glu Met Ser Gly Gly Gln Thr Asn Arg
1715                1720                1725

Thr Thr Glu Thr Glu Pro Gln Pro Thr Lys Lys Ala Ser Gly Met
1730                1735                1740

Leu Ser Phe Phe Arg Gly Thr Ala Gly Lys Ser Pro Asp Leu Ser
1745                1750                1755

Ser Gln Lys Arg Glu Thr Leu Arg Gly Ala Asp Ser Ala Tyr Tyr
1760                1765                1770

Gln Val Gly Gln Thr Gly Lys Glu Gly Thr Glu Asn Gln Gly Val
1775                1780                1785

| | | | | | | | | | | |
|---|---|---|---|---|---|---|---|---|---|---|
| Glu | Pro | Gln | Asp | Glu | Val | Asp | Gly | Gly | Asp | Thr | Gln | Lys | Lys | Gln |
| 1790 | | | | 1795 | | | | 1800 | | |

Leu Ile Asn Pro His Val Glu Leu Gln Phe Ser Asp Ala Asn Ala
    1805                 1810                 1815

Lys Phe Tyr Cys Arg Leu Tyr Tyr Ala Gly Glu Phe His Lys Met
    1820                 1825                 1830

Arg Glu Val Ile Leu Asp Ser Ser Glu Glu Asp Phe Ile Arg Ser
    1835                 1840                 1845

Leu Ser His Ser Ser Pro Trp Gln Ala Arg Gly Gly Lys Ser Gly
    1850                 1855                 1860

Ala Ala Phe Tyr Ala Thr Glu Asp Asp Arg Phe Ile Leu Lys Gln
    1865                 1870                 1875

Met Pro Arg Leu Glu Val Gln Ser Phe Leu Asp Phe Ala Pro His
    1880                 1885                 1890

Tyr Phe Asn Tyr Ile Thr Asn Ala Val Gln Gln Lys Arg Pro Thr
    1895                 1900                 1905

Ala Leu Ala Lys Ile Leu Gly Val Tyr Arg Ile Gly Tyr Lys Asn
    1910                 1915                 1920

Ser Gln Asn Asn Thr Glu Lys Lys Leu Asp Leu Leu Val Met Glu
    1925                 1930                 1935

Asn Leu Phe Tyr Gly Arg Lys Met Ala Gln Val Phe Asp Leu Lys
    1940                 1945                 1950

Gly Ser Leu Arg Asn Arg Asn Val Lys Thr Asp Thr Gly Lys Glu
    1955                 1960                 1965

Ser Cys Asp Val Val Leu Leu Asp Glu Asn Leu Leu Lys Met Val
    1970                 1975                 1980

Arg Asp Asn Pro Leu Tyr Ile Arg Ser His Ser Lys Ala Val Leu
    1985                 1990                 1995

Arg Thr Ser Ile His Ser Asp Ser His Phe Leu Ser Ser His Leu
    2000                 2005                 2010

Ile Ile Asp Tyr Ser Leu Leu Val Gly Arg Asp Asp Thr Ser Asn
    2015                 2020                 2025

Glu Leu Val Val Gly Ile Ile Asp Tyr Ile Arg Thr Phe Thr Trp
    2030                 2035                 2040

Asp Lys Lys Leu Glu Met Val Val Lys Ser Thr Gly Ile Leu Gly
    2045                 2050                 2055

Gly Gln Gly Lys Met Pro Thr Val Val Ser Pro Glu Leu Tyr Arg
    2060                 2065                 2070

Thr Arg Phe Cys Glu Ala Met Asp Lys Tyr Phe Leu Met Val Pro
    2075                 2080                 2085

Asp His Trp Thr Gly Leu Gly Leu Asn Cys
    2090                 2095

<210> SEQ ID NO 22
<211> LENGTH: 9901
<212> TYPE: DNA
<213> ORGANISM: Homo sapiens

<400> SEQUENCE: 22
caaccatgta agcagcttcg cttcctgccg caaccgtccg cggcctgagg agcccaccgc      60
cgctctcggg ggccgacttc cgggggctga gccgttgaag cggaggctgg ggcggggggc     120
agccggcgcg gccggggcag gaggcgcaga ctcatgaaat ggccacagat gataagacgt     180
ccccaacact ggactctgct aatgatttgc ctcgatctcc tactagtcct tctcatctca     240

```
cacactttaa acctttgact cctgatcaag atgagccccc ttttaaatca gcttatagtt      300
cttttgtaaa tctctttcgt tttaacaaag agagagcaga aggaggccag ggagaacagc      360
agcctttgag tggaagttgg accagccctc agctcccttc gaggacacag tctgttaggt      420
cacccacacc ttataaaaag cagcttaatg aggaactcca gcggcgctct tcagcattag      480
acacaagaag gaaagcagaa cctacctttg gaggtcatga ccctcgtaca gctgttcagc      540
ttcgaagcct cagcacagta ttaaaacgcc tcaaggaaat catggagggg aaaagccagg      600
atagtgacct gaaacaatac tggatgccag atagccaatg taaagagtgc tatgactgta      660
gtgagaaatt tacaaccttt aggcgcagac accattgccg actatgtggg cagattttct      720
gcagtcgttg ctgtaatcaa gaaatccctg gaaaatttat gggctataca ggagacctcc      780
gagcttgcac atattgtaga aaatagcct taagttatgc tcattccaca gacagtaatt      840
ctattgggga agacttgaat gctctttcag attctgcttg ctctgtgtct gtgcttgatc      900
caagtgaacc ccgaacacct gttgggagta ggaaagccag ccgtaacata ttttagagg       960
atgatttggc ctggcaaagt tgattcatc cagattcctc aaatactcct ctttcaacaa     1020
gacttgtatc tgtgcaagag gatgctggga atctcctgc tcgaaataga tcagccagca     1080
ttactaacct gtcactggat agatctggtt ctcctatggt accttcatat gagacatctg     1140
tcagtcccca ggctaaccga acatatgtta ggacagagac cactgaggat gaacgcaaaa     1200
ttcttctgga cagtgtgcag ttaaaagacc tgtggaaaaa atctgccat cacagcagtg      1260
gaatggagtt tcaggatcac cgctactggt tgagaacgca tcccaactgc attgtaggaa     1320
aggaattagt caactggcta atccgaaatg ggcatattgc cacaagggca caagctatag     1380
caattggaca agcaatggtt gatggacgtt ggctggattg tgttagtcat cacgaccagc     1440
ttttcagaga tgagtatgcg ctgtatagac cactgcagag tacagaattt tctgagacgc     1500
cttctcccga cagtgactca gtgaactccg tggaaggaca ctctgagcca tcctggttta     1560
aagacataaa gtttgatgac agtgacacag aacagatagc tgaagaaggt gacgataatt     1620
tggctaattc tgccagtcct agcaagcgca catcagtcag cagtttccag tccacagtgg     1680
acagtgactc agccgcttct atcagcctga acgtggagct ggacaacgtg aacttccata     1740
tcaagaagcc ctccaagtac ccacatgtgc ccctcaccc tgctgaccaa aaagagtatt     1800
tgatttctga cactggagga caacagctct caataagtga cgctttcatc aaagaatcct     1860
tatttaatcg ccgagtagag gaaaaatcca agagctgcc tttcacacct tgggctggc      1920
atcataacaa cctggagctc ctgagggagg agaatgggga gaaacaagcc atggagaggt     1980
tgctttcagc taatcataac cacatgatgg cactactcca gcagttgctc catagtgact     2040
cactgtcatc atcttggagg gacatcatcg tgtcattggt ctgccaggtt gttcagacag     2100
tccgacctga tgtcaagaac caggatgatg acatggatat ccgtcagttt gtccacatca     2160
aaaaatccc aggtggaaag aagtttgatt ctgtggttgt caatggcttt gtttgtacca     2220
agaacattgc acataaaaag atgagttctt gtattaaaaa ccccaaaatt cttctgttga     2280
agtgttccat tgagtatctc tacagagaag aaactaagtt tacttgcatt gatcctattg     2340
tgcttcagga aagggaattc ttgaagaatt atgtccagcg aatagttgat gttcgaccca     2400
ccttggttct tgttgagaaa acagtgtctc ggattgccca ggacatgtta ttggaacatg     2460
gcattacttt ggtcattaat gtaaagtcac aagttttgga acgaatcagt cgaatgaccc     2520
aaggtgattt agtgatgtca atggaccagc tgcttacgaa accacacctg gcacttgtc      2580
acaaatttta tatgcagata tttcagttgc ctaatgaaca aaccaagaca ctgatgtttt     2640
```

```
ttgaaggttg tccacagcac ctaggctgta caatcaagct aagaggaggc tctgattatg    2700
agctggctcg agttaaggag atcctaatat ttatgatctg tgttgcttat cattctcaac    2760
tagaaatatc ctttctcatg gatgaatttg ctatgcctcc cacattaatg caaaaccctt    2820
cattccattc cctgattgag ggacgagggc atgagggggc tgtccaagag cagtacggtg    2880
gaggttccat cccctgggat cctgacatcc ctcctgagtc tctgccctgt gatgatagca    2940
gtttgctgga attgaggatt gtgtttgaga agggtgagca ggaaaataaa aatcttccgc    3000
aggctgttgc ctctgtgaag catcaagaac atagcacaac agcttgcccg gcgggtctcc    3060
cttgtgcttt ctttgcacct gtaccggaat cattgttgcc actccctgtg gatgaccaac    3120
aagatgcttt aggcagcgag cagccagaga cttttgcagca aacagttgtg ctgcaggatc    3180
ccaaaagcca gataagagcc tttagagacc ctctacagga tgacactgga ttatatgtta    3240
ctgaggaagt cacctcctct gaagataaac gaaagactta ttcttttggcc tttaagcagg    3300
aattaaaaga tgtgatcctc tgtatctccc cagtaatcac attccgagaa ccctttcttt    3360
taactgaaaa ggggatgaga tgctctaccc gagattattt tgcagagcag gtttactggt    3420
ctcctctcct caataaagaa ttcaaagaaa tggagaacag gaggaagaaa cagctgctca    3480
gggatctctc tggacttcag ggcatgaatg aagtattca ggccaagtct attcaagtct    3540
taccctcaca tgagctagtg agcactagaa ttgctgagca tctgggcgat agccagagct    3600
tgggtagaat gctggccgat tatcgagcca gaggaggaag aattcagccc aaaaattcag    3660
accctttgc tcattcaaag gatgcatcaa gtacttcaag tggccaatca ggaagcaaaa    3720
atgagggtga tgaagagaga gggcttattc tgagtgatgc tgtgtggtca acaaaggtgg    3780
actgtctgaa tcccattaat caccagagac tttgtgtgct cttcagcagc tcttctgccc    3840
agtccagcaa tgctcctagt gcctgtgtca gtccttggat tgtaacaatg gaattttatg    3900
gaaagaatga tcttacatta ggaatatttt tagagagata ctgtttcagg ccttcttatc    3960
agtgtccaag catgttctgt gataccccca tggtacatca tattcggcgc tttgttcatg    4020
gccaaggctg tgtgcagata atcctgaagg agttggattc tccagtacct ggatatcagc    4080
atacaattct tacatattcc tggtgtagaa tctgcaaaca ggtaacacca gttgttgctc    4140
tttccaatga gtcctggtct atgtcatttg caaaatacct tgaacttagg ttttatgggc    4200
accagtatac tcgcagagcc aacgctgagc cctgtggtca ctccatccat catgattatc    4260
accagtattt ctcctataac cagatggtgg cgtctttcag ttattctccc attcggcttc    4320
ttgaagtatg tgttccactc cccaaaaatat tcattaagcg tcaggcccca ttaaaagtgt    4380
cccttcttca ggatctgaag gacttctttc aaaaagtttc acaggtatat gttgccattg    4440
atgaaagact tgcatctttg aaaactgata catttagtaa aacaagagag gaaaaaatgg    4500
aagatatttt tgcacagaaa gagatggaag aaggtgagtt caagaactgg attgagaaga    4560
tgcaagcaag gctcatgtct tcctctgtag atacccctca gcaactgcag tcggtctttg    4620
agtcactcat tgccaagaaa caaagtctct gtgaagtgct gcaagcttgg aataacaggt    4680
tgcaggacct tttccaacag gaaagggta gaaagagacc ttcagttcct ccaagtcctg    4740
gaagactgag acaaggggaa gaaagcaaga taagtgcgat ggatgcatct ccacggaata    4800
tttctccagg acttcagaat ggagaaaaag aggatcgctt cttaacaact ttgtccagcc    4860
agagctccac cagttctact catctccaat tgcctacgcc acctgaagtc atgtctgaac    4920
agtcagtggg agggccccct gagctagata cagccagcag ttccgaagat gtgtttgatg    4980
```

```
ggcatttgct gggatccaca gacagccaag tgaaggaaaa gtcaaccatg aaagccatct    5040
ttgcaaattt gcttccagga aatagctata atcctattcc atttccttt gatccagata    5100 aacactactt aatgtatgaa catgaacgag tgcccattgc agtctgcgag aaggaaccca    5160
gctccatcat tgcttttgct ctcagttgta aagaataccg aaatgcctta gaggaattgt    5220
ctaaagcgac tcagtggaac agtgccgaag aagggcttcc aacaaatagt acttcagata    5280
gcagaccaaa gagtagcagc cctatcagat tacctgaaat gagtggagga cagacaaatc    5340
gtacaacaga aacagaacca caaccaacca aaaaggcttc tggaatgttg tccttcttca    5400
gagggacagc agggaaaagc cccgatctct cttcccagaa gagagagacc ttacgtggag    5460
cagatagtgc ttactaccag gttgggcaga cgggcaagga ggggaccgag aatcaaggcg    5520
ttgagcctca agatgaagta gatggaggag atacacaaaa gaagcaactc ataaatcctc    5580
atgtggaact tcaattttca gatgctaatg ccaagtttta ctgtcggctc tactatgcgg    5640
gagagtttca taagatgcgt gaagtgattc tggacagcag tgaagaagat ttcattcgtt    5700
ccctctccca ctcatcaccc tggcaggccc ggggaggcaa atcaggagct gccttctatg    5760
caactgagga tgatagattt attttgaagc aaatgcctcg tctggaagtc cagtccttcc    5820
tcgactttgc accacattac ttcaattata ttacaaatgc tgttcaacaa aagaggccca    5880
cggcgttggc caaaattctt ggagtttaca gaattggtta taagaactct cagaacaaca    5940
ctgagaagaa gttagatctc cttgtcatgg aaaatctttt ctacgggaga agatggcac    6000 aggtttttga tttgaagggc tctcttagga atcggaatgt aaaaactgac actggaaaag    6060
agagttgtga tgtggtcctg ctagatgaaa atctcctaaa gatggttcga dacaacccctc    6120 tatatattcg ttctcattcc aaagctgtgc tgagaacctc gatccatagt gactcccatt    6180 tccttctag ccacctcatt atagattatt ctttgctggt tgggcgagat gatactagca    6240
atgagctagt agttggaatt atagattata ttcgaacatt tacatgggac aaaaagcttg    6300
agatggttgt gaaatcaaca ggaattttag gtggacaagg taaaatgcca acagtggtgt    6360
ctccggagtt gtacaggact aggttttgtg aggcaatgga caagtatttc ctaatggtac    6420
cagaccactg gacaggcttg ggtctgaatt gctgaaatca agcacatatt ttgaaatgga    6480
ctgtgaagga aaaggggaca ggaacaaagg accaaaaata agctacatgt tttatttctt    6540
catcgtgttc accactgtat gccaaggctt tcagttctg tggctgttta gactgtccgt    6600
aatggaatgg taaaactcca tgaatttgca ctttggtttt tgatacctgt ggagctgtct    6660
gtaggttggg aagtggcatg aaaattttct taagctaaaa tacagacatg tttcaaaggg    6720
ctaaagttgg agatgagtag ataggtgaa aaatggtta aatttgctag cttaattgtt    6780
ttaagaagaa aacagtgtct cataaattga ctatcctggc atcacattta acatgttatc    6840
tacttagaaa gcatttgtag agctgctgaa tttgttttgt gttttctgt aataatttaa    6900 tgttacttat tatcagaatt tctgaaacct ttacaaaaat tctgatttat tccattaatg    6960
gccagttaaa cacgtgggca tttattgttt tattgaggaa tttgacttaa actgggaatc    7020
ctgtcatgtt gtttatcttt ccagcttgcc tgttttgag tatgtttgat gttttaaaa    7080 ttttgtcttc tctgtggatg acaggaggct acagcaatta actttaagcc tccttttaga    7140
gatattttta aagcttgttt aaaattttg tgcaattcat atattaaatt gcacttactt    7200
gcatacgctc atattctagg ttttttctc tattttagg gtatcatagt aaatcattag    7260
taaatgagtc tgtagttact aaaccctaat ggaataatta ttaatgaaag atttttgaaa    7320
tataaaaaat aaattaggcc caatccaaga aattgagtga gaaggaaaca cttgttttat    7380
```

```
tcacagaggt aaagtgtctt ttcaatataa ccagcaattt aggtggcatc tataaaataa    7440
aaaatttcta ctgtggacat ccccttttcc aactttctac ataatggcta gttctgacta    7500
ctaagaaatg ttaagaaata ggccaagtgc ggtggctcac gcctataatc ctatcacttt    7560
gggaggccta ggcaggcaga tcacctgagg tcaggagttc aagaccagcc tggccaacat    7620
gaggaaaccc catctctact aaaaagacaa aaaattagct gggcatggtg gcatatacct    7680
gtaaccccaa ctactgggt ggctgaggca ggagaattgt tgaacctgg gaggcggagg      7740 ctgcagtgag ctgggattac accattgcat tccagcctgg gcaacagagc aagactgtct    7800
caaaaaacaa aacgaaacaa aaaaagaaag ttattcttag taaggaactt cttgtttaat    7860
agcatttttg tttatttaa aaagtgatca gaagtagtaa actatctttg aggaaatact     7920
gtaaccccag aatatttcct cttgacttct ttttgtaaca aggataattt agggatttat    7980
aaagttgtaa ggatttcact gttttcggac tgcctataat aatagcacat taaccttcac    8040
ataataagaa atctggacaa gttcagttac acagtatgat gaatacttga attaggaaca    8100
ttgtggaaaa tttgctttag agaatcaagg cagtagtttg gtatttggtg cttattaaaa    8160
atgtggtttg ttttgaactg gaagcaagtt gaccaaggac ttatgactaa tgtgatgcta    8220
agttccactt ggccccttt aaaaacgtgt atgtgccttt tgaagataca caaaacactg     8280
aggattttag ttttgaaatc aaagactatt aaaggagctg tacagaggta aaaaaataaa    8340
tgtggaacat tattaactta ttttgtgtct aggaacaatg gattttgtat ctgatttaaa    8400
atgccaacac tgttttgtct ctgttcattt tttctgtgag gatacttaag gttattattc    8460
ctgtctgttt cctgtactcc cctagtcatg agcacttgaa gtacaaggtg tctcccccta    8520
ggtgcaatta ggttgtttct tgttttttag tttcaattct atgtgcatag caggaatgct    8580
ccacaggaat ggcttctgac aataatctgt cctgttgatt ttgttttcct tgcccatgac    8640
ttgaacaact gtgttttaaa gtactgtagt ctagtaggta actttgtggc aaaaattttc    8700
aatataatac attctgaaac aatagttgct gccttgcaaa ggtaatctct cattttaaaa    8760
ttggacagta ttaatgaagg ggaaatatac aatttatttc tattgagtgg tagaactata    8820
tgtctggtcc cttgctgctc ttgtttaggc cactatcata gatatatttc aaatattgta    8880
ctactcagtg ttaagtattg aatgactgtt tcccttttcct tcaaggccta gagtatattc    8940
tgaaaattta ggaatgagga agaaatctta atacttcctt ccttaacata caacatgagt    9000
cccgagaata attgatagta gcaagagaaa actatgtcag taacatgttg ctttgtataa    9060
aaatcttatt tataaatgtg aagctttttg atgccatcaa aacttattaa aaaataggat    9120 ttacttttt ctaattctga cctaagaaaa ataatgagaa caagctgttg caagctcttt     9180
tgtagtctat tgaatatttt atagatattc aaaatttcct acaaactata atttttttcca   9240 tgatttagca gtgagtgatt ttctagcttt ggctcttatt aggtattgta aatagtaggg    9300
ttatatcgat atcagctttt gtgatggcat tgtggtcatc agcttcatga catttttaccc   9360 atttgcagtg atcctgtgta aaactgccaa ggaaagtaat tacctgtagg agtttgctga    9420
gcttgaagag tgaaaactgt tgtgaatgag cctgatcata aaacggacca ggccattcat    9480
tattcctcaa gtgttaatat actgacttat gcagtattca aaccatctag tgcaatgttt    9540
ttgtttttgt ttttttttg gtaacacagg tgcagtgtat tatagaaaaa ataaaaacta    9600
caatcattag cagttttaat actgctgtgt cagttttgta aaaaatgtac attatgtctt    9660
ttgacatgtt gaatttttaaa ctagggaaat gacattgtaa atcatagtag cctcttttaa   9720
```

-continued

```
tttaatatga aaaatgccac tatattgaaa gtacttaatg tattgtatat atttctctac    9780
tttggttcta gctattttat atgattgaca tgttatttaa aagataactg ccttgaactt    9840
ttggagactt gtactgtaaa taaagaaatc ttaacaataa actcagaatc tacttactcc    9900
a                                                                   9901
```

<210> SEQ ID NO 23
<211> LENGTH: 907
<212> TYPE: PRT
<213> ORGANISM: Homo sapiens

<400> SEQUENCE: 23

```
Met Pro Thr Ala Ala Pro Ile Ile Ser Ser Val Gln Lys Leu Val
1               5                   10                  15

Leu Tyr Glu Thr Arg Ala Arg Tyr Phe Leu Val Gly Ser Asn Asn Ala
                20                  25                  30

Glu Thr Lys Tyr Arg Val Leu Lys Ile Asp Arg Thr Glu Pro Lys Asp
            35                  40                  45

Leu Val Ile Ile Asp Asp Arg His Val Tyr Thr Gln Gln Glu Val Arg
    50                  55                  60

Glu Leu Leu Gly Arg Leu Asp Leu Gly Asn Arg Thr Lys Met Gly Gln
65                  70                  75                  80

Lys Gly Ser Ser Gly Leu Phe Arg Ala Val Ser Ala Phe Gly Val Val
                85                  90                  95

Gly Phe Val Arg Phe Leu Glu Gly Tyr Tyr Ile Val Leu Ile Thr Lys
                100                 105                 110

Arg Arg Lys Met Ala Asp Ile Gly Gly His Ala Ile Tyr Lys Val Glu
            115                 120                 125

Asp Thr Asn Met Ile Tyr Ile Pro Asn Asp Ser Val Arg Val Thr His
    130                 135                 140

Pro Asp Glu Ala Arg Tyr Leu Arg Ile Phe Gln Asn Val Asp Leu Ser
145                 150                 155                 160

Ser Asn Phe Tyr Phe Ser Tyr Ser Tyr Asp Leu Ser His Ser Leu Gln
                165                 170                 175

Tyr Asn Leu Thr Val Leu Arg Met Pro Leu Glu Met Leu Lys Ser Glu
                180                 185                 190

Met Thr Gln Asn Arg Gln Glu Ser Phe Asp Ile Phe Glu Asp Glu Gly
            195                 200                 205

Leu Ile Thr Gln Gly Gly Ser Gly Val Phe Gly Ile Cys Ser Glu Pro
    210                 215                 220

Tyr Met Lys Tyr Val Trp Asn Gly Glu Leu Leu Asp Ile Ile Lys Ser
225                 230                 235                 240

Thr Val His Arg Asp Trp Leu Leu Tyr Ile Ile His Gly Phe Cys Gly
                245                 250                 255

Gln Ser Lys Leu Leu Ile Tyr Gly Arg Pro Val Tyr Val Thr Leu Ile
                260                 265                 270

Ala Arg Arg Ser Ser Lys Phe Ala Gly Thr Arg Phe Leu Lys Arg Gly
            275                 280                 285

Ala Asn Cys Glu Gly Asp Val Ala Asn Glu Val Glu Thr Glu Gln Ile
    290                 295                 300

Leu Cys Asp Ala Ser Val Met Ser Phe Thr Ala Gly Ser Tyr Ser Ser
305                 310                 315                 320

Tyr Val Gln Val Arg Gly Ser Val Pro Leu Tyr Trp Ser Gln Asp Ile
                325                 330                 335
```

```
Ser Thr Met Met Pro Lys Pro Pro Ile Thr Leu Asp Gln Ala Asp Pro
            340                 345                 350

Phe Ala His Val Ala Ala Leu His Phe Asp Gln Met Phe Gln Arg Phe
            355                 360                 365

Gly Ser Pro Ile Ile Ile Leu Asn Leu Val Lys Glu Arg Glu Lys Arg
            370                 375                 380

Lys His Glu Arg Ile Leu Ser Glu Glu Leu Val Ala Ala Val Thr Tyr
385                 390                 395                 400

Leu Asn Gln Phe Leu Pro Pro Glu His Thr Ile Val Tyr Ile Pro Trp
                405                 410                 415

Asp Met Ala Lys Tyr Thr Lys Ser Lys Leu Cys Asn Val Leu Asp Arg
                420                 425                 430

Leu Asn Val Ile Ala Glu Ser Val Val Lys Lys Thr Gly Phe Phe Val
                435                 440                 445

Asn Arg Pro Asp Ser Tyr Cys Ser Ile Leu Arg Pro Asp Glu Lys Trp
            450                 455                 460

Asn Glu Leu Gly Gly Cys Val Ile Pro Thr Gly Arg Leu Gln Thr Gly
465                 470                 475                 480

Ile Leu Arg Thr Asn Cys Val Asp Cys Leu Asp Arg Thr Asn Thr Ala
                485                 490                 495

Gln Phe Met Val Gly Lys Cys Ala Leu Ala Tyr Gln Leu Tyr Ser Leu
                500                 505                 510

Gly Leu Ile Asp Lys Pro Asn Leu Gln Phe Asp Thr Asp Ala Val Arg
            515                 520                 525

Leu Phe Glu Glu Leu Tyr Glu Asp His Gly Asp Thr Leu Ser Leu Gln
            530                 535                 540

Tyr Gly Gly Ser Gln Leu Val His Arg Val Lys Thr Tyr Arg Lys Ile
545                 550                 555                 560

Ala Pro Trp Thr Gln His Ser Lys Asp Ile Met Gln Thr Leu Ser Arg
                565                 570                 575

Tyr Tyr Ser Asn Ala Phe Ser Asp Ala Asp Arg Gln Asp Ser Ile Asn
                580                 585                 590

Leu Phe Leu Gly Val Phe His Pro Thr Glu Gly Lys Pro His Leu Trp
            595                 600                 605

Glu Leu Pro Thr Asp Phe Tyr Leu His His Lys Asn Thr Met Arg Leu
            610                 615                 620

Leu Pro Thr Arg Arg Ser Tyr Thr Tyr Trp Trp Thr Pro Glu Val Ile
625                 630                 635                 640

Lys His Leu Pro Leu Pro Tyr Asp Glu Val Ile Cys Ala Val Asn Leu
                645                 650                 655

Lys Lys Leu Ile Val Lys Lys Phe His Lys Tyr Glu Glu Ile Asp
            660                 665                 670

Ile His Asn Glu Phe Phe Arg Pro Tyr Glu Leu Ser Ser Phe Asp Asp
            675                 680                 685

Thr Phe Cys Leu Ala Met Thr Ser Ser Ala Arg Asp Phe Met Pro Lys
            690                 695                 700

Thr Val Gly Ile Asp Pro Ser Pro Phe Thr Val Arg Lys Pro Asp Glu
705                 710                 715                 720

Thr Gly Lys Ser Val Leu Gly Asn Lys Ser Asn Arg Glu Glu Ala Val
                725                 730                 735

Leu Gln Arg Lys Thr Ala Ala Ser Ala Pro Pro Pro Ser Glu Glu
            740                 745                 750

Ala Val Ser Ser Ser Ser Glu Asp Asp Ser Gly Thr Asp Arg Glu Glu
```

|  |  | 755 |  |  |  | 760 |  |  |  | 765 |  |
|---|---|---|---|---|---|---|---|---|---|---|---|

Glu Gly Ser Val Ser Gln Arg Ser Thr Pro Val Lys Met Thr Asp Ala
   770                     775                     780

Gly Asp Ser Ala Lys Val Thr Glu Asn Val Val Gln Pro Met Lys Glu
785                     790                     795                     800

Leu Tyr Gly Ile Asn Leu Ser Asp Gly Leu Ser Glu Glu Asp Phe Ser
               805                     810                     815

Ile Tyr Ser Arg Phe Val Gln Leu Gly Gln Ser Gln His Lys Gln Asp
          820                     825                     830

Lys Asn Ser Gln Gln Pro Cys Ser Arg Cys Ser Asp Gly Val Ile Lys
835                     840                              845

Leu Thr Pro Ile Ser Ala Phe Ser Gln Asp Asn Ile Tyr Glu Val Gln
   850                     855                     860

Pro Pro Arg Val Asp Arg Lys Ser Thr Glu Ile Phe Gln Ala His Ile
865                     870                     875                     880

Gln Ala Ser Gln Gly Ile Met Gln Pro Leu Gly Lys Glu Asp Ser Ser
               885                     890                     895

Met Tyr Arg Glu Tyr Ile Arg Asn Arg Tyr Leu
   900                     905

<210> SEQ ID NO 24
<211> LENGTH: 3123
<212> TYPE: DNA
<213> ORGANISM: Homo sapiens

<400> SEQUENCE: 24

```
acgtcctcca gccccgctcc cgacgtgagg ggcggggctt gcctggaggc ggggcgcagg      60
gatccggaaa cacctgatca tctataggtt tagtgcctaa tgggtgttgt tcctggctgg     120
acttgatgtc cagggcctga ggggttttct cgccgagtct cctggggcgg tccggaggct     180
cgtgccctgt tgtggggccc ccatttgccg ccgccatgcc cacggccgcc gcccccatca     240
tcagctcggt ccagaagctg gttctgtatg agactagagc tagatacttt ctagtttgga     300
gcaataatgc agaaacgaaa tatcgtgtct tgaagattga tagaacagaa ccaaaagatt     360
tggtcataat tgatgacagg catgtctata ctcaacaaga agtaagggaa cttcttggcc     420
gcttggatct tggaaataga acaaagatgg gacagaaagg atcctcgggc ttatttcgag     480
cggtttcagc ttttggtgtt gtgggttttg tcaggttctt agaaggctat tatattgtgt     540
taataactaa aaggaggaag atggcggata ttggaggtca tgcaatctat aaggtcgaag     600
atacaaatat gatctatata cccaatgatt ctgtacgggt tactcatcct gatgaagcta     660
ggtatctacg aatatttcaa aatgtggacc tatctagcaa ttttttacttt agttacagct     720
atgatttgtc ccactcactt caatataatc tcactgtctt gcgaatgccc ctggagatgt     780
taaagtcaga aatgacccag aatcgccaag agagctttga catctttgaa gatgaaggat     840
taattacaca aggtggaagc gggggtatttg ggatctgtag tgagcctttat atgaaatatg     900
tatggaatgg tgaacttctg gatataatta aaagtactgt gcatcgtgac tggcttttgt     960
atattattca tgggttctgt gggcagtcaa agctgttgat ctatggacga ccagtgtatg    1020
tcactctaat agctagaaga tccagtaaat ttgctgcac ccgttttctt aaaagaggtg    1080
caaactgtga gggtgatgtt gcaaatgaag tggagactga acaaatactc tgcgatgctt    1140
ctgtgatgtc tttcactgca ggaagttatt cttcatatgt acaagttaga ggatctgtgc    1200
ccttatactg gtctcaggac atttcaacta tgatgcctaa accacctatt acattggatc    1260
```

-continued

| | |
|---|---|
| aggcagatcc atttgcacat gtggctgccc ttcactttga ccagatgttc cagaggtttg | 1320 |
| gctctcccat catcatcttg aatttagtga aggaacgaga gaaaagaaag catgaaagaa | 1380 |
| ttctgagtga agaacttgtt gctgctgtga cctatctcaa ccaattttg cctcctgagc | 1440 |
| acactattgt ttatattccc tgggacatgg ccaagtatac caaaagcaag ctgtgtaatg | 1500 |
| ttcttgatcg actaaatgtg attgcagaaa gtgtggtgaa gaaaacaggt ttctttgtaa | 1560 |
| accgccctga ttcttactgt agcattttgc ggccagatga aaagtggaat gaactaggag | 1620 |
| gatgtgtgat tcccactggt cgcctgcaga ctggcatcct tcgaaccaac tgtgtggact | 1680 |
| gtttagatcg caccaacaca gcacagttta tggtgggaaa atgtgctctg cctatcagc | 1740 |
| tgtattcact gggactgatt gacaaaccta atctacagtt tgatacagat gcagttaggt | 1800 |
| tatttgagga actctatgaa gatcatggtg ataccctatc ccttcagtat ggtggttctc | 1860 |
| aacttgttca tcgtgtgaaa acctacagaa agatagcacc atggacccag cactccaaag | 1920 |
| acatcatgca aaccctgtct agatattaca gcaatgcttt ttcagatgcc gatagacaag | 1980 |
| attccattaa tctcttcctg ggagttttcc atcccactga agggaaacct catctctggg | 2040 |
| agctcccaac agattttttat ttgcatcaca aaaataccat gagacttttg ccaacaagaa | 2100 |
| gaagttatac ttactggtgg acaccagagg tgataaagca tttaccattg ccctatgatg | 2160 |
| aagttatctg tgctgtgaac ttaaagaagt tgatagtgaa gaaattccac aaatatgaag | 2220 |
| aagagattga tatccacaat gagttctttc ggccatatga gttgagcagc tttgatgata | 2280 |
| cctttttgctt ggctatgaca agctcagcac gtgactttat gcctaagacc gttggaattg | 2340 |
| atccaagtcc atttactgtg cgtaaaccag atgaaactgg aaaatcagta ttgggaaaca | 2400 |
| aaagcaatag agaagaagct gtattacagc ggaaaacggc agccagcgcc ccgccgcccc | 2460 |
| ccagcgagga ggctgtgtcc agcagctctg aggatgactc tgggactgat cgggaagaag | 2520 |
| agggctctgt gtctcagcgc tccactcccg tgaagatgac tgatgcagga gacagtgcca | 2580 |
| aagtgaccga gaatgtggtc caacccatga aggagctata tggaattaac ctctcagatg | 2640 |
| gcctctcaga agaagatttc tccatttatt caagatttgt tcagctgggg cagagtcaac | 2700 |
| ataaacaaga caagaatagc cagcagccct gttctaggtg ctcagatgga gttataaaac | 2760 |
| taacacccat ctcggctttc tcgcaagata acatctatga agttcagccc caagagtag | 2820 |
| acagaaaatc tacagagatc ttccaagccc acatccaggc cagccaaggt atcatgcagc | 2880 |
| ccctaggaaa agaggactcc tccatgtacc gagagtacat caggaaccgc tacctgtgaa | 2940 |
| aagagcgcag gtccacctgg tggacacgtc tgattagctt agaacctgtc ttgtctcatc | 3000 |
| ttcaaaaggt aacttattaa aagtcctttg cgtctgaagc ctttctcctt ttctgtcact | 3060 |
| tgcaaattcc aaattatagc taataaagat gactagataa tttgcaaaaa aaaaaaaaa | 3120 |
| aaa | 3123 |

<210> SEQ ID NO 25
<211> LENGTH: 1491
<212> TYPE: PRT
<213> ORGANISM: Homo sapiens

<400> SEQUENCE: 25

Met Asn Gly Val Ala Phe Cys Leu Val Gly Ile Pro Pro Arg Pro Glu
1               5                   10                  15

Pro Arg Pro Pro Gln Leu Pro Leu Gly Pro Arg Asp Gly Cys Ser Pro
            20                  25                  30

Arg Arg Pro Phe Pro Trp Gln Gly Pro Arg Thr Leu Leu Leu Tyr Lys

-continued

```
            35                  40                  45
Ser Pro Gln Asp Gly Phe Gly Phe Thr Leu Arg His Phe Ile Val Tyr
 50                  55                  60

Pro Pro Glu Ser Ala Val His Cys Ser Leu Lys Glu Glu Asn Gly
 65                  70                  75                  80

Gly Arg Gly Gly Pro Ser Pro Arg Tyr Arg Leu Glu Pro Met Asp
                 85                  90                  95

Thr Ile Phe Val Lys Asn Val Lys Glu Asp Gly Pro Ala His Arg Ala
                100                 105                 110

Gly Leu Arg Thr Gly Asp Arg Leu Val Lys Val Asn Gly Glu Ser Val
            115                 120                 125

Ile Gly Lys Thr Tyr Ser Gln Val Ile Ala Leu Ile Gln Asn Ser Asp
        130                 135                 140

Asp Thr Leu Glu Leu Ser Ile Met Pro Lys Asp Glu Asp Ile Leu Gln
145                 150                 155                 160

Leu Ala Tyr Ser Gln Asp Ala Tyr Leu Lys Gly Asn Glu Pro Tyr Ser
                165                 170                 175

Gly Glu Ala Arg Ser Ile Pro Glu Pro Pro Ile Cys Tyr Pro Arg
            180                 185                 190

Lys Thr Tyr Ala Pro Pro Ala Arg Ala Ser Thr Arg Ala Thr Met Val
                195                 200                 205

Pro Glu Pro Thr Ser Ala Leu Pro Ser Asp Pro Arg Ser Pro Ala Ala
210                 215                 220

Trp Ser Asp Pro Gly Leu Arg Val Pro Pro Ala Ala Arg Ala His Leu
225                 230                 235                 240

Asp Asn Ser Ser Leu Gly Met Ser Gln Pro Arg Pro Ser Pro Gly Ala
                245                 250                 255

Phe Pro His Leu Ser Ser Glu Pro Arg Thr Pro Arg Ala Phe Pro Glu
                260                 265                 270

Pro Gly Ser Arg Val Pro Pro Ser Arg Leu Glu Cys Gln Gln Ala Leu
            275                 280                 285

Ser His Trp Leu Ser Asn Gln Val Pro Arg Arg Ala Gly Glu Arg Arg
        290                 295                 300

Cys Pro Ala Met Ala Pro Arg Ala Arg Ser Ala Ser Gln Asp Arg Leu
305                 310                 315                 320

Glu Glu Val Ala Ala Pro Arg Pro Trp Pro Cys Ser Thr Ser Gln Asp
                325                 330                 335

Ala Leu Ser Gln Leu Gly Gln Glu Gly Trp His Arg Ala Arg Ser Asp
            340                 345                 350

Asp Tyr Leu Ser Arg Ala Thr Arg Ser Ala Glu Ala Leu Gly Pro Gly
        355                 360                 365

Ala Leu Val Ser Pro Arg Phe Glu Arg Cys Gly Trp Ala Ser Gln Arg
    370                 375                 380

Ser Ser Ala Arg Thr Pro Ala Cys Pro Thr Arg Asp Leu Pro Gly Pro
385                 390                 395                 400

Gln Ala Pro Pro Pro Ser Gly Leu Gln Gly Leu Asp Asp Leu Gly Tyr
                405                 410                 415

Ile Gly Tyr Arg Ser Tyr Ser Pro Ser Phe Gln Arg Arg Thr Gly Leu
            420                 425                 430

Leu His Ala Leu Ser Phe Arg Asp Ser Pro Phe Gly Gly Leu Pro Thr
        435                 440                 445

Phe Asn Leu Ala Gln Ser Pro Ala Ser Phe Pro Pro Glu Ala Ser Glu
450                 455                 460
```

-continued

```
Pro Pro Arg Val Val Arg Pro Glu Pro Ser Thr Arg Ala Leu Glu Pro
465                 470                 475                 480

Pro Ala Glu Asp Arg Gly Asp Glu Val Val Leu Arg Gln Lys Pro Pro
            485                 490                 495

Thr Gly Arg Lys Val Gln Leu Thr Pro Ala Arg Gln Met Asn Leu Gly
                500                 505                 510

Phe Gly Asp Glu Ser Pro Glu Pro Glu Ala Ser Gly Arg Gly Glu Arg
            515                 520                 525

Leu Gly Arg Lys Val Ala Pro Leu Ala Thr Thr Glu Asp Ser Leu Ala
            530                 535                 540

Ser Ile Pro Phe Ile Asp Glu Pro Thr Ser Pro Ser Ile Asp Leu Gln
545                 550                 555                 560

Ala Lys His Val Pro Ala Ser Ala Val Val Ser Ser Ala Met Asn Ser
                565                 570                 575

Ala Pro Val Leu Gly Thr Ser Pro Ser Ser Pro Thr Phe Thr Phe Thr
            580                 585                 590

Leu Gly Arg His Tyr Ser Gln Asp Cys Ser Ser Ile Lys Ala Gly Arg
            595                 600                 605

Arg Ser Ser Tyr Leu Leu Ala Ile Thr Thr Glu Arg Ser Lys Ser Cys
610                 615                 620

Asp Asp Gly Leu Asn Thr Phe Arg Asp Glu Gly Arg Val Leu Arg Arg
625                 630                 635                 640

Leu Pro Asn Arg Ile Pro Ser Leu Arg Met Leu Arg Ser Phe Phe Thr
                645                 650                 655

Asp Gly Ser Leu Asp Ser Trp Gly Thr Ser Glu Asp Ala Asp Ala Pro
            660                 665                 670

Ser Lys Arg His Ser Thr Ser Asp Leu Ser Asp Ala Thr Phe Ser Asp
            675                 680                 685

Ile Arg Arg Glu Gly Trp Leu Tyr Tyr Lys Gln Ile Leu Thr Lys Lys
690                 695                 700

Gly Lys Lys Ala Gly Ser Gly Leu Arg Gln Trp Lys Arg Val Tyr Ala
705                 710                 715                 720

Ala Leu Arg Ala Arg Ser Leu Ser Leu Ser Lys Glu Arg Arg Glu Pro
                725                 730                 735

Gly Pro Ala Ala Ala Gly Ala Ala Ala Gly Ala Gly Glu Asp Glu
            740                 745                 750

Ala Ala Pro Val Cys Ile Gly Ser Cys Leu Val Asp Ile Ser Tyr Ser
            755                 760                 765

Glu Thr Lys Arg Arg His Val Phe Arg Leu Thr Thr Ala Asp Phe Cys
770                 775                 780

Glu Tyr Leu Phe Gln Ala Glu Asp Arg Asp Met Leu Gly Trp Ile
785                 790                 795                 800

Arg Ala Ile Arg Glu Asn Ser Arg Ala Glu Gly Asp Pro Gly Cys
                805                 810                 815

Ala Asn Gln Ala Leu Ile Ser Lys Lys Leu Asn Asp Tyr Arg Lys Val
            820                 825                 830

Ser His Ser Ser Gly Pro Lys Ala Asp Ser Ser Pro Lys Gly Ser Arg
            835                 840                 845

Gly Leu Gly Gly Leu Lys Ser Glu Phe Leu Lys Gln Ser Ala Ala Arg
            850                 855                 860

Gly Leu Arg Thr Gln Asp Leu Pro Ala Gly Ser Lys Asp Asp Ser Ala
865                 870                 875                 880
```

```
Ala Ala Pro Lys Thr Pro Trp Gly Ile Asn Ile Lys Lys Asn Lys
            885             890             895

Lys Ala Ala Pro Arg Ala Phe Gly Val Arg Leu Glu Glu Cys Gln Pro
        900             905             910

Ala Thr Glu Asn Gln Arg Val Pro Leu Ile Val Ala Ala Cys Cys Arg
        915             920             925

Ile Val Glu Ala Arg Gly Leu Glu Ser Thr Gly Ile Tyr Arg Val Pro
    930             935             940

Gly Asn Asn Ala Val Val Ser Ser Leu Gln Glu Gln Leu Asn Arg Gly
945             950             955             960

Pro Gly Asp Ile Asn Leu Gln Asp Glu Arg Trp Gln Asp Leu Asn Val
            965             970             975

Ile Ser Ser Leu Leu Lys Ser Phe Phe Arg Lys Leu Pro Glu Pro Leu
            980             985             990

Phe Thr Asp Asp Lys Tyr Asn Asp Phe Ile Glu Ala Asn Arg Ile Glu
            995             1000            1005

Asp Ala Arg Glu Arg Met Arg Thr Leu Arg Lys Leu Ile Arg Asp
    1010            1015            1020

Leu Pro Gly His Tyr Tyr Glu Thr Leu Lys Phe Leu Val Gly His
    1025            1030            1035

Leu Lys Thr Ile Ala Asp His Ser Glu Lys Asn Lys Met Glu Pro
    1040            1045            1050

Arg Asn Leu Ala Leu Val Phe Gly Pro Thr Leu Val Arg Thr Ser
    1055            1060            1065

Glu Asp Asn Met Thr Asp Met Val Thr His Met Pro Asp Arg Tyr
    1070            1075            1080

Lys Ile Val Glu Thr Leu Ile Gln His Ser Asp Trp Phe Phe Ser
    1085            1090            1095

Asp Glu Glu Asp Lys Gly Glu Arg Thr Pro Val Gly Asp Lys Glu
    1100            1105            1110

Pro Gln Ala Val Pro Asn Ile Glu Tyr Leu Leu Pro Asn Ile Gly
    1115            1120            1125

Arg Thr Val Pro Pro Gly Asp Pro Gly Ser Asp Ser Thr Thr Cys
    1130            1135            1140

Ser Ser Ala Lys Ser Lys Gly Ser Trp Ala Pro Lys Lys Glu Pro
    1145            1150            1155

Tyr Ala Arg Glu Met Leu Ala Ile Ser Phe Ile Ser Ala Val Asn
    1160            1165            1170

Arg Lys Arg Lys Lys Arg Glu Ala Arg Gly Leu Gly Ser Ser
    1175            1180            1185

Thr Asp Asp Asp Ser Glu Gln Glu Ala His Lys Pro Gly Ala Gly
    1190            1195            1200

Ala Thr Ala Pro Gly Thr Gln Glu Arg Pro Gln Gly Pro Leu Pro
    1205            1210            1215

Gly Ala Val Ala Pro Glu Ala Pro Gly Arg Leu Ser Pro Pro Ala
    1220            1225            1230

Ala Pro Glu Glu Arg Pro Ala Ala Asp Thr Arg Ser Ile Val Ser
    1235            1240            1245

Gly Tyr Ser Thr Leu Ser Thr Met Asp Arg Ser Val Cys Ser Gly
    1250            1255            1260

Ala Ser Gly Arg Arg Ala Gly Ala Gly Asp Glu Ala Asp Asp Glu
    1265            1270            1275
```

```
Arg Ser Glu Leu Ser His Val Glu Thr Asp Thr Glu Gly Ala Ala
    1280                1285                1290

Gly Ala Gly Pro Gly Gly Arg Leu Thr Arg Arg Pro Ser Phe Ser
    1295                1300                1305

Ser His His Leu Met Pro Cys Asp Thr Leu Ala Arg Arg Arg Leu
    1310                1315                1320

Ala Arg Gly Arg Pro Asp Gly Glu Gly Ala Gly Arg Gly Gly Pro
    1325                1330                1335

Arg Ala Pro Glu Pro Pro Gly Ser Ala Ser Ser Ser Gln Glu
    1340                1345                1350

Ser Leu Arg Pro Pro Ala Ala Ala Leu Ala Ser Arg Pro Ser Arg
    1355                1360                1365

Met Glu Ala Leu Arg Leu Arg Leu Arg Gly Thr Ala Asp Asp Met
    1370                1375                1380

Leu Ala Val Arg Leu Arg Arg Pro Leu Ser Pro Glu Thr Arg Arg
    1385                1390                1395

Arg Arg Ser Ser Trp Arg Arg His Thr Val Val Val Gln Ser Pro
    1400                1405                1410

Leu Thr Asp Leu Asn Phe Asn Glu Trp Lys Glu Leu Gly Gly Gly
    1415                1420                1425

Gly Pro Pro Glu Pro Ala Gly Ala Arg Ala His Ser Asp Asn Lys
    1430                1435                1440

Asp Ser Gly Leu Ser Ser Leu Glu Ser Thr Lys Ala Arg Ala Pro
    1445                1450                1455

Ser Ser Ala Ala Ser Gln Pro Pro Ala Pro Gly Asp Thr Gly Ser
    1460                1465                1470

Leu Gln Ser Gln Pro Pro Arg Arg Ser Ala Ala Ser Arg Leu His
    1475                1480                1485

Gln Cys Leu
    1490

<210> SEQ ID NO 26
<211> LENGTH: 5913
<212> TYPE: DNA
<213> ORGANISM: Homo sapiens

<400> SEQUENCE: 26
ctgccacccg atgaatggag tcgccttctg cctggtcggg atcccgcccc gcccggagcc      60
ccggccccca cagctgccac tgggcccaag agatgggtgc tctcctaggc gcccttccc     120 ctggcagggg ccgaggacgc tgctgctgta caaaagtccc caggacggct ttggcttcac     180
tctgcgccac ttcatcgtgt acccacccga gtcggccgtg cactgcagcc tgaaggagga     240
agagaatgga ggccgtggag gaggaccctc cccccggtac cgcctggagc ccatggacac     300
catctttgtc aagaatgtga aggaagacgc ccctgcccat agggcggggc ttcgcacagg     360
agaccggctg gtaaaggtga atgggaaag cgtcattggg aagacctact ctcaggtcat     420
agctctgatc cagaatagtg atgacactct ggagctgtct atcatgccca aggacgagga     480
catcctccag ctggcctact cccaggatgc ctacctgaaa gggacgagc cgtattctgg     540 agaggcccgc agcatccag agccaccgcc gatctgctac ccccgcaaga cctacgcccc     600
tcctgcccgg gcctccacca gggccactat ggtgcctgag cccacctcag cactgcccag     660 tgaccccga gtcctgctg cctggagtga cccggggctc cgtgtgccac ctgctgcccg     720
tgcccacctg gacaactctt ccttggggat gagccagccc cgccccagcc ctggtgcctt     780
```

```
cccccacctc tcctcggagc cccggacgcc ccgtgccttc ccagagcctg cagccgggt    840
gcccccccagc agactggagt gccagcaggc cttgtcacac tggctgtcaa accaggtacc  900
ccgccgggcg ggggagagac ggtgcccagc catggccccc cgggcccgca gcgcctccca   960
ggaccggttg gaggaggtgg ctgccccccg ccgtggccc tgctccacct cccaggatgc   1020
tttgagccag ctgggccagg agggctggca ccgagctcgc tcagatgact acttgagccg  1080
ggccacccgt tctgccgagg cactgggggcc aggggcactg tgtcacccc gctttgagcg  1140
gtgtggctgg gcttcccagc gttcgtctgc ccgcaccccc gcctgccaa ctcgggacct   1200
gccagggccc caggccccac ccccgtctgg cctgcagggc ctggatgacc tcgggtacat  1260
cggctaccgg agctacagcc catcattcca gcgccggacc ggcctcctcc atgcgctctc  1320
cttccgggac tcacccttg gggggctgcc taccttcaac ctggcccagt ccctgcgtc   1380
attcccacca gaggcctccg agccacccag ggttgtacgg ccggaaccca gcacccgggc  1440
cctggagcct cctgcggagg atcgcggcga tgaggtggtc ctgaggcaga agccccccgac 1500
gggccgcaag gttcagctga ccccccgcaag acagatgaac cttggatttg gtgacgagtc 1560
cccagagcca gaggccagtg ggcgagggga acgcctgggc aggaaggtgg cccctttggc  1620
caccaccgaa gactctctgg cttccatccc ctttattgat gagcccacca gccccagcat  1680
tgacctccaa gccaagcacg tccctgcctc tgctgtggtc tccagtgcca tgaactcagc  1740
ccctgtcctg ggcaccagcc catcttcccc gaccttcact ttcaccctcg gacgccatta   1800
ctcgcaggac tgcagcagca tcaaggctgg ccgccgctcc tcctacctgc tggccatcac  1860
cacggagcgc tccaagtcct gcgatgatgg actcaacacc ttccgcgacg agggccgggt  1920
tctgcggcgc ctgccaaacc gcatacccag cctgcggatg ctccggagct tcttcaccga  1980
cgggtccttg gatagctggg gcacctctga agatgctgac gctccttcta agcgacactc  2040
aacctctgac ctctcagatg cgaccttcag cgatatcagg agagaaggct ggttgtatta  2100
taagcagatt ctcaccaaga aggggaagaa agcgggcagc ggcctgcgcc agtggaagcg  2160
ggtgtacgcc gcgctgcggg cgcgctcgct ctcgctgagc aaggagcggc gggagcccgg  2220
gccggcggcg gcggggctg cggcggccgg cgcaggtgag gacgaggcgg cgcccgtctg  2280
catcggctcc tgcctcgtgg acatctccta cagcgagacc aagaggaggc acgtgttccg  2340
gctgaccacc gctgacttct gtgaatatct ctttcaggct gaggaccggg atgacatgct  2400
gggctggatc agagcgatcc gggagaacag cagggccgag ggcgaggacc ccggctgtgc  2460
caaccaagct ctgatcagca agaagcttaa cgattatcgc aaagtgagcc atagctctgg  2520
gccccaaagct gattcctccc ccaaaggctc tcgcggcctg gggggcctca gtctgagtt  2580
cctcaagcag agtgcggcac gtggcctcag gactcaggac ctgcccgcag ggagcaagga  2640
tgacagtgct gcagccccca aaccccctg gggcatcaac atcatcaaga aaataagaa   2700
ggccgctccg agggcgtttg gggtcaggct ggaggagtgc cagccagcca cggagaacca  2760
gcgcgtcccc ttaatcgtgg ctgcatgctg tcgcattgtg gaggcacgag ggctggagtc  2820
cacaggcatt taccgagtgc ccggcaacaa tgcagtggtg tccagcctac aggagcagct  2880
caaccgcggg cctggtgaca tcaacctgca ggatgagcgc tggcaagacc tcaatgtgat  2940
cagcagcctg ctcaagtcct tcttccgaaa gctgcccgag cctctttca ctgatgacaa   3000
atacaacgac ttcatcgagg ccaaccgcat tgaggacgcg cgggagcgaa tgaggacgct  3060
gcggaagctg atccgggatc tcccaggaca ctactatgaa acgctcaaat tccttgtggg  3120
ccatctcaag accatcgctg accactctga gaaaaacaag atggaacccc ggaacctggc  3180
```

```
cctggtcttt gggccgacac tggtgaggac gtctgaggac aacatgacag acatggtgac    3240
ccacatgcct gaccgctaca agatcgtgga gacactgatc cagcactcag actggttctt    3300
cagtgacgaa gaggacaagg gagagagaac ccctgtgggc gacaaggagc ctcaggcagt    3360
gcccaacatt gagtacctcc tgcccaacat tggcaggaca gtgccccctg cgacccggg     3420 gtcagattct accacctgta gttcagccaa gtccaagggt tcgtgggccc ccaagaagga    3480
gccgtacgcc cggagatgc tggcgatctc cttcatctcg gccgtcaacc gcaagcgcaa     3540
gaagcggcgg gaggcgcggg ggctgggcag cagcaccgac gacgactcgg agcaggaggc    3600
gcacaagcct ggggcggggg ccacagcgcc ggggactcag gagcggccgc aggggccgct    3660
gcctggcgcc gtcgccccg aggcccccgg acgcctcagt ccccggcgg cgccggagga     3720 gcggccggcc gcggacacgc gctccattgt gtcgggctac tccaccctgt ccaccatgga    3780
ccgcagcgtg tgctcgggcg ctagcggtcg gcgggcaggg gcggggatg aggcggacga    3840 cgagcgtagc gagctgagcc acgtggagac ggacactgag ggcgcggcgg gcgcggggcc    3900 tgggggcgc ctgacacgcc ggccgtcctt cagctcgcac cacctcatgc cctgcgacac     3960
tctggcgcgc cgccgcctgg cccgggggccg cccagacggc gagggcgcgg gccggggcgg    4020
tccccgcgcc ccggagccgc ccggctcggc gtcgtccagc agccaggagt cgctgcggcc    4080
cccggcggcg gcgctggcct cccggccctc gcgcatggag gcgctgcgtc taaggctccg    4140
cggcacggcg gacgacatgc tcgccgtgcg cctgcggcgg ccgctgtcgc ccgagacccg    4200
gcggcgccgg agcagctggc gccgccacac cgtggtggtg cagagcccgc tgactgacct    4260
caacttcaac gagtggaagg agctgggcgg agggggcccc ccggagcctg cgggcgcgcg    4320
ggcgcacagt gacaacaagg actccggact cagcagcctg gagtccacca aggcgcgggc    4380
cccgtcgtcc gctgcctcgc agccgcccgc gcccggggac acgggtccc tgcagagcca    4440 gcccccgcgc cgctcggccg cctcccgcct gcatcagtgt ctgtgatccc cacctcccgc    4500
gccgctcggg cgccacccct ccctagagcc ccttttggaac caggaggctt caccagcctg    4560
cacctcctct tctgtggccc ctgggtgcat ggtgtgggtg gagggcgcag caggcagtgt    4620
ctctagttgg tgtgctggaa ctggcagggc agaggagaag gctggggccg gactaattga    4680
atggaagggg gttccagagg tgatgagcag aagaggaggg ggcgtgggct gctgggtct    4740 gtgtccctgc acacatgcgc ccgataggtc cttctgagcc tttctgtggc tgcacttggg    4800 gaccccttgtg gaccatgggg tgtggctagg gaaccctaa gtttcagact aaaggaaaga   4860
tcctgggtga tgctggcttt ttgcttcttt cttctgccct cccacctcag cttgtaagcg    4920
gggatgtgtg tatgtctggg gagaggaggt gtagggtgcg tatgtccatg gggggagggg    4980
cttgtgtgtg cagtcattgt cccaaggtgt ttccagtagc gacttctgtc cccctatccc    5040
caccctggtc cccactttgc gccccgggc tccctgcctt tggtgcacac aggatcctgc     5100 ccgccccct tgccagagcc agagaagggg gttgggccca ttccaaggag gcaggactga    5160
aaccctcacc agggttactc cccaacatcc ttttgcctga gtcaccctct aagcgcttta    5220
accacgggca gctgcctgtt ccccagacag ttttttggtgg gggggggtcca gggtccccct    5280 tgctggtacc tccctcaccc ctctttttgt ttttccatct gtgcctgttc cttccacagc    5340
ccaggcacac agaagcccac cttcttcccc ttaggaggag ggatagtcaa cacccctgct    5400
gtctctctgt cactcacaca ctgatttatg gggtctgagc tgggctgttc ctgcaggatg    5460
gacaggaccc agcgccctct tctccccaca ggctgtaaat agacttccaa tcaccaggcc    5520
agcccccaca caccctcact cattccaggg aagcccaggt aggtggtgaa cccgctgcca    5580
```

```
cgtctatcag tcctcttgtt ttatgcaaag atttactgta aagtagattt ctttccctcc    5640
ctcccccatt cttttattgt aaatattgtc tctaaatgtg taacatatta taaagaattt    5700
ataaggattt ttaaagatgt tttgctcatt tacaaaagtg ttgtaacagt gttggacaaa    5760
gccttccacc ccatgtccgc atggctcctt tcactgtgtc cttgacacac ctctctggca    5820
acaactaaaa tttcctgctt ctgaaaagtc ctgtcttaaa agtacagtct atatcttgga    5880
aataaatagc tttcctcaag gcatgaaaaa aaa                                 5913
```

<210> SEQ ID NO 27
<211> LENGTH: 21
<212> TYPE: DNA
<213> ORGANISM: artificial sequence
<220> FEATURE:
<223> OTHER INFORMATION: NPC-F1 primer

<400> SEQUENCE: 27

```
gaagttggtc tggcgatgga g                                              21
```

<210> SEQ ID NO 28
<211> LENGTH: 23
<212> TYPE: DNA
<213> ORGANISM: artificial sequence
<220> FEATURE:
<223> OTHER INFORMATION: NPC1-R2 primer

<400> SEQUENCE: 28

```
aaggtcctga tctaaaactc tag                                            23
```

<210> SEQ ID NO 29
<211> LENGTH: 21
<212> TYPE: DNA
<213> ORGANISM: artificial sequence
<220> FEATURE:
<223> OTHER INFORMATION: VPS33A-F1 primer

<400> SEQUENCE: 29

```
tgtcctacgg ccgagtgaac c                                              21
```

<210> SEQ ID NO 30
<211> LENGTH: 22
<212> TYPE: DNA
<213> ORGANISM: artificial sequence
<220> FEATURE:
<223> OTHER INFORMATION: VPS33A-R1 primer

<400> SEQUENCE: 30

```
ctgtacactt tgctcagttt cc                                             22
```

<210> SEQ ID NO 31
<211> LENGTH: 23
<212> TYPE: DNA
<213> ORGANISM: artificial sequence
<220> FEATURE:
<223> OTHER INFORMATION: VPS11-F1 primer

<400> SEQUENCE: 31

```
gaaggagccg ctgagcaatg atg                                            23
```

<210> SEQ ID NO 32
<211> LENGTH: 23
<212> TYPE: DNA
<213> ORGANISM: artificial sequence
<220> FEATURE:
<223> OTHER INFORMATION: VPS11-R1 primer

```
<400> SEQUENCE: 32
ggccagaatt tagtagcagc aac                                          23

<210> SEQ ID NO 33
<211> LENGTH: 20
<212> TYPE: DNA
<213> ORGANISM: artificial sequence
<220> FEATURE:
<223> OTHER INFORMATION: PGT-F1 primer

<400> SEQUENCE: 33
tctccaaatc tcggtggaac                                              20

<210> SEQ ID NO 34
<211> LENGTH: 20
<212> TYPE: DNA
<213> ORGANISM: artificial sequence
<220> FEATURE:
<223> OTHER INFORMATION: VPS11 primer

<400> SEQUENCE: 34
ctgcttccaa gttcctttgc                                              20

<210> SEQ ID NO 35
<211> LENGTH: 20
<212> TYPE: DNA
<213> ORGANISM: artificial sequence
<220> FEATURE:
<223> OTHER INFORMATION: VPS11 primer

<400> SEQUENCE: 35
aagattcgag tgcagagtgg                                              20

<210> SEQ ID NO 36
<211> LENGTH: 17
<212> TYPE: DNA
<213> ORGANISM: artificial sequence
<220> FEATURE:
<223> OTHER INFORMATION: NPC1 primer

<400> SEQUENCE: 36
ccacagcatg accgctc                                                 17

<210> SEQ ID NO 37
<211> LENGTH: 21
<212> TYPE: DNA
<213> ORGANISM: artificial sequence
<220> FEATURE:
<223> OTHER INFORMATION: NPC1 primer

<400> SEQUENCE: 37
cagctcacaa aacaggttca g                                            21

<210> SEQ ID NO 38
<211> LENGTH: 21
<212> TYPE: DNA
<213> ORGANISM: artificial sequence
<220> FEATURE:
<223> OTHER INFORMATION: VPS33A primer

<400> SEQUENCE: 38
ttaacacctc ttgccactca g                                            21
```

```
<210> SEQ ID NO 39
<211> LENGTH: 21
<212> TYPE: DNA
<213> ORGANISM: artificial sequence
<220> FEATURE:
<223> OTHER INFORMATION: VPS33A primer

<400> SEQUENCE: 39
tgtgtctttc ctcgaatgct g                                           21
```

METHODS AND ASSAYS FOR TREATING FILOVIRIDAE INFECTIONS

CROSS-REFERENCE TO RELATED APPLICATION

This application is a U.S. national stage entry under 35 U.S.C. §371 of PCT International Patent Application No. PCT/US2012/022349, filed Jan. 24, 2012, which claims priority to U.S. Provisional Patent Application No. 61/435,858, filed Jan. 25, 2011, the contents of which are incorporated herein by reference into the subject application.

STATEMENT OF GOVERNMENT SUPPORT

This invention was made with government support under grant numbers AI088027, AI081842, AI057159 and HG004938 awarded by the National Institutes of Health. The government has certain rights in the invention.

BACKGROUND OF THE INVENTION

Throughout this application various publications are referred to in superscripts. Full citations for these references may be found at the end of the specification. The disclosures of these publications are hereby incorporated by reference in their entirety into the subject application to more fully describe the art to which the subject invention pertains.

Infections by the Ebola (EboV) and Marburg (MarV) filoviruses cause a rapidly fatal hemorrhagic fever in humans for which no approved vaccines or antivirals are available[1]. Filovirus entry into cells is mediated by the viral spike glycoprotein (GP), which attaches viral particles to the cell surface, delivers them to endosomes, and catalyzes fusion between viral and endosomal membranes[2]. Additional host factors in the endosomal compartment, including a putative entry receptor, are likely required for viral membrane fusion. However, despite considerable efforts, these critical host factors have defied molecular identification[3-5].

The present invention addresses the need for methods and assays for treating subjects infected with filoviruses or who are at risk for infection with filoviruses.

SUMMARY OF THE INVENTION

The present invention provides methods for treating a subject infected with a filovirus or for preventing an infection with a filovirus in a subject at risk for infection with a filovirus, where the methods comprise administering to the subject an agent that inhibits one or more of Niemann-Pick C1 (NPC1), VPS11, VPS16, VPS18, VPS33A, VPS39, VPS41, BLOC1S1, BLOC1S2, GNPTAB, PIKFYVE, ARHGAP23 or FIG4 in an amount effective to treat and/or prevent infection with the filovirus.

The present invention also provides methods for screening for an agent that treats and/or prevents infection of a subject with a filovirus, where the methods comprise determining whether or not the agent inhibits one or more of Niemann-Pick C1 (NPC1), VPS11, VPS16, VPS18, VPS33A, VPS39, VPS41, BLOC1S1, BLOC1S2, GNPTAB, PIKFYVE, ARHGAP23 or FIG4, wherein an agent that inhibits one or more of NPC1, VPS11, VPS16, VPS18, VPS33A, VPS39, VPS41, BLOC1S1, BLOC1S2, GNPTAB, PIKFYVE, ARHGAP23 or FIG4 is a candidate for treating and/or preventing an infection with a filovirus and wherein an agent that does not inhibit NPC1, VPS11, VPS16, VPS18, VPS33A, VPS39, VPS41, BLOC1S1, BLOC1S2, GNPTAB, PIK- FYVE, ARHGAP23 or FIG4 is not a candidate for treating and/or preventing an infection with a filovirus.

BRIEF DESCRIPTION OF THE DRAWINGS

FIG. 1A-1D. Genome-wide haploid genetic screen identifies the HOPS complex and NPC1 as host factors for filovirus entry. a) Genes significantly enriched for gene-trap insertion event in the rVSV-GP-EboV-selected cell population as compared to the non-selected mutagenized cell population. Circles represent genes and their size corresponds to the number of insertions identified in that gene in the rVSV-GP-EboV selected population. Significantly enriched genes (p-value<0.01) are labeled with gene name. The number of independent insertions is indicated in parentheses. Genes are ranked on the X-axis based on their chromosomal position. b) RT-PCR analysis of the expression levels of NPC1, VPS33A and VPS11 in clones that contain gene trap insertions in the corresponding genes. c) Infectivity of VSV pseudotyped with the indicated filovirus glycoproteins in WT and mutant HAP1 clones. Means±standard deviation (SD) are shown. EboV, Ebola virus (Zaire), SunV, Sudan virus, MarV, Marburg virus. Asterisks indicate that infectivity was below the limit of detection. d) The indicated HAP1 clones were exposed to a set of unrelated enveloped and nonenveloped viruses including recombinant VSV viruses carrying Rabies or Borna disease virus glycoproteins. Surviving adherent cells were stained with crystal violet.

FIG. 2A-2D. Viral infection mediated by filovirus glycoproteins requires NPC1 but not NPC2. a) Skin fibroblasts from an apparently normal individual (control) and from patients carrying homozygous mutations in NPC1 or NPC2 were stained with filipin to visualize intracellular cholesterol, or challenged with rVSV-G or rVSV-GP-EboV. Filipin-stained and infected cells were visualized by fluorescence microscopy. Filipin-stained images were inverted for clarity. Hoechst 33342 nuclear counterstain. b) Infectivity of VSV pseudotyped with the indicated viral glycoproteins in control and Niemann-Pick fibroblasts. Asterisks indicate that infectivity was below the limit of detection. c) NPC1 patient fibroblasts stably expressing an empty vector control or human NPC1 were stained with filipin or challenged with rVSV-GP-EboV. d) Infectivity of rVSV-G and rVSV-GP-EboV in Vero cells preincubated for 30 min with the indicated concentrations of U18666A. Scale bars, 200 µm (a, c). Means±standard deviation (SD) are shown (b, d).

FIG. 3A-3D. Ebola virus entry is arrested at a late step in cells deficient for the HOPS complex and NPC1. a) Viral particles attach and internalize into HOPS- and NPC1-deficient cells. The indicated HAP1 clones were inoculated with rVSV-GP-EboV and examined by transmission electron microscopy. Representative images of early steps in entry are shown. b, In vitro-cleaved rVSV-GP-EboV cannot bypass the block to infection observed in VPS11$^{GT}$, VPS33A$^{GT}$ and NPC1$^{GT}$ cells. Infectivity of mock- or thermolysin-cleaved rVSV-GP-EboV in the indicated mutant HAP1 clones. c) Viral escape into the cytoplasm is blocked in HOPS complex- and NPC1-deficient cells. Wild type HAP1 cells were treated with U18666A (10 µg/ml), and the indicated mutant HAP1 clones were exposed to VSV or rVSV-GP-EboV virus for 3 h and processed for VSV M staining. Diffuse M staining indicates successful release of viral nucleocapsids into the cytoplasm. Punctuate staining, indicating viral particles trapped within endosomes and lysosomes, is shown by the arrows. d) Electron micrographs of rVSV-GP-EboV-infected VPS33A- and NPC1-deficient HAP1 cells and NPC1-deficient fibroblasts showing agglomerations of bullet-shaped VSV particles in vesicular compartments. All images were taken at 3 h post-inoculation. Asterisks highlight rVSV-GP-EboV particles in cross-section.

FIG. 4A-4C. NPC1 function is required for infection by authentic Ebola and Marburg viruses. a) Fibroblasts from a healthy individual or an NPC1 patient were exposed to EboV or MarV. Cell supernatants were harvested at the indicated times post-infection and yields of infectious virus were measured. Means±standard deviation (SD) are shown. Asterisks indicate that infectivity was below the limit of detection. b) Vero cells treated with DMSO vehicle (no drug) or U18666A (20 µM) were exposed to EboV or MarV. Cell supernatants were harvested at the indicated times post-infection and yields of infectious virus were measured. Means±standard deviation (SD) are shown. c) A speculative model for the roles of CatB, the HOPS complex, and NPC1 in Ebola virus entry.

FIG. 6. Outline of the haploid genetic screen to identify host factors for Ebola virus entry. 100 million early passage HAP1 cells were infected with gene-trap virus and further expanded. A subset of cells was used to characterize the distribution of gene-trap insertion across the human genome. Sequences flanking the gene-traps were amplified, sequenced in parallel and aligned to the human genome. Independent insertion events into annotated genes were counted. 100 million cells were exposed to rVSV-GP-EboV virus and resistant clones were pooled and expanded. Most of these cells were used to amplify sequences flanking the gene-traps, sequence the insertion sites in parallel, and align these sequences to the human genome. A subset of the cells were used to obtain $NPC^{GT}$ and $VPS^{GT}$ cells through subcloning. Gene disruption events in the selected population were compared to the unselected cell population and genes that were significantly enriched for mutations were identified.

FIG. 8A-8B. NPC1 deficiency of HAP1 and CHO cells confers resistance to viral infection mediated by Ebola and Marburg virus glycoproteins. a) Immunoblot analysis of NPC1 in HAP1 cells, HAP1 cells carrying a gene-trap insertion in the NPC1 locus and the same cell line infected with the NPC1-expressing retrovirus. CDK4 was used as a loading control. b) Wild type or NPC1-deficient CHO cells were challenged with VSV pseudotyped with the indicated viral glycoproteins, and viral infectivity was measured 24 h later.

FIG. 14A-14B. NPC1 pathway inhibitor U18666A blocks authentic EboV and MarV infection of primary human cells. Human peripheral blood monocyte-derived dendritic cells (DC) (b) and umbilical-vein endothelial cells (HUVEC) (a) were infected in the presence or absence of U18666A (10 µM) at an MOI of 3 and the percentage of infected cells was determined by immunostaining.

FIG. 16. NPC1 pathway inhibitor imipramine blocks authentic EboV and MarV infection. Vero cells were infected in the presence or absence of U18666A (10 μM) at an MOI of 3 and the percentage of infected cells at each timepoint was determined by immunostaining.

FIG. 17A-17B. NPC1 is required for in vivo infection and pathogenesis by EboV (a) and MarV (b). Survival of NPC1$^{+/+}$ and NPC1$^{-/+}$ mice (n=10 for each group) inoculated intraperitoneally (i.p.) with ~1000 pfu of mouse-adapted EboV or MarV.

FIG. 20A-20C. NPC1 luminal loop domain C is required for filovirus entry, but full-length NPC1 is dispensable. (a) NPC1-null CHO CT43 cells were engineered to express mutant forms of human NPC1-flag lacking domains A, C, or I. Capacity of mutant NPC1 proteins to rescue viral entry and transport lysosomal cholesterol was determined. (Left) Infection of NPC1-null CHO CT43 cells expressing mutant NPC1-flag proteins by recombinant VSVs bearing VSV G or filovirus glycoproteins. Infected cells were visualized by fluorescence microscopy. (Right) Cholesterol clearance by mutant NPC1-flag proteins in CT43 cells was determined by filipin staining and fluorescence microscopy. Images were inverted for clarity. Scale bars, 20 μm. (b-c) Infectivity of VSV pseudotypes bearing VSV or filovirus glycoproteins (b) and wild type MARV (c) in CT43 cells expressing mutant NPC-flag proteins. SUDV, Sudan virus. Error bars indicate SD. Asterisks indicate values below the limit of detection.

FIG. 21A-21D. NPC1 binds specifically to a cleaved form of the Ebola virus glycoprotein. (a) Co-immunoprecipitation (IP) of NPC1 by EBOV GP. Magnetic beads coated with GP-specific monoclonal antibody KZ52 were incubated with detergent extracts containing no virus (None), uncleaved rVSV-GP, or cleaved rVSV-GP$_{CL}$. The resulting control or glycoprotein-decorated beads were mixed with cell lysates containing human NPC1-flag at pH 7.5 or pH 5.1 and 4° C. Beads were then retrieved and NPC1-flag in the immune pellets and supernatants was detected by immunoblotting (IB) with an anti-flag antibody. (b) GP$_{CL}$ captures NPC1 in an ELISA. Plates coated with rVSV-GP or rVSV-GP$_{CL}$ were incubated with cell extracts containing NPC1-flag, and bound flag-tagged proteins were detected with an anti-flag antibody. (c-d) GP$_{CL}$ but not GP captures affinity-purified NPC1-flag in an ELISA. (c) NPC1-flag was purified from CT43 CHO cell lysates by flag affinity chromatography and visualized by SDS-PAGE and staining with Krypton infrared protein stain. (d) ELISA plates coated with rVSV-GP or rVSV-GP$_{CL}$ were incubated with NPC1-flag purified in (c), and bound flag-tagged proteins were detected with an anti-flag antibody.

FIG. 22A-22C. Soluble forms of NPC1 domain C bind directly to GP and selectively neutralize infection by viral particles containing cleaved glycoproteins. (a) The capacity of rVSV-GP and rVSV-GP$_{CL}$ to capture a purified, soluble form of domain C containing flag and hexahistidine tags was determined in an ELISA. (b) The capacity of a purified, soluble form of GP lacking the transmembrane domain (GP-ΔTM) to associate with purified, soluble domain C was determined by co-immunoprecipitation. (c) rVSV-GP and rVSV-GP$_{CL}$ were preincubated with soluble domain C, and virus-protein mixtures were exposed to Vero cells. Viral infection was enumerated by fluorescence microscopy.

FIG. 23A-23B. A synthetic single-pass membrane protein containing NPC1 domain C can mediate EboV and MarV entry. CT43 cells expressing synthetic membrane proteins containing individual NPC1 luminal domains were exposed to rVSVs bearing uncleaved or cleaved Filovirus glycoproteins. Infected cells were visualized (a) and enumerated (b) by fluorescence microscopy. Asterisks in panel b indicate values below the limit of detection.

DETAILED DESCRIPTION OF THE INVENTION

The present invention provides a method for treating a subject infected with a filovirus or for preventing an infection with a filovirus in a subject at risk for infection with a filovirus comprising administering to the subject an agent that inhibits one or more of Niemann-Pick C1 (NPC1), VPS11, VPS16, VPS18, VPS33A, VPS39, VPS41, BLOC1S1, BLOC1S2, GNPTAB, PIKFYVE, ARHGAP23 or FIG4 in an amount effective to treat and/or prevent infection with the filovirus.

The family Filoviridae is a family of viruses including genera Ebolavirus and Marburgvirus.

To treat a subject with a filovirus infection means to reduce or stop the spread of filovirus in the subject, or to eliminate the filovirus from the subject, or to reduce or eliminate a sign or symptom of filovirus infection in the subject. Filovirus infection is characterized by hemorrhagic fever, including abnormalities in blood coagulation.

Subjects who are at risk for infection with filoviruses include subjects who have been exposed to filovirus or are at risk of exposure to filovirus. In addition to the natural occurrence of filoviruses, there is the potential for exposure to these pathogens if they are used as agents of bioterrorism or biological warfare.

Figure 19:
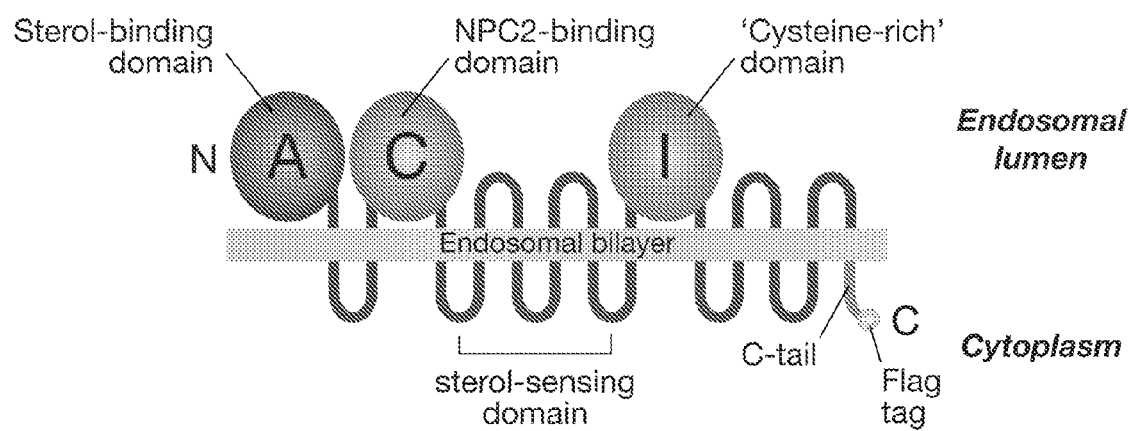
FIG. 19. Topological model of NPC1. Domain A contains a sterol-binding domain, but the specific functions of domains C and I are unknown. In the present studies, a flag epitope tag was appended to the C-terminus of NPC1.

The NPC1 gene encodes NPC1 protein, which is located in the membrane of endosomes and lysosomes and mediates intracellular cholesterol trafficking, in part via binding of cholesterol to its N-terminal domain[38,39]. NPC1 protein has a cytoplasmic C-terminus, 13 transmembrane domains, and 3 large loops in the lumen of the endosome[38] (see FIG. 19).

Defects in the NPC1 gene cause Niemann-Pick type C disease[8], a rare autosomal recessive neurodegenerative disorder characterized by over accumulation of cholesterol and glycosphingolipids in endosomal/lysosomal compartments.

Human NPC1 protein has the amino acid sequence (SEQ ID NO:1) (NCBI Reference Sequence: NM_000271.4):

```
MTARGLALGL LLLLLCPAQV FSQSCVWYGE CGIAYGDKRY NCEYSGPPKP LPKDGYDLVQ   60
ELCPGFFFGN VSLCCDVRQL QTLKDNLQLP LQFLSRCPSC FYNLLNLFCE LTCSPRQSQF  120
LNVTATEDYV DPVTNQTKTN VKELQYYVGQ SFANAMYNAC RDVEAPSSND KALGLLCGKD  180
ADACNATNWI EYMFNKDNGQ APFTITPVFS DFPVHGMEPM NNATKGCDES VDEVTAPCSC  240
QDCSIVCGPK PQPPPPPAPW TILGLDAMYV IMWITYMAFL LVFFGAFFAV WCYRKRYFVS  300
EYTPIDSNIA FSVNASDKGE ASCCDPVSAA FEGCLRRLFT RWGSFCVRNP GCVIFFSLVF  360
ITACSSGLVF VRVTTNPVDL WSAPSSQARL EKEYFDQHFG PFFRTEQLII RAPLTDKHIY  420
QPYPSGADVP FGPPLDIQIL HQVLDLQIAI ENITASYDNE TVTLQDICLA PLSPYNTNCT  480
ILSVLNYFQN SHSVLDHKKG DDFFVYADYH THFLYCVRAP ASLNDTSLLH DPCLGTFGGP  540
VFPWLVLGGY DDQNYNNATA LVITFPVNNY YNDTEKLQRA QAWEKEFINF VKNYKNPNLT  600
ISFTAERSIE DELNRESDSD VFTVVISYAI MFLYISLALG HMKSCRRLLV DSKVSLGIAG  660
ILIVLSSVAC SLGVFSYIGL PLTLIVIEVI PFLVLAVGVD NIFILVQAYQ RDERLQGETL  720
DQQLGRVLGE VAPSMFLSSF SETVAFFLGA LSVMPAVHTF SLFAGLAVFI DFLLQITCFV  780
SLLGLDIKRQ EKNRLDIFCC VRGAEDGTSV QASESCLFRF FKNSYSPLLL KDWMRPIVIA  840
IFVGVLSFSI AVLNKVDIGL DQSLSMPDDS YMVDYFKSIS QYLHAGPPVY FVLEEGHDYT  900
SSKGQNMVCG GMGCNNDSLV QQIFNAAQLD NYTRIGFAPS SWIDDYFDWV KPQSSCCRVD  960
NITDQFCNAS VVDPACVRCR PLTPEGKQRP QGGDFMRFLP MFLSDNPNPK CGKGGHAAYS 1020
SAVNILLGHG TRVGATYFMT YHTVLQTSAD FIDALKKARL IASNVTETMG INGSAYRVFP 1080
YSVFYVFYEQ YLTIIDDTIF NLGVSLGAIF LVTMVLLGCE LWSAVIMCAT IAMVLVNMFG 1140
VMWLWGISLN AVSLVNLVMS CGISVEFCSH ITRAFTVSMK GSRVERAEEA LAHMGSSVFS 1200
GITLTKFGGI VVLAFAKSQI FQIFYFRMYL AMVLLGATHG LIFLPVLLSY IGPSVNKAKS 1260
CATEERYKGT ERERLLNF                                               1278
```

Nucleic acid (mRNA) encoding human NPC1 protein has the nucleotide sequence (SEQ ID NO:2) (NCBI Reference Sequence: NM_000271.4):

```
  1 gaagggcaac acggggacct tgaagcgggg tcgcggcggc gccccagccc gggccaggga
 61 gtcccggcag cggcacctcc cagaaagggc ggagccgacg acgccttctt ccttcctgac
121 cggcgcgcgc agcctgctgc cgcggtcagc gcctgctcct gctcctccgc tcctcctgcg
181 cggggtgctg aaacagcccg gggaagtaga gccgcctccg gggagcccaa ccagccgaac
241 gccgccggcg tcagcagcct tgcgcggcca cagcatgacc gctcgcggcc tggcccttgg
301 cctcctcctg ctgctactgt gtccagcgca ggtgttttca cagtcctgtg tttggtatgg
361 agagtgtgga attgcatatg gggacaagag gtacaattgc gaatattctg gcccaccaaa
421 accattgcca aaggatggat atgacttagt gcaggaactc tgtccaggat tcttctttgg
481 caatgtcagt ctctgttgtg atgttcggca gcttcagaca ctaaaagaca acctgcagct
541 gcctctacag tttctgtcca gatgtccatc ctgtttttat aacctactga acctgttttg
601 tgagctgaca tgtagccctc gacagagtca gttttgaat gttacagcta ctgaagatta
```

-continued

```
 661 tgttgatcct gttacaaacc agacgaaaac aaatgtgaaa gagttacaat actacgtcgg
 721 acagagtttt gccaatgcaa tgtacaatgc ctgccgggat gtggaggccc cctcaagtaa
 781 tgacaaggcc ctgggactcc tgtgtgggaa ggacgctgac gcctgtaatg ccaccaactg
 841 gattgaatac atgttcaata aggacaatgg acaggcacct tttaccatca ctcctgtgtt
 901 ttcagatttt ccagtccatg ggatggagcc catgaacaat gccaccaaag gctgtgacga
 961 gtctgtggat gaggtcacag caccatgtag ctgccaagac tgctctattg tctgtggccc
1021 caagccccag cccccacctc ctcctgctcc ctggacgatc cttggcttgg acgccatgta
1081 tgtcatcatg tggatcacct acatggcgtt tttgcttgtg tttttttggag cattttttgc
1141 agtgtggtgc tacagaaaac ggtattttgt ctccgagtac actcccatcg atagcaatat
1201 agcttttttct gttaatgcaa gtgacaaagg agaggcgtcc tgctgtgacc ctgtcagcgc
1261 agcatttgag ggctgcttga ggcggctgtt cacacgctgg gggtctttct gcgtccgaaa
1321 ccctggctgt gtcattttct tctcgctggt cttcattact gcgtgttcgt caggcctggt
1381 gtttgtccgg gtcacaacca atccagttga cctctggtca gcccccagca gccaggctcg
1441 cctggaaaaa gagtactttg accagcactt tgggcctttc ttccggacgg agcagctcat
1501 catccgggcc cctctcactg acaaacacat ttaccagcca taccccttcgg gagctgatgt
1561 acccttttgga cctccgcttg acatacagat actgcaccag gttcttgact tacaaatagc
1621 catcgaaaac attactgcct cttatgacaa tgagactgtg cacttcaag acatctgctt
1681 ggccctctct tcaccgtata acacgaactg caccattttg agtgtgttaa attacttcca
1741 gaacagccat tccgtgctgg accacaagaa aggggacgac ttctttgtgt atgccgatta
1801 ccacacgcac tttctgtact gcgtacgggc tcctgcctct ctgaatgata caagtttgct
1861 ccatgaccct tgtctgggta cgtttggtgg accagtgttc ccgtggcttg tgttgggagg
1921 ctatgatgat caaaactaca ataacgccac tgcccttgtg attaccttcc ctgtcaataa
1981 ttactataat gatacagaga agctccagag ggcccaggcc tgggaaaaag agtttattaa
2041 ttttgtgaaa aactacaaga atcccaatct gaccatttcc ttcactgctg aacgaagtat
2101 tgaagatgaa ctaaatcgtg aaagtgacag tgatgtcttc accgttgtaa ttagctatgc
2161 catcatgttt ctatatattt ccctagcctt ggggcacatg aaaagctgtc gcaggcttct
2221 ggtggattcg aaggtctcac taggcatcgc gggcatcttg atcgtgctga gctcggtggc
2281 ttgctccttg ggtgtcttca gctacattgg gttgcccttg accctcattg tgattgaagt
2341 catcccgttc ctggtgctgg ctgttggagt ggacaacatc ttcattctgg tgcaggccta
2401 ccagagagat gaacgtcttc aaggggaaac cctggatcag cagctgggca gggtcctagg
2461 agaagtggct cccagtatgt tcctgtcatc ctttttctgag actgtagcat ttttcttagg
2521 agcattgtcc gtgatgccag ccgtgcacac cttctctctc tttgcgggat tggcagtctt
2581 cattgacttt cttctgcaga ttacctgttt cgtgagtctc ttggggttag acattaaacg
2641 tcaagagaaa aatcggctag acatcttttg ctgtgtcaga ggtgctgaag atggaacaag
2701 cgtccaggcc tcagagagct gtttgtttcg cttcttcaaa aactcctatt ctccacttct
2761 gctaaaggac tggatgagac caattgtgat agcaatattt gtgggtgttc tgtcattcag
2821 catcgcagtc ctgaacaaag tagatattgg attggatcag tctctttcga tgccagatga
2881 ctcctacatg gtggattatt tcaaatccat cagtcagtac ctgcatgcgg tccgcctgt
2941 gtactttgtc ctggaggaag ggcacgacta cacttcttcc aagggcaga acatggtgtg
3001 cggcggcatg ggctgcaaca atgattccct ggtgcagcag atatttaacg cggcgcagct
3061 ggacaactat acccgaatag gcttcgcccc ctcgtcctgg atcgacgatt atttcgactg
```

-continued

```
3121 ggtgaagcca cagtcgtctt gctgtcgagt ggacaatatc actgaccagt tctgcaatgc
3181 ttcagtggtt gaccctgcct gcgttcgctg caggcctctg actccggaag gcaaacagag
3241 gcctcagggg ggagacttca tgagattcct gcccatgttc ctttcggata accctaaccc
3301 caagtgtggc aaaggggac atgctgccta tagttctgca gttaacatcc tccttggcca
3361 tggcaccagg gtcggagcca cgtacttcat gacctaccac accgtgctgc agacctctgc
3421 tgactttatt gacgctctga agaaagcccg acttatagcc agtaatgtca ccgaaaccat
3481 gggcattaac ggcagtgcct accgagtatt tccttacagt gtgttttatg tcttctacga
3541 acagtacctg accatcattg acgacactat cttcaacctc ggtgtgtccc tgggcgcgat
3601 atttctggtg accatggtcc tcctgggctg tgagctctgg tctgcagtca tcatgtgtgc
3661 caccatcgcc atggtcttgg tcaacatgtt tggagttatg tggctctggg catcagtct
3721 gaacgctgta tccttggtca acctggtgat gagctgtggc atctccgtgg agttctgcag
3781 ccacataacc agagcgttca cggtgagcat gaaaggcagc cgcgtggagc gcgcggaaga
3841 ggcacttgcc cacatgggca gctccgtgtt cagtggaatc acacttacaa aatttggagg
3901 gattgtggtg ttggcttttg ccaaatctca aattttccag atattctact tcaggatgta
3961 tttggccatg gtcttactgg gagccactca cggattaata tttctccctg tcttactcag
4021 ttacataggg ccatcagtaa ataaagccaa aagttgtgcc actgaagagc gatacaaagg
4081 aacagagcgc gaacggcttc taaatttcta gccctctcgc agggcatcct gactgaactg
4141 tgtctaaggg tcggtcggtt taccactgga cgggtgctgc atcggcaagg ccaagttgaa
4201 caccggatgg tgccaaccat cggttgtttg gcagcagctt tgaacgtagc gcctgtgaac
4261 tcaggaatgc acagttgact tgggaagcag tattactaga tctggaggca accacaggac
4321 actaaacttc tcccagcctc ttcaggaaag aaacctcatt ctttggcaag caggaggtga
4381 cactagatgg ctgtgaatgt gatccgctca ctgacactct gtaaaggcca atcaatgcac
4441 tgtctgtctc tccttttagg agtaagccat cccacaagtt ctataccata tttttagtga
4501 cagttgaggt tgtagataca ctttataaca ttttatagtt taaagagctt tattaatgca
4561 ataaattaac tttgtacaca ttttatata aaaaaacagc aagtgatttc agaatgttgt
4621 aggcctcatt agagcttggt ctccaaaaat ctgtttgaaa aaagcaacat gttcttcaca
4681 gtgttcccct agaaaggaag agatttaatt gccagttaga tgtggcatga aatgagggac
4741 aaagaaagca tctcgtaggt gtgtctactg ggttttaact tatttttctt taataaaata
4801 cattgttttc ctaaaaaaaa aaaaaaa
```

Human vacuolar protein sorting 11 (VPS11) protein has the amino acid sequence (SEQ ID NO:3) (NCBI Reference Sequence: NM_021729.4):

```
MAAYLQWRRF VFFDKELVKE PLSNDGAAPG ATPASGSAAS KFLCLPPGIT VCDSGRGSLV   60

FGDMEGQIWF LPRSLQLTGF QAYKLRVTHL YQLKQHNILA SVGEDEEGIN PLVKIWNLEK  120

RDGGNPLCTR IFPAIPGTEP TVVSCLTVHE NLNFMAIGFT DGSVTLNKGD ITRDRHSKTQ  180

ILHKGNYPVT GLAFRQAGKT THLFVVTTEN VQSYIVSGKD YPRVELDTHG CGLRCSALSD  240

PSQDLQFIVA GDECVYLYQP DERGPCFAFE GHKLIAHWFR GYLIIVSRDR KVSPKSEFTS  300

RDSQSSDKQI LNIYDLCNKF IAYSTVFEDV VDVLAEWGSL YVLTRDGRVH ALQEKDTQTK  360

LEMLFKKNLF EMAINLAKSQ HLDSDGLAQI FMQYGDHLYS KGNHDGAVQQ YIRTIGKLEP  420

SYVIRKFLDA QRIHNLTAYL QTLHRQSLAN ADHTTLLLNC YTKLKDSSKL EEFIKKKSES  480
```

-continued

```
EVHFDVETAI KVLRQAGYYS HALYLAENHA HHEWYLKIQL EDIKNYQEAL RYIGKLPFEQ  540

AESNMKRYGK ILMHHIPEQT TQLLKGLCTD YRPSLEGRSD REAPGCRANS EEFIPIFANN  600

PRELKAFLEH MSEVQPDSPQ GIYDTLLELR LQNWAHEKDP QVKEKLHAEA ISLLKSGRFC  660

DVFDKALVLC QMHDFQDGVL YLYEQGKLFQ QIMHYHMQHE QYRQVISVCE RHGEQDPSLW  720

EQALSYFARK EEDCKEYVAA VLKHIENKNL MPPLLVVQTL AHNSTATLSV IRDYLVQKLQ  780

KQSQQIAQDE LRVRRYREET TRIRQEIQEL KASPKIFQKT KCSICNSALE LPSVHFLCGH  840

SFHQHCFESY SESDADCPTC LPENRKVMDM IRAQEQKRDL HDQFQHQLKC SNDSFSVIAD  900

YFGRGVFNKL TLLTDPPTAR LTSSLEAGLQ RDLLMHSRRG T                     941
```

Nucleic acid (mRNA) encoding human VPS11 protein has the nucleotide sequence (SEQ ID NO:4) (NCBI Reference Sequence: NM_021729.4):

```
   1 ctcacgtgac aaagctcccg gaggtgggag ccctgggcca aaatggcggc ctacctgcag
  61 tggcggcgct tcgttttctt cgacaaggag ctggtgaagg agccgctgag caatgatggg
 121 gccgctcccg gggccacacc tgcttctgga tccgctgctt ccaagttcct ttgcctccct
 181 cctggcatca ctgtctgcga ctcaggccga gggagcctgg tctttggaga tatgaaggc
 241 cagatctggt tcttgccacg ttccctacag cttacaggct tccaagccta caaactacgg
 301 gtgacacacc tgtaccaact gaagcagcac aatattctgg catctgttgg agaagatgaa
 361 gagggcatca acccttggt taagatctgg aacctggaga agagagatgg tggcaatcca
 421 ctctgcactc gaatcttccc tgctattcca ggaacagagc caactgttgt atcttgtttg
 481 actgtccatg aaaatctcaa ctttatgcc attggtttca cagatggcag tgttacattg
 541 aacaaggag acatcacccg ggaccggcat agcaagaccc agattttgca caagggcaac
 601 tatcctgtaa ctggattggc ctttcgccaa gcaggaaaga ccactcactt gtttgttgtg
 661 acaacagaga acgtccagtc ctatatagtt tctggaaaag actaccctcg cgtggagttg
 721 gacacccatg gttgtggcct gcgctgctca gccctaagtg acccttctca ggacctgcag
 781 ttcattgtgg ccggggatga gtgtgtctac ttgtaccagc ctgatgaacg tgggccctgc
 841 ttcgcctttg agggccataa gctcattgcc cactggttta gaggctacct tatcattgtc
 901 tcccgtgacc ggaaggtttc tcccaagtca gagtttacca gcagggattc acagagctcc
 961 gacaagcaga ttctaaacat ctatgacctg tgcaacaagt tcatagccta tagcaccgtc
1021 tttgaggatg tagtggatgt gcttgctgag tggggctccc tgtacgtgct gacgcgggat
1081 gggcgggtcc acgcactgca ggagaaggac acacagacca aactggagat gctgtttaag
1141 aagaacctat ttgagatggc gattaacctt gccaagagcc agcatctgga cagtgatggg
1201 ctggcccaga ttttcatgca gtatggagac atctctaca gcaagggcaa ccacgatggg
1261 gctgtccagc aatatatccg aaccattgga aagttggagc catcctacgt gatccgcaag
1321 tttctggatg cccagcgcat tcacaacctg actgcctacc tgcagaccct gcaccgacaa
1381 tccctggcca atgccgacca taccaccctg ctcctcaact gctataccaa gctcaaggac
1441 agctcgaagc tggaggagtt catcaagaaa aagagtgaga gtgaagtcca ctttgatgtg
1501 gagacagcca tcaaggtcct ccggcaggct ggctactact cccatgccct gtatctggcg
1561 gagaaccatg cacatcatga gtggtacctg aagatccagc tagaagacat taagaattat
1621 caggaagccc ttcgatacat cggcaagctg ccttttgagc aggcagagag caacatgaag
1681 cgctacggca agatcctcat gcaccacata ccagagcaga caactcagtt gctgaaggga
```

-continued

```
1741 ctttgtactg attatcggcc cagcctcgaa ggccgcagcg atagggaggc cccaggctgc 1801 agggccaact ctgaggagtt catccccatc tttgccaata cccgcgaga gctgaaagcc 1861 ttcctagagc acatgagtga agtgcagcca gactcacccc aggggatcta cgacacactc 1921 cttgagctgc gactgcagaa ctgggcccac gagaaggatc cacaggtcaa agagaagctt 1981 cacgcagagg ccatttccct gctgaagagt ggtcgcttct gcgacgtctt tgacaaggcc 2041 ctggtcctgt gccagatgca cgacttccag gatggtgtcc tttaccttta tgagcagggg 2101 aagctgttcc agcagatcat gcactaccac atgcagcacg agcagtaccg gcaggtcatc 2161 agcgtgtgtg agcgccatgg ggagcaggac ccctccttgt gggagcaggc cctcagctac 2221 ttcgctcgca aggaggagga ctgcaaggag tatgtgcag ctgtcctcaa gcatatcgag 2281 aacaagaacc tcatgccacc tcttctagtg gtgcagaccc tggcccacaa ctccacagcc 2341 acactctccg tcatcaggga ctacctggtc caaaaactac agaaacagag ccagcagatt 2401 gcacaggatg agctgcgggt gcggcggtac cgagaggaga ccacccgtat ccgccaggag 2461 atccaagagc tcaaggccag tcctaagatt ttccaaaaga ccaagtgcag catctgtaac 2521 agtgccttgg agttgccctc agtccacttc ctgtgtggcc actccttcca ccaacactgc 2581 tttgagagtt actcggaaag tgatgctgac tgccccacct gcctccctga aaaccggaag 2641 gtcatggata tgatccgggc ccaggaacag aaacgagatc tccatgatca attccagcat 2701 cagctcaagt gctccaatga cagcttttct gtgattgctg actactttgg cagaggtgtt 2761 ttcaacaaat tgactctgct gaccgaccct cccacagcca gactgacctc cagcctggag 2821 gctgggctgc aacgcgacct actcatgcac tccaggaggg gcacttaagc agcctggagg 2881 aagatgtggg caacagtgga ggaccaagag aacagacaca tgggacctg gcgggcgtt 2941 acacagaagg ctggctgaca tgcccagggc tccactctca tctaatgtca cagccctcag 3001 aactaaagcg gactttcttt ccctgccttc ttatttagtc agcttgccat ccctcctctt 3061 cactagcagt gtagatcatt ccagatcagt ggggagggc acctcagcaa cctctgagtg 3121 tggacaatag ctgctttctt ctctatccaa gagcaccagg ctgtgcttgg gtccttgctc 3181 tcagagtcta taaataaaag aatataatga tttgggagct taaaaaaaaa aaaaaaaaa 3241 aaaaaaaaaa aaaaaaaaaa aaaaaaaaaa aaaaaaaa
```

Human vacuolar protein sorting 16 (VPS16) protein has the amino acid sequence (SEQ ID NO:5) (NCBI Reference Sequence: NM_022575.2):

```
MDCYTANWNP LGDSAFYRKY ELYSMDWDLK EELRDCLVAA APYGGPIALL RNPWRKEKAA  60

SVRPVLDIYS ASGMPLASLL WKSGPVVSLG WSAEEELLCV QEDGAVLVYG LHGDFRRHFS 120

MGNEVLQNRV LDARIFHTEF GSGVAILTGA HRFTLSANVG DLKLRRMPEV PGLQSAPSCW 180

TVLCQDRVAH ILLAVGPDLY LLDHAACSAV TPPGLAPGVS SFLQMAVSFT YRHLALFTDT 240

GYIWMGTASL KEKLCEFNCN IRAPPKQMVW CSRPRSKERA VVVAWERRLM VVGDAPESIQ 300

FVLDEDSYLV PELDGVRIFS RSTHEFLHEV PAASEEIFKI ASMAPGALLL EAQKEYEKES 360

QKADEYLREI QELGQLTQAV QQCIEAAGHE HQPDMQKSLL RAASFGKCFL DRFPPDSFVH 420

MCQDLRVLNA VRDYHIGIPL TYSQYKQLTI QVLLDRLVLR RLYPLAIQIC EYLRLPEVQG 480

VSRILAHWAC YKVQQKDVSD EDVARAINQK LGDTPGVSYS DIAARAYGCG RTELAIKLLE 540

YEPRSGEQVP LLLKMKRSKL ALSKAIESGD TDLVFTVLLH LKNELNRGDF FMTLRNQPMA 600

LSLYRQFCKH QELETLKDLY NQDDNHQELG SFHIRASYAA EERIEGRVAA LQTAADAFYK 660
```

```
AKNEFAAKAT EDQMRLLRLQ RRLEDELGGQ FLDLSLHDTV TTLILGGHNK RAEQLARDFR    720

IPDKRLWWLK LTALADLEDW EELEKFSKSK KSPIGYLPFV EICMKQHNKY EAKKYASRVG    780

PEQKVKALLL VGDVAQAADV AIEHRNEAEL SLVLSHCTGA TDGATADKIQ RARAQAQKK    839
```

Nucleic acid (mRNA) encoding human VPS16 protein has the nucleotide sequence (SEQ ID NO:6) (NCBI Reference Sequence: NM_022575.2):

```
   1 ctaggtgggt gtccctcgg tgcttccag ctgccgtctg caccagccat ggactgctac
  61 acggcgaact ggaacccact cggggactct gccttttacc ggaaatatga gctgtacagc
 121 atggactggg acctgaagga ggaactcagg gattgcctgg tggctgctgc acctatggg
 181 ggccccattg cactgctgag gaacccctgg cggaaggaga aagctgctag tgtgaggcca
 241 gtgctcgata tatactctgc ttccggcatg cctctggcca gcctgctgtg gaagagtgga
 301 cccgtggtgt ccctgggctg gtcagctgag gaggagctgc tctgtgtgca ggaagatggt
 361 gctgtactgg tttatgggct tcatggtgac ttccggagac acttcagcat gggcaatgaa
 421 gtgctccaga accgggttct ggatgcccgg atctttcaca ctgagtttgg ttccggagtg
 481 gccatcctca caggggccca ccgcttcacc ctcagtgcca atgtgggtga cctcaaactc
 541 cgccggatgc cagaggtgcc aggtctgcaa agtgcaccct cctgctggac tgtgctgtgc
 601 caggaccgag tggcacacat tcttctggct gtggggcctg acctttacct cttggaccat
 661 gcagcctgct ccgcagtgac gccccctggc ctgcccccag gagtaagcag cttcctacag
 721 atggctgtct ccttcaccta ccgacacctg gcactcttca cagacacagg ctacatctgg
 781 atggggacag catcactcaa ggagaagcta tgtgagttca actgcaacat ccgggcacct
 841 ccaaagcaga tggtctggtg cagccgtcct cgtagcaagg agagggccgt ggtggtggcc
 901 tgggaaaggc ggctgatggt ggtgggcgat gcacccgaga gcatccagtt tgtgctggat
 961 gaggactcct acctggtgcc tgagctcgat ggggtccgca tcttctcccg cagcacccac
1021 gagttcctgc atgaggttcc agcggccagc gaggaaatct tcaaaattgc ctcaatggcc
1081 cccggggcgc tgctcctgga ggctcagaag gagtatgaga agagagcca gaaggcggac
1141 gagtacctgc gggagatcca ggagctgggc cagctgaccc caggccgtgca gcagtgcatt
1201 gaggctgcag gacatgagca ccagccagac atgcagaaga gtctgctcag gccgcctcc
1261 ttcggaaagt gttcctggga cagatttcca cccgacagct tcgtgcacat gtgtcaggac
1321 ctgcgtgtgc tcaatgctgt tcgggactat cacatcggga tcccgctcac ctatagccaa
1381 tataagcagc tcaccatcca ggtgctgctg gacaggctcg tgttgcggag acttttacccc
1441 ctggccatcc agatatgcga gtacttgcgc cttcctgaag tacagggcgt cagcaggatc
1501 ctggcccact gggcctgcta caaggtgcaa cagaaggatg tctcagatga ggatgtggct
1561 cgagccatta accagaagct gggggacacg cctggtgtct cttactccga cattgctgca
1621 cgagcctatg gttgtggccg cacggagctg gccatcaagc tgctggagta tgagccacgc
1681 tcaggggagc aggtacccct tctcctaaag atgaagagga gcaaactggc actaagcaag
1741 gccatcgaga gcgggacac tgacctggtg ttcacggtgt tgctgcacct gaagaacgag
1801 ctgaaccgag gagattttttt catgacccctt cggaatcagc ccatggccct cagtttgtac
1861 cgacagttct gtaagcatca ggagctagac acgctgaagg acctttacaa tcaggatgac
1921 aatcaccagg aattgggcag cttccacatc cgagccagct atgctgcaga gagcgtatt
1981 gaggggcgag tagcagctct gcagacagcc gccgatgcct tctacaaggc caagaatgag
```

-continued

```
2041 tttgcagcca aggctacaga ggatcaaatg cggctcctac ggctgcagcg gcgcctagaa 2101 gacgagctgg ggggccagtt cctagacctg tctctacatg acacagttac caccctcatt 2161 cttggcggtc acaacaagcg tgcagagcag ctggcacgtg acttccgcat ccctgacaag 2221 aggctctggt ggctgaagct gactgccctg gcagatttgg aagattggga agagctagag 2281 aagtttttcca agagcaagaa atcacccatt ggctacctgc cttttgtgga gatctgcatg 2341 aaacaacata acaaatacga agccaagaag tatgcttccc gcgtgggtcc cgagcagaag 2401 gtcaaggctt tgcttcttgt tggcgatgtg gctcaggctg cagatgtggc catcgaacac 2461 cggaatgagg ctgagctgag cctcgtattg tcccactgca cgggagccac agatggggcc 2521 acagctgaca agattcaacg ggccagggca caagcccaga agaagtgagg agtccatcct 2581 gtacatctca agcaagggt tcctccccta gcacctgggc ttggcagaag ggccatagtt 2641 catccagctc ctcccctaga gcaatgctga ggagcgggg catggtagca gggctgtctg 2701 gttttaaata aagttggaac acttcaaaaa aaaaaaaaaa aaaaaaaaaa aaaaaaaaaa 2761 aaaaaaaaa
```

Human vacuolar protein sorting 18 (VPS18) protein has the amino acid sequence (SEQ ID NO:7) (NCBI Reference Sequence: NM_020857.2):

```
MASILDEYEN SLSRSAVLQP GCPSVGIPHS GYVNAQLEKE VPIFTKQRID FTPSERITSL   60

VVSSNQLCMS LGKDTLLRID LGKANEPNHV ELGRKDDAKV HKMFLDHTGS HLLIALSSTE  120

VLYVNRNGQK VRPLARWKGQ LVESVGWNKA LGTESSTGPI LVGTAQGHIF EAELSASEGG  180

LFGPAPDLYF RPLYVLNEEG GPAPVCSLEA ERGPDGRSFV IATTRQRLFQ FIGRAAEGAE  240

AQGFSGLFAA YTDHPPPFRE FPSNLGYSEL AFYTPKLRSA PRAFAWMMGD GVLYGALDCG  300

RPDSLLSEER VWEYPEGVGP GASPPLAIVL TQFHFLLLLA DRVEAVCTLT GQVVLRDHFL  360

EKFGPLKHMV KDSSTGQLWA YTERAVFRYH VQREARDVWR TYLDMNRFDL AKEYCRERPD  420

CLDTVLAREA DFCFRQRRYL ESARCYALTQ SYFEEIALKF LEARQEEALA EFLQRKLASL  480

KPAERTQATL LTTWLTELYL SRLGALQGDP EALTLYRETK ECFRTFLSSP RHKEWLFASR  540

ASIHELLASH GDTEHMVYFA VIMQDYERVV AYHCQHEAYE EALAVLARHR DPQLFYKFSP  600

ILIRHIPRQL VDAWIEMGSR LDARQLIPAL VNYSQGGEVQ QVSQAIRYME FCVNVLGETE  660

QAIHNYLLSL YARGRPDSLL AYLEQAGASP HRVHYDLKYA LRLCAEHGHH RACVHVYKVL  720

ELYEEAVDLA LQVDVDLAKQ CADLPEEDEE LRKKLWLKIA RHVVQEEEDV QTAMACLASC  780

PLLKIEDVLP FFPDFVTIDH FKEAICSSLK AYNHHIQELQ REMEEATASA QRIRRDLQEL  840

RGRYGTVEPQ DKCATCDFPL LNRPFYLFLC GHMFHADCLL QAVRPGLPAY KQARLEELQR  900

KLGAAPPPAK GSARAKEAEG GAATAGPSRE QLKADLDELV AAECVYCGEL MIRSIDRPFI  960

DPQRYEEEQL SWL                                                     973
```

Nucleic acid (mRNA) encoding human VPS18 protein has the nucleotide sequence (SEQ ID NO:8) (NCBI Reference Sequence: NM_020857.2):

```
  1 gcccgcgtca cgggggcggg agtcagctga gctgccgggg cgaggttggg atcacctggc 61 accggctgaa gggagcctgt gatttttttg tagcgggggc ggggagtaag gtgcaagact 121 gcgccagatt caaggacgag ggctgcccga ttatctcgct gcataaggca agagcaagag 181 gatcctcagg attttaaaga ggaggcgacg gctgcaggtt cccaggatct gtcagaggct
```

-continued

```
 241 ggggagttac agcttccatt ctggggcgac ggggaccccg ggggggtagc cctttttgtaa
 301 tccccaggcc ccggacaaag agcccagagg ccgggcacca tggcgtccat cctggatgag
 361 tacgagaact cgctgtcccg ctcggccgtc ttgcagcccg gctgccctag cgtgggcatc
 421 ccccactcgg ggtatgtgaa tgcccagctg gagaaggaag tgcccatctt cacaaagcag
 481 cgcattgact tcaccccttc cgagcgcatt accagtcttg tcgtctccag caatcagctg
 541 tgcatgagcc tgggcaagga tacactgctc cgcattgact gggcaaggc aaatgagccc
 601 aaccacgtgg agctgggacg taaggatgac gcaaaagttc acaagatgtt ccttgaccat
 661 actggctctc acctgctgat tgccctgagc agcacggagg tcctctacgt gaaccgaaat
 721 ggacagaagg tacggccact agcacgctgg aaggggcagc tggtggagag tgtgggttgg
 781 aacaaggcac tgggcacgga gagcagcaca ggccccatcc tggtcgggac tgcccaaggc
 841 cacatctttg aagcagagct ctcagccagc gaaggtgggc ttttcggccc tgctccggat
 901 ctctacttcc gcccattgta cgtgctaaat gaagaagggg gtccagcacc tgtgtgctcc
 961 cttgaggccg agcggggccc tgatgggcgt agctttgtta ttgccaccac tcggcagcgc
1021 ctcttccagt tcataggccg agcagcagag ggggctgagg cccagggttt ctcagggctc
1081 tttgcagctt acacggacca cccacccccca ttccgtgagt ttcccagcaa cctgggctac
1141 agtgagttgg ccttctacac ccccaagctg cgctccgcac cccgggcctt cgcctggatg
1201 atggggatg gtgtgttgta tggggcattg gactgtgggc gccctgactc tctgctgagc
1261 gaggagcgag tctgggagta cccagagggg gtagggcctg gggccagccc acccctagcc
1321 atcgtcttga cccagttcca cttcctgctg ctactggcag accgggtgga ggcagtgtgc
1381 acactgaccg ggcaggtggt gctgcgggat cacttcctgg agaaatttgg gccgctgaag
1441 cacatggtga aggactcctc cacaggccag ctgtgggcct acactgagcg ggctgtcttc
1501 cgctaccacg tgcaacggga ggcccgagat gtctggcgca cctatctgga catgaaccgc
1561 ttcgatctgg ccaaagagta ttgtcgagag cggcccgact gcctgacac ggtcctggcc
1621 cgggaggccg atttctgctt tcgccagcgt cgctacctgg agagcgcacg ctgctatgcc
1681 ctgacccaga gctactttga ggagattgcc ctcaagttcc tggaggcccg acaggaggag
1741 gctctggctg agttcctgca gcgaaaactg gccagtttga agccagccga acgtacccag
1801 gccacactgc tgaccacctg gctgacagag ctctacctga gccggcttgg ggctctgcag
1861 ggcgacccag aggccctgac tctctaccga gaaaccaagg aatgctttcg aaccttcctc
1921 agcagccccc gccacaaaga gtggctcttt gccagccggg cctctatcca tgagctgctc
1981 gccagtcatg gggacacaga acacatggtg tactttgcag tgatcatgca ggactatgag
2041 cgggtggtgg cttaccactg tcagcacgag gcctacgagg aggccctggc cgtgctcgcc
2101 cgccaccgtg acccccagct cttctacaag ttctcaccca tcctcatccg tcacatcccc
2161 cgccagcttg tagatgcctg gattgagatg ggcagccggc tggatgctcg tcagctcatt
2221 cctgccctgg tgaactacag ccagggtggt gaggtccagc aggtgagcca ggccatccgc
2281 tacatggagt tctgcgtgaa cgtgctgggg gagactgagc aggccatcca caactacctg
2341 ctgtcactgt atgcccgtgg ccggccggac tcactactgg cctatctgga gcaggctggg
2401 gccagccccc accgggtgca ttacgacctc aagtatgcgc tgcggctctg cgccgagcat
2461 ggccaccacc gcgcttgtgt ccatgtctac aaggtcctag agctgtatga ggaggccgtg
2521 gacctggccc tgcaggtgga tgtggacctg gccaagcagt gtgcagacct gcctgaggag
2581 gatgaggaat tgcgcaagaa gctgtggctg aagatcgcac ggcacgtggt gcaggaagag
2641 gaagatgtac agacagccat ggcttgcctg gctagctgcc ccttgctcaa gattgaggat
```

```
2701 gtgctgccct tctttcctga tttcgtcacc atcgaccact tcaaggaggc gatctgcagc 2761 tcacttaagg cctacaacca ccacatccag gagctgcagc gggagatgga agaggctaca 2821 gccagtgccc agcgcatccg gcgagacctg caggagctgc ggggccgcta cggcactgtg 2881 gagcccagg acaaatgtgc cacctgcgac ttcccctgc tcaaccgccc tttttacctc 2941 ttcctctgtg gccatatgtt ccatgctgac tgcctgctgc aggctgtgcg acctggcctg 3001 ccagcctaca agcaggcccg gctgaggag ctgcagagga agctggggc tgctccaccc 3061 ccagccaagg gctctgcccg ggccaaggag gccgagggtg gggctgccac ggcagggccc 3121 agccgggaac agctcaaggc tgacctggat gagttggtgg ccgctgagtg tgtgtactgt 3181 ggggagctga tgatccgctc tatcgaccgg ccgttcatcg accccagcg ctacgaggag 3241 gagcagctca gttggctgta ggagggtgtc acctttgatg ggggtgggc aatgggagc 3301 agtggcttga acccacttga gaaggctgcc tcctaggctc tgctcagtca tcttgcaatt 3361 gccacactgt gaccacgttg acgggagtag agtagcgctg ttggccagga ggtgtcaggt 3421 gtgagtgtat tctgccagct tttcatgctg ttcttcagag ctgcagttat gccagaccat 3481 cagcctgcct cccagtagag gcccttcacc tggagaagtc agaaatctga cccaattcca 3541 ccccctgcct ctagcacctc ttctgtccct gtcattcccc acacacgtcc tgttcacctc 3601 gagagagaga gagagagagc acctttcttc cgtctgttca ctctgcggcc tctggaatcc 3661 cagctcttct ctctcagaag aagccttctc ttcctcctgc ctgtaggtgt cccagaagtg 3721 agaaggcagc cttcgaagtc ctgggcattg ggtgagaaag tgatgctagt tggggcatgc 3781 ttttgtgcac actctctggg gctccagtgt gaagggtgcc ctggggctga gggccttgtg 3841 gaggatggtc ggtggtggtg atggaggtgg agagcattaa actgtctgca ctgcaaaaaa 3901 aaaaaaaaaa aaaaaaaaaa aa
```

Human vacuolar protein sorting 33A (VPS33A) protein has the amino acid sequence (SEQ ID NO:9) (NCBI Reference Sequence: NM_022916.4):

```
MAAHLSYGRV NLNVLREAVR RELREFLDKC AGSKAIVWDE YLTGPFGLIA QYSLLKEHEV  60

EKMFTLKGNR LPAADVKNII FFVRPRLELM DIIAENVLSE DRRGPTRDFH ILFVPRRSLL 120

CEQRLKDLGV LGSFIHREEY SLDLIPFDGD LLSMESEGAF KECYLEGDQT SLYHAAKGLM 180

TLQALYGTIP QIFGKGECAR QVANMMIRMK REFTGSQNSI FPVFDNLLLL DRNVDLLTPL 240

ATQLTYEGLI DEIYGIQNSY VKLPPEKFAP KKQGDGGKDL PTEAKKLQLN SAEELYAEIR 300

DKNFNAVGSV LSKKAKIISA AFEERHNAKT VGEIKQFVSQ LPHMQAARGS LANHTSIAEL 360

IKDVTTSEDF FDKLTVEQEF MSGIDTDKVN NYIEDCIAQK HSLIKVLRLV CLQSVCNSGL 420

KQKVLDYYKR EILQTYGYEH ILTLHNLEKA GLLKPQTGGR NNYPTIRKTL RLWMDDVNEQ 480

NPTDISYVYS GYAPLSVRLA QLLSRPGWRS IEEVLRILPG PHFEERQPLP TGLQKKRQPG 540

ENRVTLIFFL GGVTFAEIAA LRFLSQLEDG GTEYVIATTK LMNGTSWIEA LMEKPF     596
```

Nucleic acid (mRNA) encoding human VPS33A protein has the nucleotide sequence (SEQ ID NO:10) (NCBI Reference Sequence: NM_022916.4):

```
  1 gtgcgctgcc gtaccggtca cgtggacgtt tggtcacgtg actgcgtccg tggtcctccc 61 gtaggaaccg gcggactcgg ttggcgttgt ggggcagggg gtggtggagc aagatggcgg 121 ctcatctgtc ctacggccga gtgaacctaa acgtgttgcg cgaggcggtg cgtcgcgagc
```

-continued

```
 181 tgcgcgagtt cctggacaag tgcgcaggaa gcaaggcaat agtttgggat gaatacctaa
 241 ctggaccctt tggcctgatt gcacagtatt cactattgaa ggaacatgaa gtggaaaaaa
 301 tgttcacact taaaggaaat cgtttgccgg cagctgatgt gaagaatata atttttttg
 361 tcagacccag gctagagttg atggatataa tcgctgaaaa cgtgctcagt gaagatagac
 421 gaggcccaac gagagatttt catattctgt tgtgccacg ccgtagcctg ttgtgcgaac
 481 agcggttgaa ggatctgggt gtcttgggat cctttattca cagggaggag tacagcttag
 541 atctcattcc attcgatggg gatctcttat ccatggaatc agagggtgca ttcaaagagt
 601 gctacctgga gggtgaccag acgagcctgt accacgcagc caaggggctg atgaccctgc
 661 aagctctgta tggaacgatc ccccagatct tgggaaagg agaatgcgct cggcaagtgg
 721 ccaatatgat gatcaggatg aagagagagt ttacaggaag ccagaattca atatttcctg
 781 tttttgataa tctcttgttg cttgatcgga atgtggattt attaacacct cttgccactc
 841 agctgacata tgaaggactc attgatgaaa tttatggcat tcagaacagt tatgtgaaat
 901 tacctccaga gaaatttgca cctaagaaac agggcgatgg tggtaaggac ctccccacgg
 961 aagcaaagaa gctgcagctg aattctgcag aggagctcta tgctgagatc cgagataaga
1021 acttcaacgc agttggctct gtgctcagca agaaagcaaa gatcatctct gcagcattcg
1081 aggaaagaca caatgctaag accgtggggg agatcaagca gtttgtttcc cagttgcccc
1141 acatgcaggc agcaaggggc tcgcttgcaa accatacctc aattgcagaa ttgatcaaag
1201 atgtcactac ttctgaagac ttttttgata aattaaccgt ggaacaggag tttatgtctg
1261 gaatagacac tgataaggtc aacaattaca ttgaggattg tatcgcccaa aagcactcgt
1321 tgatcaaggt gttaagacta gtttgcctcc aatccgtgtg taatagtggg ctcaaacaaa
1381 aagttttgga ttattacaaa agagagattc tccagacata cggctatgag cacatattga
1441 ccttacacaa cctggagaag gccggcctgc tgaaaccgca gacgggggc agaaacaatt
1501 acccaactat acggaaaaca ttacgcctct ggatggatga tgttaatgag caaaccccca
1561 cggacatatc gtatgtgtac agtgggtatg ccccgctcag tgtgcggctg cccagctgc
1621 tttcccggcc tggctggcgg agcatcgagg aggtcctccg catcctccca gggccccact
1681 ttgaggagcg gcagccactg cccacaggac tgcagaagaa acgtcaaccg ggagaaaacc
1741 gagtgactct gatatttttc cttgggggcg taaccttcgc tgaaattgct gccctgcgat
1801 ttctctccca gttggaagat ggaggtacag aatatgtcat tgccaccact aaactaatga
1861 atggaaccag ttgatagag gctctgatgg aaaaacctt ctaggatgtt cagaggagac
1921 ttaacaagtg tactgcagaa taaactacct ctttgaagaa attgctgaaa ggaagtaaaa
1981 ccccatagaa gaaacatggg aatacagaat atattctggg gtcagcttct taaattatac
2041 tactgtttac tgctttctcc gtctcttttg tattcccttt ttttttcc tttgagacgg
2101 agtcttgctc tgtcacccag actagagtgc agtggcacgg tctcacctca ctgcaacctc
2161 cacctcctag gttcaagcaa ttctcctgcc tcagcctcct gagtagctgg gactacaggc
2221 atgcaccacc acacccggct aattttgta ttttagtag ccatggtgtt tcaccatgtt
2281 ggccaggctg gtctcaaact cctgacctca ggtgatccac ctgcctcggc ctcccacagt
2341 gctgggatta caggcctgag ccaccgtgcc tggcccctaa tctgctgaag aagaagaat
2401 agaagaaaat caacctgagt aaaagcagca ctggttttga gttttctaag ctcagggtct
2461 tcattagaga cctctggaaa tacattaagg atggtggggg tagataatcc attcagccag
2521 acaaacgggg ccagctctta aaataagaaa gctgagactg aggaggtgaa actgaaaata
2581 aaaagagaaa gttcatcctc taaaaaaaaa aaaaaaaaa aaaaaaa
```

Human vacuolar protein sorting 39 (VPS39) protein has the amino acid sequence (SEQ ID NO:11) (NCBI Reference Sequence: NM_015289.2):

```
MHDAFEPVPI LEKLPLQIDC LAAWEEWLLV GTKQGHLLLY RIRKDVGCNR FEVTLEKSNK  60
NFSKKIQQIH VVSQFKILVS LLENNIYVHD LLTFQQITTV SKAKGASLFT CDLQHTETGE 120
EVLRMCVAVK KKLQLYFWKD REFHELQGDF SVPDVPKSMA WCENSICVGF KRDYYLIRVD 180
GKGSIKELFP TGKQLEPLVA PLADGKVAVG QDDLTVVLNE EGICTQKCAL NWTDIPVAME 240
HQPPYIIAVL PRYVEIRTFE PRLLVQSIEL QRPRFITSGG SNIIYVASNH FVWRLIPVPM 300
ATQIQQLLQD KQFELALQLA EMKDDSDSEK QQQIHHIKNL YAFNLFCQKR FDESMQVFAK 360
LGTDPTHVMG LYPDLLPTDY RKQLQYPNPL PVLSGAELEK AHLALIDYLT QKRSQLVKKL 420
NDSDHQSSTS PLMEGTPTIK SKKKLLQIID TTLLKCYLHT NVALVAPLLR LENNHCHIEE 480
SEHVLKKAHK YSELIILYEK KGLHEKALQV LVDQSKKANS PLKGHERTVQ YLQHLGTENL 540
HLIFSYSVWV LRDFPEDGLK IFTEDLPEVE SLPRDRVLGF LIENFKGLAI PYLEHIIHVW 600
EETGSRFHNC LIQLYCEKVQ GLMKEYLLSF PAGKTPVPAG EEEGELGEYR QKLLMFLEIS 660
SYYDPGRLIC DFPFDGLLEE RALLLGRMGK HEQALFIYVH ILKDTRMAEE YCHKHYDRNK 720
DGNKDVYLSL LRMYLSPPSI HCLGPIKLEL LEPKANLQAA LQVLELHHSK LDTTKALNLL 780
PANTQINDIR IFLEKVLEEN AQKKRFNQVL KNLLHAEFLR VQEERILHQQ VKCIITEEKV 840
CMVCKKKIGN SAFARYPNGV VVHYFCSKEV NPADT                          875
```

Nucleic acid (mRNA) encoding human VPS39 protein has the nucleotide sequence (SEQ ID NO:12) (NCBI Reference Sequence: NM_015289.2):

```
   1 ggggttgacg atggctgtgt tgttgaaggg cctgtagccg gggggttcct ggccggatcc
  61 cggtctaccc ttagcccaga ctcgttccgg accccagccc ggcccggaac actctgggcg
 121 agacggcggt ggcaactctc cccttgccgc catgcacgac gctttcgagc cagtgccgat
 181 cctagaaaag ctgcctctgc aaatcgactg tctggctgcc tgggaggaat ggcttcttgt
 241 gggaaccaaa caaggacatc ttcttctcta taggattcgg aaggacgttg gttgcaacag
 301 atttgaagtg acactagaga atccaataa gaacttctcc aaaaagattc agcagatcca
 361 tgtggtttcc cagtttaaga ttctggtcag cttgttagaa ataacatttt atgtccatga
 421 cctattgaca tttcaacaaa tcactacggt ttcaaaggca aagggagcat cactgtttac
 481 ttgtgacctc cagcacacag agaccggtga ggaggtgtta cggatgtgtg tggcagtaaa
 541 aaagaagctg cagctctatt tctggaagga cagggaattt catgaattgc aggggggactt
 601 tagtgtgcca gatgtgccca gtccatggc gtggtgtgaa aattctatct gtgtgggttt
 661 caagagagac tactacctaa taagggtgga tggaaagggg tccatcaaag agctctttcc
 721 aacaggaaaa cagctggagc ccttagttgc acctctggca gatggaaaag tggctgtggg
 781 ccaggatgat ctcaccgtgg tactcaatga ggaagggatc tgcacacaga aatgtgccct
 841 gaactggacg gacataccag tggccatgga gcaccagcct ccctacatca ttgcagtgtt
 901 gcctcgatat gttgagatcc gaacatttga accgaggctt ctggtccaaa gcattgaatt
 961 gcaaaggccc cgtttcatta cctcaggagg atcaaacatt atctatgtgg ccagcaatca
1021 ttttgtttgg agactcatcc ctgtccccat ggcaacccaa atccaacaac ttctccagga
1081 caagcagttt gaattggctc tgcagctcgc agaaatgaaa gatgattctg acagtgaaaa
1141 gcagcaacaa attcatcaca tcaagaactt gtatgccttc aacctcttct gccagaagcg
```

-continued

```
1201 ttttgatgag tccatgcagg tctttgctaa acttggcaca gatcccaccc atgtgatggg
1261 cctgtaccct gacctgctgc ccacagacta cagaaagcag ttgcagtatc caacccatt
1321 gcctgtgctc tccggggctg aattggagaa ggctcactta gctctgattg actacctgac
1381 acagaaacga agtcaattgg taaagaagct gaatgactct gatcaccagt caagcacctc
1441 accgctcatg gaaggcactc ccaccatcaa atccaagaag aagctgctac aaatcatcga
1501 caccaccctg ctcaagtgct atctccatac aaatgtggcc ctggtggccc ccttgctacg
1561 cctggagaac aatcactgcc acatcgagga gagcgagcac gtgctaaaga aggctcacaa
1621 gtacagtgag cttatcatcc tgtatgaaga aaggggctc cacgagaaag ctctgcaggt
1681 gctcgtggac cagtccaaga aagccaactc ccctctgaaa ggccacgaga ggacagtgca
1741 gtatctgcag catctgggca cagaaaacct gcatttgatt ttctcctact cagtgtgggt
1801 gctgagagac ttcccagaag atggcctgaa gatatttact gaagatctcc cggaagtgga
1861 gtctctgcca cgtgatcgag tcctcggctt cttaatagag aattttaagg gtctggctat
1921 tccttatctg gaacacatca tccatgtttg ggaggagaca ggctctcggt tccacaactg
1981 cctgatccag ctatactgtg agaaggtgca aggtctgatg aaggagtatc tcctgtcctt
2041 ccctgcaggc aaaaccccag tcccagctgg agaggaagag ggtgagctgg gagaataccg
2101 gcaaaagctc ctcatgttct tggagatttc cagctactat gatccaggcc ggctcatctg
2161 tgattttccc tttgatggcc tcttagaaga acgagctctc ctgttggggc gcatggggaa
2221 acatgaacaa gctcttttca tttatgtcca catcttgaag gatacaagga tggctgagga
2281 gtactgccac aaacactatg accgaaacaa agatggcaac aaagatgtgt atctgtccct
2341 gcttcggatg tacctgtcgc cccccagcat tcactgcctg gggccaatca agctggaact
2401 actggagcca aaagccaacc tccaggccgc tctgcaggtc ctcgagctac accacagcaa
2461 actggacacc accaaggccc tcaaccttct gccagcaaac actcagatca atgacatacg
2521 catcttcctg gaaaaggtct tggaagaaaa tgcacaaaag aaacggttca atcaagtgct
2581 caagaacctt ctccatgcag aattcctgag ggtccaggaa gagcggattt tacaccagca
2641 ggtgaagtgc atcatcacag aggagaaggt gtgcatggtg tgtaagaaga agattgggaa
2701 cagtgcattt gcaagatacc ccaatggagt ggtcgtccat tacttctgtt ccaaagaggt
2761 aaacccagct gacacttgag cccagcatcc tggggatcca gcggatggac agttggctc
2821 tcccagagag gtgaaggagc acctggcctt aggaatcctg gctgccacca ccacaaggct
2881 ccccatttgg acattactgg ctatcttgtg ccctggaaca actctgaatt aattagactc
2941 atggtctggc attgccagct ttttaatggg aaaagagatt agttatacct tataccatta
3001 tgttgtgggc aattccagag aattcagtac ctgcttggtc aggaggatgt gcaccatctt
3061 gcctttgcac accagtcacc tgaacaagga aacttgtcac aagtgtttgt aaccatgggg
3121 ttgttcatca agggcttttc tattaagtac atgacttcac aaggaccgct cagcatggct
3181 cactggagag ttccatgaga gaacagcact caagcttctg gccgcatgga cccgatggct
3241 cgcattctgt gtagtgtttt acgtctccat ggtaactgtg ccctgcaccc ctcggtagcc
3301 gccctgttag tttttcagtct ccttttcttt ctcaccattt atcacttccc tcactgccct
3361 acccaggctt tctctcccac ttccctgact ctgggaataa ctaatattta agcaaggtaa
3421 gatgagaagc aaggggtctc agttctagga atacagtgct agttgattgt caggtatgtt
3481 gtaaatagac cctcttttggc catacactcc atgcctagat gcctcggaga gcatcattct
3541 ctgcctaggc aaggccctgc atcccttgcc tcaggccggg ctgagtgtga ctgcagctcc
3601 tgaggatggg cctgccctgt ctggggtatg cgtgatccct agatacatgt tcccacagag
```

```
-continued
3661 gtgcctgctc cgtcttcgct caccagacac tcaggcaggc tggcttagtc tttgtgcgtg 3721 gcgattttgt gctctgggcc ctttctcttt ttccagccag tttccattca cttgccttac 3781 agcctgccct ggccgtcact ccccagcttt gttcagcaat ggtgtggttg gagagttgtg 3841 ctgggatagc gcaggaaggt gggtcccggc aacacgcagg ggatgagtgg acctggaact 3901 gacaatggcg tgctgccaag tgttcctgag aggtgtttag gcacagcaga ggggacgcgg 3961 ggggcaagaa cagcaggacg ctggtttaaa ataactcac cgccaaacct gtggagcagt 4021 gtggggcatc ctgccagagg tgcacaggct ggagtttcag gcactgcagg ctgatgacac 4081 acagggagag tggccctgcc tcctgtcctc cccggggttt ttgcagactc gaagtctcac 4141 tgcaccagtg tctttgatgg tggtgagggt gggtgatggt gcccagcacc aacagtttta 4201 gtggcctgtc cttgacctgc cgtggtcctt tgtaaactat ggctccatgc tgtgtgacag 4261 atcaacgtgc tgatggtaag tagactaggc ttccccaggc atgccgtccg tgggggcctg 4321 aagagacagt gagtgccatt ggccccattc gcagatgtgg gagactctgc tcaggcctgt 4381 gaggctgggc agcccttcac cagagttcgg aggagcagtg tgtggcgcca cgtcccgact 4441 ggccataccc acacagaagc agtgctgccc ggggcctcat ctgggccagc ttggactctg 4501 cttcctccag gagcagcagg gaagctctgg gccacctccc tggatagcag gaacttgacc 4561 tgccatgtgt gccctgcctt cctggccagc tgtgcttgtt atcttccatt ctcacaaact 4621 gtctttgaag caatagaata aagaatgtgt gttttctttc ctggtataca tacatgatcc 4681 catgctccca agctccattc ttccttccct caactctctg ccctccacag agctatggag 4741 aaggctggag atgaaagctt tgtagtgagg actgataaag atctcatcac tgctccttat 4801 aataaaccta ataaagcaag aaaccaagcc taaaaaaaaa aaaaaaaaa a
```

Human vacuolar protein sorting 41 (VPS41) protein has the amino acid sequence (SEQ ID NO:13) (NCBI Reference Sequence: NM_014396.3):

```
MAEAEEQETG SLEESTDESE EEESEEEPKL KYERLSNGVT EILQKDAASC MTVHDKFLAL  60

GTHYGKVYLL DVQGNITQKF DVSPVKINQI SLDESGEHMG VCSEDGKVQV FGLYSGEEFH 120

ETFDCPIKII AVHPHFVRSS CKQFVTGGKK LLLFERSWMN RWKSAVLHEG EGNIRSVKWR 180

GHLIAWANNM GVKIFDIISK QRITNVPRDD ISLRPDMYPC SLCWKDNVTL IIGWGTSVKV 240

CSVKERHASE MRDLPSRYVE IVSQFETEFY ISGLAPLCDQ LVVLSYVKEI SEKTEREYCA 300

RPRLDIIQPL SETCEEISSD ALTVRGFQEN ECRDYHLEYS EGESLFYIVS PRDVVVAKER 360

DQDDHIDWLL EKKKYEEALM AAEISQKNIK RHKILDIGLA YINHLVERGD YDIAARKCQK 420

ILGKNAALWE YEVYKFKEIG QLKAISPYLP RGDPVLKPLI YEMILHEFLE SDYEGFATLI 480

REWPGDLYNN SVIVQAVRDH LKKDSQNKTL LKTLAELYTY DKNYGNALEI YLTLRHKDVF 540

QLIHKHNLFS SIKDKIVLLM DFDSEKAVDM LLDNEDKISI KKVVEELEDR PELQHVYLHK 600

LFKRDHHKGQ RYHEKQISLY AEYDRPNLLP FLRDSTHCPL EKALEICQQR NFVEETVYLL 660

SRMGNSRSAL KMIMEELHDV DKAIEFAKEQ DDGELWEDLI LYSIDKPPFI TGLLNNIGTH 720

VDPILLIHRI KEGMEIPNLR DSLVKILQDY NLQILLREGC KKILVADSLS LLKKMHRTQM 780

KGVLVDEENI CESCLSPILP SDAAKPFSVV VFHCRHMFHK ECLPMPSMNS AAQFCNICSA 840

KNRGPGSAIL EMKK                                                  854
```

Nucleic acid (mRNA) encoding human VPS41 protein has the nucleotide sequence (SEQ ID NO:14) (NCBI Reference Sequence: NM_014396.3):

```
   1 ctgtcaggtg actctcccgt ggcgccatgg cggaagcaga ggagcaggaa actgggtccc
  61 ttgaagaatc tacagatgag tctgaggaag aagagagcga agaggaaccc aagctgaagt
 121 atgaaaggct ttccaatggg gtaactgaaa tacttcagaa ggatgcagct agctgcatga
 181 cagtccatga caagtttttg gcatgggca cacattatgg caaggtttat ttacttgatg
 241 tccaggggaa catcactcag aagtttgatg taagtcctgt gaagataaat cagattagct
 301 tggatgaaag tggagagcac atgggtgtgt gttcagagga tggcaaggtg caggtatttg
 361 gactgtattc tggagaagaa tttcacgaga cttttgactg tcccattaaa attattgctg
 421 tgcacccaca tttcgtgaga tccagttgca agcagtttgt gaccggaggg aagaagctgc
 481 tactgtttga acggtcttgg atgaacagat ggaagtctgc tgttctgcat gaaggggaag
 541 ggaacataag gagtgtgaag tggagaggcc atctgattgc ttgggccaat aatatgggtg
 601 tgaagatttt tgacatcatc tcaaagcaaa gaatcaccaa tgtgcccgg gatgatataa
 661 gtcttcgccc agacatgtat ccctgcagcc tctgctggaa ggacaatgtg acactgatta
 721 ttggctgggg gacttctgtc aaggtgtgct cagtgaagga acggcatgcc agtgaaatga
 781 gggatttgcc aagtcgatat gttgaaatag tgtctcagtt tgaaactgaa ttctacatca
 841 gtggacttgc acctctctgt gatcagcttg ttgtactttc gtatgtaaag gagatttcag
 901 aaaaaacgga aagagaatac tgtgccaggc ctagactgga catcatccag ccactttctg
 961 agacttgtga agagatctct tctgatgctt tgacagtcag aggcttttcag gagaatgaat
1021 gtagagatta tcatttagaa tactctgaag gggaatcact tttttacatc gtgagtccga
1081 gagatgttgt agtggccaag gaacgagacc aagatgatca cattgactgg ctccttgaaa
1141 agaagaaata tgaagaagca ttgatggcag ctgaaattag ccaaaaaaat attaaaagac
1201 ataagattct ggatattggc ttggcatata taaatcacct ggtggagaga ggagactatg
1261 acatagcagc acgcaaatgc cagaaaattc ttgggaaaaa tgcagcactc tgggaatatg
1321 aagtttataa atttaaagaa attggacagc ttaaggctat tagtccttat ttgccaagag
1381 gtgatccagt tctgaaacca ctcatctatg aaatgatctt acatgaattt ttggagagtg
1441 attatgaggg ttttgccaca ttgatccgag aatggcctgg agatctgtat aataattcag
1501 tcatagttca agcagttcgg gatcatttga gaaaagatag tcagaacaag actttactta
1561 aaaccctggc agaattgtac acctatgaca agaactatgg caatgctctg gaaatatact
1621 taacattaag acataaagac gtttttcagt tgatccacaa gcataatctt ttcagttcta
1681 tcaaggataa aattgtttta ttaatggatt ttgattcaga gaaagctgtt gacatgcttt
1741 tggacaatga agataaaatt tcaattaaaa aggtagtgga agaattggaa gacagaccag
1801 agctacagca tgtgtatttg cataagcttt tcaagagaga ccaccataag gggcagcgtt
1861 accatgaaaa acagatcagt ctttatgctg aatatgatcg accaaactta cttcccttc
1921 tccgagacag tacccattgc ccacttgaaa aggctcttga gatctgtcaa cagagaaact
1981 ttgtagaaga gacagtttat cttctgagcc gaatgggtaa tagccgaagt gccctgaaga
2041 tgattatgga ggaattacat gatgttgata aagcaatcga atttgccaag gagcaagatg
2101 atggagagct gtgggaagat ttgattttat attccattga caaaccacca tttattactg
2161 gcttgttaaa caacattggc acacatgttg acccaattct actgattcac cgtattaagg
2221 aaggaatgga gatccccaat ttgagagatt ccttggttaa aattctgcaa gactacaatt
```

-continued

```
2281 tgcaaattct gcttcgtgaa ggctgcaaga agattctcgt agctgactct ttgtccttac 2341 tgaagaaaat gcaccgaact caaatgaaag gtgttcttgt tgatgaggag aacatctgtg 2401 agtcgtgcct ttcccctatt cttccatcag atgcagctaa gcccttcagc gtggtggtct 2461 tccattgccg gcacatgttc cacaaggagt gcctgcccat gcccagcatg aactctgctg 2521 cacagttctg caacatctgc agtgctaaga accgtggacc aggaagtgca attttggaga 2581 tgaaaaaata gctcatttct ccttgtcagt ctccttgtca ccactctttt tgagactgtt 2641 tttgcaacaa caaaagcatt tgttgacact cgtgctgtta agagatttgt ttatgtttat 2701 attatactca aaaacaattt cttcatctat tcctgtacta atggtttctc tttgcagttc 2761 acagagaatt tggggctctc ttcatgcctt gaaattttgg ggtccatagt gaatattttg 2821 ttatttattt gtttggctca ttctttatat agtaatggaa acataagtct aggagttaga 2881 aatgaatttt ttagacctta gtaaaaccat ttaaccataa aatggacaac tgagaattct 2941 cccagctgcc tgaaagcgtc gccaactgtg gttatcctgc aagctgctac ctgcaacttg 3001 gacgttgttt ccacgtgctc tgctggctac gattcttgca ttctgggttt ggctttttc 3061 tgtgtcatca actatggtta tcctctaaat aggcatttaa tgaaacattg tacaaattgt 3121 cactcatttg atgacacctg gaataacat tagcaggctg atgtcctgca ccattatgtt 3181 tactaatcac atgttctgtg tgctgtgacg actgtcaaag agtatctggc catggcggac 3241 actcagcatt tgttgattga ataaatgtta gctcttctca ttgtgaagga ctcactttta 3301 ctgggataaa caaatgcagt taagaattct ggcacccttg taaggaagaa aagagagttc 3361 aacaccttcg agtctgagcg cttgtggcta gagtttgcca ggaggagga aaccagtgac 3421 cctgaaaact gagggtgcct caggagcagt gggaccacct gatgctgaag gacggactaa 3481 tgatgtttcc tcttgccttc tctggtgcct ccattgccct catggaacag agcatatcat 3541 agagggagaa aagtcaaact tgtaattgtg tcttacagtt actggcttca tcttccttgg 3601 gatatatggt catcctctaa tgagtgtaaa agtgcgcaaa acacatcctt attgttcctg 3661 atctcttagt cccataaatg ggaacaaata cagctttctg cttcttttctt tttggggaaa 3721 ggacagggtg ctagtgagta ctgacagcat gccagctacc gaagtcaccc agccattccc 3781 atgagcagca gttcatttaa ttgtcacagc gtcgccagga agaagatctg ataaacctag 3841 gtttacagat aaagaaagca aaatgtagag atgttgttga ggtcacagag gtgactgcct 3901 aacttcagag cagggcttct gatcccttta agaaattaca gggccagccg gcatggtgg 3961 ctcacgcccg taatcccagg gctttgggag gccttggcag gtggatcacc tgagatcgca 4021 cgttcgagac cagcctgacc aacatggaga acccccatct ctactaaaaa cacaaattag 4081 ccaggcgtgg tggtacatgc ctgtaatccc agctactcag gaggctgagg caggagaatc 4141 acttgacccc aggagacgta ggttgtggtg agctgagatc gcgccattgc actccagcct 4201 gggcaacaag agcaaaactc cgtctcaaaa aagaaaagaa aagaaaagaa atcatagggc 4261 caagttcaaa ggaaatgcac agaacatatc ttcacattag agttaagaat tctctagcaa 4321 acaacagatt ttttgttgt tgttagtcac aaatacttag aactggaagg ctctttgtta 4381 ttattgaatg taccctcag ccttctcagc atttccttat cccaagacta gtgtgctttc 4441 tgctacactg ctagttttca gttttgttct tacccaattg ttttttcttt tcaacattac 4501 caatttacag attcagttta ttacatttac attaatcctc acttatgatt tgagcaagct 4561 catttccaga aaagtttact ttaagatcat caataggatt tgctaatttc agtgaagtca 4621 ttttgcttca ggggtaaatt atcctagtta ccaagtccta tttggacata agaaaatcc 4681 tacttataga aaaggagaaa ataattaaac agtcttcatt tttaagtaac tgatttaaaa
```

-continued

```
4741 ggaaaataat aaaatatgtt cgtttatcat ttcagaaatt gctgtaacac actggaaaat 4801 tcctgaacaa tatagatttt atcgttaata aaaaacacta gctttcgttc cttagaatgt 4861 cttttctttt gaataaacag tattgggtga ttta
```

Human BLOC1S1 protein has the amino acid sequence (SEQ ID NO:15) (NCBI Reference Sequence: NM_001487.3):

```
MAPGSRGERS SFRSRRGPGV PSPQPDVTML SRLLKEHQAK QNERKELQEK RRREAITAAT    60
CLTEALVDHL NVGVAQAYMN QRKLDHEVKT LQVQAAQFAK QTGQWIGMVE NFNQALKEIG   120
DVENWARSIE LDMRTIATAL EYVYKGQLQS APS                                153
```

Nucleic acid (mRNA) encoding human BLOC1S1 protein has the nucleotide sequence (SEQ ID NO:16) (NCBI Reference Sequence: NM_001487.3):

```
  1 acacagcggt cacgtgacat ggccccgggg agccgaggtg agcgttccag cttccggagc 61 cggagggggc ccggcgtacc cagccccag cccgacgtga ccatgctgtc ccgcctccta 121 aaagaacacc aggccaagca gaatgaacgc aaggagctgc aggaaaagag gaggcgagag 181 gctatcactg cagcgacctg cctgacagaa gctttggtgg atcacctcaa tgtgggtgtg 241 gcccaggcct acatgaacca gagaaagctg gaccatgagg tgaagaccct acaggtccag 301 gctgcccaat tgccaagca gacaggccag tggatcggaa tggtggagaa cttcaaccag 361 gcactcaagg aaattgggga tgtggagaac tgggctcgga gcatcgagct ggacatgcgc 421 accattgcca ctgcactgga atatgtctac aaagggcagc tgcagtctgc cccttcctag 481 cccctgttcc ctcccccaac cctatccctc ctacctcacc cgcaggggga aggagggagg 541 ctgacaagcc ttgaataaaa cacaagcctc cgtttctcaa aaaaaaaaa
```

Human BLOC1S2 protein has the amino acid sequence (SEQ ID NO:17) (NCBI Reference Sequence: NM_173809.2):

```
MAAAAEGVLA TRSDEPARDD AAVETAEEAK EPAEADITEL CRDMFSKMAT YLTGELTATS    60
EDYKLLENMN KLTSLKYLEM KDIAINISRN LKDLNQKYAG LQPYLDQINV IEEQVAALEQ   120
AAYKLDAYSK KLEAKYKKLE KR                                            142
```

Nucleic acid (mRNA) encoding human BLOC1S2 protein has the nucleotide sequence (SEQ ID NO:18) (NCBI Reference Sequence: NM_173809.2):

```
  1 ccggaaacag cgcggggtcc gctatggcgg cggcagccga gggcgtactg gcgacccgga 61 gtgatgagcc cgcccgagac gatgccgccg tggagacagc tgaggaagca aaggagcctg 121 ctgaagctga catcactgag ctctgccggg acatgttctc caaaatggcc acttacctga 181 ctggggaact gacggccacc agtgaagact ataagctcct ggaaaatatg aataaactca 241 ccagcttgaa gtatcttgaa atgaaagata ttgctataaa cattagtagg aacttaaagg 301 acttaaacca gaaatatgct ggactgcagc cttatctgga tcagatcaat gtcattgaag 361 agcaggtagc agctcttgag caggcagctt acaagttgga tgcatattca aaaaaactgg 421 aagccaagta caagaagctg gagaagcgat gagaaactta tttctatggg acagagtctt 481 ttttttttaa tgtggaagaa tgtcttataa aacctgaatc ctgaggctga tgaattgtga
```

-continued

```
 541 aaattcctca aaaggaaatt atgctggtca tcacaggaac atctcaacgt tcgagtaaac 601 tggaggactg tggctattcc tgaaccttct ttgagacaga atccctcaga atctcacact 661 tataacttcc tacctttac  ttgaatgctt tgccatattc aggacagaga ctctcacaaa 721 gttcagaaaa cagctggact taccagtaaa atcaaatgag aggacctatt ttctctggta 781 gtggttgatt actacattat tttcttaagt ggctggtttt ttagttacta tgtaaatggt 841 cgtttttctg ttaatgatgc taatgtgttg taaacaagat tctaaattta aaaggaaaa 901 caaacaaac  ttgttctttg cagcttatca ccttgtgaat gtcggtaact tacttttcca 961 taatattgca ataacataa  aatcttaaaa taattccaag ctgagtcttc tagattgagc 1021 agaaatggtg aaaggagtat tgataacttg gcgtatgtga tgggcccctc ttgtttattt 1081 tctatgtgag tcacattgac atgcgatcag tttgggaaat gtgatgaaaa caaagactag 1141 atgggtatgt gtgtttatgt gttgggtagg gaggtgacga ttgccactca taaaataaag 1201 gattttataa aataccttcc tactgtgtat gtaggatttg gggggatctt agggacctaa 1261 tcgacttctt tgcacactaa aaacatcaga caatgggaca tactgactga ccagtctagg 1321 ttgaaagata ggcagcctta cccagaacac aacattagca gctgggaagg tgtctgaggt 1381 ccccaattac atatcccaaa gagtttctta cttctgtttc tgtcatttcc cctctgttcc 1441 agacagtcat catttatcct ctgttcttcc tggactgttg ctgtggtctc ttctcatctt 1501 aactgtccct tccaaccacc ctccacactg ctgccagagc aatcttaaaa atgtaaactg 1561 gccctattac tcctgcttag aaccctgtag tgacttatca tggcctctga aaaatctaga 1621 ctttcattat gcatacaagt cccttgtgtt tttttgtttg tttatagaca gggtctctat 1681 tgtcacccag gctggagtgt ggtggtgtga taatagctca ccttgacctc ctaggctcaa 1741 ctgatcttcc cacctcagcc tcctgaatag ctgggactac cagcacgctc caccatgcct 1801 tgctaattat tttttataca gatggagtct cactatgttg tccaggctgg tcttgaactg 1861 gcctcaagtg attctcttac cacagcctgc cagagtgctg agattgtagg catgaaccac 1921 cgtgcctaac ataaggcccc tatttaaaca tttttctt
```

40

Human N-acetylglucosamine-1-phosphate transferase, alpha and beta subunits (GNPTAB) protein has the amino acid sequence (SEQ ID NO:19) (NCBI Reference Sequence: NM_024312.4):

```
MLFKLLQRQT YTCLSHRYGL YVCFLGVVVT IVSAFQFGEV VLEWSRDQYH VLFDSYRDNI      60

AGKSFQNRLC LPMPIDVVYT WVNGTDLELL KELQQVREQM EEEQKAMREI LGKNTTEPTK     120

KSEKQLECLL THCIKVPMLV LDPALPANIT LKDLPSLYPS FHSASDIFNV AKPKNPSTNV     180

SVVVFDSTKD VEDAHSGLLK GNSRQTVWRG YLTTDKEVPG LVLMQDLAFL SGFPPTFKET     240

NQLKTKLPEN LSSKVKLLQL YSEASVALLK LNNPKDFQEL NKQTKKNMTI DGKELTISPA     300

YLLWDLSAIS QSKQDEDISA SRFEDNEELR YSLRSIERHA PWVRNIFIVT NGQIPSWLNL     360

DNPRVTIVTH QDVFRNLSHL PTFSSPAIES HIHRIEGLSQ KFIYLNDDVM FGKDVWPDDF     420

YSHSKGQKVY LTWPVPNCAE GCPGSWIKDG YCDKACNNSA CDWDGGDCSG NSGGSRYIAG     480

GGGTGSIGVG QPWQFGGGIN SVSYCNQGCA NSWLADKFCD QACNVLSCGF DAGDCGQDHF     540

HELYKVILLP NQTHYIIPKG ECLPYFSFAE VAKRGVEGAY SDNPIIRHAS IANKWKTIHL     600

IMHSGMNATT IHFNLTFQNT NDEEFKMQIT VEVDTREGPK LNSTAQKGYE NLVSPITLLP     660

EAEILFEDIP KEKRFPKFKR HDVNSTRRAQ EEVKIPLVNI SLLPKDAQLS LNTLDLQLEH     720

GDITLKGYNL SKSALLRSFL MNSQHAKIKN QAIITDETND SLVAPQEKQV HKSILPNSLG     780
```

-continued

```
VSERLQRLTF PAVSVKVNGH DQGQNPPLDL ETTARFRVET HTQKTIGGNV TKEKPPSLIV    840

PLESQMTKEK KITGKEKENS RMEENAENHI GVTEVLLGRK LQHYTDSYLG FLPWEKKKYF    900

QDLLDEEESL KTQLAYFTDS KNTGRQLKDT FADSLRYVNK ILNSKFGFTS RKVPAHMPHM    960

IDRIVMQELQ DMFPEEFDKT SFHKVRHSED MQFAFSYFYY LMSAVQPLNI SQVFDEVDTD   1020

QSGVLSDREI RTLATRIHEL PLSLQDLTGL EHMLINCSKM LPADITQLNN IPPTQESYYD   1080

PNLPPVTKSL VTNCKPVTDK IHKAYKDKNK YRFEIMGEEE IAFKMIRTNV SHVVGQLDDI   1140

RKNPRKFVCL NDNIDHNHKD AQTVKAVLRD FYESMFPIPS QFELPREYRN RFLHMHELQE   1200

WRAYRDKLKF WTHCVLATLI MFTIFSFFAE QLIALKRKIF PRRRIHKEAS PNRIRV       1256
```

Nucleic acid (mRNA) encoding human GNPTAB protein has the nucleotide sequence (SEQ ID NO:20) (NCBI Reference Sequence: NM_024312.4):

```
   1 gctcccggaa gcggcggccg cggcgcggag ccgagcgggc gtccgtcgcc ggagctgcaa 61 tgagcggcgc ccggaggctg tgacctgcgc gcggcggccc gaccgggcc cctgaatggc 121 ggctcgctga ggcggcggcg gcggcggcgg cggctcaggc tcctcgggc gtggcgtggc 181 ggtgaagggg tgatgctgtt caagctcctg cagagacaga cctatacctg cctgtcccac 241 aggtatgggc tctacgtgtg cttcttgggc gtcgttgtca ccatcgtctc cgccttccag 301 ttcggagagg tggttctgga atggagccga gatcaatacc atgttttgtt tgattcctat 361 agagacaata ttgctggaaa gtcctttcag aatcggcttt gtctgcccat gccgattgac 421 gttgtttaca cctgggtgaa tggcacagat cttgaactac tgaaggaact acagcaggtc 481 agaaacagac tggaggagga gcagaaagca atgagagaaa tccttgggaa aaacacaacg 541 gaacctacta agaagagtga aagcagtta gagtgtttgc taacacactg cattaaggtg 601 ccaatgcttg tcctggaccc agccctgcca gccaacatca ccctgaagga cctgccatct 661 ctttatcctt cttttcattc tgccagtgac attttcaatg ttgcaaaacc aaaaaaccct 721 tctaccaatg tctcagttgt tgttttttgac agtactaagg atgttgaaga tgcccactct 781 ggactgctta aaggaaatag cagacagaca gtatggaggg gctacttgac aacagataaa 841 gaagtccctg gattagtgct aatgcaagat ttggctttcc tgagtggatt ccaccaaca 901 ttcaaggaaa caaatcaact aaaaacaaaa ttgccagaaa atctttcctc taaagtcaaa 961 ctgttgcagt tgtattcaga ggccagtgta gcgcttctaa aactgaataa ccccaaggat 1021 tttcaagaat tgaataagca aactaagaag aacatgacca ttgatggaaa agaactgacc 1081 ataagtcctg catatttatt atgggatctg agcgccatca gccagtctaa gcaggatgaa 1141 gacatctctg ccagtcgttt tgaagataac gaagaactga ggtactcatt gcgatctatc 1201 gagaggcatg caccatgggt tcggaatatt tcattgtca ccaacgggca gattccatcc 1261 tggctgaacc ttgacaatcc tcgagtgaca atagtaacac accaggatgt ttttcgaaat 1321 ttgagccact tgcctacctt tagttcacct gctattgaaa gtcacattca tcgcatcgaa 1381 gggctgtccc agaagtttat ttacctaaat gatgatgtca tgtttgggaa ggatgtctgg 1441 ccagatgatt tttacagtca ctccaaaggc cagaaggttt atttgacatg gcctgtgcca 1501 aactgtgccg agggctgccc aggttcctgg attaaggatg ctattgtga caaggcttgt 1561 aataattcag cctgcgattg ggatggtggg gattgctctg gaaacagtgg agggagtcgc 1621 tatattgcag gaggtggagg tactgggagt attggagttg acagccctg gcagtttggt 1681 ggaggaataa acagtgtctc ttactgtaat cagggatgtg cgaattcctg gctcgctgat
```

-continued

```
1741 aagttctgtg accaagcatg caatgtcttg tcctgtgggt ttgatgctgg cgactgtggg 1801 caagatcatt ttcatgaatt gtataaagtg atccttctcc caaaccagac tcactatatt 1861 attccaaaag gtgaatgcct gccttatttc agctttgcag aagtagccaa aagaggagtt 1921 gaaggtgcct atagtgacaa tccaataatt cgacatgctt ctattgccaa caagtggaaa 1981 accatccacc tcataatgca cagtggaatg aatgccacca caatacattt taatctcacg 2041 tttcaaaata caaacgatga agagttcaaa atgcagataa cagtggaggt ggacacaagg 2101 gagggaccaa aactgaattc tacagcccag aagggttacg aaaatttagt tagtcccata 2161 acacttcttc cagaggcgga aatccttttt gaggatattc ccaaagaaaa acgcttcccg 2221 aagtttaaga gacatgatgt taactcaaca aggagagccc aggaagaggt gaaaattccc 2281 ctggtaaata tttcactcct tccaaaagac gcccagttga gtctcaatac cttggatttg 2341 caactggaac atggagacat cactttgaaa ggatacaatt tgtccaagtc agccttgctg 2401 agatcatttc tgatgaactc acagcatgct aaaataaaaa atcaagctat aataacagat 2461 gaaacaaatg acagtttggt ggctccacag gaaaaacagg ttcataaaag catcttgcca 2521 aacagcttag gagtgtctga aagattgcag aggttgactt ttcctgcagt gagtgtaaaa 2581 gtgaatggtc atgaccaggg tcagaatcca cccctggact tggagaccac agcaagattt 2641 agagtggaaa ctcacaccca aaaaaccata ggcggaaatg tgacaaaaga aaagccccca 2701 tctctgattg ttccactgga aagccagatg acaaaagaaa agaaaatcac agggaaagaa 2761 aaagagaaca gtagaatgga ggaaaatgct gaaaatcaca taggcgttac tgaagtgtta 2821 cttggaagaa agctgcagca ttacacagat agttacttgg gcttttttgcc atgggagaaa 2881 aaaaagtatt tccaagatct tctcgacgaa gaagagtcat tgaagacaca attggcatac 2941 ttcactgata gcaaaaatac tgggaggcaa ctaaaagata catttgcaga ttccctcaga 3001 tatgtaaata aaattctaaa tagcaagttt ggattcacat cgcggaaagt ccctgctcac 3061 atgcctcaca tgattgaccg gattgttatg caagaactgc aagatatgtt ccctgaagaa 3121 tttgacaaga cgtcatttca caaagtgcgc cattctgagg atatgcagtt tgccttctct 3181 tatttttatt atctcatgag tgcagtgcag ccactgaata tatctcaagt ctttgatgaa 3241 gttgatacag atcaatctgg tgtcttgtct gacagagaaa tccgaacact ggctaccaga 3301 attcacgaac tgccgttaag tttgcaggat ttgacaggtc tggaacacat gctaataaat 3361 tgctcaaaaa tgcttcctgc tgatatcacg cagctaaata atattccacc aactcaggaa 3421 tcctactatg atcccaacct gccaccggtc actaaaagtc tagtaacaaa ctgtaaacca 3481 gtaactgaca aaatccacaa agcatataag gacaaaaaca aatataggtt tgaaatcatg 3541 ggagaagaag aaatcgcttt taaaatgatt cgtaccaacg tttctcatgt ggttggccag 3601 ttggatgaca taagaaaaaa ccctaggaag tttgtttgcc tgaatgacaa cattgaccac 3661 aatcataaag atgctcagac agtgaaggct gttctcaggg acttctatga atccatgttc 3721 cccatacctt cccaatttga actgccaaga gagtatcgaa accgtttcct tcatatgcat 3781 gagctgcagg aatggagggc ttatcgagac aaattgaagt tttggaccca ttgtgtacta 3841 gcaacattga ttatgtttac tatattctca tttttttgctg agcagttaat tgcacttaag 3901 cggaagatat ttcccagaag gaggatacac aaagaagcta gtcccaatcg aatcagagta 3961 tagaagatct tcatttgaaa accatctacc tcagcattta ctgagcattt taaaactcag 4021 cttcacagag atgtctttgt gatgtgatgc ttagcagttt ggcccgaaga aggaaaatat 4081 ccagtaccat gctgttttgt ggcatgaata tagcccactg accaggaatt atttaaccaa 4141 cccactgaaa acttgtgtgt tgagcagctc tgaactgatt ttacttttaa agaatttgct
```

-continued

```
4201 catggacctg tcatccttt tataaaaagg ctcactgaca agagacagct gttaatttcc 4261 cacagcaatc attgcagact aactttatta ggagaagcct atgccagctg ggagtgattg 4321 ctaagaggct ccagtctttg cattccaaag cctttgcta aagttttgca ctttttttt 4381 ttcatttccc atttttaagt agttactaag ttaactagtt attcttgctt ctgagtataa 4441 cgaattggga tgtctaaacc tatttttata gatgttattt aaataatgca gcaatatcac 4501 ctcttattga caatacctaa attatgagtt ttattaatat ttaagactgt aaatggtctt 4561 aaaccactaa ctactgaaga gctcaatgat tgacatctga aatgctttgt aattattgac 4621 ttcagcccct aagaatgcta tgatttcacg tgcaggtcta atttcaaagg gctagagtta 4681 gtactactta ccagatgtaa ttatgttttg gaaatgtaca tattcaaaca gaagtgcctc 4741 attttagaaa tgagtagtgc tgatggcact ggcacattac agtggtgtct tgtttaatac 4801 tcattggtat attccagtag ctatctctct cagttggttt ttgatagaac agaggccagc 4861 aaactttctt tgtaaaaggc tggttagtaa attattgcag gccacctgtg tctttgtcat 4921 acattcttct tgctgttgtt tagtttgttt tttttcaaac aaccctctaa aaatgtaaaa 4981 accatgttta gcttgcagct gtacaaaaac tgcccaccag ccagatgtga ccctcaggcc 5041 atcatttgcc aatcactgag aattagtttt tgttgttgtt gttgttgttg ttttttgagac 5101 agagtctctc tctgttgccc aggctggagt gcagtggcgc aatctcagct cactgcaacc 5161 tccgcctccc gggttcaagc agttctgtct cagccttctg agtagctggg actacaggtg 5221 catgccacca caccctgcta attttgtat ttttagtaga cgggggtt ccaccatatt 5281 ggtcaggctt atcttgaact cctgacctca ggtgatccac ctgcctctgc ctcccaaagt 5341 gctgagatta caggcataag ccagtgcacc cagccgagaa ttagtatttt tatgtatggt 5401 taaaccttgg cgtctagcca tatttatgt cataatacaa tggatttgtg aagagcagat 5461 tccatgagta actctgacag gtattttaga tcatgatctc aacaatattc ttccaaaatg 5521 gcatacatct tttgtacaaa gaacttgaaa tgtaaatact gtgtttgtgc tgtaagagtt 5581 gtgtatttca aaaactgaaa tctcataaaa agttaaattt ttgtctgaca aaaaaaaaa 5641 aaaa
```

Human phosphoinositide kinase, FYVE finger containing (PIKFYVE) protein has the amino acid sequence (SEQ ID NO:21) (NCBI Reference Sequence: NM_015040.3):

```
MATDDKTSPT LDSANDLPRS PTSPSHLTHF KPLTPDQDEP PFKSAYSSFV NLFRFNKERA      60

EGGQGEQQPL SGSWTSPQLP SRTQSVRSPT PYKKQLNEEL QRRSSALDTR RKAEPTFGGH     120

DPRTAVQLRS LSTVLKRLKE IMEGKSQDSD LKQYWMPDSQ CKECYDCSEK FTTFRRRHHC     180

RLCGQIFCSR CCNQEIPGKF MGYTGDLRAC TYCRKIALSY AHSTDSNSIG EDLNALSDSA     240

CSVSVLDPSE PRTPVGSRKA SRNIFLEDDL AWQSLIHPDS SNTPLSTRLV SVQEDAGKSP     300

ARNRSASITN LSLDRSGSPM VPSYETSVSP QANRTYVRTE TTEDERKILL DSVQLKDLWK     360

KICHHSSGME FQDHRYWLRT HPNCIVGKEL VNWLIRNGHI ATRAQAIAIG QAMVDGRWLD     420

CVSHHDQLFR DEYALYRPLQ STEFSETPSP DSDSVNSVEG HSEPSWFKDI KFDDSDTEQI     480

AEEGDDNLAN SASPSKRTSV SSFQSTVDSD SAASISLNVE LDNVNFHIKK PSKYPHVPPH     540

PADQKEYLIS DTGGQQLSIS DAFIKESLFN RRVEEKSKEL PFTPLGWHHN NLELLREENG     600

EKQAMERLLS ANHNHMMALL QQLLHSDSLS SSWRDIIVSL VCQVVQTVRP DVKNQDDDMD     660

IRQFVHIKKI PGGKKFDSVV VNGFVCTKNI AHKKMSSCIK NPKILLLKCS IEYLYREETK     720
```

-continued

```
FTCIDPIVLQ EREFLKNYVQ RIVDVRPTLV LVEKTVSRIA QDMLLEHGIT LVINVKSQVL    780
ERISRMTQGD LVMSMDQLLT KPHLGTCHKF YMQIFQLPNE QTKTLMFFEG CPQHLGCTIK    840
LRGGSDYELA RVKEILIFMI CVAYHSQLEI SFLMDEFAMP PTLMQNPSFH SLIEGRGHEG    900
AVQEQYGGGS IPWDPDIPPE SLPCDDSSLL ELRIVFEKGE QENKNLPQAV ASVKHQEHST    960
TACPAGLPCA FFAPVPESLL PLPVDDQQDA LGSEQPETLQ QTVVLQDPKS QIRAFRDPLQ   1020
DDTGLYVTEE VTSSEDKRKT YSLAFKQELK DVILCISPVI TFREPFLLTE KGMRCSTRDY   1080
FAEQVYWSPL LNKEFKEMEN RRKKQLLRDL SGLQGMNGSI QAKSIQVLPS HELVSTRIAE   1140
HLGDSQSLGR MLADYRARGG RIQPKNSDPF AHSKDASSTS SGQSGSKNEG DEERGLILSD   1200
AVWSTKVDCL NPINHQRLCV LFSSSSAQSS NAPSACVSPW IVTMEFYGKN DLTLGIFLER   1260
YCFRPSYQCP SMFCDTPMVH HIRRFVHGQG CVQIILKELD SPVPGYQHTI LTYSWCRICK   1320
QVTPVVALSN ESWSMSFAKY LELRFYGHQY TRRANAEPCG HSIHHDYHQY FSYNQMVASF   1380
SYSPIRLLEV CVPLPKIFIK RQAPLKVSLL QDLKDFFQKV SQVYVAIDER LASLKTDTFS   1440
KTREEKMEDI FAQKEMEEGE FKNWIEKMQA RLMSSSVDTP QQLQSVFESL IAKKQSLCEV   1500
LQAWNNRLQD LFQQEKGRKR PSVPPSPGRL RQGEESKISA MDASPRNISP GLQNGEKEDR   1560
FLTTLSSQSS TSSTHLQLPT PPEVMSEQSV GGPPELDTAS SSEDVFDGHL LGSTDSQVKE   1620
KSTMKAIFAN LLPGNSYNPI PFPFDPDKHY LMYEHERVPI AVCEKEPSSI IAFALSCKEY   1680
RNALEELSKA TQWNSAEEGL PTNSTSDSRP KSSSPIRLPE MSGGQTNRTT ETEPQPTKKA   1740
SGMLSFFRGT AGKSPDLSSQ KRETLRGADS AYYQVGQTGK EGTENQGVEP QDEVDGGDTQ   1800
KKQLINPHVE LQFSDANAKF YCRLYYAGEF HKMREVILDS SEEDFIRSLS HSSPWQARGG   1860
KSGAAFYATE DDRFILKQMP RLEVQSFLDF APHYFNYITN AVQQKRPTAL AKILGVYRIG   1920
YKNSQNNTEK KLDLLVMENL FYGRKMAQVF DLKGSLRNRN VKTDTGKESC DVVLLDENLL   1980
KMVRDNPLYI RSHSKAVLRT SIHSDSHFLS SHLIIDYSLL VGRDDTSNEL VVGIIDYIRT   2040
FTWDKKLEMV VKSTGILGGQ GKMPTVVSPE LYRTRFCEAM DKYFLMVPDH WTGLGLNC    2098
```

Nucleic acid (mRNA) encoding human PIKFYVE protein has the nucleotide sequence (SEQ ID NO:22) (NCBI Reference Sequence: NM_015040.3):

```
  1 caaccatgta agcagcttcg cttcctgccg caaccgtccg cggcctgagg agcccaccgc
 61 cgctctcggg ggccgacttc cgggggctga gccgttgaag cggaggctgg ggcgggggc
121 agccggcgcg gccggggcag gaggcgcaga ctcatgaaat ggccacagat gataagacgt
181 ccccaacact ggactctgct aatgatttgc ctcgatctcc tactagtcct tctcatctca
241 cacactttaa acctttgact cctgatcaag atgagccccc ttttaaatca gcttatagtt
301 cttttgtaaa tctctttcgt tttaacaaag agagagcaga aggaggccag ggagaacagc
361 agcctttgag tggaagttgg accagccctc agctcccttc gaggacacag tctgttaggt
421 cacccacacc ttataaaaag cagcttaatg aggaactcca gcggcgctct tcagcattag
481 acacaagaag gaaagcagaa cctaccttg gaggtcatga ccctcgtaca gctgttcagc
541 ttcgaagcct cagcacagta ttaaaacgcc tcaaggaaat catggagggg aaaagccagg
601 atagtgacct gaaacaatac tggatgccag atagccaatg taaagagtgc tatgactgta
661 gtgagaaatt tacaaccttt aggcgcagac accattgccg actatgtggg cagattttct
721 gcagtcgttg ctgtaatcaa gaaatccctg gaaaatttat gggctataca ggagacctcc
781 gagcttgcac atattgtaga aaaatagcct taagttatgc tcattccaca gacagtaatt
```

```
 841 ctattgggga agacttgaat gctctttcag attctgcttg ctctgtgtct gtgcttgatc 901 caagtgaacc ccgaacacct gttgggagta ggaaagccag ccgtaacata tttttagagg 961 atgatttggc ctggcaaagt tgattcatc cagattcctc aaatactcct ctttcaacaa 1021 gacttgtatc tgtgcaagag gatgctggga atctcctgc tcgaaataga tcagccagca 1081 ttactaacct gtcactggat agatctggtt ctcctatggt accttcatat gagacatctg 1141 tcagtcccca ggctaaccga acatatgtta ggacagagac cactgaggat gaacgcaaaa 1201 ttcttctgga cagtgtgcag ttaaaagacc tgtggaaaaa atctgccat cacagcagtg 1261 gaatggagtt tcaggatcac cgctactggt tgagaacgca tcccaactgc attgtaggaa 1321 aggaattagt caactggcta atccgaaatg gcatattgc cacaagggca caagctatag 1381 caattggaca agcaatggtt gatggacgtt ggctggattg tgttagtcat cacgaccagc 1441 ttttcagaga tgagtatgcg ctgtatagac cactgcagag tacagaattt tctgagacgc 1501 cttctcccga cagtgactca gtgaactccg tggaaggaca ctctgagcca tcctggttta 1561 aagacataaa gtttgatgac agtgacacag aacagatagc tgaagaaggt gacgataatt 1621 tggctaattc tgccagtcct agcaagcgca catcagtcag cagtttccag tccacagtgg 1681 acagtgactc agccgcttct atcagcctga acgtggagct ggacaacgtg aacttccata 1741 tcaagaagcc ctccaagtac ccacatgtgc cccctcaccc tgctgaccaa aaagagtatt 1801 tgatttctga cactggagga caacagctct caataagtga cgctttcatc aaagaatcct 1861 tatttaatcg ccgagtagag gaaaaatcca aagagctgcc tttcacacct tgggctggc 1921 atcataacaa cctggagctc ctgagggagg agaatgggga gaaacaagcc atggagaggt 1981 tgctttcagc taatcataac cacatgatgg cactactcca gcagttgctc catagtgact 2041 cactgtcatc atcttggagg gacatcatcg tgtcattggt ctgccaggtt gttcagacag 2101 tccgacctga tgtcaagaac caggatgatg acatggatat ccgtcagttt gtccacatca 2161 aaaaaatccc aggtggaaag aagtttgatt ctgtggttgt caatggcttt gtttgtacca 2221 agaacattgc acataaaaag atgagttctt gtattaaaaa ccccaaaatt cttctgttga 2281 agtgttccat tgagtatctc tacagagaag aaactaagtt tacttgcatt gatcctattg 2341 tgcttcagga aagggaattc ttgaagaatt atgtccagcg aatagttgat gttcgaccca 2401 ccttggttct tgttgagaaa acagtgtctc ggattgccca ggacatgtta ttggaacatg 2461 gcattacttt ggtcattaat gtaaagtcac aagttttgga acgaatcagt cgaatgaccc 2521 aaggtgattt agtgatgtca atggaccagc tgcttacgaa accacacctg gcacttgtc 2581 acaaatttta tatgcagata tttcagttgc ctaatgaaca aaccaagaca ctgatgtttt 2641 ttgaaggttg tccacagcac ctaggctgta caatcaagct aagaggaggc tctgattatg 2701 agctggctcg agttaaggag atcctaatat ttatgatctg tgttgcttat cattctcaac 2761 tagaaatatc ctttctcatg gatgaatttg ctatgcctcc cacattaatg caaaaccctt 2821 cattccattc cctgattgag ggacgagggc atgaggggc tgtccaagag cagtacggtg 2881 gaggttccat cccctgggat cctgacatcc ctcctgagtc tctgccctgt gatgatagca 2941 gtttgctgga attgaggatt gtgtttgaga agggtgagca ggaaaataaa atcttccgc 3001 aggctgttgc ctctgtgaag catcaagaac atagcacaac agcttgcccg gcgggtctcc 3061 cttgtgcttt ctttgcacct gtaccggaat cattgttgcc actccctgtg gatgaccaac 3121 aagatgcttt aggcagcgag cagccagaga ctttgcagca aacagttgtg ctgcaggatc 3181 ccaaaagcca gataagagcc tttagagacc ctctacagga tgacactgga ttatatgtta
```

-continued

```
3241 ctgaggaagt cacctcctct gaagataaac gaaagactta ttctttggcc tttaagcagg
3301 aattaaaaga tgtgatcctc tgtatctccc cagtaatcac attccgagaa ccctttcttt
3361 taactgaaaa ggggatgaga tgctctaccc gagattattt tgcagagcag gtttactggt
3421 ctcctctcct caataaagaa ttcaaagaaa tggagaacag gaggaagaaa cagctgctca
3481 gggatctctc tggacttcag ggcatgaatg gaagtattca ggccaagtct attcaagtct
3541 taccctcaca tgagctagtg agcactagaa ttgctgagca tctgggcgat agccagagct
3601 tgggtagaat gctggccgat tatcgagcca gaggaggaag aattcagccc aaaaattcag
3661 acccttttgc tcattcaaag gatgcatcaa gtacttcaag tggccaatca ggaagcaaaa
3721 atgagggtga tgaagagaga gggcttattc tgagtgatgc tgtgtggtca acaaaggtgg
3781 actgtctgaa tcccattaat caccagagac tttgtgtgct cttcagcagc tcttctgccc
3841 agtccagcaa tgctcctagt gcctgtgtca gtccttggat tgtaacaatg gaattttatg
3901 gaaagaatga tcttacatta ggaatatttt tagagagata ctgtttcagg ccttcttatc
3961 agtgtccaag catgttctgt gatacccca tggtacatca tattcggcgc tttgttcatg
4021 gccaaggctg tgtgcagata atcctgaagg agttggattc tccagtacct ggatatcagc
4081 atacaattct tacatattcc tggtgtagaa tctgcaaaca ggtaacacca gttgttgctc
4141 tttccaatga gtcctggtct atgtcatttg caaatacct tgaacttagg ttttatgggc
4201 accagtatac tcgcagagcc aacgctgagc cctgtggtca ctccatccat catgattatc
4261 accagtattt ctcctataac cagatggtgg cgtctttcag ttattctccc attcggcttc
4321 ttgaagtatg tgttccactc cccaaaatat tcattaagcg tcaggcccca ttaaaagtgt
4381 cccttcttca ggatctgaag gacttctttc aaaaagtttc acaggtatat gttgccattg
4441 atgaaagact tgcatctttg aaaactgata catttagtaa acaagagag gaaaaaatgg
4501 aagatatttt tgcacagaaa gagatggaag aaggtgagtt caagaactgg attgagaaga
4561 tgcaagcaag gctcatgtct tcctctgtag atacccctca gcaactgcag tcggtctttg
4621 agtcactcat tgccaagaaa caaagtctct gtgaagtgct gcaagcttgg aataacaggt
4681 tgcaggacct tttccaacag gaaaagggta gaaagagacc ttcagttcct ccaagtcctg
4741 gaagactgag acaaggggaa gaaagcaaga taagtgcgat ggatgcatct ccacggaata
4801 tttctccagg acttcagaat ggagaaaaag aggatcgctt cttaacaact tgtccagcc
4861 agagctccac cagttctact catctccaat tgcctacgcc acctgaagtc atgtctgaac
4921 agtcagtggg agggccccct gagctagata cagccagcag ttccgaagat gtgtttgatg
4981 ggcatttgct gggatccaca gacagccaag tgaaggaaaa gtcaaccatg aaagccatct
5041 ttgcaaattt gcttccagga aatagctata atcctattcc atttccttt gatccagata
5101 aacactactt aatgtatgaa catgaacgag tgcccattgc agtctgcgag aaggaaccca
5161 gctccatcat tgcttttgct ctcagttgta agaataccg aaatgcctta gaggaattgt
5221 ctaaagcgac tcagtggaac agtgccgaag aagggcttcc aacaaatagt acttcagata
5281 gcagaccaaa gagtagcagc cctatcagat tacctgaaat gagtggagga cagacaaatc
5341 gtacaacaga aacagaacca caaccaacca aaaaggcttc tggaatgttg tccttcttca
5401 gagggacagc agggaaaagc cccgatctct cttcccagaa gagagagacc ttacgtggag
5461 cagatagtgc ttactaccag gttgggcaga cgggcaagga ggggaccgag aatcaaggcg
5521 ttgagcctca agatgaagta gatggaggag atacacaaaa gaagcaactc ataaatcctc
5581 atgtggaact tcaattttca gatgctaatg ccaagtttta ctgtcggctc tactatgcgg
5641 gagagtttca taagatgcgt gaagtgattc tggacagcag tgaagaagat ttcattcgtt
```

-continued

```
5701 ccctctccca ctcatcaccc tggcaggccc ggggaggcaa atcaggagct gccttctatg 5761 caactgagga tgatagattt attttgaagc aaatgcctcg tctggaagtc cagtccttcc 5821 tcgactttgc accacattac ttcaattata ttacaaatgc tgttcaacaa aagaggccca 5881 cggcgttggc caaaattctt ggagtttaca gaattggtta taagaactct cagaacaaca 5941 ctgagaagaa gttagatctc cttgtcatgg aaaatctttt ctacgggaga agatggcac 6001 aggttttga tttgaagggc tctcttagga atcggaatgt aaaaactgac actggaaaag 6061 agagttgtga tgtggtcctg ctagatgaaa atctcctaaa gatggttcga dacaaccctc 6121 tatatattcg ttctcattcc aaagctgtgc tgagaacctc gatccatagt gactcccatt 6181 tcctttctag ccacctcatt atagattatt ctttgctggt tgggcgagat gatactagca 6241 atgagctagt agttggaatt atagattata ttcgaacatt tacatgggac aaaaagcttg 6301 agatggttgt gaaatcaaca ggaattttag gtggacaagg taaaatgcca acagtggtgt 6361 ctccggagtt gtacaggact aggttttgtg aggcaatgga caagtatttc ctaatggtac 6421 cagaccactg gacaggcttg ggtctgaatt gctgaaatca agcacatatt ttgaaatgga 6481 ctgtgaagga aaaggggaca ggaacaaagg accaaaaata agctacatgt tttatttctt 6541 catcgtgttc accactgtat gccaaggctt ttcagttctg tggctgttta gactgtccgt 6601 aatggaatgg taaaactcca tgaatttgca ctttggtttt tgatacctgt ggagctgtct 6661 gtaggttggg aagtggcatg aaaatttct taagctaaaa tacagacatg tttcaaaggg 6721 ctaaagttgg agatgagtag ataggtgaa aaatgggtta aatttgctag cttaattgtt 6781 ttaagaagaa aacagtgtct cataaattga ctatcctggc atcacattta acatgttatc 6841 tacttagaaa gcatttgtag agctgctgaa tttgttttgt gttttctgt aataatttaa 6901 tgttacttat tatcagaatt tctgaaacct ttacaaaaat tctgatttat tccattaatg 6961 gccagttaaa cacgtgggca tttattgttt tattgaggaa tttgacttaa actgggaatc 7021 ctgtcatgtt gtttatcttt ccagcttgcc tgttttgag tatgtttgat gttttaaaa 7081 ttttgtcttc tctgtggatg acaggaggct acagcaatta actttaagcc tccttttaga 7141 gatattttta aagcttgttt aaaattttg tgcaattcat atattaaatt gcacttactt 7201 gcatacgctc atattctagg gttttttctc tattttagg gtatcatagt aaatcattag 7261 taaatgagtc tgtagttact aaaccctaat ggaataatta ttaatgaaag attttgaaa 7321 tataaaaaat aaattaggcc caatccaaga aattgagtga aaggaaaca cttgttttat 7381 tcacagaggt aaagtgtctt ttcaatataa ccagcaattt aggtggcatc tataaaataa 7441 aaaatttcta ctgtggacat cccctttcc aactttctac ataatggcta gttctgacta 7501 ctaagaaatg ttaagaaata ggccaagtgc ggtggctcac gcctataatc ctatcacttt 7561 gggaggccta ggcaggcaga tcacctgagg tcaggagttc aagaccagcc tggccaacat 7621 gaggaaaccc catctctact aaaaagacaa aaaattagct gggcatggtg gcatatacct 7681 gtaaccccaa ctacttgggt ggctgaggca ggagaattgt tgaacctgg gaggcggagg 7741 ctgcagtgag ctgggattac accattgcat tccagcctgg gcaacagagc aagactgtct 7801 caaaaaacaa aacgaaacaa aaaagaaag ttattcttag taaggaactt cttgtttaat 7861 agcatttttg tttattttaa aaagtgatca gaagtagtaa actatctttg aggaaatact 7921 gtaacccag aatatttcct cttgacttct ttttgtaaca aggataattt agggatttat 7981 aaagttgtaa ggatttcact gttttcggac tgcctataat aatagcacat taaccttcac 8041 ataataagaa atctgacaa gttcagttac acagtatgat gaatacttga attaggaaca 8101 ttgtggaaaa tttgctttag agaatcaagg cagtagtttg gtatttggtg cttattaaaa
```

-continued

```
8161 atgtggtttg ttttgaactg gaagcaagtt gaccaaggac ttatgactaa tgtgatgcta 8221 agttccactt ggccccttt aaaaacgtgt atgtgccttt tgaagataca caaaacactg 8281 aggattttag ttttgaaatc aaagactatt aaaggagctg tacagaggta aaaaaataaa 8341 tgtggaacat tattaactta ttttgtgtct aggaacaatg gattttgtat ctgatttaaa 8401 atgccaacac tgttttgtct ctgttcattt tttctgtgag gatacttaag gttattattc 8461 ctgtctgttt cctgtactcc cctagtcatg agcacttgaa gtacaaggtg tctccccta 8521 ggtgcaatta ggttgtttct ttgtttttag tttcaattct atgtgcatag caggaatgct 8581 ccacaggaat ggcttctgac aataatcgt cctgttgatt ttgttttcct tgcccatgac 8641 ttgaacaact gtgttttaaa gtactgtagt ctagtaggta actttgtggc aaaaattttc 8701 aatataatac attctgaaac aatagttgct gccttgcaaa ggtaatctct catttaaaa 8761 ttggacagta ttaatgaagg ggaaatatac aatttatttc tattgagtgg tagaactata 8821 tgtctggtcc cttgctgctc ttgtttaggc cactatcata gatatattc aaatattgta 8881 ctactcagtg ttaagtattg aatgactgtt tcccttcct tcaaggccta gagtatattc 8941 tgaaaattta ggaatgagga agaaatctta atacttcctt ccttaacata caacatgagt 9001 cccgagaata attgatagta gcaagagaaa actatgtcag taacatgttg ctttgtataa 9061 aaatcttatt tataaatgtg aagcttttg atgccatcaa aacttattaa aaaataggat 9121 ttacttttt ctaattctga cctaagaaaa ataatgagaa caagctgttg caagctcttt 9181 tgtagtctat tgaatatttt atagatattc aaaatttcct acaaactata attttttcca 9241 tgatttagca gtgagtgatt ttctagcttt ggctcttatt aggtattgta aatagtaggg 9301 ttatatcgat atcagctttt gtgatggcat tgtggtcatc agcttcatga catttttaccc 9361 atttgcagtg atcctgtgta aaactgccaa ggaaagtaat tacctgtagg agtttgctga 9421 gcttgaagag tgaaaactgt tgtgaatgag cctgatcata aaacggacca ggccattcat 9481 tattcctcaa gtgttaatat actgacttat gcagtattca aaccatctag tgcaatgttt 9541 ttgtttttgt tttttttttg gtaacacagg tgcagtgtat tatagaaaaa ataaaaacta 9601 caatcattag cagtttaat actgctgtgt cagttttgta aaaaatgtac attatgtctt 9661 ttgacatgtt gaatttaaa ctagggaaat gacattgtaa atcatagtag cctctttaa 9721 tttaatatga aaaatgccac tatattgaaa gtacttaatg tattgtatat atttctctac 9781 tttggttcta gctatttat atgattgaca tgttatttaa aagataactg ccttgaactt 9841 ttggagactt gtactgtaaa taaagaaatc ttaacaataa actcagaatc tacttactcc 9901 a
```

Human FIG4 protein has the amino acid sequence (SEQ ID NO:23) (NCBI Reference Sequence: NM_014845.5):

```
MPTAAAPIIS SVQKLVLYET RARYFLVGSN NAETKYRVLK IDRTEPKDLV IIDDRHVYTQ    60

QEVRELLGRL DLGNRTKMGQ KGSSGLFRAV SAFGVVGFVR FLEGYYIVLI TKRRKMADIG   120

GHAIYKVEDT NMIYIPNDSV RVTHPDEARY LRIFQNVDLS SNFYFSYSYD LSHSLQYNLT   180

VLRMPLEMLK SEMTQNRQES FDIFEDEGLI TQGGSGVFGI CSEPYMKYVW NGELLDIIKS   240

TVHRDWLLYI IHGFCGQSKL LIYGRPVYVT LIARRSSKFA GTRFLKRGAN CEGDVANEVE   300

TEQILCDASV MSFTAGSYSS YVQVRGSVPL YWSQDISTMM PKPPITLDQA DPFAHVAALH   360

FDQMFQRFGS PIIILNLVKE REKRKHERIL SEELVAAVTY LNQFLPPEHT IVYIPWDMAK   420

YTKSKLCNVL DRLNVIAESV VKKTGFFVNR PDSYCSILRP DEKWNELGGC VIPTGRLQTG   480
```

```
ILRTNCVDCL DRTNTAQFMV GKCALAYQLY SLGLIDKPNL QFDTDAVRLF EELYEDHGDT    540

LSLQYGGSQL VHRVKTYRKI APWTQHSKDI MQTLSRYYSN AFSDADRQDS INLFLGVFHP    600

TEGKPHLWEL PTDFYLHHKN TMRLLPTRRS YTYWWTPEVI KHLPLPYDEV ICAVNLKKLI    660

VKKFHKYEEE IDIHNEFFRP YELSSFDDTF CLAMTSSARD FMPKTVGIDP SPFTVRKPDE    720

TGKSVLGNKS NREEAVLQRK TAASAPPPPS EEAVSSSSED DSGTDREEEG SVSQRSTPVK    780

MTDAGDSAKV TENVVQPMKE LYGINLSDGL SEEDFSIYSR FVQLGQSQHK QDKNSQQPCS    840

RCSDGVIKLT PISAFSQDNI YEVQPPRVDR KSTEIFQAHI QASQGIMQPL GKEDSSMYRE    900

YIRNRYL                                                             907
```

Nucleic acid (mRNA) encoding human FIG4 protein has the nucleotide sequence (SEQ ID NO:24) (NCBI Reference Sequence: NM_014845.5):

```
   1 acgtcctcca gccccgctcc cgacgtgagg ggcggggctt gcctggaggc ggggcgcagg
  61 gatccggaaa cacctgatca tctataggtt tagtgcctaa tgggtgttgt tcctggctgg
 121 acttgatgtc cagggcctga ggggttttct cgccgagtcc cctggggcgg tccggaggct
 181 cgtgccctgt tgtggggccc ccatttgccg ccgccatgcc cacggccgcc gccccatca
 241 tcagctcggt ccagaagctg gttctgtatg agactagagc tagatacttt ctagttggga
 301 gcaataatgc agaaacgaaa tatcgtgtct tgaagattga tagaacagaa ccaaaagatt
 361 tggtcataat tgatgacagg catgtctata ctcaacaaga agtaagggaa cttcttggcc
 421 gcttggatct tggaaataga acaaagatgg gacagaaagg atcctcgggc ttatttcgag
 481 cggtttcagc ttttggtgtt gtgggttttg tcaggttctt agaaggctat tatattgtgt
 541 taataactaa aaggaggaag atggcggata ttggaggtca tgcaatctat aaggtcgaag
 601 atacaaatat gatctatata cccaatgatt ctgtacgggt tactcatcct gatgaagcta
 661 ggtatctacg aatatttcaa atgtggacc tatctagcaa tttttacttt agttacagct
 721 atgatttgtc ccactcactt caatataatc tcactgtctt gcgaatgccc ctggagatgt
 781 taaagtcaga aatgacccag aatcgccaag agagctttga catctttgaa gatgaaggat
 841 taattacaca aggtggaagc ggggtatttg ggatctgtag tgagccttat atgaaatatg
 901 tatggaatgg tgaacttctg gatataatta aaagtactgt gcatcgtgac tggcttttgt
 961 atattattca tgggttctgt gggcagtcaa agctgttgat ctatggacga ccagtgtatg
1021 tcactctaat agctagaaga tccagtaaat ttgctggcac ccgttttctt aaaagaggtg
1081 caaactgtga gggtgatgtt gcaaatgaag tggagactga acaaatactc tgcgatgctt
1141 ctgtgatgtc tttcactgca ggaagttatt cttcatatgt acaagttaga ggatctgtgc
1201 ccttatactg gtctcaggac atttcaacta tgatgcctaa ccacctatt acattggatc
1261 aggcagatcc atttgcacat gtggctgccc ttcactttga ccagatgttc cagaggtttg
1321 gctctcccat catcatcttg aatttagtga aggaacgaga gaaagaaag catgaaagaa
1381 ttctgagtga agaacttgtt gctgctgtga cctatctcaa ccaattttg cctcctgagc
1441 acactattgt ttatattccc tgggacatgg ccaagtatac caaaagcaag ctgtgtaatg
1501 ttcttgatcg actaaatgtg attgcagaaa gtgtggtgaa gaaaacaggt ttctttgtaa
1561 accgccctga ttcttactgt agcatttttgc ggccagatga aaagtggaat gaactaggag
1621 gatgtgtgat tcccactggt cgcctgcaga ctggcatcct tcgaaccaac tgtgtggact
1681 gtttagatcg caccaacaca gcacagttta tggtgggaaa atgtgctctg gcctatcagc
```

-continued

```
1741 tgtattcact gggactgatt gacaaaccta atctacagtt tgatacagat gcagttaggt 1801 tatttgagga actctatgaa gatcatggtg ataccctatc ccttcagtat ggtggttctc 1861 aacttgttca tcgtgtgaaa acctacagaa agatagcacc atggacccag cactccaaag 1921 acatcatgca aaccctgtct agatattaca gcaatgcttt ttcagatgcc gatagacaag 1981 attccattaa tctcttcctg ggagttttcc atcccactga agggaaacct catctctggg 2041 agctcccaac agattttttat ttgcatcaca aaaataccat gagacttttg ccaacaagaa 2101 gaagttatac ttactggtgg acaccagagg tgataaagca tttaccattg ccctatgatg 2161 aagttatctg tgctgtgaac ttaaagaagt tgatagtgaa gaaattccac aaatatgaag 2221 aagagattga tatccacaat gagttcttc ggccatatga gttgagcagc tttgatgata 2281 ccttttgctt ggctatgaca agctcagcac gtgactttat gcctaagacc gttggaattg 2341 atccaagtcc atttactgtg cgtaaaccag atgaaactgg aaaatcagta ttgggaaaca 2401 aaagcaatag agaagaagct gtattacagc ggaaaacggc agccagcgcc ccgccgcccc 2461 ccagcgagga ggctgtgtcc agcagctctg aggatgactc tgggactgat cgggaagaag 2521 agggctctgt gtctcagcgc tccactcccg tgaagatgac tgatgcagga gacagtgcca 2581 aagtgaccga gaatgtggtc caacccatga aggagctata tggaattaac ctctcagatg 2641 gcctctcaga agaagatttc tccatttatt caagatttgt tcagctgggg cagagtcaac 2701 ataaacaaga caagaatagc cagcagcct gttctaggtg ctcagatgga gttataaaac 2761 taacacccat ctcggctttc tcgcaagata acatctatga agttcagccc caagagtag 2821 acagaaaatc tacagagatc ttccaagccc acatccaggc cagccaaggt atcatgcagc 2881 ccctaggaaa agaggactcc tccatgtacc gagagtacat caggaaccgc tacctgtgaa 2941 aagagcgcag gtccacctgg tggacacgtc tgattagctt agaacctgtc ttgtctcatc 3001 ttcaaaaggt aacttattaa aagtcctttg cgtctgaagc ctttctcctt ttctgtcact 3061 tgcaaattcc aaattatagc taataaagat gactagataa tttgcaaaaa aaaaaaaaa 3121 aaa
```

Human Rho GTPase activating protein 23 (ARHGAP23) protein has the amino acid sequence (SEQ ID NO:25) (NCBI Reference Sequence: NM_001199417.1):

```
MNGVAFCLVG IPPRPEPRPP QLPLGPRDGC SPRRPFPWQG PRTLLLYKSP QDGFGFTLRH    60

FIVYPPESAV HCSLKEEENG GRGGGPSPRY RLEPMDTIFV KNVKEDGPAH RAGLRTGDRL   120

VKVNGESVIG KTYSQVIALI QNSDDTLELS IMPKDEDILQ LAYSQDAYLK GNEPYSGEAR   180

SIPEPPPICY PRKTYAPPAR ASTRATMVPE PTSALPSDPR SPAAWSDPGL RVPPAARAHL   240

DNSSLGMSQP RPSPGAFPHL SSEPRTPRAF PEPGSRVPPS RLECQQALSH WLSNQVPRRA   300

GERRCPAMAP RARSASQDRL EEVAAPRPWP CSTSQDALSQ LGQEGWHRAR SDDYLSRATR   360

SAEALGPGAL VSPRFERCGW ASQRSSARTP ACPTRDLPGP QAPPPSGLQG LDDLGYIGYR   420

SYSPSFQRRT GLLHALSFRD SPFGGLPTFN LAQSPASFPP EASEPPRVVR PEPSTRALEP   480

PAEDRGDEVV LRQKPPTGRK VQLTPARQMN LGFGDESPEP EASGRGERLG RKVAPLATTE   540

DSLASIPFID EPTSPSIDLQ AKHVPASAVV SSAMNSAPVL GTSPSSPTFT FTLGRHYSQD   600

CSSIKAGRRS SYLLAITTER SKSCDDGLNT FRDEGRVLRR LPNRIPSLRM LRSFFTDGSL   660

DSWGTSEDAD APSKRHSTSD LSDATFSDIR REGWLYYKQI LTKKGKKAGS GLRQWKRVYA   720

ALRARSLSLS KERREPGPAA AGAAAAGAGE DEAAPVCIGS CLVDISYSET KRRHVFRLTT   780
```

```
ADFCEYLFQA EDRDDMLGWI RAIRENSRAE GEDPGCANQA LISKKLNDYR KVSHSSGPKA    840

DSSPKGSRGL GGLKSEFLKQ SAARGLRTQD LPAGSKDDSA AAPKTPWGIN IIKKNKKAAP    900

RAFGVRLEEC QPATENQRVP LIVAACCRIV EARGLESTGI YRVPGNNAVV SSLQEQLNRG    960

PGDINLQDER WQDLNVISSL LKSFFRKLPE PLFTDDKYND FIEANRIEDA RERMRTLRKL   1020

IRDLPGHYYE TLKFLVGHLK TIADHSEKNK MEPRNLALVF GPTLVRTSED NMTDMVTHMP   1080

DRYKIVETLI QHSDWFFSDE EDKGERTPVG DKEPQAVPNI EYLLPNIGRT VPPGDPGSDS   1140

TTCSSAKSKG SWAPKKEPYA REMLAISFIS AVNRKRKKRR EARGLGSSTD DDSEQEAHKP   1200

GAGATAPGTQ ERPQGPLPGA VAPEAPGRLS PPAAPEERPA ADTRSIVSGY STLSTMDRSV   1260

CSGASGRRAG AGDEADDERS ELSHVETDTE GAAGAGPGGR LTRRPSFSSH HLMPCDTLAR   1320

RRLARGRPDG EGAGRGGPRA PEPPGSASSS SQESLRPPAA ALASRPSRME ALRLRLRGTA   1380

DDMLAVRLRR PLSPETRRRR SSWRRHTVVV QSPLTDLNFN EWKELGGGGP PEPAGARAHS   1440

DNKDSGLSSL ESTKARAPSS AASQPPAPGD TGSLQSQPPR RSAASRLHQC L            1491
```

Nucleic acid (mRNA) encoding human ARHGAP23 protein has the nucleotide sequence (SEQ ID NO:26) (NCBI Reference Sequence: NM_001199417.1):

```
   1 ctgccacccg atgaatggag tcgccttctg cctggtcggg atcccgcccc gcccggagcc
  61 ccggccccca cagctgccac tgggcccaag agatgggtgc tctcctaggc gccccttccc
 121 ctggcagggg ccgaggacgc tgctgctgta caaaagtccc caggacggct ttggcttcac
 181 tctgcgccac ttcatcgtgt acccacccga gtcggccgtg cactgcagcc tgaaggagga
 241 agagaatgga ggccgtggag gaggaccctc ccccggtac cgcctggagc catggacac
 301 catctttgtc aagaatgtga aggaagacgg ccctgcccat agggcgggc ttcgcacagg
 361 agaccggctg gtaaaggtga atggggaaag cgtcattggg aagacctact ctcaggtcat
 421 agctctgatc cagaatagtg atgacactct ggagctgtct atcatgccca aggacgagga
 481 catcctccag ctggcctact cccaggatgc ctacctgaaa gggaacgagc cgtattctgg
 541 agaggcccgc agcatcccag agccaccgcc gatctgctac cccgcaaga cctacgcccc
 601 tcctgcccgg gcctccacca gggccactat ggtgcctgag cccacctcag cactgcccag
 661 tgaccccgg agtcctgctg cctggagtga cccggggctc cgtgtgccac tgctgcccg
 721 tgcccacctg acaactcttt ccttggggat gagccagccc cgcccagcc ctggtgcctt
 781 cccccacctc tcctcggagc cccggacgcc ccgtgccttc ccagagcctg gcagccgggt
 841 gccccccagc agactggagt gccagcaggc cttgtcacac tggctgtcaa accaggtacc
 901 ccgccgggcg gggagagac ggtgcccagc catggccccc cgggcccgca gcgcctccca
 961 ggaccggttg gaggaggtgg ctgcccccg cccgtggccc tgctccacct cccaggatgc
1021 tttgagccag ctgggccagg agggctggca ccgagctcgc tcagatgact acttgagccg
1081 ggccacccgt tctgccgagg cactgggggcc aggggcactg tgtcacccc gctttgagcg
1141 gtgtggctgg gcttcccagc gttcgtctgc ccgcaccccc gcctgccaa tcgggacct
1201 gccaggccc caggccccac ccccgtctgg cctgcagggc ctggatgacc tcgggtacat
1261 cggctaccgg agctacagcc catcattcca gcgccggacc ggcctcctcc atgcgctctc
1321 cttccgggac tcacccttg gggggctgcc taccttcaac ctggcccagt ccctgcgtc
1381 attcccacca gaggcctccg agccaccag ggttgtacgg ccggaaccca gcacccgggc
1441 cctggagcct cctgcggagg atcgcggcga tgaggtggtc ctgaggcaga agcccccgac
```

```
1501 gggccgcaag gttcagctga cccccgcaag acagatgaac cttggatttg gtgacgagtc
1561 cccagagcca gaggccagtg ggcgagggga acgcctgggc aggaaggtgg cccctttggc
1621 caccaccgaa gactctctgg cttccatccc ctttattgat gagcccacca gccccagcat
1681 tgacctccaa gccaagcacg tccctgcctc tgctgtggtc tccagtgcca tgaactcagc
1741 ccctgtcctg ggcaccagcc catcttcccc gaccttcact ttcaccctcg gacgccatta
1801 ctcgcaggac tgcagcagca tcaaggctgg ccgccgctcc tcctacctgc tggccatcac
1861 cacggagcgc tccaagtcct gcgatgatgg actcaacacc ttccgcgacg agggccgggt
1921 tctgcgcgc ctgccaaacc gcatacccag cctgcggatg ctccggagct tcttcaccga
1981 cgggtccttg gatagctggg gcacctctga agatgctgac gctccttcta agcgacactc
2041 aacctctgac ctctcagatg cgaccttcag cgatatcagg agagaaggct ggttgtatta
2101 taagcagatt ctcaccaaga agggaagaa agcgggcagc ggcctgcgcc agtggaagcg
2161 ggtgtacgcc gcgctgcggg cgcgctcgct ctcgctgagc aaggagcggc gggagcccgg
2221 gccggcggcg gcggggctg cggcggccgg cgcaggtgag gacgaggcgg cgcccgtctg
2281 catcggctcc tgcctcgtgg acatctccta cagcgagacc aagaggaggc acgtgttccg
2341 gctgaccacc gctgacttct gtgaatatct ctttcaggct gaggaccggg atgacatgct
2401 gggctggatc agagcgatcc gggagaacag cagggccgag ggcgaggacc ccggctgtgc
2461 caaccaagct ctgatcagca agaagcttaa cgattatcgc aaagtgagcc atagctctgg
2521 gcccaaagct gattcctccc ccaaaggctc tcgcggcctg gggggcctca gtctgagtt
2581 cctcaagcag agtgcggcac gtggcctcag gactcaggac ctgcccgcag ggagcaagga
2641 tgacagtgct gcagccccca aaccccctg ggcatcaac atcatcaaga aaataagaa
2701 ggccgctccg agggcgtttg gggtcaggct ggaggagtgc cagccagcca cggagaacca
2761 gcgcgtcccc ttaatcgtgg ctgcatgctg tcgcattgtg gaggcacgag ggctggagtc
2821 cacaggcatt taccgagtgc ccggcaacaa tgcagtggtg tccagcctac aggagcagct
2881 caaccgcggg cctggtgaca tcaacctgca ggatgagcgc tggcaagacc tcaatgtgat
2941 cagcagcctg ctcaagtcct tcttccgaaa gctgcccgag cctctttca ctgatgacaa
3001 atacaacgac ttcatcgagg ccaaccgcat tgaggacgcg cgggagcgaa tgaggacgct
3061 gcggaagctg atccgggatc tcccaggaca ctactatgaa acgctcaaat tccttgtggg
3121 ccatctcaag accatcgctg accactctga gaaaaacaag atggaacccc ggaacctggc
3181 cctggtcttt gggccgacac tggtgaggac gtctgaggac aacatgacag acatggtgac
3241 ccacatgcct gaccgctaca gatcgtgga gacactgatc cagcactcag actggttctt
3301 cagtgacgaa gaggacaagg gagagagaac ccctgtgggc gacaaggagc ctcaggcagt
3361 gcccaacatt gagtacctcc tgcccaacat tggcaggaca gtgcccccctg cgacccggg
3421 gtcagattct accacctgta gttcagccaa gtccaagggt tcgtgggccc caagaagga
3481 gccgtacgcc cgggagatgc tggcgatctc cttcatctcg gccgtcaacc gcaagcgcaa
3541 gaagcggcgg gaggcgcggg ggctgggcag cagcaccgac gacgactcgg agcaggaggc
3601 gcacaagcct ggggcggggg ccacagcgcc ggggactcag gagcggccgc aggggccgct
3661 gcctggcgcc gtcgcccccg aggccccgg acgcctcagt ccccggcgg cgccggagga
3721 gcggccggcc gcggacacgc gctccattgt gtcgggctac tccaccctgt ccaccatgga
3781 ccgcagcgtg tgctcgggcg ctagcggtcg gcgggcaggg gcggggatg aggcggacga
3841 cgagcgtagc gagctgagcc acgtggagac ggacactgag ggcgcggcgg gcgcggggcc
3901 tggggggcgc ctgacacgcc ggccgtcctt cagctcgcac cacctcatgc cctgcgacac
```

-continued
```
3961 tctggcgcgc cgccgcctgg cccggggccg cccagacggc gagggcgcgg gccggggcgg 4021 tccccgcgcc ccggagccgc ccggctcggc gtcgtccagc agccaggagt cgctgcggcc 4081 cccggcggcg gcgctggcct cccggccctc gcgcatggag gcgctgcgtc taaggctccg 4141 cggcacggcg gacgacatgc tcgccgtgcg cctgcggcgg ccgctgtcgc ccgagacccg 4201 gcggcgccgg agcagctggc gccgccacac cgtggtggtg cagagcccgc tgactgacct 4261 caacttcaac gagtggaagg agctgggcgg aggggccccc ccggagcctg cgggcgcgcg 4321 ggcgcacagt gacaacaagg actccggact cagcagcctg gagtccacca aggcgcgggc 4381 cccgtcgtcc gctgcctcgc agccgcccgc gccggggac acggggtccc tgcagagcca 4441 gccccgcgc cgctcggccg cctcccgcct gcatcagtgt ctgtgatccc cacctcccgc 4501 gccgctcggg cgccacccct ccctagagcc cctttggaac caggaggctt caccagcctg 4561 cacctcctct tctgtggccc ctgggtgcat ggtgtgggtg gagggcgcag caggcagtgt 4621 ctctagttgg tgtgctggaa ctggcagggc agaggagaag gctggggccg gactaattga 4681 atggaagggg gttccagagg tgatgagcag aagaggaggg ggcgtgggct gctggggtct 4741 gtgtccctgc acacatgcgc ccgataggtc cttctgagcc tttctgtggc tgcacttggg 4801 gaccctttgtg gaccatgggg tgtggctagg gaaccctaa gtttcagact aaaggaaaga 4861 tcctgggtga tgctggcttt ttgcttcttt cttctgccct cccacctcag cttgtaagcg 4921 gggatgtgtg tatgtctggg gagaggaggt gtagggtgcg tatgtccatg ggggagggg 4981 cttgtgtgtg cagtcattgt cccaaggtgt ttccagtagc gacttctgtc cccctatccc 5041 caccctggtc cccactttgc gccccgggc tccctgcctt tggtgcacac aggatcctgc 5101 ccgccccct tgccagagcc agagaagggg gttggggcca ttccaaggag gcaggactga 5161 aaccctcacc agggttactc cccaacatcc ttttgcctga gtcaccctct aagcgcttta 5221 accacgggca gctgcctgtt ccccagacag ttttttggtgg gggggtcca gggtccccct 5281 tgctggtacc tccctcaccc ctctttttgt ttttccatct gtgcctgttc cttccacagc 5341 ccaggcacac agaagcccac cttcttcccc ttaggaggag ggatagtcaa caccctgct 5401 gtctctctgt cactcacaca ctgatttatg gggtctgagc tgggctgttc ctgcaggatg 5461 gacaggaccc agcgccctct tctccccaca ggctgtaaat agacttccaa tcaccaggcc 5521 agccccaca caccctcact cattccaggg aagcccaggt aggtggtgaa cccgctgcca 5581 cgtctatcag tcctcttgtt ttatgcaaag atttactgta aagtagattt ctttccctcc 5641 ctcccccatt cttttattgt aaatattgtc tctaaatgtg taacatatta taaagaattt 5701 ataaggattt ttaaagatgt tttgctcatt tacaaaagtg ttgtaacagt gttggacaaa 5761 gccttccacc ccatgtccgc atggctcctt tcactgtgtc cttgacacac ctctctggca 5821 acaactaaaa tttcctgctt ctgaaaagtc ctgtcttaaa agtacagtct atatcttgga 5881 aataaatagc tttcctcaag gcatgaaaaa aaa
```

The invention also encompasses splice variants of NPC1, VPS11, VPS16, VPS18, VPS33A, VPS39, VPS41, BLOC1S1, BLOC1S2, GNPTAB, PIKFYVE, ARHGAP23 and/or FIG4.

Known inhibitors of NPC1 include U18666A[25] (3-β-[2-(diethylamino)ethoxy]androst-5-en-17-one) and the antidepressant imipramine[26] (a tricyclic antidepressant).

VPS11, VPS16, VPS18, VPS33A, VPS39, and VPS41 are subunits of the homotypic fusion and vacuole protein sorting (HOPS) complex. The mammalian HOPS complex plays a critical role in fusion of endosomes and lysosomes[6]. One or more inhibitors may be used, for example, to inhibit one or more subunits of HOPS.

PIKFYVE is involved in the biogenesis of endosomes,[14,15] and BLOC1S1 and BLOC1S2 are involved in the biogenesis of lysosomes.[16] GNPTAB is involved in targeting of luminal cargo to the endocytic pathway.[17]

Inhibition of NPC1, VPS11, VPS16, VPS18, VPS33A, VPS39, VPS41, BLOC1S1, BLOC1S2, GNPTAB, PIKFYVE, ARHGAP23 or FIG4 can occur at the level of the protein or at the level of nucleic acid (DNA or RNA) encoding the protein.

For example, the agent can be an antisense molecule, a ribozyme, or a RNA interference (RNAi) molecule, such as a small interfering RNA (siRNA) molecule, that specifically inhibits expression of NPC1, VPS11, VPS16, VPS18, VPS33A, VPS39, VPS41, BLOC1S1, BLOC1S2, GNPTAB, PIKFYVE, ARHGAP23 or FIG4 protein. The agent can be comprised of nucleic acid (e.g., DNA or RNA) or nucleic acid mimetics (e.g., phosphorothionate mimetics) such as those known in the art.

The agent can also be, for example, an antibody, antibody fragment, aptamer or small molecule that specifically binds to NPC1, VPS11, VPS16, VPS18, VPS33A, VPS39, VPS41, BLOC1S1, BLOC1S2, GNPTAB, PIKFYVE, ARHGAP23 or FIG4 and reduces its activity or interferes with its normal function. Antibody fragments include, but are not limited to, F(ab')$_2$ and Fab' fragments and single chain antibodies. F(ab')$_2$ is an antigen binding fragment of an antibody molecule with deleted crystallizable fragment (Fc) region and preserved binding region. Fab' is ½ of the F(ab')$_2$ molecule possessing only ½ of the binding region. The term antibody is further meant to encompass polyclonal antibodies and monoclonal antibodies. The antibody can be a human antibody or a non-human antibody such as a goat antibody or a mouse antibody. Antibodies can be "humanized" using standard recombinant DNA techniques. Aptamers are single stranded oligonucleotides or oligonucleotide analogs that bind to a particular target molecule, such as a protein. Thus, aptamers are the oligonucleotide analogy to antibodies. However, aptamers are smaller than antibodies. Their binding is highly dependent on the secondary structure formed by the aptamer oligonucleotide. Both RNA and single stranded DNA (or analog) aptamers can be used. Aptamers that bind to virtually any particular target can be selected using an iterative process called SELEX, which stands for Systematic Evolution of Ligands by EXponential enrichment.

Possible modes of action of antiviral compounds include those illustrated, for example, in FIG. 24A-24D.

Rapidly acting small molecule inhibitors of NPC1, VPS11, VPS16, VPS18, VPS33A, VPS39, VPS41, BLOC1S1, BLOC1S2, GNPTAB, PIKFYVE, ARHGAP23 or FIG4 protein may be preferred for treatment of viral infections due to the rapid speed of viral replication.

It is envisioned that administration of the agent to the subject would normally be limited to periods when the subject either has a filovirus infection or when the subject has been exposed to filovirus or is at risk of exposure to filovirus, in order to minimize any deleterious effect of administration of the agent. Ebola/marburgvirus infections are typically acute in nature, so drug treatment of infection for only a short period of time is appropriate.

The agent can be administered to the subject in a pharmaceutical composition comprising a pharmaceutically acceptable carrier. Examples of acceptable pharmaceutical carriers include, but are not limited to, additive solution-3 (AS-3), saline, phosphate buffered saline, Ringer's solution, lactated Ringer's solution, Locke-Ringer's solution, Krebs Ringer's solution, Hartmann's balanced saline solution, and heparinized sodium citrate acid dextrose solution. The pharmaceutically acceptable carrier used can depend on the route of administration. The pharmaceutical composition can be formulated for administration by any method known in the art, including but not limited to, oral administration, parenteral administration, intravenous administration, transdermal administration, intranasal administration, and administration through an osmotic mini-pump. The compounds can be applied to the skin, for example, in compositions formulated as skin creams, or as sustained release formulations or patches.

The present invention also provides a method for screening for an agent that treats and/or prevents infection of a subject with a filovirus, the method comprising determining whether or not the agent inhibits one or more of Niemann-Pick C1 (NPC1), VPS11, VPS16, VPS18, VPS33A, VPS39, VPS41, BLOC1S1, BLOC1S2, GNPTAB, PIKFYVE, ARHGAP23 or FIG4, wherein an agent that inhibits NPC1, VPS11, VPS16, VPS18, VPS33A, VPS39, VPS41, BLOC1S1, BLOC1S2, GNPTAB, PIKFYVE, ARHGAP23 or FIG4 is a candidate for treating and/or preventing an infection with a filovirus and wherein an agent that does not inhibit NPC1, VPS11, VPS16, VPS18, VPS33A, VPS39, VPS41, BLOC1S1, BLOC1S2, GNPTAB, PIKFYVE, ARHGAP23 or FIG4 is not a candidate for treating and/or preventing an infection with a filovirus.

The agent used for treatment or in screening can be, for example, an agent that targets domain C of NPC1 or nucleic acid encoding domain C of NPC1. Domain C of NPC1 (FIG. 19) is a 248-amino acid domain from residue 373 to residue 620 of SEQ ID NO:1.

The method can be carried out with respect to NPC1, for example, by measuring cholesterol transport, where a decrease in cholesterol transport in the presence of the agent indicates that the agent inhibits NPC1. The assay can be carried out using a cell line that expresses NPC1.

NPC1's cholesterol transport function is separable from its viral host factor function. Preferably, the agent selectively targets NPC1's viral host factor function, without blocking NPC1's cholesterol transport function.

The method can also be carried out, for example, by measuring binding between NPC1, VPS11, VPS16, VPS18, VPS33A, VPS39, VPS41, BLOC1S1, BLOC1S2, GNPTAB, PIKFYVE, ARHGAP23 or FIG4, and the filovirus or a filovirus glycoprotein (GP), where a decrease in binding in the presence of the agent indicates that the agent inhibits NPC1, VPS11, VPS16, VPS18, VPS33A, VPS39, VPS41, BLOC1S1, BLOC1S2, GNPTAB, PIKFYVE, ARHGAP23 or FIG4. The method can be carried out, for example, using a enzyme-linked-immunosorbent assay (ELISA). The method can be carried out, for example, using a electrochemiluminescence (ECL) assay.

The method can also be carried out, for example, by measuring filovirus infection in tissue culture, where a reduction in filovirus infection in the presence of the agent indicates that the agent inhibits NPC1, VPS11, VPS16, VPS18, VPS33A, VPS39, VPS41, BLOC1S1, BLOC1S2, GNPTAB, PIKFYVE, ARHGAP23 and/or FIG4.

The invention also provides an agent for treating and/or preventing infection of a subject with a filovirus identified by any of the methods disclosed herein for screening for an agent that treats and/or prevents infection of a subject with a filovirus. The invention further provides a pharmaceutical composition for treating and/or preventing infection of a subject with a filovirus comprising a pharmaceutically acceptable carrier and an agent identified by any of the methods disclosed herein for screening for an agent that treats and/or prevents infection of a subject with a filovirus.

This invention will be better understood from the Experimental Details, which follow. However, one skilled in the art will readily appreciate that the specific methods and results discussed are merely illustrative of the invention as described more fully in the claims that follow thereafter.

Experimental Details

Introduction

A genome-wide haploid genetic screen in human cells is described for identifying host factors required for EboV entry. The screen uncovered 67 mutations disrupting all six members of the HOPS multisubunit tethering complex, which is involved in fusion of endosomes to lysosomes[6], and 39 independent mutations that disrupt the endo/lysosomal cholesterol transporter protein Niemann-Pick C1 (NPC1)[7,8]. Cells defective for the HOPS complex or NPC1 function, including primary fibroblasts derived from human Niemann-Pick type C1 disease patients, are resistant to infection by EboV and MarV, but remain fully susceptible to a suite of unrelated viruses. Membrane fusion mediated by filovirus glycoproteins and viral escape from the vesicular compartment were shown to require the NPC1 protein, independent of its known function in cholesterol transport. The findings uncover unique features of the entry pathway used by filoviruses and indicate antiviral strategies to combat these deadly agents.

Methods

Summary: Adherent HAP1 cells were generated by the introduction of OCT4/SOX2/c-Myc and KLF4 transcription factors. 100 million cells were mutagenized using a promotor-less retroviral gene-trap vector carrying a GFP reporter. Cells were not selected for reporter gene expression, and insertion sites were mapped for approximately 1% of the unselected population using parallel sequencing. Cells were exposed to rVSV-GP-EboV and the resistant cell population was expanded and used to sequence insertion sites. Genes that were statistically enriched for mutation events in the selected population were identified, and the roles of selected genes in filovirus entry were characterized.

Cells: KBM7 cells and derivatives were maintained in IMDM supplemented with 10% FCS, L-glutamine, and penicillin-streptomycin. Vero grivet monkey cells and human dermal fibroblasts (Coriell Institute for Medical Research) were maintained in DMEM supplemented with 10% FCS, L-glutamine, and penicillin-streptomycin. Wild type and NPC1-null (CT43) Chinese hamster ovary (CHO) fibroblasts were maintained in DMEM-Ham's F-12 medium (50-50 mix) supplemented with 10% FCS, L-glutamine, and penicillin-streptomycin[21].

Viruses: A recombinant VSV expressing eGFP and EboV GP lacking the mucin domain (Δ309-489) (rVSV-GP-EboV) was recovered and amplified as described previously[11]. Recombinant rVSV-BDV was generously provided by Juan Carlos de la Torre. rVSV-GP-Rabies was generated by replacement of the VSV G ORF in VSV-eGFP (REF PMC 116335) with that of the SAD-B19 strain of Rabies virus, and recombinant virus was recovered and amplified as described[29].

The following non-recombinant viruses were used: Adenovirus type 5 (ATCC), Coxsackievirus B1 (ATCC), Poliovirus 1 Mahoney (generously provided by Christian Schlieker), HSV-1 KOS (generously provided by Hidde Ploegh), Influenza A PR8 (Charles Rivers) and Rift valley fever virus MP-12 (generously provided by Jason Wojcechowskyj).

Generation of HAP1 cells: Retroviruses encoding SOX2, C-MYC, OCT4 and KLF4 were produced as described earlier[12]. Concentrated virus was used to infect near haploid KBM7 cells in three consecutive rounds of spin-infection with an interval of 12 hours. Conditions were used that resulted in an infection percentage of >95% of pLIB-EGFP (Clontech) that was taken along in a separate infection as a control. Cells were plated at low density in regular medium (IMDM 10% FCS, L-glutamine, and penicillin-streptomycin). Expression of the four transcription factors markedly changed morphology of the KBM7 cells from round, non-adherent cells typical for CML cells, to more flattened and adherent cells. Colonies were picked and tested for ploidy. One clonally derived cell line (referred to as HAP1) with a haploid DNA content as determined using DNA staining and flow cytometry was further grown and characterized. Karyotyping of this line demonstrated that the majority of the analyzed cells (27/39) were fully haploid, a smaller population (9/39) was haploid for all chromosomes except chromosome 8, like the parental KBM7 cells. Less than 10% (3/39) was diploid for all chromosomes except for chromosome 8 that was tetraploid. All cells carried the Philadelphia chromosome present in the parental KBM7 cells.

Haploid genetic screen: Gene trap virus was produced by transfection of 293T cells in T175 dishes using turbofectin 8 (origene) with a mixture of pGT-GFP, pGT-GFP+1 and pGT-GFP+2 (6.7 μg) combined with 1.7 μg pAdvantage, 2.6 μg CMV-VSVG and 4 μg Gag-pol. The virus-containing supernatant was concentrated using ultracentrifugation for 1.5 h at 25,000 r.p.m. in a Beckman SW28 rotor. To create a mutagenized cell population ~100 million HAP1 cells were infected with the gene-trap virus. After expansion for 7 days, a proportion of the cells was harvested for genomic DNA isolation to create a control dataset containing sequences flanking the gene-trap insertions in unselected cells. For the screen, hundred million mutagenized cells were exposed to rVSV-GP-EboV at an MOI ~100. The resistant colonies that grew out were expanded and ~30 million cells were used for genomic DNA isolation.

Sequence analysis of gene trap insertion sites: Insertion sites were identified en masse by sequencing the genomic DNA flanking gene trap proviral DNA as described before[9]. In short, a control dataset was generated containing insertion sites in mutagenized HAP1 cells before selection with rVSV-GP-EboV. For this purpose genomic DNA was isolated from ~40 million cells and subjected to a linear PCR followed by linker ligation, PCR and sequencing using the Genome Analyzer platform (Illumina). The insertions sites were mapped on the human genome and insertion sites were identified that were located in genomic regions annotated to contain genes. The insertions in this control dataset comprise of ~400,000 independent insertions that meet this criteria. To generate the experimental dataset, insertions in the mutagenized HAP1 cells after selection with rVSV-GP-EboV were identified using an inverse PCR protocol followed by sequencing using the Genome Analyzer. The number of inactivating mutations (=sense orientation or present in exon) per individual gene was counted as well as the total number of inactivating insertions for all genes. Enrichment of a gene in the screen was calculated by comparing how often that gene was mutated in the screen compared to how often the genes carries an insertion in the control dataset. For each gene a p-value (corrected for false discovery rate) was calculated using the one-sided Fisher exact test.

Characterization of the HAP1 mutant lines: Clonal cell lines with gene trap insertion in NPC1, VPS11 and VPS33A were derived and genomic DNA was isolated using Qiamp DNA mini kit (Qiagen). To confirm that the cells were truly clonal and to confirm the absence of the wild type DNA locus, a PCR was performed with primers flanking the insertion site using the following primers:

```
                                           (SEQ ID NO: 27)
    NPC-F1,  5'-GAAGTTGGTCTGGCGATGGAG-3';

(SEQ ID NO: 28)
    NPC1-R2, 5'-AAGGTCCTGATCTAAAACTCTAG-3';

(SEQ ID NO: 29)
    VPS33A-F1, 5'-TGTCCTACGGCCGAGTGAACC-3';
```

```
                                             (SEQ ID NO: 30)
VPS33A-R1, 5'-CTGTACACTTTGCTCAGTTTCC-3';

(SEQ ID NO: 31)
VPS11-F1,  5'-GAAGGAGCCGCTGAGCAATGATG-3';

(SEQ ID NO: 32)
VPS11-R1,  5'-GGCCAGAATTTAGTAGCAGCAAC-3'.
```

To confirm the correct insertion of the gene trap at the different loci a PCR was performed using the reverse (R1) primers of NPC1, VPS11 and VPS33A in combination with a primer specific for the gene trap vector: PGT-F1; 5'-TCTC-CAAATCTCGGTGGAAC-3' (SEQ ID NO:33). To determine RNA expression levels of NPC1, VPS11 and VPS33A in the respective mutants, total RNA was extracted using RNeasy (Qiagen), reverse transcribed using Superscript III (Invitrogen) and PCR amplified using gene specific primers:

```
                                             (SEQ ID NO: 34)
VPS11: 5'-CTGCTTCCAAGTTCCTTTGC-3'
and (SEQ ID NO: 35)
5'-AAGATTCGAGTGCAGAGTGG-3';

(SEQ ID NO: 36)
NPC1:  5'-CCACAGCATGACCGCTC-3'
and (SEQ ID NO: 37)
5'-CAGCTCACAAAACAGGTTCAG-3';

(SEQ ID NO: 38)
VPS33A: 5'-TTAACACCTCTTGCCACTCAG-3'
and (SEQ ID NO: 39)
5'-TGTGTCTTTCCTCGAATGCTG-3'.
```

NPC1 constructs: Human NPC1 cDNA was ligated in-frame to a triple flag sequence, and the resulting gene encoding C-terminally FLAG-tagged NPC1 was subcloned into the BamHI and SalI restriction sites of the pBABE-puro retroviral vector[30]. Constructs encoding flag-tagged NPC1 'loop-minus' mutants in pBABE-puro [ΔA, lacking NPC1 amino acid residues 24-252); ΔC, lacking residues 381-611); ΔI, (lacking residues 865-1088)] were generated by replacing the indicated sequence with a BglII restriction site. To engineer the individual loop domain constructs, a cassette vector encoding the following sequence elements was first generated and cloned into the BamHI and SalI sites of pBABE-puro: NPC1 signal peptide (encoding NPC1 amino acid residues 1-24), MluI restriction site, the first NPC1 transmembrane domain (residues 267-295), NPC1 C-tail (residues 1252-1278), gly-gly-gly-ser linker, and triple flag tag. Each loop domain (A, residues 25-266; C, residues 373-620; I, residues 854-1098) was cloned into the MluI site of this cassette vector. All constructs were verified by automated DNA sequencing.

CT43 cell populations stably expressing NPC1 proteins: For transduction of VH-2 cells, the full-length human NPC1 cDNA (Origene) was cloned into the retroviral vector pMX-sIRESblasti-FLAG[10]. For transduction of CHO WT and CT43 cells, the pBABE-puro-based retroviral vectors described above were used. Retroviruses packaging the transgenes were produced by triple transfection in 293T cells, and target cells were directly exposed to sterile-filtered retrovirus-laden supernatants in the presence of polybrene (6 μg/mL). Transduced cell populations were selected with blasticidin (20 μg/mL; for pMX) or puromycin (10 μg/mL; for pBABE-puro).

Cell viability assays for virus treatments: KBM7 and HAP1 cells were seeded at 10,000 cells per well in a 96-well tissue culture plate and treated with the indicated concentrations of rVSV-GP-EboV or left untreated. Three days after treatment the cell viability was measured using an XTT colorimetric assay (Roche) according to manufacturer's protocol. Viability is plotted as percentage viability compared to untreated control. To compare susceptibility of the HAP1 mutants to different viruses, they were seeded at 10,000 cells per well and treated with different cytolytic viruses at a concentration that in pilot experiments was the lowest concentration to produce extensive cytopathic effects. Three days after treatment, viable, adherent cells were fixed with 4% formaldehyde in phosphate-buffered saline (PBS) followed by staining with 0.5% crystal violet dye in 70% ethanol for 30 min. After three gentle washes with water, air-dried plates were scanned.

Viral infectivity measurements: Infectivities of VSV pseudotypes were measured by manual counting of eGFP-positive cells using fluorescence microscopy at 16-26 h post-infection, as described previously[3]. rVSV-GP-EboV infectivity was measured by fluorescent-focus assay (FFA), as described previously[11].

Filipin staining: Filipin staining to visualize intracellular cholesterol was done essentially as described[31]. Briefly, cells were fixed with paraformaldehyde (3%) for 15 min at room temperature. After three PBS washes, cells were incubated with filipin complex from *Streptomyces filipinensis* (Sigma-Aldrich) (50 μg/mL) in the dark for 1 h at room temp. After three PBS washes, cells were visualized by fluorescence microscopy in the DAPI channel.

Measurements of cysteine cathepsin activity: The enzymatic activities of CatB and CatL in acidified postnuclear extracts of Vero cells, human fibroblasts, and CHO lines were assayed with fluorogenic peptide substrates Z-Arg-Arg-AMC (Bachem Inc., Torrance, Calif.) and (Z-Phe-Arg)2-R110 (Invitrogen), respectively, as described previously[32]. As a control for assay specificity, enzyme activities were also assessed in extracts pretreated with E-64 (10 μM), a broad-spectrum cysteine protease inhibitor, as previously described[11]. Active CatB and CatL within intact cells were labeled with the fluorescently-labeled activity-based probe GB111 (1 μM) and visualized by gel electrophoresis and fluoroimaging, as described previously[33].

Purification and dye conjugation of rVSV-GP-EboV: rVSV-GP-EboV was propagated, purified and labeled with Alexa Fluor 647 (Molecular Probes, Invitrogen Corporation) as described previously[34] with minor modifications. Briefly, Alexa Fluor 647 (Molecular Probes, Invitrogen Corporation) was solubilized in DMSO at 10 mg/mL and incubated at a final concentration of 31.25 μg/ml with purified rVSV-GP-EboV (0.5 mg/ml) in 0.1 M NaHCO3 (pH 8.3) for 90 min. at RT. Virus was separated from free dye by ultracentrifugation. Labeled viruses were resuspended in NTE (10 mM Tris pH 7.4, 100 mM NaCl, 1 mM EDTA) and stored at −80° C.

Virus binding/internalization assay: Cells were inoculated with an MOI of 200-500 of Alexa 647-labeled rVSV-GP-EboV at 4° C. for 30 min. to allow binding of virus particles to the cell surface. Cells were subsequent fixed in 2% paraformaldehyde (to examine virus binding) or following a 2 h incubation at 37° C. and an acid wash to remove surface-bound virus. The cellular plasma membrane was labeled by incubation of cells with 1 ug/mL Alexa Fluor 594 wheat germ agglutinin (Molecular Probes, Invitrogen) in PBS for 15 min. at RT. External virus particles were detected using a 1:2000 dilution of antibody 265.1, a mouse monoclonal specific for Ebola GP. The GP antibodies were detected by Alexa 488- conjugated goat anti-mouse secondary antibody (Molecular Probes, Invitrogen). After washing with PBS, cells were mounted onto glass slides using Prolong Antifade Reagent (Invitrogen, Molecular Probes). Fluorescence was monitored with a epifluorescence microscope (Axiovert 200M; Carl Zeiss, Inc.; Thornwood, N.Y.) and representative images were acquired using Slidebook 4.2 software (Intelligent Imaging Innovations; Denver, Colo.)[34,35].

VSV M protein-release assay: Cells grown on 12 mm coverslips coated with poly-D-lysine (Sigma-Aldrich) were pre-treated with 5 µg/ml puromycin for 30 min. and inoculated with rVSV at an MOI of 200-500 in the presence of puromycin. After 3 h, cells were washed once with PBS and fixed with 2% paraformaldehyde in PBS for 15 min. at RT. To detect VSV M protein, fixed cells were incubated with a 1:7500 dilution of monoclonal antibody 23H12 (kind gift of Doug Lyles[36]), in PBS containing 1% BSA and 0.1% Triton X-100 for 30 min. at RT. Cells were washed three times with PBS, and the anti-M antibodies were detected using a 1:750 dilution of Alexa 594-conjugated goat anti-mouse secondary antibodies. In addition, cells were counter-stained with DAPI to visualize nuclei. Cells were washed three times and mounted onto glass slides after which M localization images were acquired using a Nikon TE2000-U inverted epifluorescence microscope (Nikon Instruments, Inc.; Melville, N.Y.). Representative images were acquired with Metamorph software (Molecular Devices).

Electron microscopy: Confluent cell monolayers in 6-well plates were inoculated with rVSV-GP-EboV at a MOI of 200-500 for 3 h. Subsequently, cells were fixed for at least 1 h at RT in a mixture of 2.5% glutaraldehyde, 1.25% paraformaldehyde and 0.03% picric acid in 0.1 M sodium cacodylate buffer (pH 7.4). Samples were washed extensively in 0.1 M sodium cacodylate buffer (pH 7.4) after which they were treated with 1% osmiumtetroxide and 1.5% potassiumferrocyanide in water for 30 min. at RT. Treated samples were washed in water, stained in 1% aqueous uranyl acetate for 30 min., and dehydrated in grades of alcohol (70%, 90%, 2×100%) for 5 min. each. Cells were removed from the dish with propyleneoxide and pelleted at 3,000 rpm for 3 min. Samples were infiltrated with Epon mixed with propyleneoxide (1:1) for 2 h at RT. Samples were embedded in fresh Epon and left to polymerize for 24-48 h at 65° C. Ultrathin sections (about 60-80 nm) were cut on a Reichert Ultracut-S microtome and placed onto copper grids. Images were acquired using a Technai G2 Spirit BioTWIN (Fei, Hillsboro, Oreg.) transmission electron microscope.

Authentic filoviruses and infections: Cells were exposed to EBOV-Zaire 1995 or MARV-Ci67 at an MOI of 3 for 1 h. Viral inoculum was then removed and fresh culture media was added. At 48 h post-infection, cells were fixed with formalin, and blocked with 1% bovine serum albumin. EBOV-infected cells and uninfected controls were incubated with EBOV GP-specific monoclonal antibodies 13F6 or KZ52. MARV-infected cells and uninfected controls were incubated with MARV GP-specific monoclonal antibody 9G4. Cells were washed with PBS prior to incubation with either goat anti-mouse IgG or goat anti-human IgG conjugated to Alexa 488. Cells were counterstained with Hoechst stain (Invitrogen), washed with PBS and stored at 4° C. Infected cells were quantitated by fluorescence microscopy and automated image analysis. Images were acquired at 9 fields/well with a 10× objective lens on a Discovery-1 high content imager (Molecular Devices) or at 6 fields/well with a 20× objective lens on an Operetta (Perkin-Elmer) high content device. Discovery-1 images were analyzed with the "live/dead" module in MetaXpress software. Operetta images were analyzed with a customized scheme built from image analysis functions present in Harmony software.

Animals and filovirus challenge experiments: Mouse-adapted MarV Ci67 was provided by Sina Bavari[47]. Female and male BALB/c NPC1$^{+/-}$ mice and BALB/c NPC1$^{+/+}$ mice (5 to 8 week old) were obtained from Jackson Laboratory (Bar Harbor, Me.). Mice were housed under specific-pathogen-free conditions. Research was conducted in compliance with the Animal Welfare Act and other federal statutes and regulations relating to animals and experiments involving animals and adhered to principles stated in the Guide for the Care and Use of Laboratory Animals (National Research Council, 1996). The facility where this research was conducted is fully accredited by the Association for the Assessment and Accreditation of Laboratory Animal Care International. For infection, mice were inoculated intraperitoneally (i.p.) with a target dose of 1000 pfu (30,000×the 50% lethal dose) of mouse-adapted EboV or mouse-adapted MarV Ci67 virus in a biosafety level 4 laboratory. Mice were observed for 28 days after challenge by study personnel and by an impartial third party. Daily observations included evaluation of mice for clinical symptoms such as reduced grooming, ruffled fur, hunched posture, subdued response to stimulation, nasal discharge, and bleeding. Serum was collected from surviving mice to confirm virus clearance. Back titration of the challenge dose by plaque assay determined that EboV-infected mice received 900 pfu/mouse and MarV-infected mice received 700 pfu/mouse.

GP-NPC1 co-immunoprecipitation (co-IP) assays: Protein G-coated magnetic beads (20 µL/reaction; Spherotech) were incubated with the GP-specific monoclonal antibody KZ52 (5 µg) for 1 h, washed to remove unbound antibody, and then added to uncleaved or in vitro-cleaved rVSV-GP-EBOV or VSV-GP-EBOV particles (5 µL concentrated virus; $10^7$-$10^8$ infectious units), or to purified EBOV GPΔTM (9 µg) in NTE-CHAPS buffer (10 mM Tris.Cl [pH 7.5], 140 mM NaCl, 1 mM EDTA, 0.5% vol/vol CHAPS (3-[(3-cholamidopropyl) dimethylammonio]-1-propanesulfonate)). Bead-virus mixtures were incubated for 2 h at room temperature, and then added to crude detergent extracts of CHO CT43 cells expressing a flag-tagged NPC1 protein (NPC1-flag) (2×$10^6$ cell-equivalents in 150 µL), or to purified, soluble NPC1 domain C (5 µg/mL). After overnight incubation with mixing at 4° C., beads were retrieved with a magnet, extensively washed with NTE-CHAPS, and heated in Laemmli sample buffer to elute bound proteins. Solubilized proteins were subjected to SDS-polyacrylamide gel electrophoresis, and NPC1 and GP were detected by immunoblotting with anti-flag (Sigma-Aldrich) and anti-GP1 antibodies, respectively.

GP-NPC1 capture ELISA: 96-well high-binding ELISA plates (Corning) were coated with the GP-specific monoclonal antibody KZ52 (2 µg/mL in PBS), and then blocked with PBS containing 3% bovine serum albumin and 0.5% CHAPS (PBSA-CHAPS). Uncleaved or in vitro-cleaved rVSV-GP or VSV-GP particles solubilized in PBSA-CHAPS buffer were added to the blocked plates, and GP capture was allowed to proceed for 1 h at 37° C. After washing to remove unbound GP, serial dilutions of NPC1-flag partially purified from CT43 cells (0-100 ng/well), crude detergent extracts of 293T cells expressing flag-tagged NPC1 or NPC1L1 proteins (0-2×$10^5$ cell-equivalents), or purified, soluble domain C (0-40 µg/mL) were added to the wells. After an overnight incubation at 4° C., plates were extensively washed, and bound flag-tagged proteins were detected with an anti-flag antibody-horseradish peroxidase conjugate and Ultra-TMB substrate (Thermo).

Affinity purification of NPC1-flag: CT43 cells expressing NPC1-flag ($2 \times 10^8$ cells) were harvested and lysed as above, and the extracts were incubated with magnetic beads coated with anti-flag antibody (0.25 mL) at 4° C. with mixing for 12-16 h. Beads were then extensively washed with NTE-CHAPS, and bound proteins were eluted with 10 packed-bead volumes of triple flag peptide (5 mg/mL; Sigma). The eluate was concentrated and buffer-exchanged using a centrifugal concentrator (100 kDa molecular weight cutoff; Pall Biosciences), and NPC1-flag purity was assessed by SDS-PAGE and staining with the Krypton infrared protein-binding dye (Thermo).

Generation and purification of soluble domain C and GPΔTM proteins: A construct engineered to encode NPC1 domain C (residues 372-622) flanked by sequences that form a stable, antiparallel coiled coil, and fused to a preprotrypsin signal sequence and flag and hexahistidine tags at its N-terminus. A plasmid encoding EBOV GPΔTM (residues 1-650) fused to a hexahistidine tag at the C-terminus was kindly provided by G. G. Olinger (USAMRIID). Soluble domain C was expressed in human 293-Freestyle cells (Invitrogen) and purified from conditioned supernatants by nickel affinity chromatography. GPΔTM was expressed in 293-EBNA cells (ATCC) and purified from conditioned supernatants in a similar manner.

Neutralization of rVSV-GP-EBOV by soluble domain C: Uncleaved or cleaved rVSV-GP-EBOV particles were mixed with soluble domain C for 1 h at room temp. Subsequently, the virus mixtures were diluted and exposed to Vero cell monolayers for 1 h at 37° C., at which time $NH_4Cl$ (20 mM) was added to block additional entry events and cell-to-cell spread. Viral infectivity was determined at 12-16 h post-infection by enumerating eGFP-positive cells.

Results

Figure 5A:
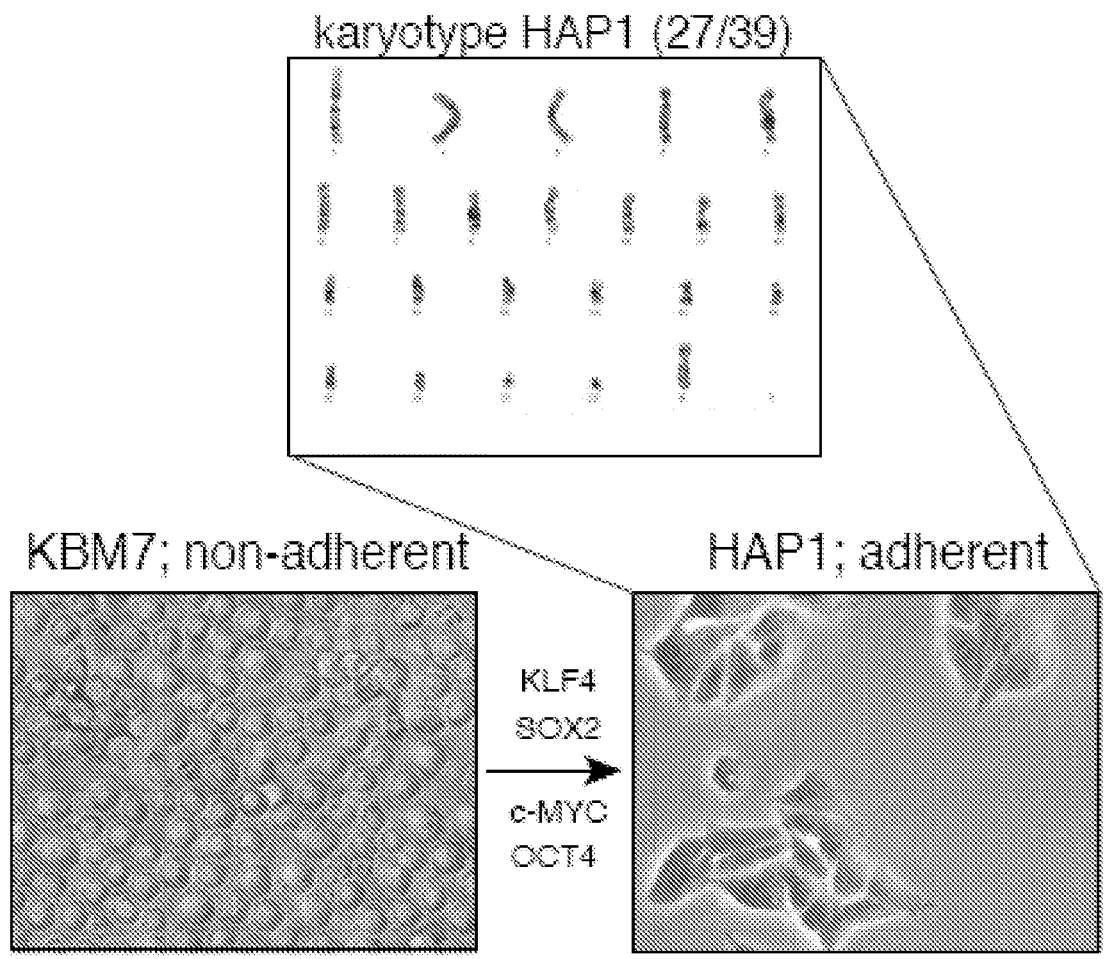
FIG. 5A-5C. Generation of HAP1 cells and susceptibility to rVSV-GP-EboV. a) Near-haploid KBM7 cells were coinfected with retroviral vectors expressing OCT4/SOX2/c-MYC and KLF4 and an adherently growing subclone was identified (HAP1 cells). Karyotypic analysis of HAP1 cells indicates that the majority of cells (27 out of 39 analyzed) is haploid for all chromosomes b) Staining of KBM7 cells and HAP1 cells with pan-hematopoietic markers CD43 and CD45. Stained cells were examined by flow-cytometry. The unstained control is indicated in grey. c) Susceptibility of HAP1 and KBM7 cells to cell-killing by rVSV-GP-EboV.
Figures 5B, 5C:
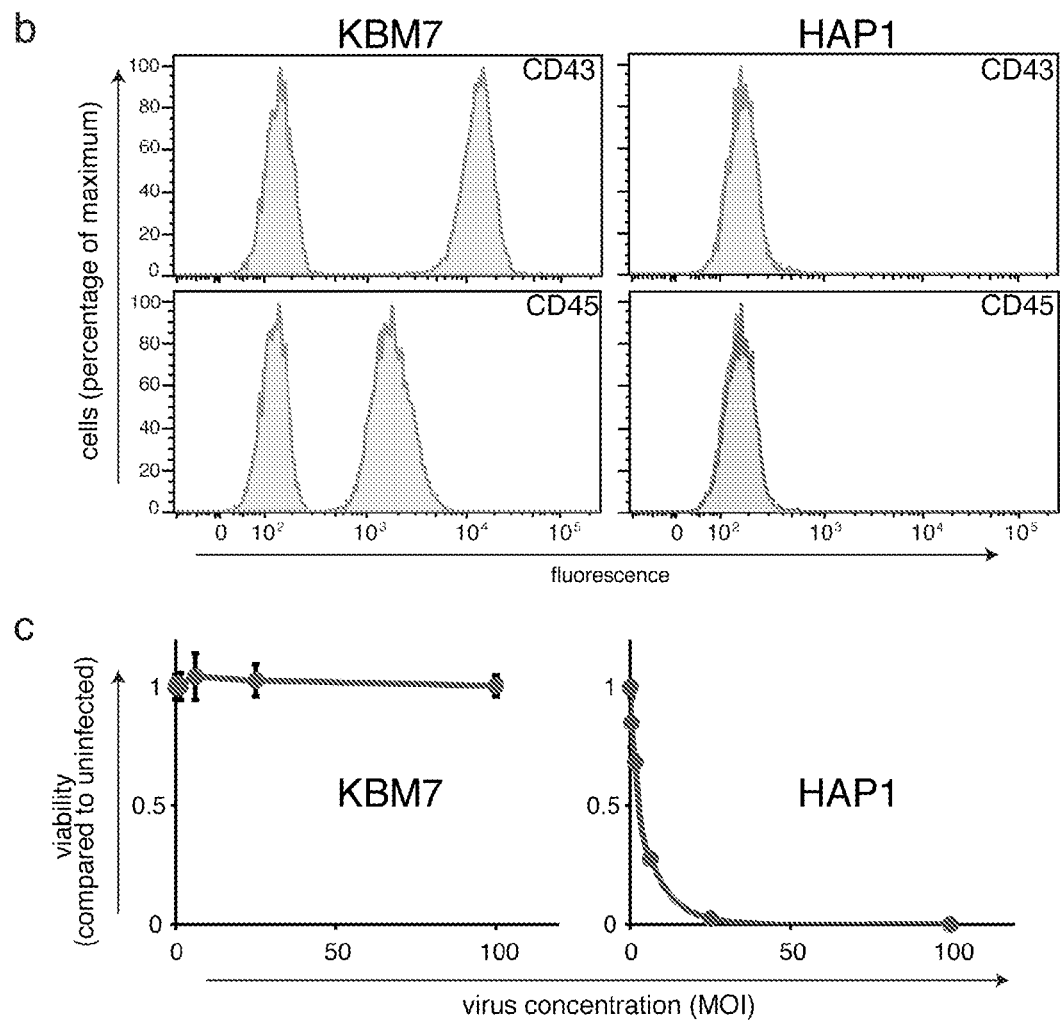

Haploid genetic screens have previously been used to gain insight into a variety of biological processes relevant to human disease[9,10]. Here this approach was used to explore the cell entry pathway used by filoviruses at an unprecedented level of detail. To interrogate millions of independent gene disruption events in human cells for associated defects in EboV entry, a replication-competent vesicular stomatitis virus bearing the EboV glycoprotein (rVSV-GP-EboV)[11] was used to select for resistant cells. Although this recombinant virus multiplies in and kills most cultured cell lines, it grew poorly in near-haploid KBM7 cell cultures (FIG. 5C). To obtain a system suitable for a haploid genetic screen using rVSV-GP-EboV, experiments were undertaken to alter the differentiation state of KBM7 cells[12]. In an unsuccessful attempt to induce pluripotency in KBM7 cells through the expression of OCT4, SOX-2, c-MYC and KLF4[13], a cell line was obtained that was termed HAP1 (FIG. 5A). HAP1 cells grow adherently, can be clonally expanded, and no longer express markers associated with hematopoietic cells (FIG. 5B). The majority of cells in early passage cultures of HAP1 cells are haploid for all chromosomes, including chromosome 8 (which is present in two copies in KBM7 cells). Unlike KBM7 cells, HAP1 cells did support robust multiplication of rVSV-GP-EboV and were rapidly killed by it (FIG. 5C), thus allowing mutagenesis-based screens for essential Filovirus host factors.

Figure 1A:
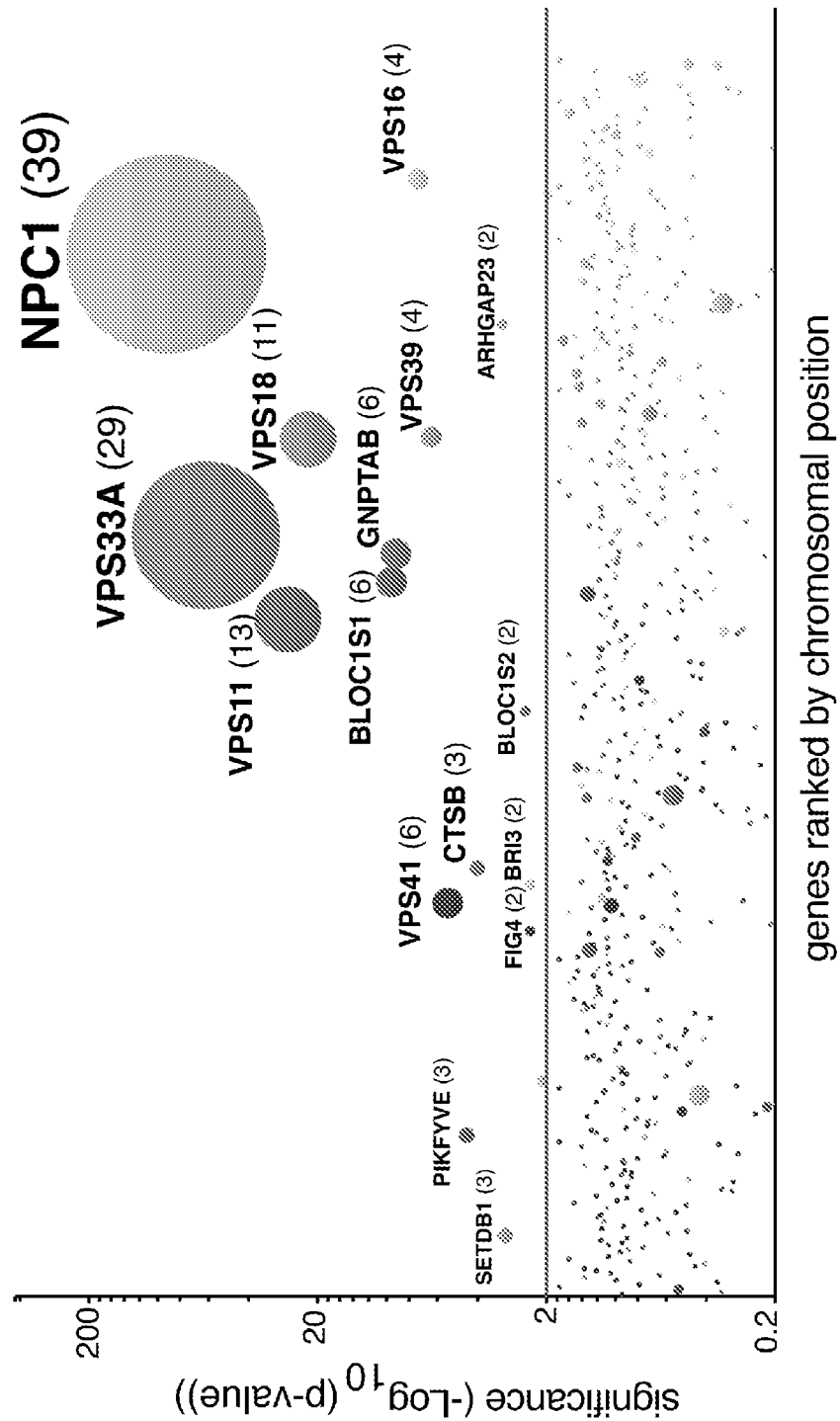
Figures 4A, 4B:
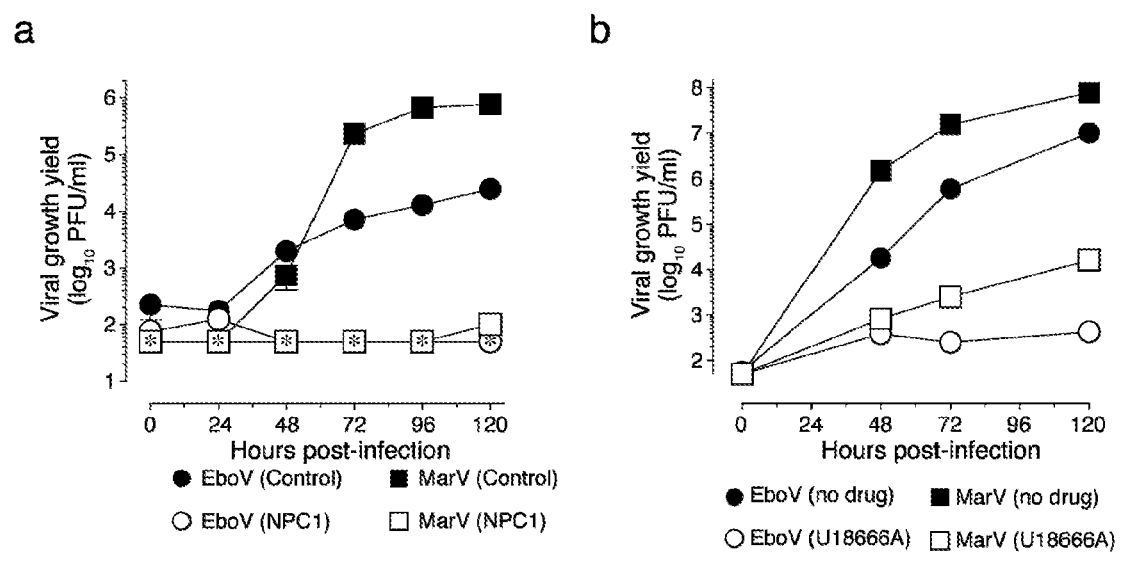
Figure 4C:
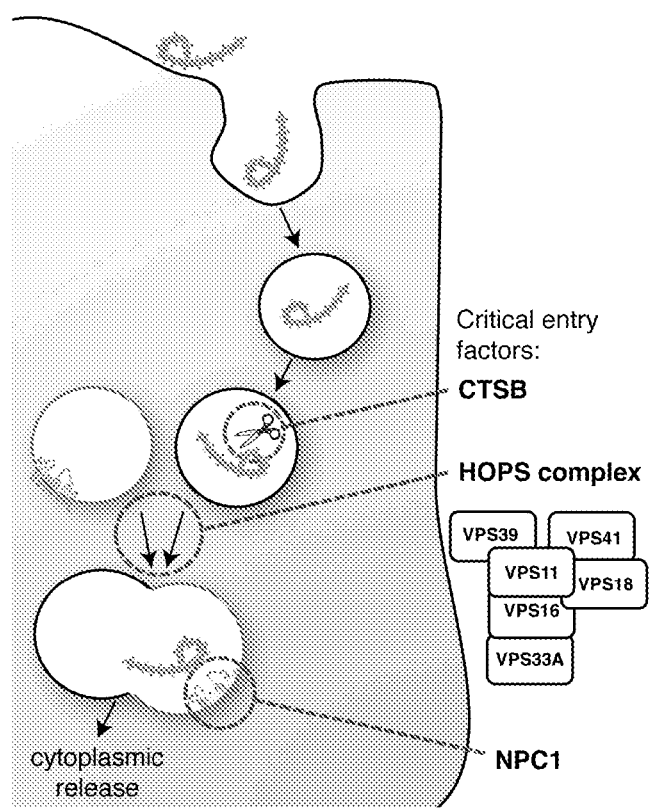

A retroviral promoter-less gene trap vector[10] was used to perform insertional mutagenesis on early-passage HAP1 cells, creating a library of cells with single-gene disruptions. To generate a control dataset, ~800,000 insertion events were mapped in unselected cells using deep sequencing. Next, ~100 million mutagenized cells were exposed to rVSV-GP-EboV. Cells resistant to killing by this virus were expanded as a pool, and insertion sites were mapped using parallel sequencing. Enrichment for mutations in a particular gene was calculated by comparing the gene's mutation frequency in resistant cells to that observed in the unselected control dataset (FIG. 6). Similar experiments in KBM7 cells have linked numerous genes to a variety of phenotypes with high confidence[9]. Using this approach, a set of genes enriched for mutations in the rVSV-GP-EboV-resistant cell population were identified (FIGS. 1A and 4C). Nearly all of the candidate host factors encoded by these genes are involved in the architecture and trafficking of endo/lysosomal compartments, highlighting the central importance of this pathway for EboV GP-dependent infection. The screen identified the endosomal cysteine protease cathepsin B (CatB), the only host factor whose genetic deletion was previously demonstrated to inhibit EboV GP-dependent entry[3]. Further inspection showed that mutations were highly enriched in all 6 subunits of the homotypic fusion and vacuole protein sorting (HOPS) complex (VPS11, VPS16, VPS18, VPS33A, VPS39 and VPS41), for which a total of 67 independent mutations were identified. Like its well-studied yeast counterpart, the mammalian HOPS complex plays a critical role in fusion of endosomes and lysosomes[6]. The identification of all 6 members of the HOPS complex demonstrates the high, and possibly saturating, coverage of the mutagenesis screen. A number of additional genes were also identified whose products are involved in the biogenesis of endosomes (PIKFYVE)[14,15] and lysosomes (BLOC1S1, BLOC1S2)[16], and in targeting of luminal cargo to the endocytic pathway (GNPTAB)[17]. Finally, the single strongest hit obtained, with 39 independent gene-trap insertions, was the Niemann-Pick disease locus NPC1, which encodes an endo/lysosomal cholesterol transporter[8].

Figures 1B, 1C, 1D:
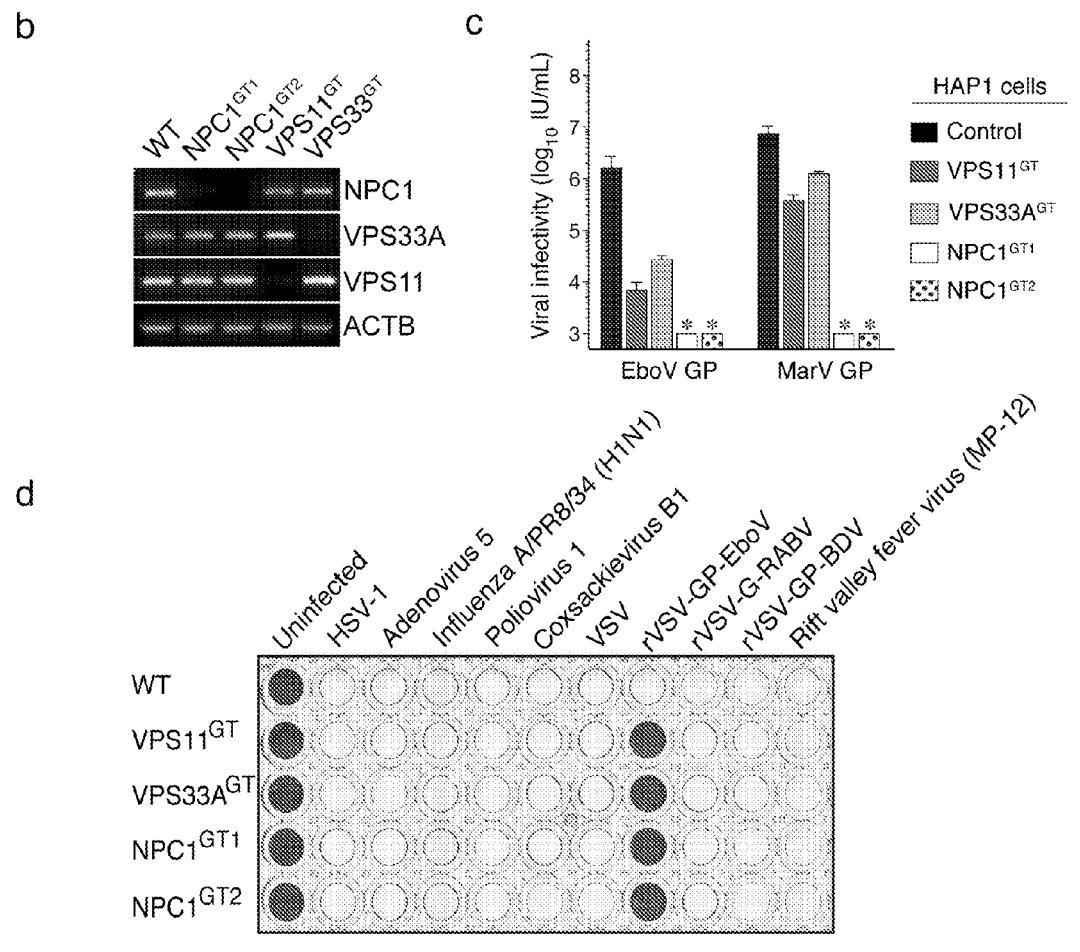
Figure 7A:
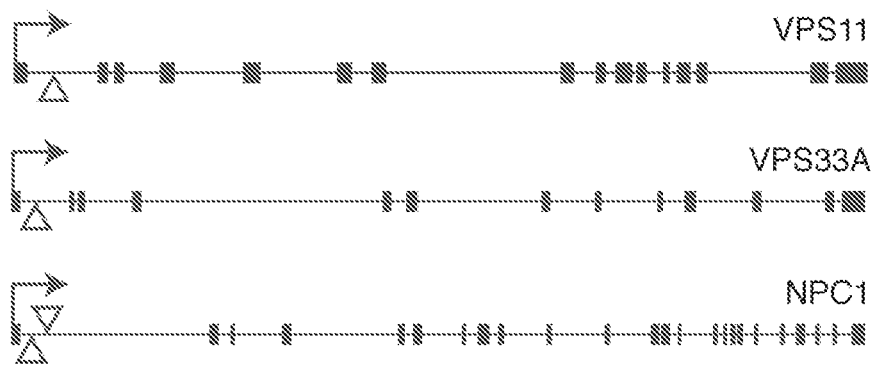
FIG. 7A-7C. Identification and characterization of HAP1 cells carrying gene-trap insertions in the NPC1, VPS11 and VPS33A loci. a) Schematic outline of the positions of gene-trap insertions in the corresponding genes. Gene traps were located in the sense orientation in intronic sequences of the 5'-end of the gene and are therefore predicted to disrupt gene function. b) Clonal cell lines carrying the gene-trap insertions in the corresponding loci were identified through subcloning. Genotyping indicates the absence of wild type genomic loci and the presence of gene-trap loci. c) Cells carrying gene-trap insertions in the corresponding loci and wild type HAP1 cells were inoculated with rVSV-GP-EboV, and infected cells were visualized by fluorescence microscopy 12 h later.
Figure 7B:
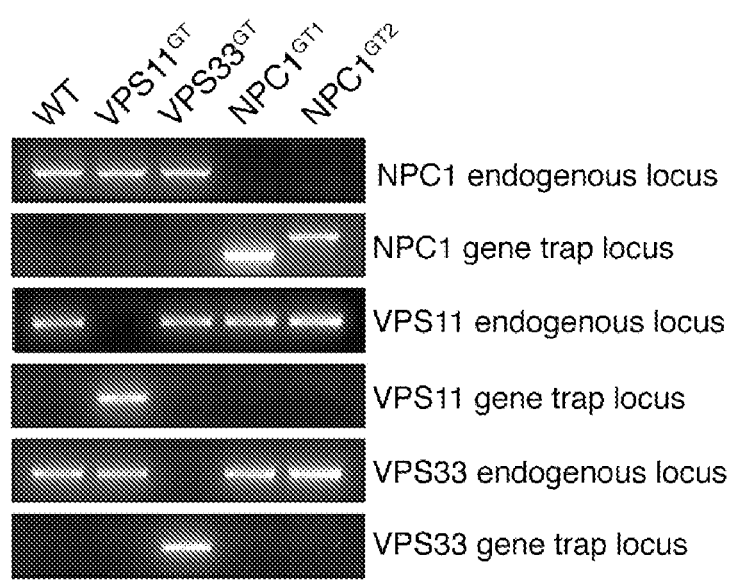
Figure 7C:
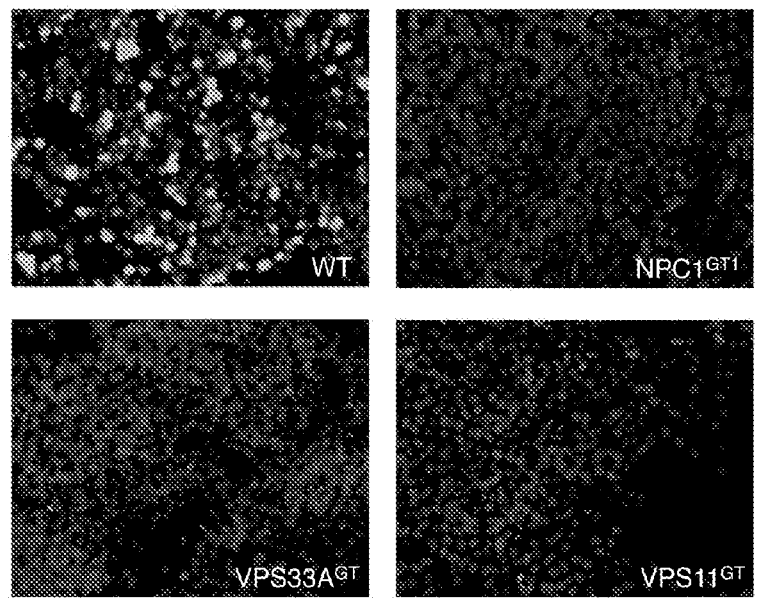
Figures 8A, 8B:
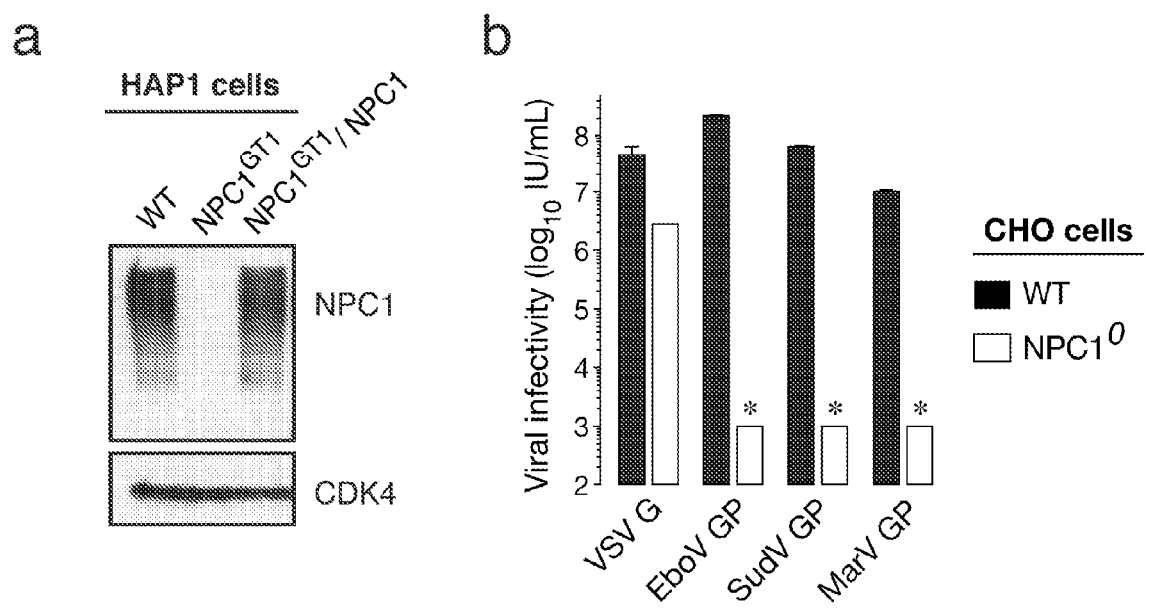

Neither the HOPS complex nor NPC1 has previously been implicated in the entry of any type of virus. To investigate their roles in filovirus entry, the resistant cell population was subcloned to obtain clones deficient for the HOPS subunits VPS11 and VPS33A, and for NPC1 (FIG. 7A, 7B). Expression of the corresponding gene products was no longer detected in these clones (FIG. 8A). NPC1-, VPS11- and VPS33A-null cells displayed marked resistance to infection by rVSV-GP-EboV and VSV pseudotypes bearing EboV or MarV GP (FIGS. 1C, and 7C). NPC1-deficient cells were completely refractory to infection by these viruses. Cells that lack a functional HOPS complex or NPC1 were nonetheless fully susceptible to infection by a large panel of other enveloped and nonenveloped viruses, including native VSV and recombinant VSVs bearing the Rabies and Borna disease virus glycoproteins[17] (FIG. 1D). These mutant cells also fully supported infection by influenza A virus, which enters cells via late endosomes[19] (FIG. 1D). Therefore, deficiency of VPS11, VPS33A, or NPC1 causes resistance specifically to viral entry mediated by filovirus glycoproteins.

Figure 2A:
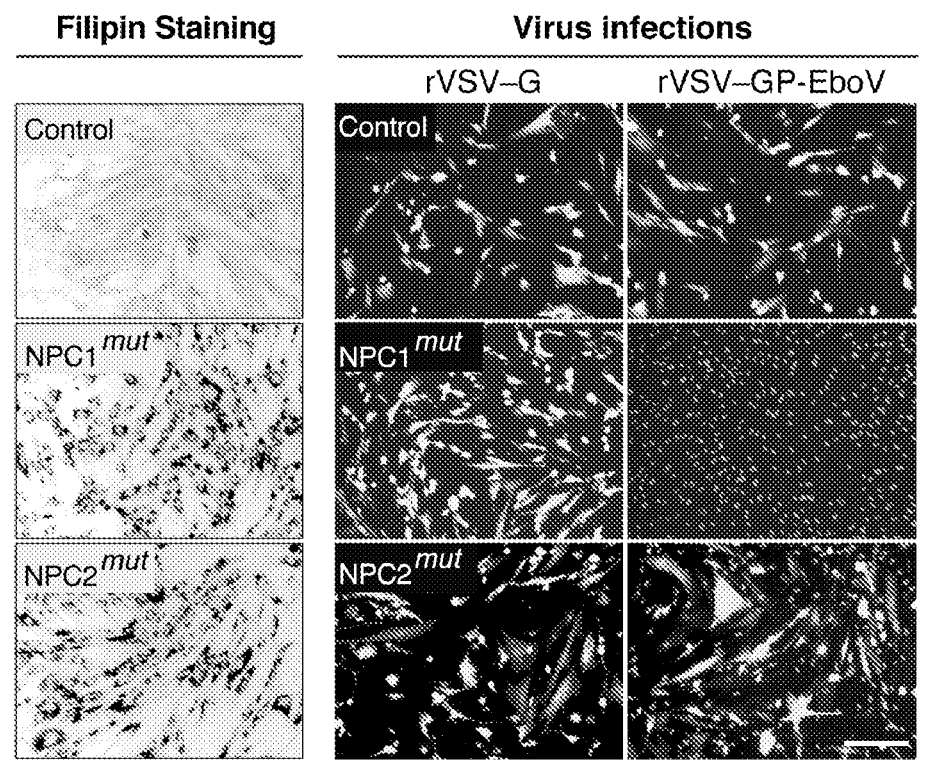
Figure 2B:
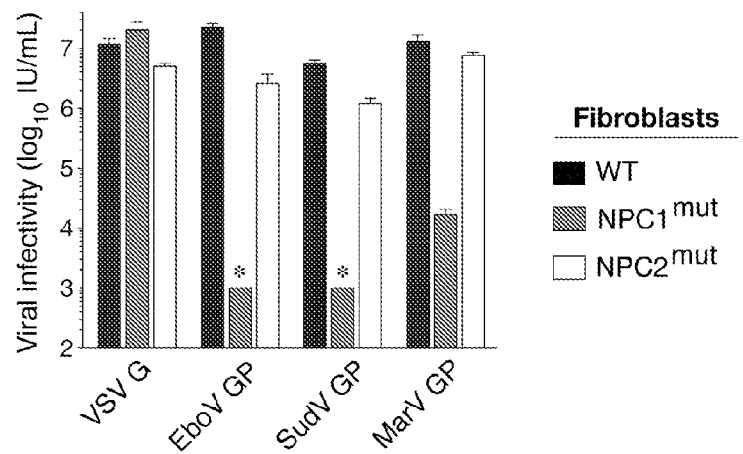
Figure 2C:
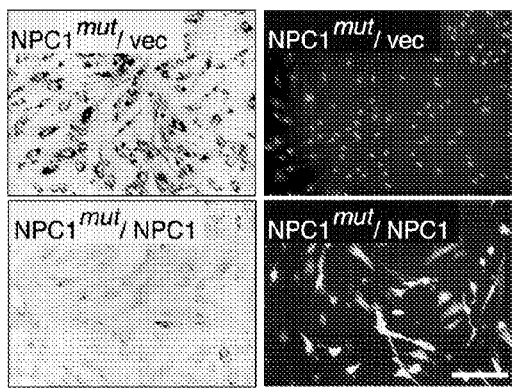

Loss of NPC1 function causes Niemann-Pick disease, a hereditary neurovisceral disorder characterized by the accumulation of cholesterol and sphingolipids within lysosomes[8,20,21]. Tests were conducted of the susceptibility of patient fibroblasts carrying homozygous mutations in NPC1 to filovirus GP-dependent infection. As expected, control cells derived from a healthy individual were readily infected by rVSV-GP-EboV and VSV pseudotyped with GP proteins derived from EboV, Sudan virus, or MarV, whereas NPC1-mutant cells were infected poorly or not at all (FIGS. 2A, B). By contrast, both types of cells were efficiently infected by native VSV. The susceptibility of NPC1-deficient fibroblasts to rVSV-GP-EboV infection was restored by retroviral expression of wild type NPC1, confirming that loss of the NPC1 protein is responsible for the infection defect (FIG. 2C).

Figure 9:
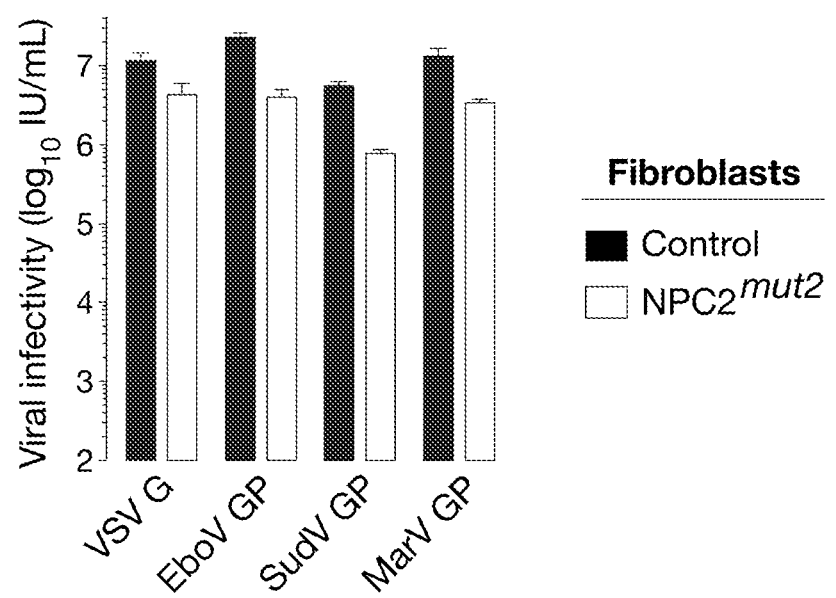
FIG. 9. NPC2-mutant fibroblasts derived from a second Niemann-Pick type C patient are susceptible to viral infection mediated by the Ebola virus glycoprotein. Fibroblasts from an apparently normal individual and a Niemann-Pick disease patient carrying homozygous mutations in NPC2 were infected with VSV pseudotypes bearing the indicated viral glycoproteins, and viral infectivity was measured 24 h later. Means±standard deviation (SD) are shown FIG. 10A-10B. Clearance of accumulated cholesterol does not render NPC1-deficient cells susceptible to infection by rVSV-GP-EboV. Wild type and NPC1-null CHO cells were cultivated either in normal growth medium (control) or in growth medium containing lipoprotein-depleted fetal bovine serum (depleted) for 6 days. Cells were then stained with filipin to visualize accumulated cholesterol (A) or exposed to rVSV-GP-EboV (B). Filipin-stained or infected cells were visualized by fluorescence microscopy. In each of (A) and (B), top panels are control and bottom panels are depleted.
Figures 10A, 10B:
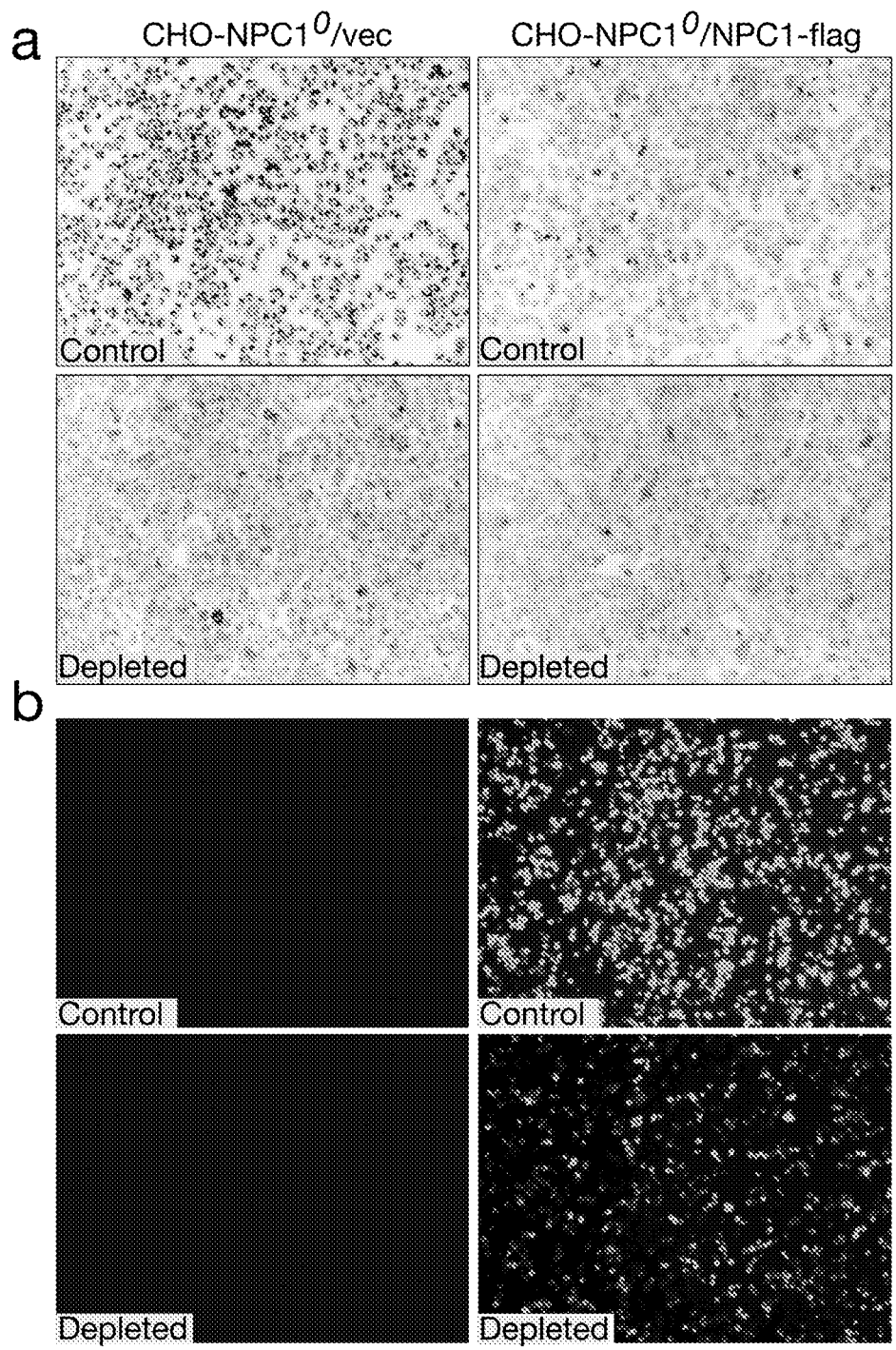

Mutations in a second gene, NPC2, cause identical clinical symptoms and phenocopy the defects in cellular lipid transport[7]. Surprisingly, NPC2-mutant fibroblasts derived from two different patients were susceptible to filovirus GP-dependent infection, despite similar capacities of the NPC2- and NPC1-mutant cells to accumulate cholesterol in lysosomes (FIGS. 2A, 2B and 9). Furthermore, clearance of accumulated cholesterol from NPC1-null cells by prolonged cultivation in lipoprotein-depleted growth medium did not confer susceptibility to rVSV-GP-EboV infection (FIG. 10A, 10B). Thus, resistance of NPC1-deficient cells to rVSV-GP-EboV is not caused by defects in lipid transport per se, consistent with the results of the screen, which did not identify NPC2 as a host factor for EboV entry (FIG. 1A).

Filoviruses display broad mammalian host and tissue tropism and can infect a wide variety of cell types in culture[22,23]. To determine if NPC1 is generally required for filovirus GP-mediated infection, rVSV-GP-EboV infection was measured in NPC1-null Chinese hamster ovary (CHO) cells[24]. Loss of NPC1 conferred complete resistance to viral infection (FIGS. 8B and 10B) that could be reversed by expression of human NPC1 (FIG. 10B). Therefore, NPC1 plays a critical role in entry mediated by filovirus glycoproteins that is conserved in mammals.

Figures 3A, 3B:
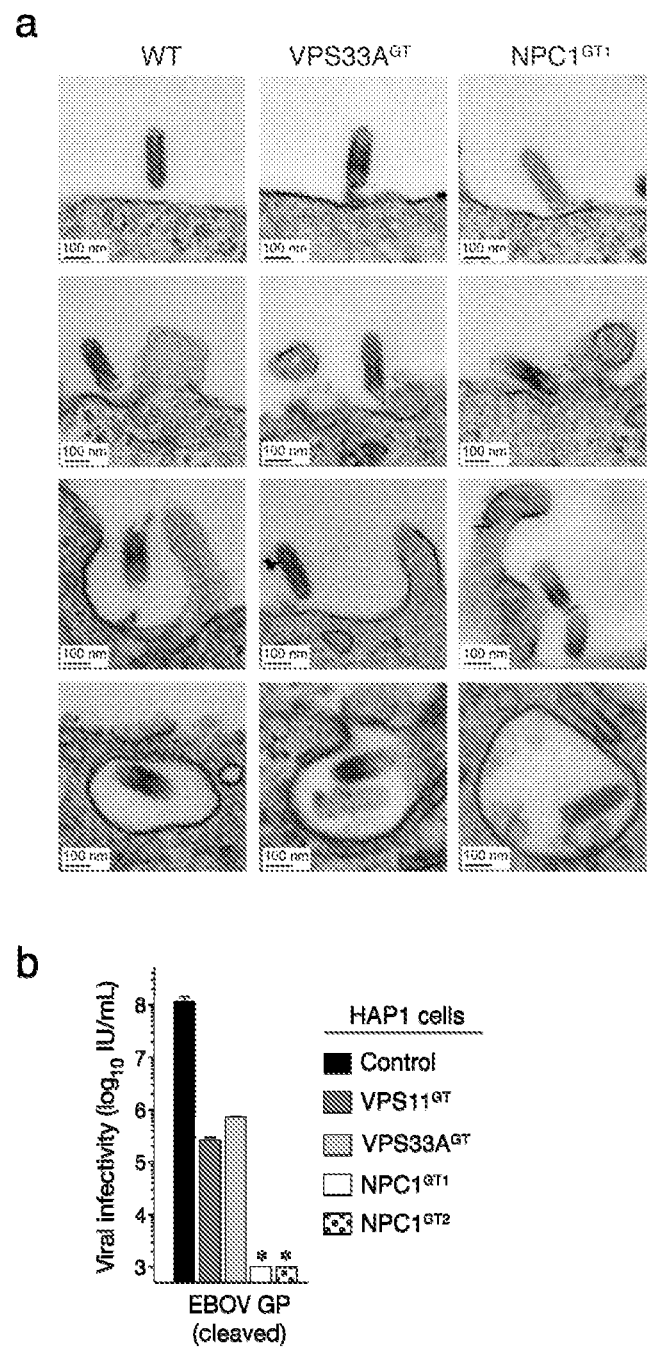

Filovirus particles can probably bind to a diverse set of cell-surface molecules[4,31], upon which they undergo internalization by a macropinocytosis-like mechanism[32,33], and traffic to late endosomal compartment(s) where GP is cleaved by endosomal cysteine proteases[3]. Cleaved GP then mediates fusion of viral and endosomal membranes, thereby releasing the viral nucleocapsid into the cytoplasm[34]. To determine which step(s) in filovirus entry require the HOPS complex and NPC1, an assessment was conducted of possible defects in attachment and internalization of rVSV-GP-EboV in VPS33A- and NPC1-null HAP1 cells. No significant difference were observed in binding of Alexa 647 fluorophore-labeled rVSV-GP-EboV to wild type and mutant cells at 4° C. (not shown). Cells with bound virus were then warmed to 37° C. to promote endocytosis and acid-washed to strip non-internalized viral particles from the cell surface. Fluorescent microscopy showed similar levels of internalized rVSV-GP-EboV in wild type and mutant cells (not shown). Consistent with these findings, bullet-shaped VSV particles were readily observed by electron microscopy at the cell periphery and within plasma membrane invaginations resembling nascent macropinosomes (FIG. 3A). Therefore, GP-mediated entry is not inhibited at binding or internalization steps in NPC1- or HOPS-defective cells, suggesting a downstream block.

Figures 11A, 11B, 11C:
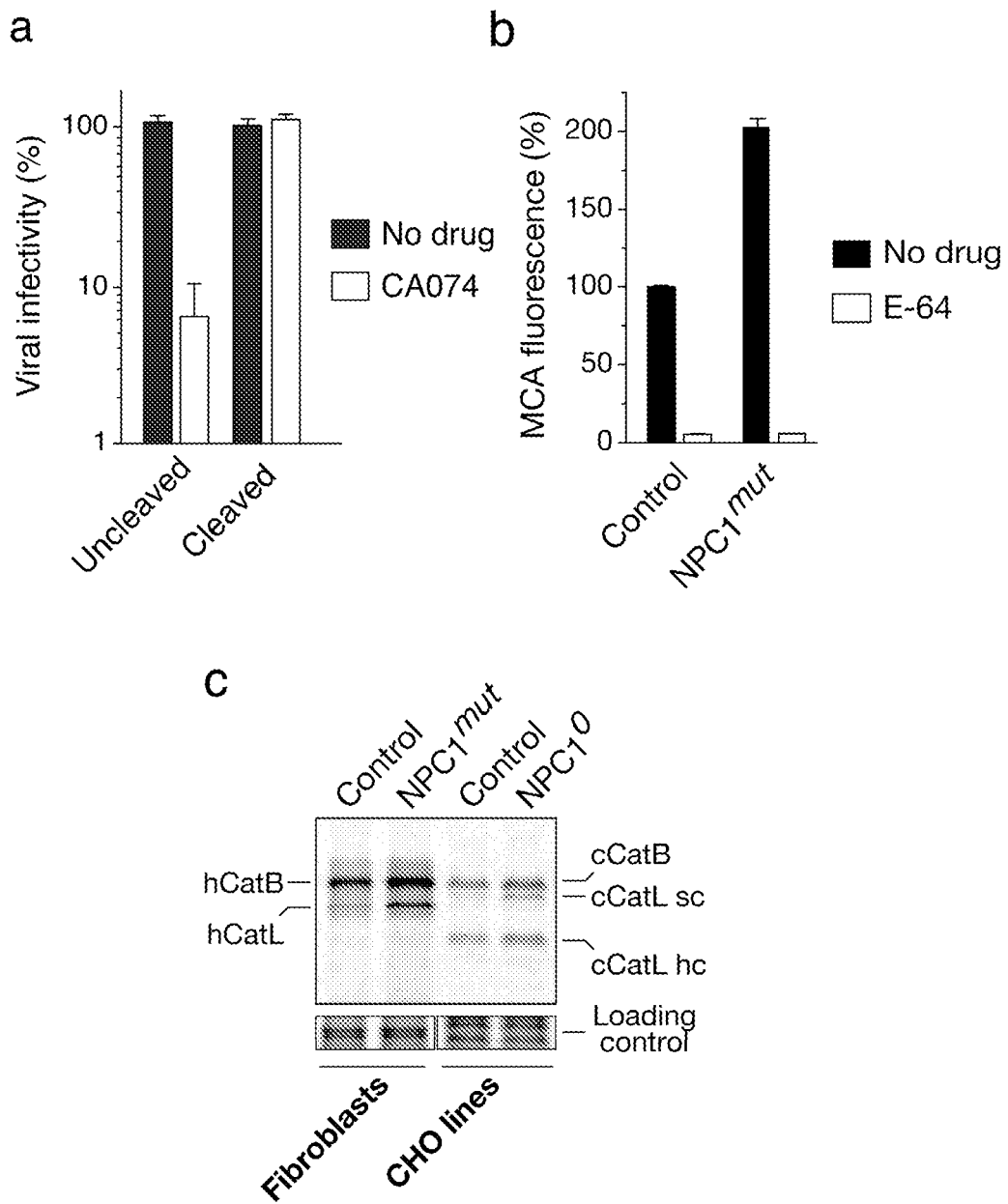
FIG. 11A-11C. The activities of endosomal cysteine cathepsins B and L are not inhibited in NPC1-defective cells. a) In vitro cleaved rVSV-GP-EboV bypasses the intracellular requirement for cathepsin B (CatB). Infectivity of mock- or thermolysin-cleaved rVSV-GP-EboV in Vero cells treated with the CatB inhibitor CA074. b) Fibroblasts from an apparently normal individual (control) and a Niemann-Pick patient carrying homozygous mutations in NPC1 were lysed at acid pH, and the capacity of these acidic extracts to cleave a fluorogenic peptide substrate for CatB and CatL was measured. Pretreatment of cell extracts with the pan-cysteine protease inhibitor E-64 abolished substrate cleavage, confirming that only cysteine cathepsin activities were being measured. c) Intact control and NPC1-deficient fibroblasts and CHO cells were incubated with a fluorophore-tagged suicide substrate for CatB/CatL. Cells were then lysed and fluorophore-labeled CatB and CatL proteins were detected by SDS-polyacrylamide gel electrophoresis and fluorescence imaging. hCatB and hCatL, human enzymes. cCatB and cCatL, CHO enzymes. sc and hc, single chain and heavy chain forms of CatL.

Cleavage of EboV GP by CatB and/or cathepsin L (CatL) is a prerequisite for viral membrane fusion[3,5]. Mutant HAP1 cells possess normal levels of CatB/CatL enzyme activity (FIG. 11B, 11C) and remained refractory to infection by in vitro-cleaved rVSV-GP-EboV particles (FIG. 3C) that no longer required CatB/CatL activity within Vero cells (FIG. 11A). Therefore, the HOPS complex and NPC1 are likely required at step(s) downstream of GP proteolytic processing.

Figures 3C, 3D:
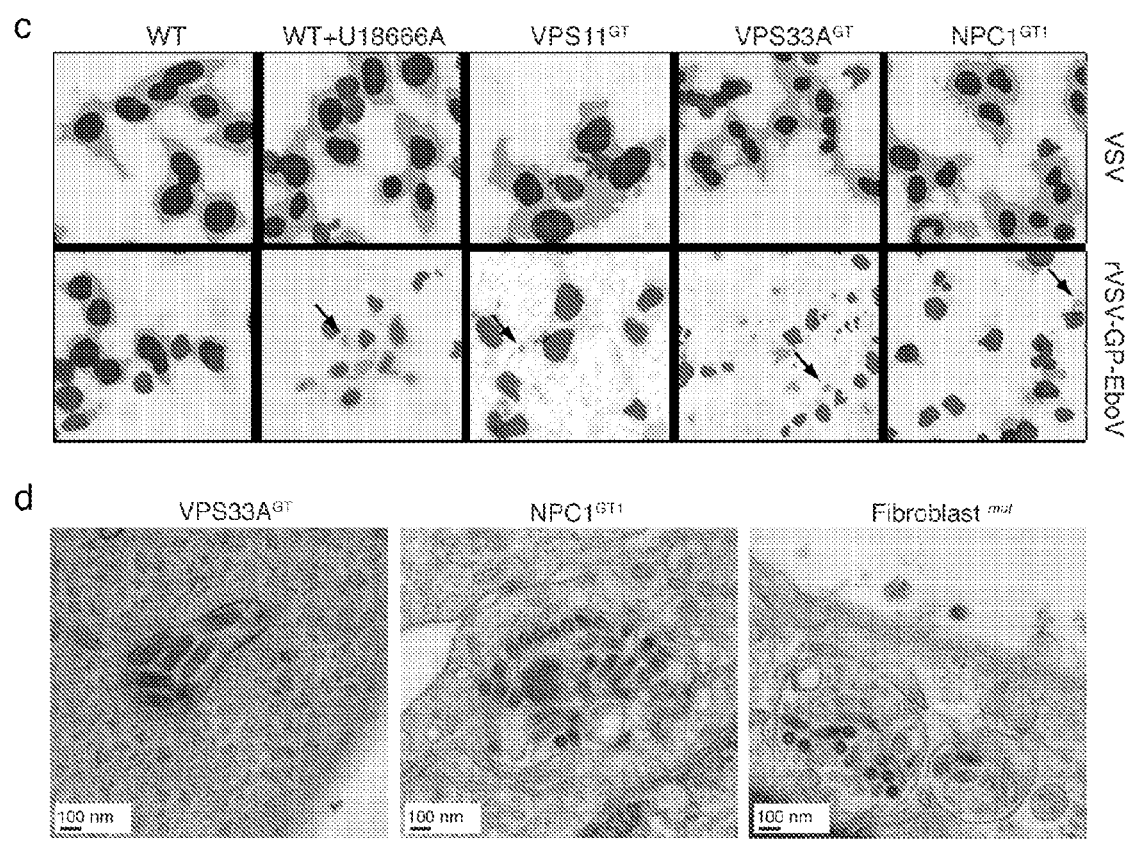
Figure 12:
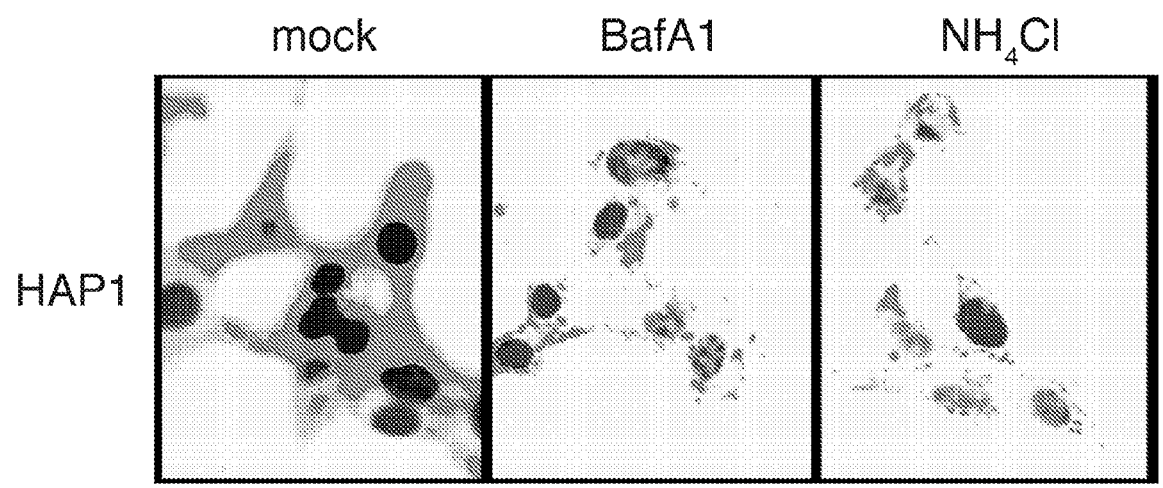
FIG. 12. Viral membrane fusion is required for VSV M release into the cytoplasm of infected cells. Wild type HAP1 cells were treated with puromycin (5 µg/ml) and inoculated with rVSV-GP-EboV in the presence or absence of bafilomycin A1 (bafA1; 100 nM) or ammonium chloride ($NH_4Cl$; 20 µg/ml). Cells were fixed 3 h post inoculation and stained with VSV M antibody 23H12. Successful fusion leads to the diffuse M staining throughout the cytoplasm. Failure to fuse leads to discrete punctuate of M staining as shown by bafA1 and $NH_4Cl$.
Figure 13:
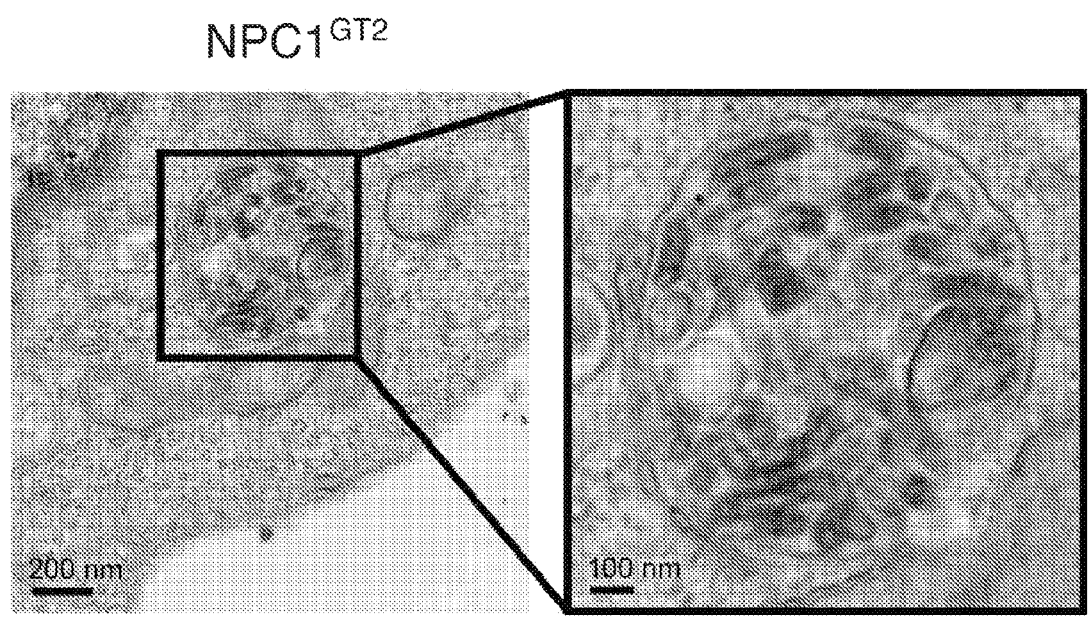
FIG. 13. Accumulation of rVSV-GP-EboV viral particles in vesicular compartments in NPC1-deficient cells. Electron micrograph of a second NPC1-deficient HAP1 clone exposed to rVSV-GP-EboV. A large agglomeration of bullet-shaped VSV particles is visible within a vesicular (endosomal) compartment. All images were taken at 3 h post-infection.

The intracellular distribution of the internal VSV M (matrix) protein was used as a marker for successful membrane fusion in VPS33A- and NPC1-null HAP1 cells (FIG. 3D). Cells were exposed to native VSV or rVSV-GP-EboV in the presence of puromycin to block protein synthesis, and then fixed and immunostained to visualize the incoming M protein. Productive entry into wild type HAP1 cells caused redistribution of the incoming viral M throughout the cytoplasm (FIG. 3C), whereas a membrane fusion block imposed by agents that elevate endosomal pH resulted in punctate M staining (FIG. 12). Diffuse M staining was also observed for VSV in U18666A-treated wild type cells, and in HOPS complex- and NPC1-null cells (FIG. 3C), consistent with the capacity of VSV to productively infect these cells (FIG. 1D). By contrast, only punctate M staining was obtained in drug-treated and mutant cells exposed to rVSV-GP-EboV (FIG. 3C). Electron micrographs of mutant cells revealed agglomerations of viral particles within vesicular compartments (FIGS. 3D and 13), reinforcing the conclusion that fusion and uncoating of the incoming rVSV-GP-EboV is arrested. Therefore, NPC1 and a functional HOPS complex are required for late step(s) in filovirus entry leading to viral membrane fusion.

The above experiments were done with recombinant or pseudotyped VSV particles bearing filovirus glycoproteins. Because these surrogate systems may not faithfully represent all aspects of filovirus infection, it was tested if infection and multiplication by authentic EboV and MarV are affected in NPC1-mutant patient fibroblasts. Consistent with the findings with VSV particles, yields of infectious viral progeny were profoundly reduced for both viruses in the mutant cells, relative to control fibroblasts (FIG. 4A). Therefore, NPC1 is essential for authentic filovirus infection.

Figure 2D:
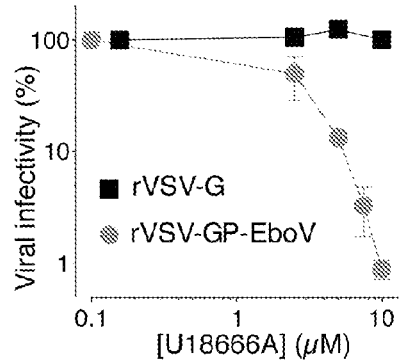
Figures 15A, 15B:
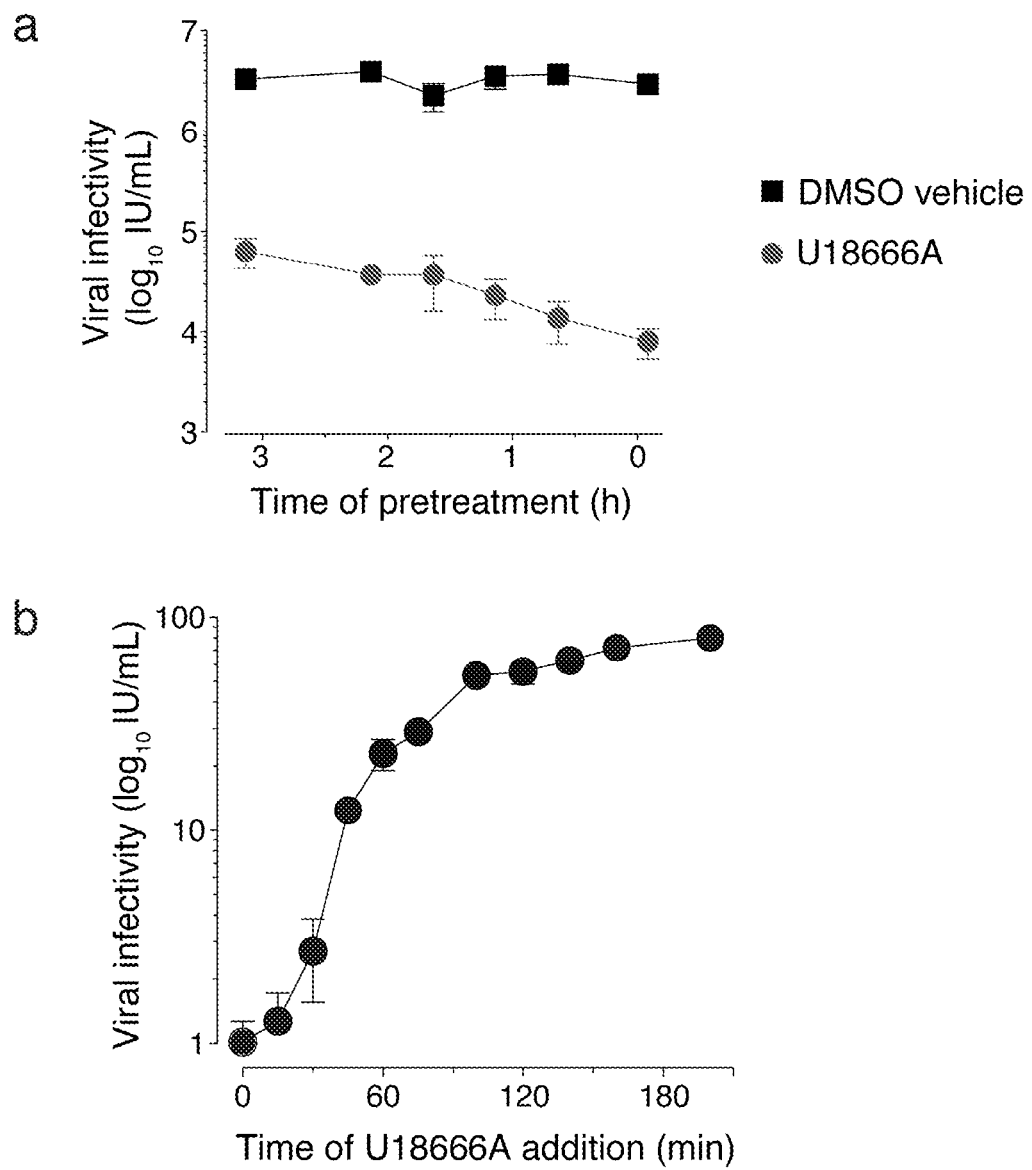
FIG. 15A-15B. U18666A acts rapidly to inhibit Ebola virus GP-dependent entry. (a) Time-of-pretreatment experiment: Vero cells were left untreated or treated with U18666A (20 µM) for the indicated times and then exposed to rVSV-GP-EboV. After 1 h, viral entry was terminated by addition of NH₄Cl (20 mM). Viral infectivity was measured 14 h later. Means±standard deviation (SD) are shown. (b) Time-of-escape experiment: Vero cells were first exposed to rVSV-GP-EboV and then left untreated or treated with U18666A for 1 h at 37° C. After 1 h, viral entry was terminated by addition of NH₄Cl (20 mM). Viral infectivity was determined as above.
Figure 18:
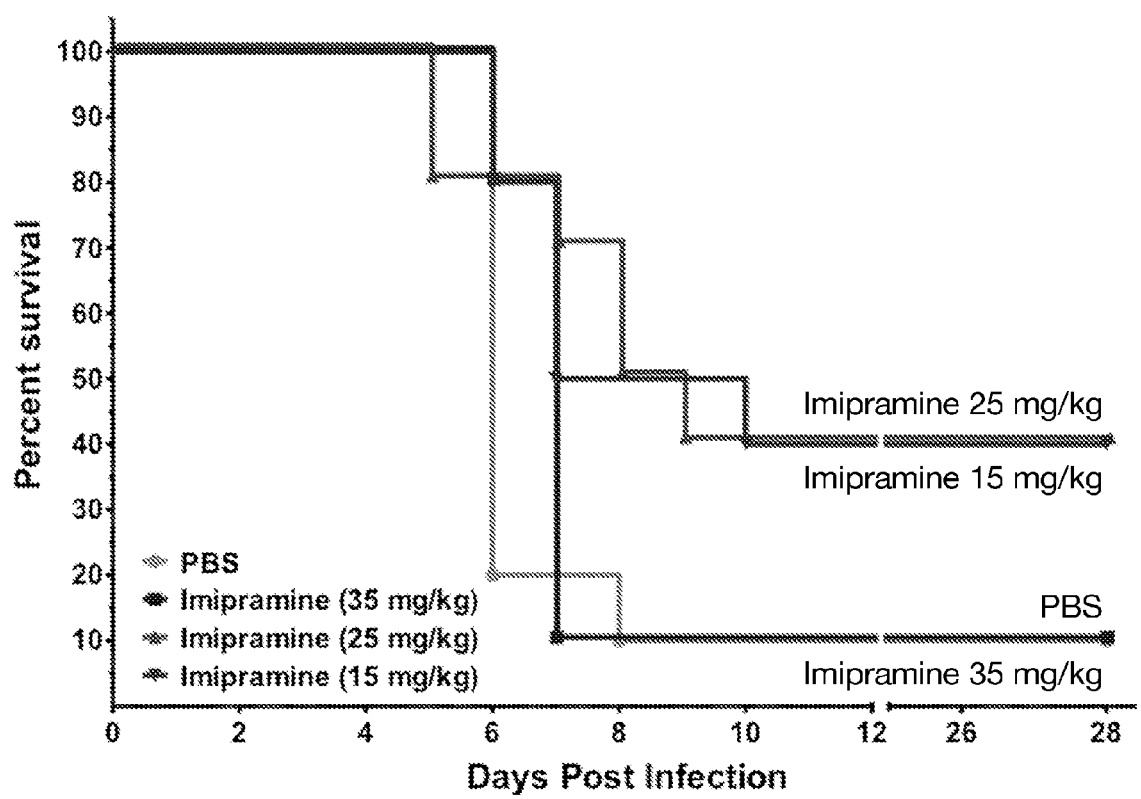
FIG. 18. NPC1 pathway inhibitor imipramine partially protects mice from EboV. Balb/c mice (n=10 for each group) were inoculated intraperitoneally (i.p.) with ~1000 pfu of mouse-adapted EboV or MarV together with vehicle (PBS) or imipramine at the indicated dose.

Certain small molecules such as U18666A[25] and the antidepressant imipramine[26] are known to cause a cellular phenotype similar to that observed in Niemann-Pick disease, in part by targeting the NPC1 protein[27,28,29]. Both compounds potently inhibited viral infection mediated by EboV GP but not VSV in Vero grivet monkey cells (FIG. 2D for U18666A; imipramine not shown). U18666A inhibited viral infection almost immediately after its addition to Vero cells (<10 min) (FIG. 15A) and before significant intracellular accumulation of cholesterol could be observed (>4 h) (data not shown)[30]. Moreover, sensitivity of viral infection to U18666A was lost by ~2 h post-infection, indicating that U18666A inhibits infection at the entry step (FIG. 15B).

Figures 14A, 14B:
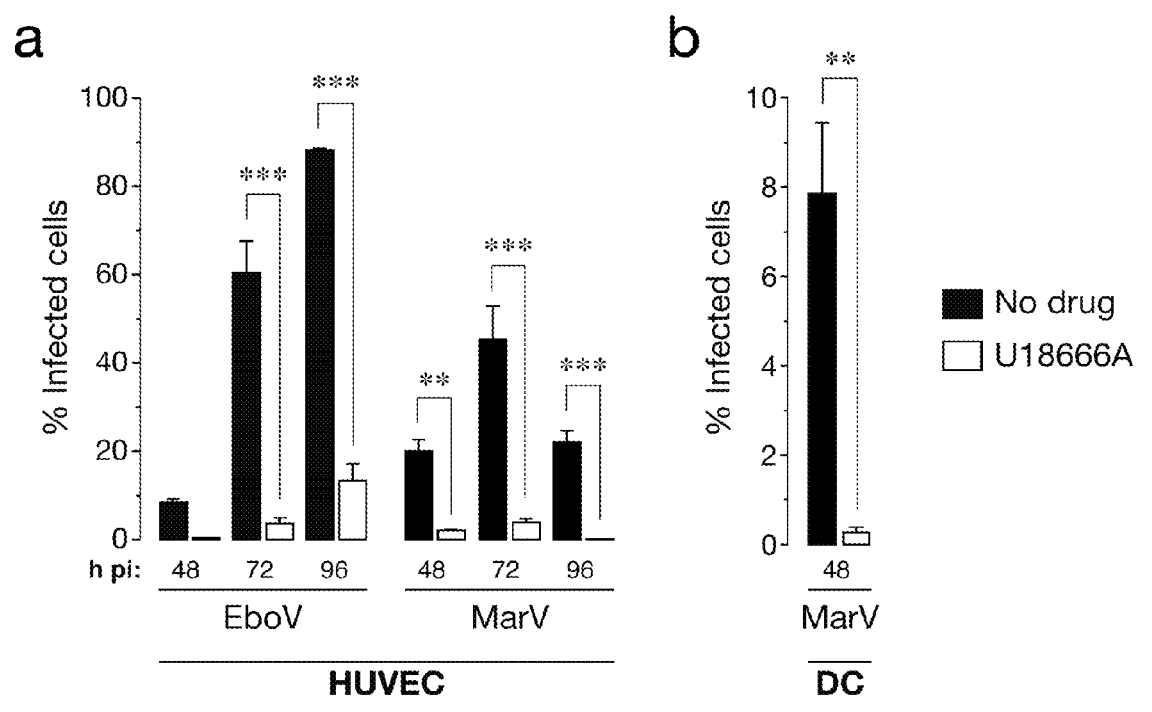
Figure 16:
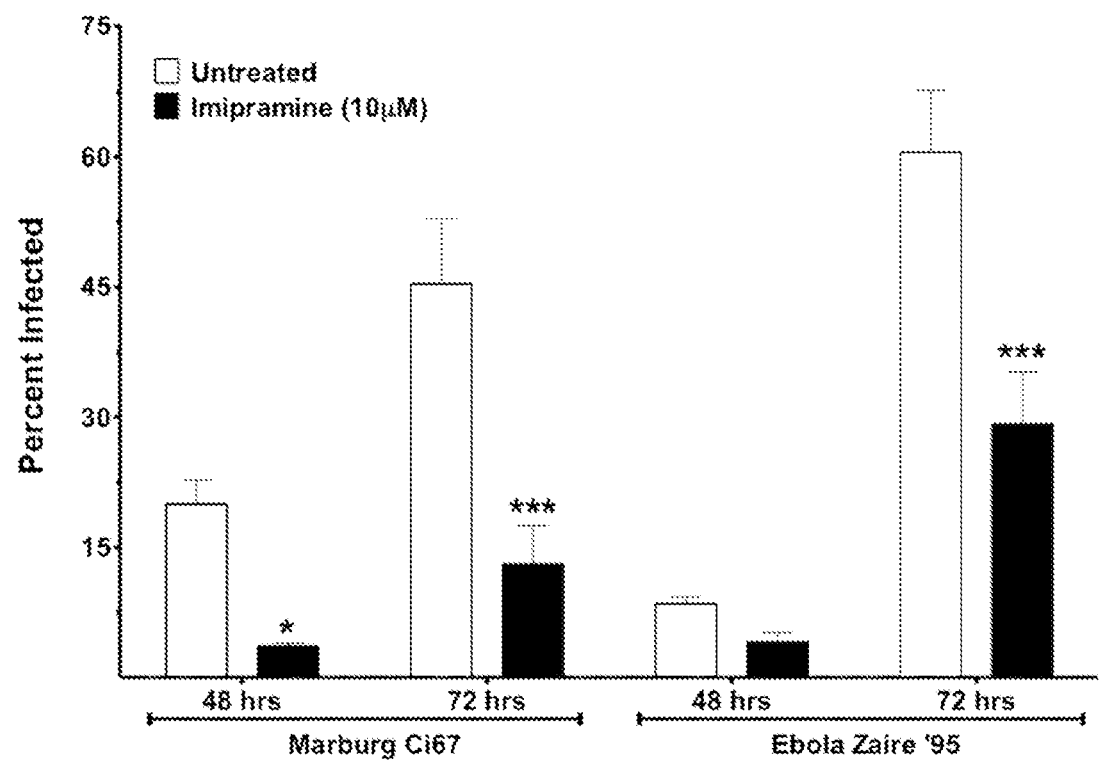

The effect of U18666A and imipramine on infection by authentic EboV and MarV was examined Stark reductions in viral yield were obtained in Vero cells treated with either drug (FIGS. 4B and 16). Moreover U18666A greatly reduced infection of human peripheral blood monocyte-derived dendritic cells and umbilical-vein endothelial cells (HUVEC) (FIG. 14A, 14B), without affecting cell number or morphology. These findings indicate that filovirus entry and infection is sensitive to perturbation by small-molecule inhibitors of NPC1.

Figures 17A, 17B:
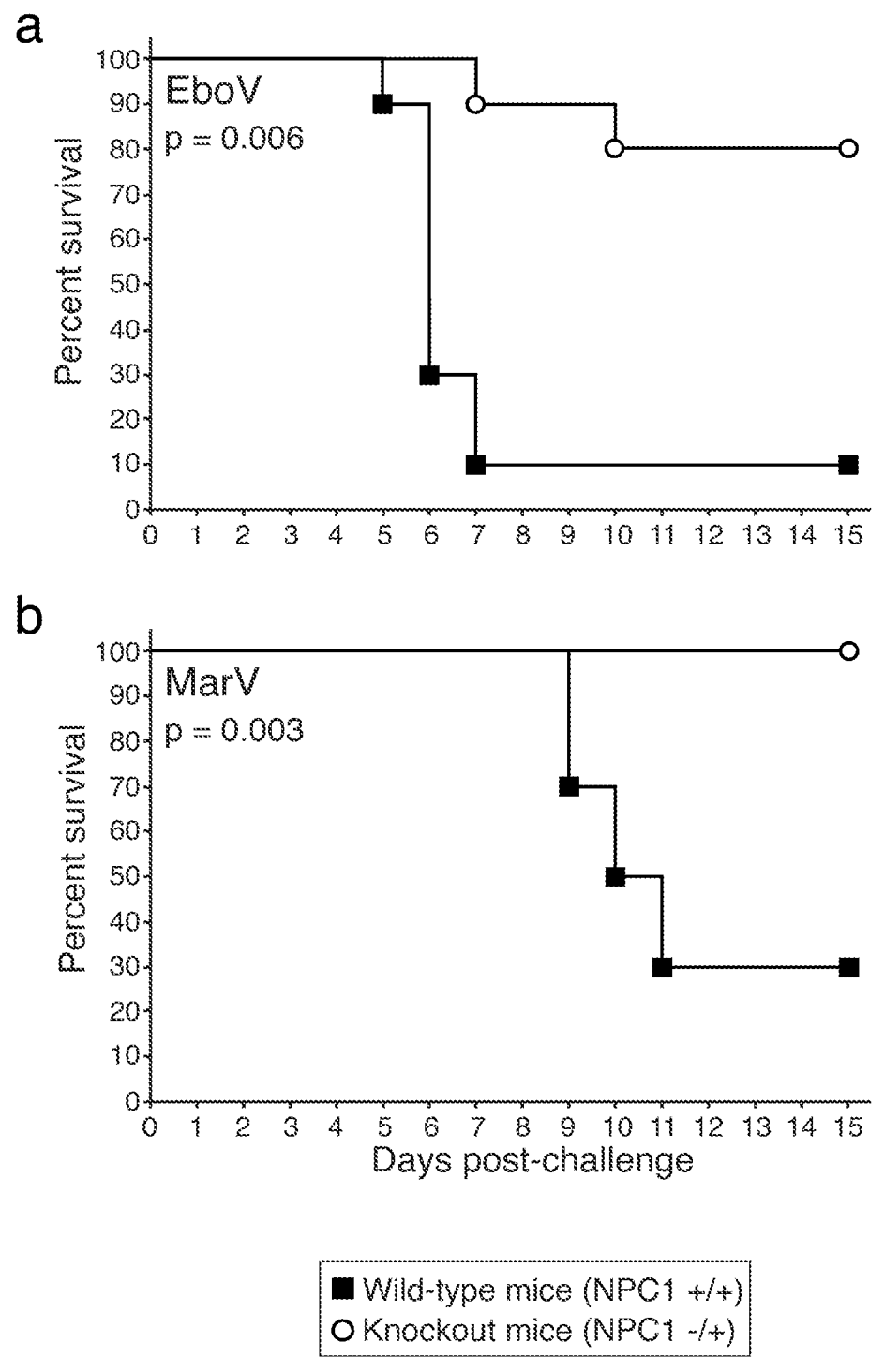

The effect of NPC1 mutation in lethal mouse models of EboV and MarV infection was assessed. Heterozygous NPC1 (NPC1$^{-/+}$) knockout mice and their wild type littermates were challenged with mouse-adapted EboV or MarV and monitored for 28 days. Whereas NPC1$^{+/+}$ mice rapidly succumbed to infection with either filovirus, NPC1$^{-/+}$ mice were largely protected (FIG. 17A, 17B). Therefore, NPC1 is critically required for filovirus in vivo pathogenesis.

Given its efficacy in tissue culture, the protective capacity of imipramine was examined in the lethal mouse model of of EboV infection. Mice administered a single dose of imipramine 2 h before EboV challenge were substantially protected from filovirus challenge. Although the efficacy of imipramine at interrupting NPC1 function in vivo was not examined, these findings provide the first evidence that pharmacological inhibition of NPC1 in vivo can confer protection against filovirus infection.

Figures 20A, 20B, 20C:
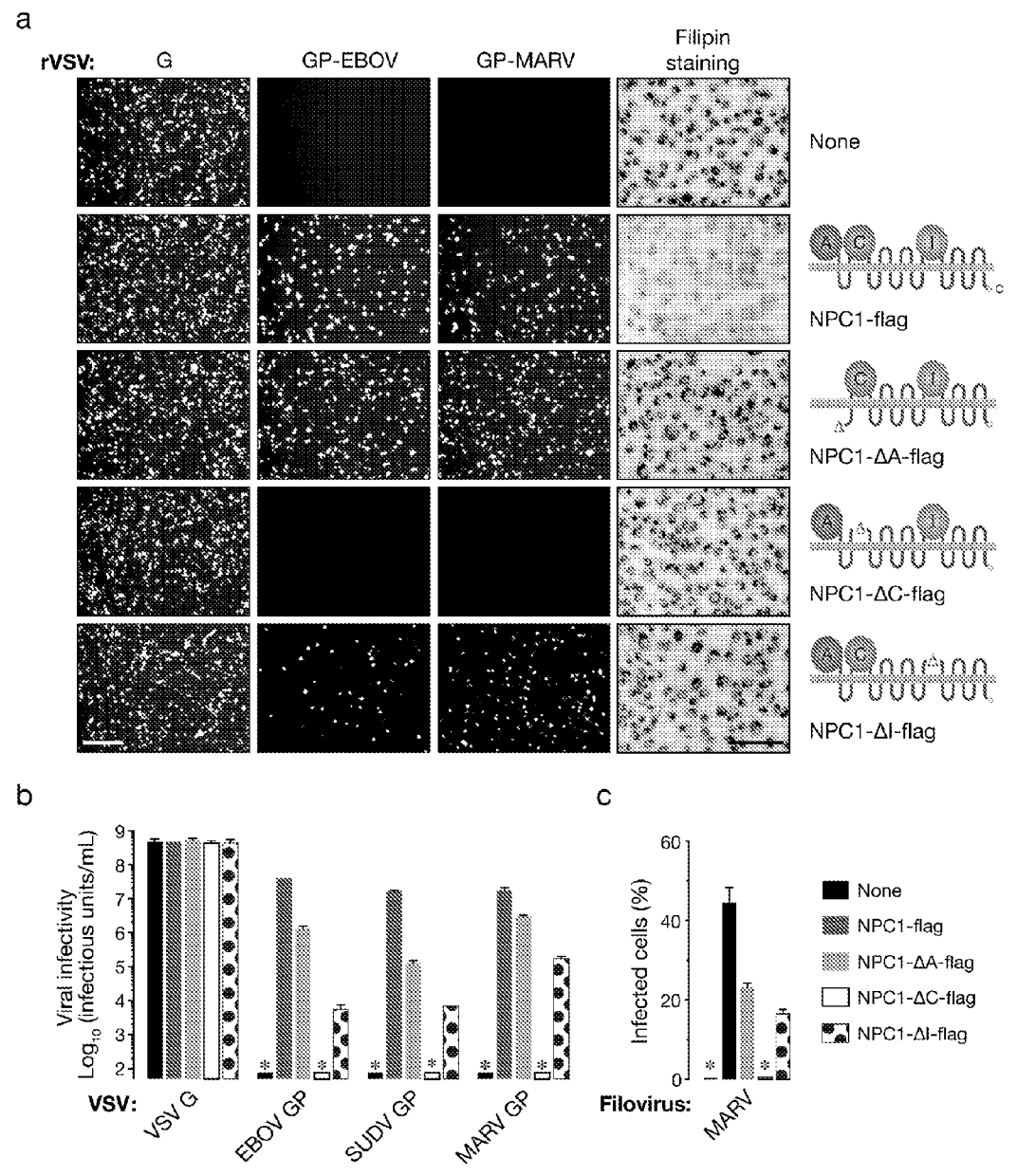

To determine if filovirus entry requires the entire NPC1 protein or can instead be attributed to a discrete region within it, NPC1 deletion mutants individually lacking the large luminal loop domains A, C, and I (FIG. 19) were expressed in an NPC1-null cell line (Chinese hamster ovary [CHO] CT43[21]), and their capacity to mediate lysosomal cholesterol transport and viral infection was examined (FIG. 20). CT43 cells accumulated lysosomal cholesterol[21], and they were completely resistant to infection by wild type EBOV/MARV and rVSV-GP-EBOV/MARV[10]. As shown previously[10], expression of flag epitope-tagged WT NPC1 (NPC1-flag) in these cells not only corrected their cholesterol transport defect but also rendered them highly susceptible to infection by wild type filoviruses and rVSVs bearing filovirus glycoproteins. All three 'loop-minus' NPC1 mutants were inactive at lysosomal cholesterol transport (FIG. 20A), despite their significant localization to LAMP1-positive late endosomal/lysosomal compartments (not shown), confirming that this cellular activity of NPC1 requires all three luminal domains A, C, and I. However, the mutants differed in their capacity to support filovirus GP-mediated entry. Both NPC1-ΔA-flag and NPC-ΔI-flag could mediate entry, albeit at reduced levels relative to WT NPC1-flag. In striking contrast, NPC1-ΔC-flag was unable to rescue viral entry (FIG. 20) even though it resembled the other mutants in expression level and intracellular distribution (not shown). Similar results were obtained in infection assays with wild type MARV (FIG. 20C). These findings unequivocally separate NPC1's functions in lysosomal cholesterol transport and filovirus entry. More importantly, they demonstrate that a discrete region within NPC1, the luminal domain C, is essential for EBOV and MARV entry.

Figures 21A, 21B:
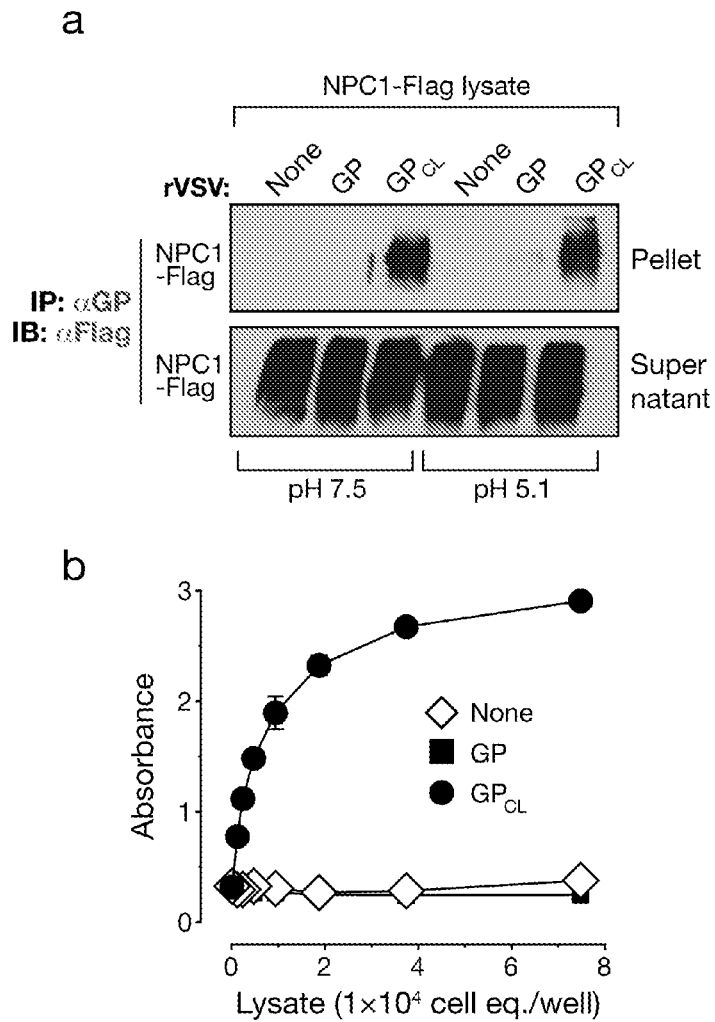
Figure 24A:
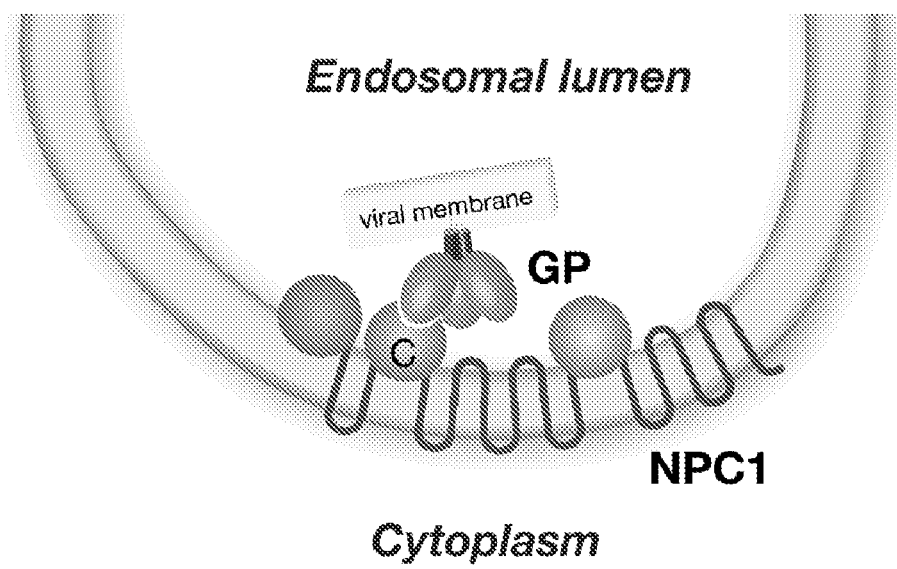
FIG. 24A-24D. Some possible modes of action of small molecule antivirals targeting NPC1. (a) Binding of EboV and MarV GP to domain C in NPC1 within endosomes or lysosomes is required for viral entry and infection. (b) A compound may direct inhibit GP-NPC1 interaction by binding to either protein. (c) A compound may indirectly inhibit GP-NPC1 interaction by binding to NPC1 (in domain C or elsewhere) or to an associated protein or lipid, thereby inducing a conformational change in NPC1. (d) A compound may induce misfolding of NPC1 or otherwise cause reduction of NPC1 levels within the endo/lysosomal compartment. Note that this figure only illustrate a few possible modes of action.
Figure 24B:
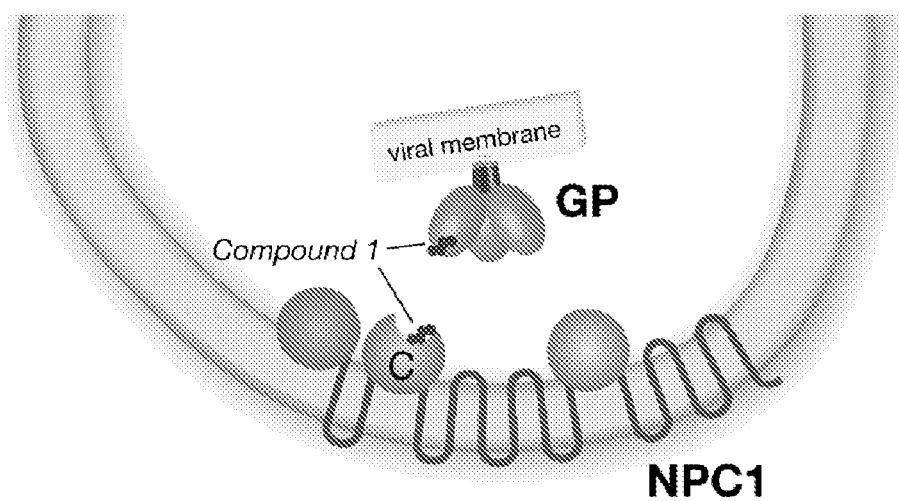
Figure 24C:
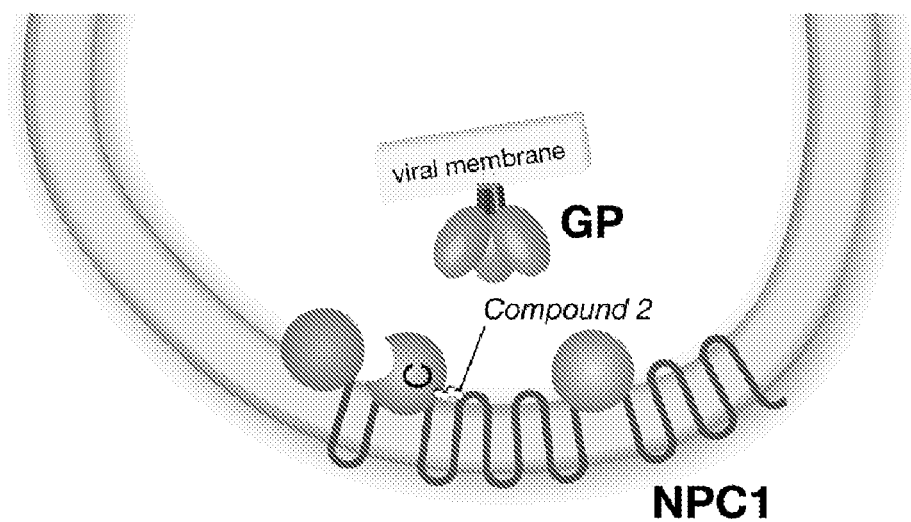
Figure 24D:
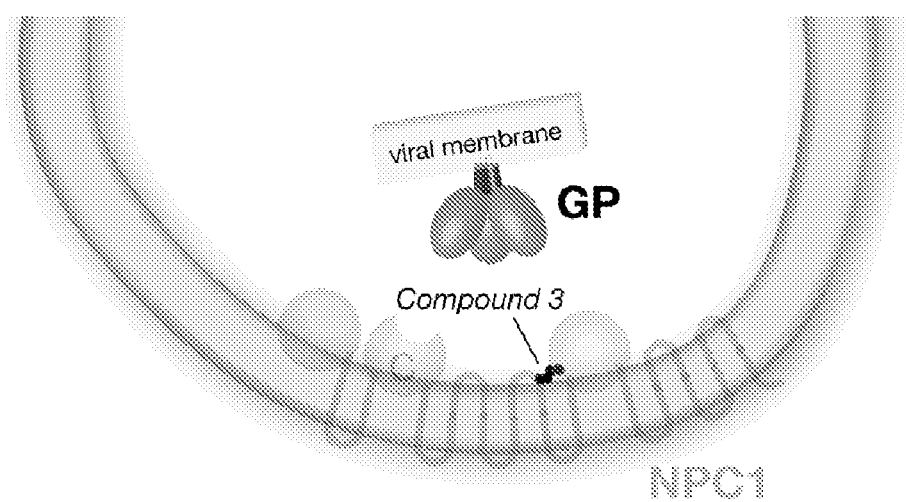

The preceding experiment raised the possibility that filovirus GP uses NPC1 to enter cells by interacting directly with this protein without regard to its normal cellular functions. To examine this hypothesis, it was first tested if EBOV GP could bind to NPC1 in a cell- and membrane-free system. Concentrated rVSV-GP-EBOV particles were solubilized in a nonionic detergent-containing buffer, and the GP protein in these extracts was captured by magnetic beads coated with the GP-specific monoclonal antibody KZ52. These GP-decorated beads did not retrieve NPC1-flag from CT43 detergent extracts in a co-immunoprecipitation (co-IP) assay (FIG. 21A). Next rVSV-GP-EBOV was incubated with the bacterial metalloprotease thermolysin to generate a GP intermediate ($GP_{CL}$) that resembles the product of endo/lysosomal GP cleavage[3,5]. $GP_{CL}$ could capture NPC1-flag at both neutral and acid pH (FIG. 21A). Similar results were obtained in a reciprocal co-IP experiment: magnetic beads displaying NPC1-flag captured $GP_{CL}$ but not GP (not shown).

Figures 21C, 21D:
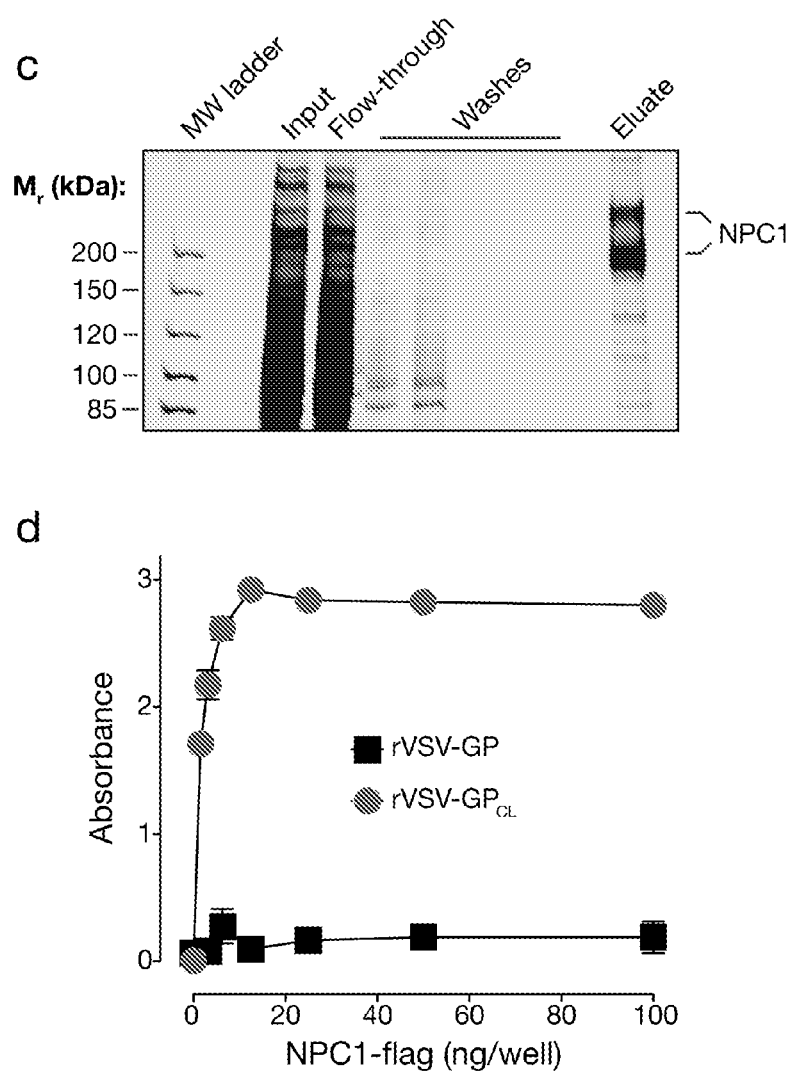

To confirm these findings, the capacity of rVSV-derived GP and $GP_{CL}$ to capture NPC1-flag from 293T human embryonic kidney cell extracts was examined using an enzyme-linked immunosorbent assay (ELISA). GP and $GP_{CL}$ were captured onto antibody KZ52-coated ELISA plates, and then incubated with CT43 extracts containing NPC1-flag. NPC1-flag bound saturably to wells coated with $GP_{CL}$ but not with GP, consistent with the results from the co-IP assay (FIG. 21B). Affinity-purified NPC1-flag (FIG. 21C) bound saturably to wells coated with $GP_{CL}$ but not GP in the ELISA, providing evidence that $GP_{CL}$ directly interacts with NPC1 (FIG. 21D). Cumulatively, these findings demonstrate that the proteolytic priming of EBOV GP creates, or unmasks, a specific and direct binding site for NPC1.

Figures 22A, 22B, 22C:
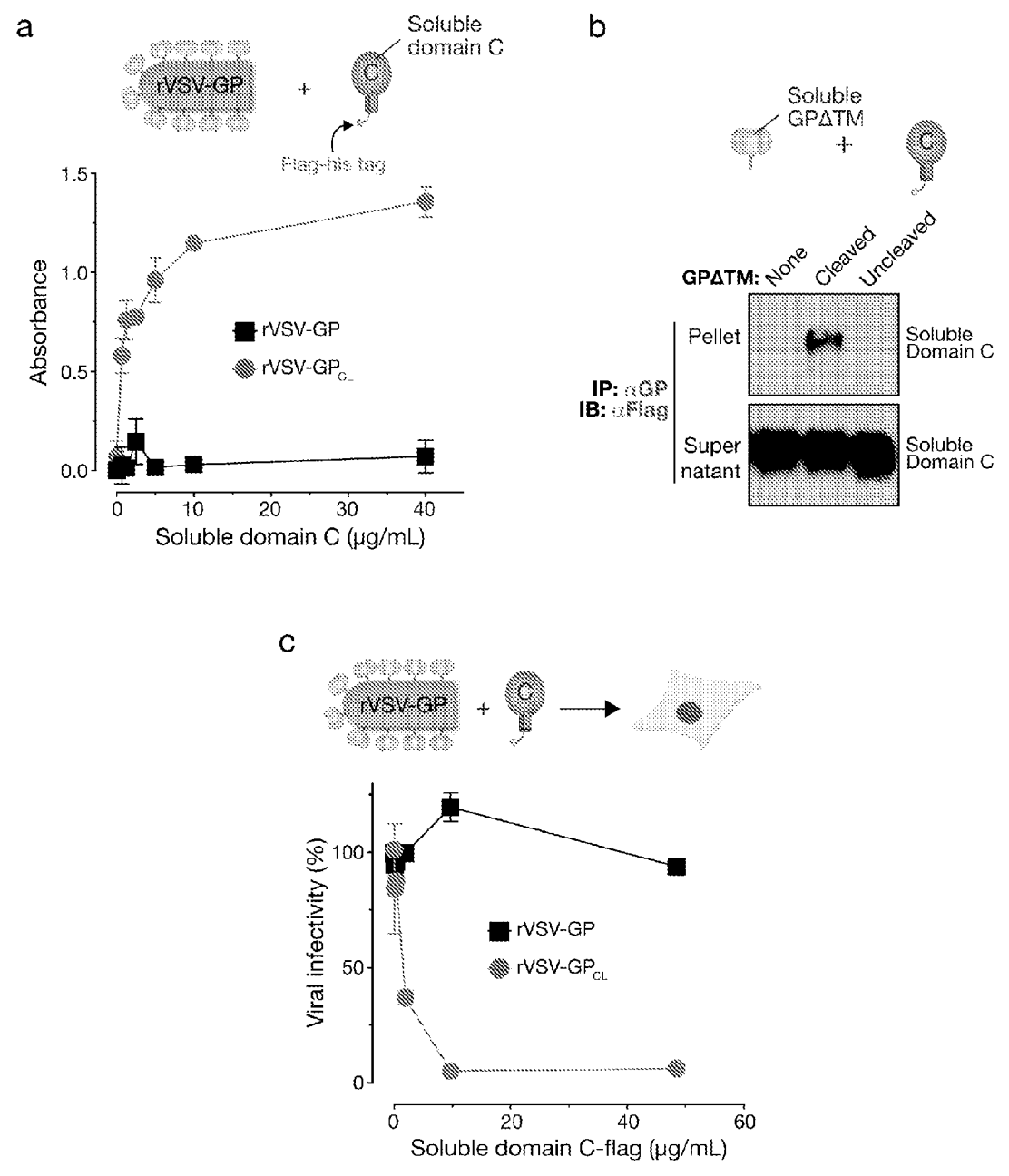

It was next tested if NPC1 domain C is not only necessary but also sufficient to mediate EBOV $GP_{CL}$-NPC1 binding. To examine the $GP_{CL}$-NPC1 interaction with 'soluble proteins' in the absence of detergent, a soluble, secreted, and biologically-active form of domain C[40] was engineered and its binding to $GP_{CL}$ was tested. Cleaved rVSV-$GP_{CL}$, but not uncleaved rVSV-GP, captured purified domain C in an ELISA (FIG. 22A). Even more stringently, $GP_{CL}$ derived from a purified, soluble GP protein lacking the transmembrane domain (GPΔTM) co-precipitated purified domain C, whereas uncleaved GPΔTM did not (FIG. 22B). Consistent with its capacity to bind directly and stably to $GP_{CL}$, soluble domain C neutralized infection by rVSV-$GP_{CL}$ but not rVSV-GP in a dose-dependent manner (FIG. 22C). Therefore, NPC1 domain C directly and specifically binds to a cleaved form of the EboV glycoprotein.

Figures 23A, 23B:
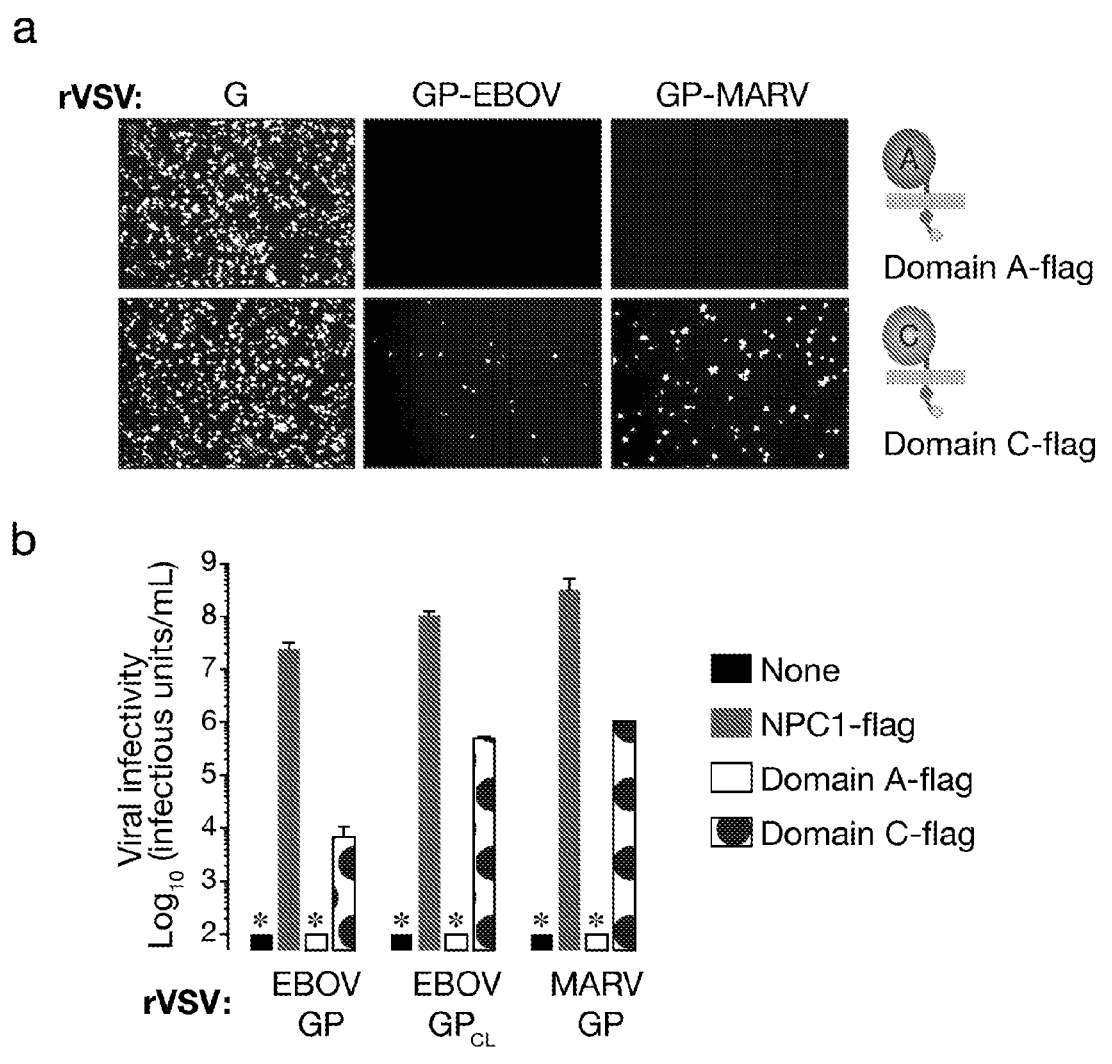

Finally, it was asked if a synthetic single-pass membrane protein containing only NPC1 domain C could mediate filovirus entry. Accordingly, NPC1 luminal domains A, C, and I were separately fused to the first transmembrane domain of NPC1, the NPC1 cytoplasmic tail, and a flag tag, and expressed in CT43 cells. All three proteins were expressed to similar levels, and domain A-flag and domain C-flag localized significantly to late endosomes and/or lysosomes (not shown). The capacity of these engineered single-domain transmembrane proteins to mediate viral entry was tested in CT43 cells (FIG. 23A, 23B). Remarkably, only domain C-flag afforded measurable, although incomplete, rescue of filovirus GP-dependent entry, in full agreement with the $GP_{CL}$-binding activity of domain C (FIG. 22). Taken together, these results indicate that sequences essential for both the EboV GP binding and entry host factor activities of NPC1 reside within domain C, a 248-amino acid domain of this 1278-amino acid protein that protrudes into the endosomal lumen. These findings, together with other functional data presented herein, also indicate that NPC1 is a critical endosomal receptor for cell entry by the Ebola and Marburg viruses.

The current work enables the development of small molecule antivirals targeting the NPC1 protein in cells and hosts (FIG. 24). A number of possible modes of action for these antivirals are envisioned, only some of which are detailed here. For example, these molecules may (1) directly inhibit the GP-NPC1 virus-receptor interaction during entry (FIG. 24A) by blocking the binding site in either protein (FIG. 24B); (2) indirectly inhibit the GP-NPC1 virus-receptor interaction during entry by binding to NPC1 and inducing a conformational change in this protein (FIG. 24C); (3) indirectly inhibit the GP-NPC1 virus-receptor interaction during entry by binding to an associated cellular component (e.g., protein or lipid) and inducing a conformational change in this protein (not pictured); and/or (4) reduce levels of the NPC1 protein by causing it to misfold, or otherwise targeting it for degradation within cells (FIG. 24D).

Figure 25:
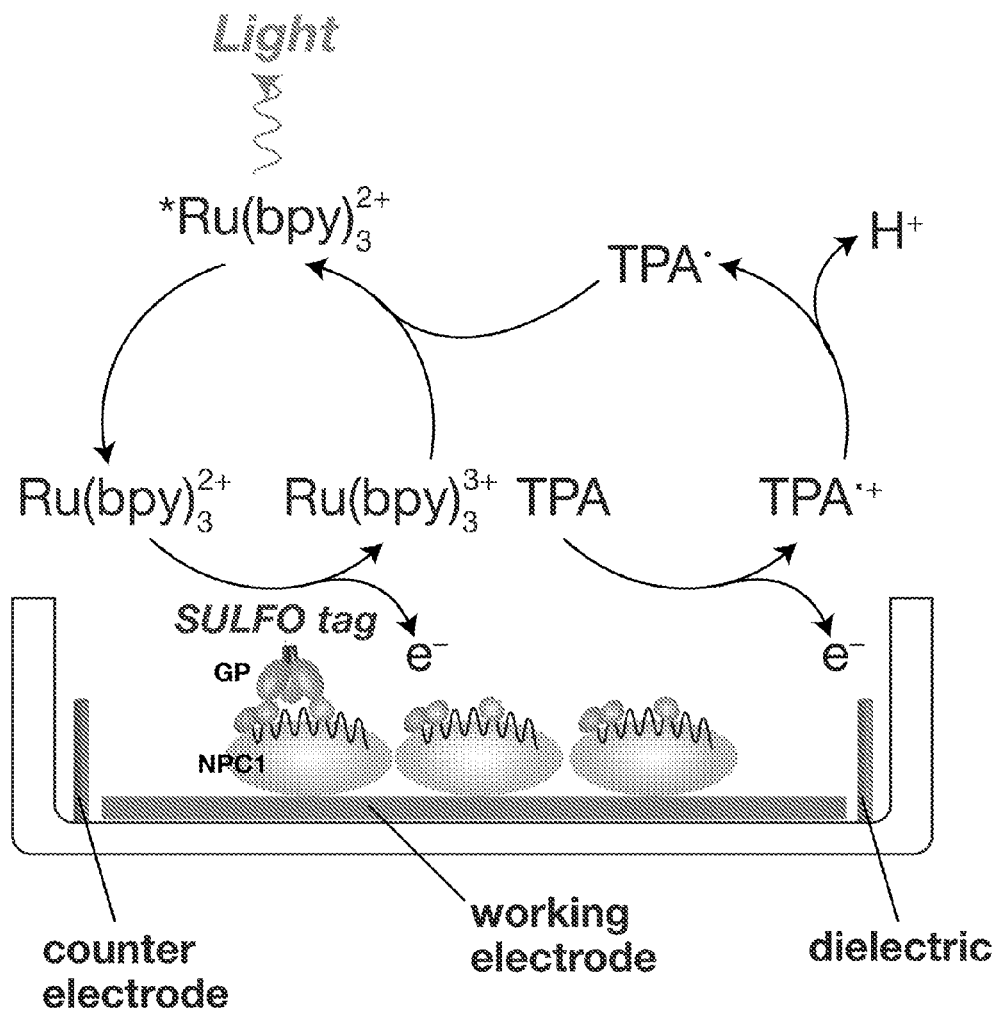
FIG. 25. A homogeneous electrochemiluminescence assay to screen for inhibitors of the GP-NPC1 interaction. Binding of a GP ectodomain labeled with a SULFO-tag™ (MesoScale Discovery Systems) to NPC1 in immobilized membranes is detected by the emission of light by *Ru(bpy)$_3^{2+}$. This activated species is electrochemically generated at the bottom of the microplate well.
Figure 26:
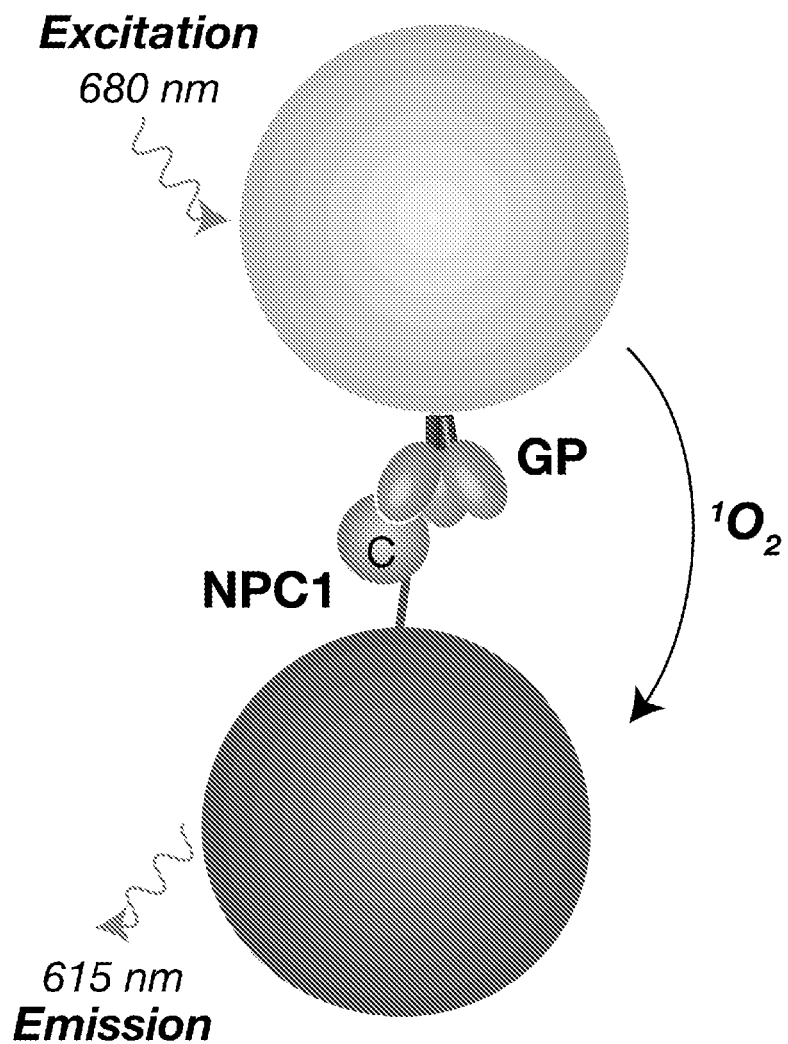
FIG. 26. A homogeneous Alphascreen™ assay (Perkin-Elmer) to screen for inhibitors of the GP-NPC1 interaction. Binding of purified NPC1 domain C tethered to Donor beads and GP ectodomain tethered to Acceptor beads is detected as follows. When Donor and Acceptor beads are brought into close proximity by the GP-NPC1 interaction, the excitation of the Donor beads provokes the release of singlet oxygen ($^1O_2$), triggering a cascade of energy transfer to the Acceptor beads and resulting in blue-shifted emission.

The current work enables the development of assays for identification of small molecule inhibitors of the GP-NPC1 interaction by high-throughput screening. For example, results are provided with an enzyme-linked immunosorbent assay (ELISA) to detect the binding of GP to intact NPC1 or NPC1 domain C-containing fragment (FIGS. 21B, 21D, 22A), which may be adapted to high-throughput screening. One possible embodiment of such a screening assay is a homogeneous electrochemiluminescence (ECL) assay to measure the binding of purified GP to immobilized endosomal membrane fragments containing the complete NPC1 protein (FIG. 25). A second possible embodiment of such a screening assay is a homogeneous assay in which interaction of GP and NPC1 domain C brings two distinct functionalized beads into proximity, resulting in the emission of light at a specific wavelength that can be measured with the appropriate instrumentation. The current work also enables other types of GP-NPC1 interaction assays.

Global disruption of nonessential human genes as described here has provided a solid genetic framework for understanding the unusual entry pathway used by the Ebola and Marburg viruses. Most of the genes that were identified affect different aspects of lysosome function, suggesting that filoviruses exploit this organelle in a manner distinct from other viruses. By uncovering unanticipated roles for these cellular genes and their products in EboV and MarV entry into host cells, the present work opens new avenues for sorely needed anti-filovirus therapeutics.

REFERENCES

1 Feldmann, H and Geisbert, T W, Ebola haemorrhagic fever. *Lancet* (2010).
2 Lee, J E and Saphire, E O, Ebolavirus glycoprotein structure and mechanism of entry. *Future Virol.* 4 (6), 621 (2009).
3 Chandran, Kartik et al., Endosomal proteolysis of the Ebola virus glycoprotein is necessary for infection. *Science*. 308 (5728), 1643 (2005).
4 Kuhn, Jens H. et al., Conserved receptor-binding domains of Lake Victoria marburgvirus and Zaire ebolavirus bind a common receptor. *The Journal of biological chemistry* 281 (23), 15951 (2006).
5 Schornberg, Kathryn et al., Role of endosomal cathepsins in entry mediated by the Ebola virus glycoprotein. *Journal of virology* 80 (8), 4174 (2006).
6 Nickerson, Daniel P., Brett, Christopher L., and Merz, Alexey J., Vps-C complexes: gatekeepers of endolysosomal traffic. *Current opinion in cell biology* 21 (4), 543 (2009).
7 Naureckiene, S. et al., Identification of HE1 as the second gene of Niemann-Pick C disease. *Science (New York, N.Y.)* 290 (5500), 2298 (2000).
8 Carstea, E. D. et al., Niemann-Pick C1 disease gene: homology to mediators of cholesterol homeostasis. *Science (New York, N.Y.)* 277 (5323), 228 (1997).
9 Carette et al, J E (submitted).
10 Carette, Jan E. et al., Haploid genetic screens in human cells identify host factors used by pathogens. *Science (New York, N.Y.)* 326 (5957), 1231 (2009).
11 Wong, Anthony C. et al., A forward genetic strategy reveals destabilizing mutations in the Ebolavirus glycoprotein that alter its protease dependence during cell entry. *Journal of virology* 84 (1), 163 (2010).
12 Carette, Jan E. et al., Generation of iPSCs from cultured human malignant cells. *Blood* 115 (20), 4039 (2010).
13 Takahashi, Kazutoshi et al., Induction of pluripotent stem cells from adult human fibroblasts by defined factors. *Cell* 131 (5), 861 (2007).
14 Sbrissa, Diego et al., Core protein machinery for mammalian phosphatidylinositol 3,5-bisphosphate synthesis and turnover that regulates the progression of endosomal transport. Novel Sac phosphatase joins the ArPIKfyve-PIKfyve complex. *The Journal of biological chemistry* 282 (33), 23878 (2007); Ikonomov, Ognian C. et al., PIKfyve controls fluid phase endocytosis but not recycling/degradation of endocytosed receptors or sorting of procathepsin D by regulating multivesicular body morphogenesis. *Molecular biology of the cell* 14 (11), 4581 (2003).
15 Dell'Angelica, Esteban C., The building BLOC(k)s of lysosomes and related organelles. *Current opinion in cell biology* 16 (4), 458 (2004).
16 Tiede, Stephan et al., Mucolipidosis II is caused by mutations in GNPTA encoding the alpha/beta GlcNAc-1-phosphotransferase. *Nature medicine* 11 (10), 1109 (2005).
17 Perez, Mar et al., Generation and characterization of a recombinant vesicular stomatitis virus expressing the glycoprotein of Borna disease virus. *Journal of virology* 81 (11), 5527 (2007).
18 Sieczkarski, Sara B. and Whittaker, Gary R., Differential requirements of Rab5 and Rab7 for endocytosis of influenza and other enveloped viruses. *Traffic (Copenhagen, Denmark)* 4 (5), 333 (2003).
19 Pentchev, P. G. et al., A defect in cholesterol esterification in Niemann-Pick disease (type C) patients. *Proceedings of the National Academy of Sciences of the United States of America* 82 (23), 8247 (1985); Blanchette-Mackie, E. J. et al., Type-C Niemann-Pick disease: low density lipoprotein uptake is associated with premature cholesterol accumulation in the Golgi complex and excessive cholesterol storage in lysosomes. *Proceedings of the National Academy of Sciences of the United States of America* 85 (21), 8022 (1988).
20 Wool-Lewis, R. J. and Bates, P., Characterization of Ebola virus entry by using pseudotyped viruses: identification of receptor-deficient cell lines. *Journal of virology* 72 (4), 3155 (1998); Takada, A. et al., A system for functional analysis of Ebola virus glycoprotein. *Proceedings of the National Academy of Sciences of the United States of America* 94 (26), 14764 (1997).
21 Cruz, J. C., Sugii, S., Yu, C., and Chang, T. Y., Role of Niemann-Pick type C1 protein in intracellular trafficking of low density lipoprotein-derived cholesterol. *The Journal of biological chemistry* 275 (6), 4013 (2000).
22 Liscum, L. and Faust, J. R., The intracellular transport of low density lipoprotein-derived cholesterol is inhibited in Chinese hamster ovary cells cultured with 3-beta-[2-(diethylamino)ethoxy]androst-5-en-17-one. *The Journal of biological chemistry* 264 (20), 11796 (1989).
23 Rodriguez-Lafrasse, C. et al., Abnormal cholesterol metabolism in imipramine-treated fibroblast cultures. Similarities with Niemann-Pick type C disease. *Biochimica et biophysica acta* 1043 (2), 123 (1990).
24 Lange, Y. Ye, J. Rigney, M. and Steck, T., Cholesterol movement in Niemann-Pick type C cells and in cells treated with amphiphiles. *The Journal of biological chemistry* 275 (23), 17468 (2000); Liu, Ronghua, Lu, Peihua, Chu, Joseph W. K., and Sharom, Frances J., Characterization of fluorescent sterol binding to purified human NPC1. *The Journal of biological chemistry* 284 (3), 1840 (2009); Cenedella, Richard J., Cholesterol synthesis inhibitor U18666A and the role of sterol metabolism and trafficking in numerous pathophysiological processes. *Lipids* 44 (6), 477 (2009).
25 Lloyd-Evans, Emyr et al., Niemann-Pick disease type C1 is a sphingosine storage disease that causes deregulation of lysosomal calcium. *Nature medicine* 14 (11), 1247 (2008).
26 Marzi, Andrea et al., DC-SIGN and DC-SIGNR interact with the glycoprotein of Marburg virus and the S protein of severe acute respiratory syndrome coronavirus. *Journal of virology* 78 (21), 12090 (2004).
27 Nanbo, Asuka et al., Ebolavirus is internalized into host cells via macropinocytosis in a viral glycoprotein-dependent manner. *PLoS pathogens* 6 (9) (2010); Saeed, Mohammad F., Kolokoltsov, Andrey A., Albrecht, Thomas, and Davey, Robert A., Cellular entry of ebola virus involves uptake by a macropinocytosis-like mechanism and subsequent trafficking through early and late endosomes. *PLoS pathogens* 6 (9) (2010).
28 Weissenhorn, W. et al., The central structural feature of the membrane fusion protein subunit from the Ebola virus glycoprotein is a long triple-stranded coiled coil. *Proceed-*

29 Whelan, S. P., Ball, L. A., Barr, J. N., and Wertz, G. T., Efficient recovery of infectious vesicular stomatitis virus entirely from cDNA clones. *Proceedings of the National Academy of Sciences of the United States of America* 92 (18), 8388 (1995).

30 Morgenstern, J. P. and Land, H., Advanced mammalian gene transfer: high titre retroviral vectors with multiple drug selection markers and a complementary helper-free packaging cell line. *Nucleic acids research* 18 (12), 3587 (1990).

31 Pentchev, P. G. et al., The cholesterol storage disorder of the mutant BALB/c mouse. A primary genetic lesion closely linked to defective esterification of exogenously derived cholesterol and its relationship to human type C Niemann-Pick disease. *The Journal of biological chemistry* 261 (6), 2772 (1986).

32 Ebert, Daniel H., Deussing, Jan, Peters, Christoph, and Dermody, Terence S., Cathepsin L and cathepsin B mediate reovirus disassembly in murine fibroblast cells. *The Journal of biological chemistry* 277 (27), 24609 (2002).

33 Blum, Galia et al., Dynamic imaging of protease activity with fluorescently quenched activity-based probes. *Nature chemical biology* 1 (4), 203 (2005).

34 Cureton, David K. et al., Vesicular stomatitis virus enters cells through vesicles incompletely coated with clathrin that depend upon actin for internalization. *PLoS pathogens* 5 (4), e1000394 (2009).

35 Ehrlich, Marcelo et al., Endocytosis by random initiation and stabilization of clathrin-coated pits. *Cell* 118 (5), 591 (2004).

36 Lefrancois, L. and Lyles, D. S., The interaction of antibody with the major surface glycoprotein of vesicular stomatitis virus. I. Analysis of neutralizing epitopes with monoclonal antibodies. *Virology* 121 (1), 157 (1982).

37 Dube D, Brecher M B, Delos S E, Rose S C, Park E W, Schornberg K L, Kuhn J H, White J M. The primed ebolavirus glycoprotein (19-kilodalton GP1,2): sequence and residues critical for host cell binding. J Virol. 2009 April; 83(7):2883-91. Epub 2009 Jan. 14.

38 Davies J P, Ioannou Y A. Topological analysis of Niemann-Pick C1 protein reveals that the membrane orientation of the putative sterol-sensing domain is identical to those of 3-hydroxy-3-methylglutaryl-CoA reductase and sterol regulatory element binding protein cleavage-activating protein. *J Biol Chem.* 2000 Aug. 11; 275(32):24367-74.

39 Kwon H J, Abi-Mosleh L, Wang M L, Deisenhofer J, Goldstein J L, Brown M S, Infante R E. Structure of N-terminal domain of NPC1 reveals distinct subdomains for binding and transfer of cholesterol. *Cell*. 2009 Jun. 26; 137(7):1213-24.

40 Deffieu, M. and Pfeffer, S. R. Niemann-Pick type C1 function requires lumenal domain residues that mediate cholesterol-dependent NPC2 binding. *Proc Natl Acad Sci USA*. 2011. 108, 18932-36.

What is claimed is:

1. A method for treating a subject infected with an ebolavirus or a marburgvirus or for preventing an infection with an ebolavirus or a marburgvirus in a subject exposed to an ebolavirus or a marburgvirus comprising administering to the subject an agent that inhibits Niemann-Pick C1 (NPC1) in an amount effective to treat and/or prevent infection with an ebolavirus or a marburgvirus.

2. The method of claim 1 for treating a subject infected with an ebolavirus or a marburgvirus.

3. The method of claim 1 for preventing an infection with an ebolavirus or a marburgvirus in a subject exposed to an ebolavirus or a marburgvirus.

4. The method of claim 3, wherein the subject is exposed to an ebolavirus or a marburgvirus as the result of bioterrorism or biological warfare.

5. The method of claim 1, wherein the agent inhibits NPC1 protein activity.

6. The method of claim 1, wherein the agent inhibits nucleic acid that encodes NPC1 protein.

7. The method of claim 1, wherein the agent targets domain C of NPC1 or nucleic acid encoding domain C of NPC1.

8. The method of claim 1, wherein the subject is infected with an ebolavirus or exposed to an ebolavirus.

9. The method of claim 1, wherein the subject is infected with a marburgvirus or exposed to a marburgvirus.

* * * * *